US006492505B1

(12) United States Patent
Reddy et al.

(10) Patent No.: US 6,492,505 B1
(45) Date of Patent: Dec. 10, 2002

(54) COMPOSITION FOR DETECTION OF GENES ENCODING MEMBRANE-ASSOCIATED PROTEINS

(75) Inventors: Roopa Reddy, Sunnyvale; Karl J. Guegler, Menlo Park; Janice Au-Young, Brisbane, all of CA (US)

(73) Assignee: Incyte Genomics, Inc., Palo Alto, CA (US)

(*) Notice: Subject to any disclaimer, the term of this patent is extended or adjusted under 35 U.S.C. 154(b) by 0 days.

(21) Appl. No.: 09/495,050

(22) Filed: Jan. 31, 2000

Related U.S. Application Data

(60) Provisional application No. 60/118,318, filed on Feb. 1, 1999.

(51) Int. Cl.[7] ......................... C07H 21/02; A61K 38/00

(52) U.S. Cl. ....................... 536/23.1; 536/530; 536/300

(58) Field of Search .............................. 536/23.1; 435/6

(56) References Cited

PUBLICATIONS

Accession No. AF112972 on GenBank, Babichev et al., Jan. 13, 1999.*

Accession No. AC002350 on GenBank, Muzny et al., May 2, 1998.*

Schena et al., "Parallel human genome analysis: Microarray–based expression monitoring of 1000 genes," Proc. Natl. Acad. Sci. USA, 1996, vol. 93, pp. 10614–10619.*

* cited by examiner

*Primary Examiner*—John S. Brusca
*Assistant Examiner*—Young Kim
(74) *Attorney, Agent, or Firm*—Incyte Genomics, Inc.

(57) ABSTRACT

The present invention relates to a composition comprising a plurality of polynucleotide sequences. The composition can be used as probes or array elements.

5 Claims, 4 Drawing Sheets

```
1514470CT1 GCAGGGGCCAGTCCCTCCACCCTCAACTCAGCCTCCATCTGGCAGGGCAATGGCCCCTTCCCTCAGATTG
1513293H1  GCAGGGGCCAGTCCCTCCACCCTCAACTCAGCCTCCATCTGGCAGGGCAATGGCCCCTTCCCTCAGATTG
1514470F6  GCANGGGCCAGTCCCTCCACCCNCAACTCANCNTCCATCTGGCAGGGCAATGGCCCCTTCCCTCAGATTG
1514470H1  GCAGGGGCCAGTCCCTCCACCCTCAACTCAGCCTCCATCTGGCAGGGCAATGGCCCCTTCCCTCAGATTG
                    10        20        30        40        50        60        70

1514470CT1 CCTGTCCCCTCGTGGTGCCTTCTCCTTCATCAGGCAACCTATAATTCTTGTGGAAGGGAGGGACGGCGTG
1513293H1  CCTGTCCCCTCGTGGTGCCTTCTCCTTCATCAGGCAACCTATAATTCTTGTNGAANGGAGGGACGGCGTG
1514470F6  CCTGTCCCCTCGTGGTGCCTTCTCCTTCATCAGGCAACCTATAATTCTTGTNGAAGGGAGGGACGGCGTG
1514470H1  CCTGTCCCCTCGTGGTGCCTTCTCCTTCATCAGGCAACCTATAATTCTTGTNGAAGGGAGGGACGGCGTG
                    80        90       100       110       120       130       140

1514470CT1 TCCCCGGGCCCTCTGATGGTTCCCTTACCCTTAGGGTGGACCAAATTGTGGGTCGGGGGCCCGGGGACAG
1513293H1  TCCCCGGGCCCTCTGATGGTTCCCTTACCCTTAGGGTGGACCAAATTGTGGGTCGGG
1514470F6  TCCCCGGGCCCTCTGATGGTTCCCTTACCCTTAGGGTGGACCAAATTGTGGGTCGGGGGCCCGGGGACAG
1514470H1  TCCCCGGGCCCTCTGATGGTTCCCTTACCCTTAGGGTGGACCAAATTGTGGGTCGGGGGCCCG
                   150       160       170       180       190       200       210

1514470CT1 GAAGGCCCGGGAGAAGGGCGACAAGGGGCCCTCCGACGCGGAGGTGGTGGATGAAATCAGCATGATGGGA
1514470F6  GAAGGCCCGGGAGAAGGGCGACAAGGGGCCCTCCGACGCGGAGGTGGTGGATGAAATCAGCATGATGGGA
                   220       230       240       250       260       270       280
```

FIGURE 1A

```
1514470CT1  CGCGTGGTCAAGGTGGAGAAGCAGGTGCAGTCCATCGAGCACAAGCTGGACCTGCTGTTGGGCTTCTATT
1514470F6   CGCGTGGTCAAGGTGGAGAAGCAGGTGCAGTCCATCGAGCACAAGCTGGACCTGCTGTTGGGCTTCTATT
3372628H1             GCCCCGT....CCCCAGGTGCAGTCCATCGAGCACAAGCTGGACCTGCTGTTGGGCTTCTATT
                      290       300       310       320       330       340       350

1514470CT1  CGCGCTGCCTGCGCTCTGGCACCTCGGCCAGCCTGGGCGCCGTGCAAGTGCCGCTGTTCGACCCCGACAT
1514470F6   CGCGCTTCCTGCGCTCTGGCACCTCGGCCAGCCTGGGCGCCGTGCAAGTGC
3372628H1   CGCGCTGCCTGCGCTCTGGCACCTCGGCCAGCCTGGGCGCCGTGCAAGTGCCGCTGTTCGACCCCGACAT
                      360       370       380       390       400       410       420

1514470CT1  CACCTCCGACTACCACAGCTCTGTGGACCACGAGGACATCTCCGTCTCTGCACAGACGCTCAGCATCTCC
3372628H1   CACCTCCGACTACCACAGCCCTGTGGACCACGAGGACATCTCCGTCTCCGCACAGACGCTCAGCATCTCC
                      430       440       450       460       470       480       490

1514470CT1  CGCTCGGTCAGCA.CAACATGGACTGAGGG.CTTCTCAGAGGCA.GGCAGCA.ACGG.CAG.CTCGCGG.
3372628H1   CGCTCGGTCAGCACCAACATGGACTGAGGGACTTCTCAGAGGCAGGGCAGCACACGGCCAGCCCCGCGGC
                      500       510       520       530       540       550       560

1514470CT1  CTGG
3372628H1   CTGGCGCTCCGA
                      570
```

FIGURE 1B

```
4970006CT1  GGAAAAGGGCAAATCACATCAGATAAGAAGAGCCGAGAGAAAATAACAGCAGAACATGAGACCACAGACG
4970006F6   GGAAAAGGGCAAATCACATCAGATAAGAAGAGCCGAGAGAAAATAACAGCAGAACATGAGACCACAGACG
4970006H1   GGNNNAGGGCAAATCACATCAGATAAGAAGAGCCGAGAGAAAATAACAGCAGAACATGAGACCACAGACG
                     10        20        30        40        50        60        70

4970006CT1  ATCTCAGTATGCTCGGTCGGGTGGTCAAGGTTGAAAAACAGGTACAGTCCATAGAATCCAAGCTGGACTG
4970006F6   ATCTCAGTATGCTCGGTCGGGTGGTCAAGGTTGAAAAACAGGTACAGTCCATAGAATCCAAGCTGGACTG
4970006H1   ATCTCAGTATGCTCGGTCGGGTGGTNNAGGTTGAAAAACAGGTACAGTCCATAGAATCCAAGCTGGACTG
                     80        90       100       110       120       130       140

4970006CT1  CCTACTAGACATCTATCAACAGGTCCTTCGGAAAGGCTCTGCCTCAGCCCTCGCTTTGGCTTCATTCCAG
4970006F6   CCTACTAGACATCTATCAACAGGTCCTTCGGAAAGGCTCTGCCTCAGCCCTCGCTTTGGCTTCATTCCAG
4970006H1   CCTACTAGACATCTATCAACAGGTCCTTCGGAAAGGCTCTGCCTCAGCCCTCGCTTTGGCTTCATTCCAG
                    150       160       170       180       190       200       210

4970006CT1  ATCCCACCTTTTGAATGTGAACAGACATCTGACTATCAAAGCCCTGTGGATAGCAAAGATCTTTCGGGTT
4970006F6   ATCCCACCTTTTGAATGTGAACAGACATCTGACTATCAAAGCCCTGTGGATAGCAAAGATCTTTCGGGTT
4970006H1   ATCCCACCTTTTGAATGTNAACAGACATCTGACTATCAAAGCCCTGTGGATAGCAAAGATCTTTC
                    220       230       240       250       260       270       280
```

FIGURE 2A

```
4970006CT1  CCGCACAAAACAGTGGCTGCTTATCCAGATCAACTAGTGCCAACATCTCGAGAGGCCTGCAGTTCATTCT
4970006F6   CCGCACAAAACAGTGGCTGCTTATCCAGATCAACTAGTGCCAACATCTCGAGAGGCCTGCAGTTCA.TCT
                      290       300       310       320       330       340       350

4970006CT1  GACGCCAAATGAGTTCAGTGCCCAGACTTTCTACGCGCTTAGCCCTACTATGCACAGTCAAGCAACACAG
4970006F6   GACGCCAAATGAGTTCAGTGCCCAGACTTTCTACG.GCTTAG.CCTACTATGCACAGTCAAGCAACACAG
                      360       370       380       390       400       410       420

4970006CT1  GTGCCAATTAGTCAAAGCGATGGCTCAGCAGTGGCAGCCACCAACACCATTGCAAACCAAATAAATACGG
4970006F6   GTGCCAA.TAGTCAAAGCGATGGCTCAGCAGTGGCAGCCACCAACACCATTGC.AACCAAATTAATACGG
                      430       440       450       460       470       480       490

4970006CT1  CACCAAAGCCAGCA.GCCCAACAACTTTACAGATCTTCCTCCTCCAGCTCTTGAGGAGCTAGAA.TACAG
4970006F6   NACCCAAGCCAGCAGGCCCCACAA.NTTACAG.TC.TCCT.CT.CAGCTCTTGAGGGGTAGGAATTACAG
                      500       510       520       530       540       550       560

4970006CT1  GGAGATGCCACAT.GCCAGTTAATT
4970006F6   GNAGATGCCCCATGGCCCGTTANTT

                      570       580
```

FIGURE 2B

SEQUENCE LISTING

```
<160> NUMBER OF SEQ ID NOS: 305

<210> SEQ ID NO 1
<211> LENGTH: 893
<212> TYPE: DNA
<213> ORGANISM: Homo sapiens
<220> FEATURE:
<221> NAME/KEY: misc_feature
<223> OTHER INFORMATION: Incyte ID No: 008915CB1      Contig5

<400> SEQUENCE: 1

aataaagttt aaaggaaata agtatctaat accattttca actagccatg caaaattggc     60

ttctctcccc aaatcctgta tttgaaaaaa taactttaac ataacgtttg gcattaactt    120

atatttgctc atcataaaaa accaaaagaa atttttatat ctcaaattgg taaactttac    180

aaaatattta acatatgagg aagaggtata tcttacagaa ttatttggct atgtcataag    240

gcagtaatga agatggaatt tttcctatca taaatctgac ataagtgaaa gtctataaca    300

tggtcattct ccataaatct gaaagcttgt tggttacagc aatatgatca tgccacactg    360

tcgtcgttat tgaactttga tgaaagtaga ctgaatgaga aaggaacaaa tttggtgcct    420

gcaccaacgt agaatttgtt ctgaaattct acccagtgga ggcgtatggc gtgaagaaac    480

gcagaaagcc cttccatgat cagaaggatg aaaatggtca aaactgcaaa gagcgcgata    540

accgggagca gtagcaagac gccataggtg gtgtcaacgc ggaggcccac gcgcatcagc    600

atggcccaca ggacatcaga caactgtgcg tgagccaggc taagcgccca gagcctcagg    660

taggaggcgg tgttggagat gcatcccaga cagtactcga tggaatggat tacttggggt    720

cattaatatt tctccaaaat taaactcttc acacgccatt tctctacatc catcttccac    780

ctggtgattt ccctcttcta tatcttggct tcccagcaat gaaacttctt cctcactatc    840

tttccttata agtgtgtagc cactccggtt caccccgaac caactacgcc cat           893


<210> SEQ ID NO 2
<211> LENGTH: 144
<212> TYPE: DNA
<213> ORGANISM: Homo sapiens
<220> FEATURE:
<221> NAME/KEY: misc_feature
<223> OTHER INFORMATION: Incyte ID No: 068454H1
<221> NAME/KEY: unsure
<222> LOCATION: 41, 59, 102, 105, 142
<223> OTHER INFORMATION: a, t, c, g, or other

<400> SEQUENCE: 2

ccagcacact ttcatattcc ccatcacatt ggctgaagtc ntcctcaggc ctcattccna     60

tccatcaaag aagacaggac tcaccttgct ggctgctgcc anttntgctt acatcagccg    120

gtaagattta catggagaaa gnca                                           144
```

-continued

```
<210> SEQ ID NO 3
<211> LENGTH: 337
<212> TYPE: DNA
<213> ORGANISM: Homo sapiens
<220> FEATURE:
<221> NAME/KEY: misc_feature
<223> OTHER INFORMATION: Incyte ID No: 098991H1
<221> NAME/KEY: unsure
<222> LOCATION: 25, 27, 29, 34, 44, 47, 54, 103, 122, 161, 169, 188-189,
      204-206, 215, 222-224, 226-227, 231, 242, 253, 257, 264, 266, 270,
      273, 276, 279, 306, 308, 312, 322, 330, 334
<223> OTHER INFORMATION: a, t, c, g, or other

<400> SEQUENCE: 3

taatcaaagc gttaatctga taccngncng accntctgag gggnggnggc cccngtaccc     60

aatttcgccc ctataggtga gtccgtatta caattcactg gtncgttgtt ttacaacgtt    120

gngacttggg aaaaccctgg ggttacccaa ctttaaatcg nctttcagna caattcccct    180

ttcgccannc ttgggtaata gcgnnngagg ccccntactt tnnngnnctt nccaacagtt    240

gngcagcctg tanaggngta atgngnaaan ttnttnagnc gagaaataat tttttgtttt    300

aaaaantncg cngtttaaaa tntttttgtn taanaat                             337


<210> SEQ ID NO 4
<211> LENGTH: 1051
<212> TYPE: DNA
<213> ORGANISM: Homo sapiens
<220> FEATURE:
<221> NAME/KEY: misc_feature
<223> OTHER INFORMATION: Incyte ID No: 121140CT1

<400> SEQUENCE: 4

gaaatatgga taattatgac atttatccct cattaagctg cctatcagtt tgatttggac     60

aacttgacat ttatttgaga cattaagcta ctttctggta atatattagg catttctgca    120

atagctcttt caggtaactg aatattatta agcatagttt tatcttgctt tgattaaacc    180

tcttaggcaa aaaatggaac ttcataagct aatacattag aaaggggtta tgattataaa    240

tcagaaatgc ttgtgacatt aagaaatgag gcacttgtga aatttctttg aaatagccag    300

ctcctctaat gtgtcttcaa aatataaagt gattcacaaa ggcatgcatc acacctattt    360

gtagcagccc attcattaca taaaccaggg catacctgtg tgggctctgt gagtgaaggg    420

aggcttcact actttctgtg agcagtaagg actggtatct ttctgtgagc aataaggact    480

ggataaagac tgcatatcct tgtgtcgtgt cagcaccaat acaataagga gggttttaat    540

gtgaagcagg caatcttcca gccccttctg gtcttggatg aaatagttgt acagagtatt    600

gcaccaaaaa tacacaatgg aggctgaaaa gttcaacata ttttaagtca attaatcaaa    660

ttgcattgat tcttgatgct ttcttagagg cctacatgat ttcttagatt gctctgataa    720

actatcataa ggggtccacc tcccctcatt tagctccccc agggatttct tttcccccat    780

gtcatacacc cagtcctaaa tcaaccccca aggctatcct tccatccctt ctgcagaggg    840

aacttttgtc agactctgca acaaactcct agctctatcc agagtgtcct ctgctgctaa    900

gattggtatc tttctcctca aaagcctgga tggtgaatgg gggtgcatta gtcagaattc    960

tccagagaaa cagaaaaaat aagattcgcg tgtgtgtgca aacatatata taaataaata   1020

aaaatatatt tattttaaaa aaaaaaaaaa a                                  1051


<210> SEQ ID NO 5
<211> LENGTH: 86
<212> TYPE: DNA
<213> ORGANISM: Homo sapiens
```

-continued

<220> FEATURE:
<221> NAME/KEY: misc_feature
<223> OTHER INFORMATION: Incyte ID No: 129059H1
<221> NAME/KEY: unsure
<222> LOCATION: 13, 53, 57, 60, 74, 76, 81
<223> OTHER INFORMATION: a, t, c, g, or other

<400> SEQUENCE: 5
gccccggtac ccntattcgg cccgtttagt gagtcgtatt acaattcact gtncgtngtn 60
ttacaacgtt tgtnantttt ngaaac 86

<210> SEQ ID NO 6
<211> LENGTH: 56
<212> TYPE: DNA
<213> ORGANISM: Homo sapiens
<220> FEATURE:
<221> NAME/KEY: misc_feature
<223> OTHER INFORMATION: Incyte ID No: 222732H1

<400> SEQUENCE: 6
caacaaggag caggggatct cccatgtagt gatggttgta aaaagaaagg aaagtt 56

<210> SEQ ID NO 7
<211> LENGTH: 1280
<212> TYPE: DNA
<213> ORGANISM: Homo sapiens
<220> FEATURE:
<221> NAME/KEY: misc_feature
<223> OTHER INFORMATION: Incyte ID No: 222748CT1

<400> SEQUENCE: 7
ctggacgtgg tcacccctga gtccttcacc cagctgagcc gcgtggggaa gcccctgatt 60
gaggacccag ctgtggatgt gatcaggaag ctcctgcaac ttcccaacac aaaatggcca 120
acccaccatt gtgacaaaga tccgtcccag acaggcttca agcgacatcg gtgccagcca 180
gaaaactctg ggaagaaggc tgtacccagt gccagtgcta cctctgcagg cagggatttt 240
aaggggatca tcttgaccct cctctgggag agcagtgaga acctgctgac agtcgcagag 300
gagttctacc gtaaagaaaa acgcccagtc accaggcctg actgcatgtg tgacaccttt 360
gaccagtgcg ccgagaacat tagcaaaaag atcctggagt atcagagcca ggcaaataag 420
taccacaact cctgcctcat agaattacgg atccagatca ggagatttga ggagctgctg 480
ccccaagtgt gttggctggt gatggagaat ttcaaggaac accactggaa aaagtttttc 540
acctctgtga aggagatccg aggacagttc gaggaacagc agaagcggct ggagaaaaga 600
aaggacaaaa atgcccagaa gctccatcta aatcttggac accccgtaca tttccaagaa 660
atggagtctc tacacttaag tgaagaggaa aggcaggaag agctggacag catgattagg 720
atgaacaagg agaagctgga ggaatgtacc agaaggaatg gccaggtttt cataaccaac 780
ttggccacct tcaccgagaa gttcctactg cagttggatg aggtggtcac cattgacgat 840
gtccaggttg caaggatgga gccccccaaa cagaaattat caatgctcat acgaaggaaa 900
ctcgctgggc tctccctgaa ggaagagagt gagaaacccc tgattgaacg tggaagcagg 960
aagtggccag ggatcaaacc caccgaagtc accatccaaa acaagattct tctccagcca 1020
acatcatcga tttccaccac caaaaccacc ctgggccacc tggcggccgt ggaagcccga 1080
gatgctgtgt acctgaaata tttagcatca tttgaggagg agctaaagag gatccaggat 1140
gactgtacat ctcagataaa ggaggctcag cgctggaagg acagctggaa gcagtccctg 1200
cacactatcc aaggcctgta tgtgtgaccc tccgccccac catgaataaa cactttctta 1260

```
tacagaaaaa aaaaaaaaaa                                                 1280


<210> SEQ ID NO 8
<211> LENGTH: 789
<212> TYPE: DNA
<213> ORGANISM: Homo sapiens
<220> FEATURE:
<221> NAME/KEY: misc_feature
<223> OTHER INFORMATION: Incyte ID No: 224587CT1
<221> NAME/KEY: unsure
<222> LOCATION: 455-594, 610, 619, 624, 631, 636-637, 651, 665, 675,
      689, 703, 729, 741, 759, 761, 777, 785-786
<223> OTHER INFORMATION: a, t, c, g, or other

<400> SEQUENCE: 8

tacgttgtta ttattaataa tcctttttat gggttacctt taaatagttt ttactattat      60

gtatgtgttg gttttaattt ttacacattt atcagttatg tcctttatga agtttctgcc     120

tttgtaacat attgggaatt ctcttctata gctagattat acagtgcttt cctctttcac     180

tgataatacc aactattaag catccacagt gtgccaggga actgtattag gtagtgagca     240

caaattggta aacaatggat aaaggtccct gcccttattt gacttaaacg ttgttagcaa     300

caacagtaaa ctattaggaa actgaaacga acaggatttt ccagaacgtt taagctgttt     360

ttattcattt tttcctcaaa gcctaaataa cataggatag gaggaatggt ttctatcagt     420

ccctagttgg ttaatcctaa aaagcactgc tggcnnnnnn nnnnnnnnnn nnnnnnnnnn     480

nnnnnnnnnn nnnnnnnnnn nnnnnnnnnn nnnnnnnnnn nnnnnnnnnn nnnnnnnnnn     540

nnnnnnnnnn nnnnnnnnnn nnnnnnnnnn nnnnnnnnnn nnnnnnnnnn nnnnaggctt     600

ggccgtggtn gggcaccanc tggnattccc nacctnnctt tggggggcct naagggtggg     660

agggnccaac ccganccaat ggggggggcna agggccacct gcnaattggg tacaaagggg     720

ggggccttnc ccaaatttaa nggggaaaaa aaaggcccnt nataactccc caccccnggg     780

gaaannggg                                                             789


<210> SEQ ID NO 9
<211> LENGTH: 708
<212> TYPE: DNA
<213> ORGANISM: Homo sapiens
<220> FEATURE:
<221> NAME/KEY: misc_feature
<223> OTHER INFORMATION: Incyte ID No: 225146CT1

<400> SEQUENCE: 9

aaataaatgc atgcaaagca aattagacac accaaaaaga ggggaggagg agaactgaaa      60

gagcagaatt attacagaag aagaactaat gggattgcaa aatgtattga gaattggagg     120

gaaacttaca agctgcattc tactaaggat accatttctt catctccctt cctttttttta    180

gtgaaaataa tattaaaatc taagagaggg ctgtctaggg ggattgtttt gtgattgact     240

gatattaaaa tagaatccat tttaggccgg gcacggtggc tcacacctgt aatcctaaca     300

ctttaggagg ccgaggtgag tggatcactt tagtccagga tttcaagacc agcctggaca     360

acatggcaaa accccgtctg tactaaaaat acaaaaatta gccgggcgtg gtggtgcacg     420

actgtaaatg cagctactta ggaagctaag gcaggagaac cgattgaacc agggaggata     480

gaggttgcaa tgagccaagg tcaattccac tgcaattcca aacccggggc aattagagcc     540

gaggagtctt ctacaaagaa aaaagaaaat agaaaaaacc ttcgaaggag aagggagacc     600

cgggttaccc caaagttata gacccactta tgaaggaagg aggtagcgaa tattaccaca     660

gatgtaaaca tttggcacac agtataggga gttgttatat acaacaag                  708
```

<210> SEQ ID NO 10
<211> LENGTH: 768
<212> TYPE: DNA
<213> ORGANISM: Homo sapiens
<220> FEATURE:
<221> NAME/KEY: misc_feature
<223> OTHER INFORMATION: Incyte ID No: 225640CT1

<400> SEQUENCE: 10

```
tggcaattta ttaacccagc atggtttgtt ctaatgcttc ttgttggcag ctgccacctg     60

tccggcgatt ctgtccagat ctctttgtcc ctgaggtgtc agtttgcggc cgccctttttt   120

ttttttttt tatgaagatg cccaaggctg aagcagccag ccgtgggtga gggtaggggg    180

tgtctttatt gcacagtacc aatgtcaggt tggggagtta ccacctgaaa agctcctgtt    240

ttcaaagaga acttgaccct gtcactcaga tccaccaaag gggccaggat ccacccctgg    300

gcggcccctg gtccatgctc taggctgatg gcccctgcca ggacatctaa cttctgccag    360

gcaagaccag caaactgttc aacggcatct ggttcatgct gtggcatcca cagccacctt    420

agcaccaggc ccatggaggg gtgactaagg caggaagagt agtcaccagc cttccagggg    480

gctttcttca ccacttccca aggccacaaa gggcttcttg cacagatccc caggttgtgc    540

tagctcctga gctctggggc ccccagggtc ttggtcagga gcctccctct ttcgcttgtg    600

caaggaaggg ctctcctcac ccagccgacc ctcagggagg ccctggctcc gcagacagac    660

gatggctgca gcctgctccg ccagtttctt ggacttgtcc cacaaggtag actgatactt    720

ttgttcagca acggtgacaa tagaggagaa caggcgatct agagggcg                 768
```

<210> SEQ ID NO 11
<211> LENGTH: 622
<212> TYPE: DNA
<213> ORGANISM: Homo sapiens
<220> FEATURE:
<221> NAME/KEY: misc_feature
<223> OTHER INFORMATION: Incyte ID No: 225650CT1
<221> NAME/KEY: unsure
<222> LOCATION: 448
<223> OTHER INFORMATION: a, t, c, g, or other

<400> SEQUENCE: 11

```
ccagtagata actttactag taagtaaaga ttagaggata tgttaagaaa acagtttaag     60

atagaacaga acccatagag tgggatcagt atacaaaaac atatactctg gctttatcag    120

ctcccatcca cagacaacac actcagcttc tgcctcctcc tgggtcggga cctctctgga    180

tagcccaggc tggcctgtct gtcatttctt tctgtggtgg tcagctttac actggctata    240

aactgctgct gctctgagac ctaccctttg aaaacttact taagaggcct ttattagggc    300

aaaaggagag gaataataac tgtgcttatt ttataattat aagtaatgtt ataatcctta    360

gtgttaaggt gctaaatgca tataaaagtg gtactgaggc caagtgtggt ggcttacacc    420

tgtaatccca gcactttggg aggctgangc gggcggatca cttgaggtcg ggaggtttag    480

acccacctgg cgaaaccctg tctctactag aagcacaaat actagctggg cgtggtgtgt    540

gacctgtagc ccagctactg ggaagcctga gccgagaatc gcttactcca ggggctgttt    600

gtgtgaccta gatcgaccac gg                                              622
```

<210> SEQ ID NO 12
<211> LENGTH: 495
<212> TYPE: DNA
<213> ORGANISM: Homo sapiens
<220> FEATURE:
<221> NAME/KEY: misc_feature
<223> OTHER INFORMATION: Incyte ID No: 226179CT1

<400> SEQUENCE: 12
aaacaatcca gatgtccatc agtaggggat tagtcaaaga aattatggaa aaaccatata 60
atggaatacc atgcagctgt aagaaaaagg caaaattctg ggctgcatat atttatattc 120
atattttttt tacactcaca aacttggaaa ggatggacaa ggaaatctta acatgcgtta 180
cctggagaaa ggggagagga actgaatacg tggaaagatt gggagggagg ctttttttggt 240 ttgttttgtc ttgagacaga gtttcgcttg gagtgcagtg gcgtgatctc agctcactac 300
aatgtctgcc tccccaattc aagtgattct cctgcctcag cctctcgagt agccgggatt 360
acaggcatcc caccacgcca ggctaatttc tggactatta cgaagaatgg tgtttcacca 420
tgttgttggc caggctggtc tcgaactcct acccaagggt attcgccggt ttttccccccc 480 agaggggggg gaaat 495

<210> SEQ ID NO 13
<211> LENGTH: 803
<212> TYPE: DNA
<213> ORGANISM: Homo sapiens
<220> FEATURE:
<221> NAME/KEY: misc_feature
<223> OTHER INFORMATION: Incyte ID No: 226815CT1

<400> SEQUENCE: 13
agagtagaaa ggaaacattg agtttggttc tggacatttt agaatggggc acccaaatgg 60
agagaaccag cagacggaaa catattcaca tgtgtgtgaa tgggtgagat tatataagga 120
gagcttgctg agcaaaacga gagagggtca tgcagaggac tctgggacac tccaacattt 180
aaagggcaca ctcgggaaaa gagccattta agaacagttt caaaaggaga gatagccaca 240
agaggtcaag ctgagatgag caggaatacg aagccattgg aacagagtga gaccctgtct 300
caaacaaaca aaaacaacaa caaaactttt tcaaaagaat ttgttgtaag atttttaaaa 360
ataccaagca cttttcagta tgtgtgtgtg tagcgggggt aaatatatac ataacataaa 420
ctttaccatt taatcattct tgagtggttt ttttggcatt aagtacattc acattgttgt 480
gcaaccatta ccaccataca tctccagaac cttttcactt tccatgattg aaactctggc 540
tgggcgtggt ggctcacgcc tgtaatccca gcgctttggg aggccaaggc aggcggatcg 600
cgaggtcggg agttcgggac caccctgacc aacgtggtga agccctgtct ctactaaaaa 660
tataaaaatt agcagggcgt ggtggtgcgc acctgtgatc ccagctactc gggggggctga 720 ggcgggagag tcgcttgaac ccggggggtg gaggttgcgg tgagccggga tcacgccacc 780
acattccagt ctggacgaga gtg 803

<210> SEQ ID NO 14
<211> LENGTH: 607
<212> TYPE: DNA
<213> ORGANISM: Homo sapiens
<220> FEATURE:
<221> NAME/KEY: misc_feature
<223> OTHER INFORMATION: Incyte ID No: 227559CB1
<221> NAME/KEY: unsure
<222> LOCATION: 292, 384
<223> OTHER INFORMATION: a, t, c, g, or other

<400> SEQUENCE: 14
cattataaga atggaatcct tatctggatt acaaaaatgt gaaaagcaga ggtttctctt 60

-continued

```
ttaaaaaaat ttgtagtaga tttcctgtag caattttatg gcacggaatt caccagaagg    120

taggtttatc aagttggttt attactagaa gtattaaaaa ataattggta taggccgggc    180

gcagttgctc aagcctgtaa tcccagcact ttgggaggcc gatgcaggcg gatcataagg    240

tcaggaggtc gagaccatcc tggctaacac ggtgaaaccc tgtctctact anaaatacaa    300

aaaaattagc tgggagtggt ggcgggcgtc tgtagtccca gctactcagg aggctgaggt    360

aggagaatgg tgtgaacccg ggangtggag cttgcagtga gctgagacca cgccactgca    420

ctccggcctg ggcgacagag cgagactctg tctcaaaaaa caaaaaaaaa actcgggggg    480

ggcccgtaac cattcgccta taggggtcga atacaatcac tggcgtcgtt tacacgtcgt    540

actgggaaac ctgcgtacca ttaatggctg agaaatccct tgcagtgcgt atacaaagcc    600

gacgtgc                                                              607
```

```
<210> SEQ ID NO 15
<211> LENGTH: 676
<212> TYPE: DNA
<213> ORGANISM: Homo sapiens
<220> FEATURE:
<221> NAME/KEY: misc_feature
<223> OTHER INFORMATION: Incyte ID No: 227799CB1

<400> SEQUENCE: 15

atttttttcct atatatccaa catagtcatg agaaaaacaa gatttgcttt tattcttaaa     60

tttgaagaca aatgctattt taattgctag agaattggcc actaatatac aatatataat    120

agtggcaatt ttttacacaa attttgtttt tatggaacag tactttttcc tttcttttgc    180

aacttttgtc ggcttctttt tcttgaaagc ataagcattt acactgccat atattgacat    240

gaggtttttc tttagtgttt ggctgttgtt gggaagaata ttattaaaat gctttccatt    300

accatatcta tagtcttttg tgccaacata ttcattgata tgactgtaat atgtaagtta    360

aagtctctct aagagaaatg ttttctacac atataaggag acaaaaggcc agacatggtg    420

gctcatgcct gtaattccag cacgttggga ggccgaggtg ggcagatcac ttgaggccag    480

gagttcgaga tcagcaggcc aacatgggga aactcagtct ctactaaaaa tacaaaaatc    540

agccaggctt ggtggcacat tcctgtaatc ccagctacta gggcagctga ggcaggagaa    600

ttgcttgaac cagggaggcg gaggttgcag tgagccgaga tcgcaccact gcactctagc    660

atggcaacag agcaag                                                    676
```

```
<210> SEQ ID NO 16
<211> LENGTH: 493
<212> TYPE: DNA
<213> ORGANISM: Homo sapiens
<220> FEATURE:
<221> NAME/KEY: misc_feature
<223> OTHER INFORMATION: Incyte ID No: 227892CT1

<400> SEQUENCE: 16

atagaagtag tccaagaaga gttttgtaag aaatggcaga gaagagtgta agtaatttgg     60

catggtaatg tgtgtaagaa aatggaaagc tgatgggttg gctacctgaa caattatgtc    120

tggaatctca gccagcagag aacaggagac tggttggttt ggtagagttg ttaacaaaac    180

tttctggtgt tttgagtttt ggtctacatt ttaggaatta tagcctttca taatagaatg    240

aatataaatc aacccttgag ggttataggc tttcaaattg gtggtggtta aatataatat    300

tctcaagatt ctatgatggg agtcccagcc tggctcttgg aaagaagatc tcattgtaca    360

ggtgtacttc acctgaccca atgatgtgtt ctcaaagatt tgtgtgagaa ttggcctcca    420
```

-continued

```
aatttaggat gaaataggag agcttgccat ttctagtaat gctattatga atcattttct    480

aaggaaaaaa tct                                                        493


<210> SEQ ID NO 17
<211> LENGTH: 495
<212> TYPE: DNA
<213> ORGANISM: Homo sapiens
<220> FEATURE:
<221> NAME/KEY: misc_feature
<223> OTHER INFORMATION: Incyte ID No: 228282CT1

<400> SEQUENCE: 17

tccatttttt aaagactaaa ccatctcaca gattgttctg tatcagtaaa taaagatctt     60

tcccccaccc ttgcccagtg tgtcattgtc ttaatagacc attattagtt ccctattggt    120

ggacacttaa tggcttttat ttttctgttg taagcaaaac tgcatataca gcatccttgt    180

ctttaggcac atgtgcaaga tatttataag gtaattctca ggctgggcac agtggctcat    240

gcctgtaatc ccagcacttt gggaggccga ggtgggtgga tcatttgagg tcaggagttc    300

gagaccagcc tggtcaacat agtgaaaccc cacctctact aaaaatacca aaataattag    360

ccagcatgat ggagggcacg tgtagtccca gctactcagg aggccgaggc aggagaaatt    420

gcttgaacct gggagatgaa ggttgcaatg agctgagatt gcaccactgc actgcagact    480

ggcgggacga cgagt                                                      495


<210> SEQ ID NO 18
<211> LENGTH: 305
<212> TYPE: DNA
<213> ORGANISM: Homo sapiens
<220> FEATURE:
<221> NAME/KEY: misc_feature
<223> OTHER INFORMATION: Incyte ID No: 229665CT1

<400> SEQUENCE: 18

tttctacttc gttttgtctc atgagaaaac atagtctgat tatcaattgg ggatcctttg     60

aatatcttcc cacttgctcc tagattttct agcaagatga taattagcac ttgccgtggc    120

acaaagggca ctcgctcact catttattga aagtgtatcc attgctactg cagtcctgct    180

attcctagaa accctcaaac tatatatgtg catgtgtgtc taagtgtaaa tatgtatgca    240

cacatttgta ttgatgttta tttttatatc tatatagaat atcatgaggt cgggccaggt    300

atggt                                                                 305


<210> SEQ ID NO 19
<211> LENGTH: 741
<212> TYPE: DNA
<213> ORGANISM: Homo sapiens
<220> FEATURE:
<221> NAME/KEY: misc_feature
<223> OTHER INFORMATION: Incyte ID No: 229779CT1
<221> NAME/KEY: unsure
<222> LOCATION: 492, 502, 538, 547, 559, 566, 574, 584, 592, 599-600,
      604-605, 611-614, 623, 645, 649, 658, 660, 671-672, 676, 678, 681,
      685, 695, 698, 705-707, 709, 719, 724
<223> OTHER INFORMATION: a, t, c, g, or other

<400> SEQUENCE: 19

tttaaatcaa ccctcaccat aagtgtaatt tggaggccac gtattgaaaa aatatattag     60

taacattagt gctcaataaa tacttccaga acctaaaata tgctgatgga ctgtttcttt    120

caagccaaga agggatgctc tcctaatctc actaacaggt tgttaccagt aagtgtagta    180
```

-continued

```
gcatgaacca atggcctaac attttaatgt ctcgtgtgga tgactaaacc aagaaaggcc    240

aatgagtctg cctgcccatc ctcagtcaca gctaacccag ttcttattcc agtttaccaa    300

accatttttt attgcatgtt gactggttta cagctgactc ttcgaggcat gagtgaagcg    360

ttagttgaca agcgggttgc tccggccctg ttaccttgtc cagtgatcct gaattgtgag    420

tttcacagac tgcggcctta agttatcctg tctgtctttt tgagcattct ccttggtctg    480

ctttttttaaa tntatttaat tngcaatgct agagcctaat acaggatatt accctggnac    540

ttacttnaat atacatttna ataaanaccc cggngtcca accncaaaaa cntccaggnn    600

cccnncccgg nnnnaaaatc ccnaaacaag gtcctggcca agggnttgnc caacaaantn    660

cccaggccct nngggnancc naatnaatgg ggaancangg gaaannncna aaagggggng    720

ggtnccctgg ggaaaggagg g                                              741
```

<210> SEQ ID NO 20
<211> LENGTH: 689
<212> TYPE: DNA
<213> ORGANISM: Homo sapiens
<220> FEATURE:
<221> NAME/KEY: misc_feature
<223> OTHER INFORMATION: Incyte ID No: 240829CT1

<400> SEQUENCE: 20

```
tttttttttt tttttttttt ttaacaaaac taagatggac atttcacaca acgcagagct     60

acgagaacat ctcttatgct ccttgccatg ggattttaat gccccaaggt tcataactac    120

agcaaagaaa gtaagtcaaa aataaactga gcttaaagaa ggtggcaggc caattttccc    180

aaaaagactg tggactgtgg gctgctgtgt agcctttgct acaaggctga ggaagcagaa    240

gaaagatgaa ttgggcaatt ggtgatgaaa agtatttgcc attttcaaag gcttctcagt    300

gtggccatag attttgctag tcaattttta aaaaattata tttttagctc aacacacagc    360

tctaaagcag ggttcagtgt agtgtgttct ctaccgaaat ggttatatac agatggtatg    420

gaaatggttt taaagattac tcataaacta tccttttaaa gaaaaactag actcggtcat    480

atttgttaaa atgagcaatg tcaccaaaca gaaatgtagg tgggaaatac tgaaccacaa    540

acatttggag ttgcaggcat agactagcag agcatgaata gtcatcactg tttctataat    600

actgaaacac tcaaatctgt ttctgaggtt taaaacacag agctatatta tattcataaa    660

cttcccccctc cacttaagtt atatttgcc                                      689
```

<210> SEQ ID NO 21
<211> LENGTH: 1130
<212> TYPE: DNA
<213> ORGANISM: Homo sapiens
<220> FEATURE:
<221> NAME/KEY: misc_feature
<223> OTHER INFORMATION: Incyte ID No: 341490CT1

<400> SEQUENCE: 21

```
catacttcaa ttctcatggg atttcttgag ctaggaaagg tggttggctt acggcacagt     60

agagagcttc cagggctggc tggcgtggga tacccgtacc acagaaatgc agggaccatt    120

gcttcttcca ggcctctgct ttctgctgag cctctttgga gctgtgactc agaaaaccaa    180

aacttcctgt gctaagtgcc ccccaaatgc ttcctgtgtc aataacactc actgcacctg    240

caaccatgga tatacttctg gatctgggca gaaactattc acattcccct tggagacatg    300

taacgacatt aatgaatgta caccacccta tagtgtatat tgtggattta acgctgtgtg    360

ttacaatgtc gaaggaagtt tctactgtca atgtgtccca ggatatagac tgcattctgg    420
```

-continued

```
gaatgaacaa ttcagtaatt ccaatgagaa cacctgtcag gacaccacct cctcaaagac    480

aacccagggc aggaaagagc tgcaaaagat tgtggacaaa tttgagtcac ttctcaccaa    540

tcagacttta tggagaacag aagggagaca agaaatctca tccacagcta ccactattct    600

ccgggatgtg gaatcgaaag ttctagaaac tgccttgaaa gatccagaac aaaaagtcct    660

gaaaatccaa aacgatagtg tagctattga aactcaagcg attacagaca attgctctga    720

agaaagaaag acattcaact tgaacgtcca aatgaactca atggacatcc gttgcagtga    780

catcatccag ggagacacac aaggtcccag tgccattgcc tttatctcat attcttctct    840

tggaaacatc ataaatgcaa cttttttga agagatggat aagaaagatc aagtgtatct    900

gaactctcag gttgtgagtg ctgctattgg acccaaaagg aacgtgtctc tctccaagtc    960

tgtgacgctg actttccagc acgtgaagat gacccccagt accaaaaagg tcttctgtgt   1020

ctactggaag agcacagggc agggcagcca gtggtccagg gatggctgct tcctgataca   1080

cgtgaacaag agtcacacca tgtgtaattg tcagtcacct gtccagcttc              1130
```

```
<210> SEQ ID NO 22
<211> LENGTH: 279
<212> TYPE: DNA
<213> ORGANISM: Homo sapiens
<220> FEATURE:
<221> NAME/KEY: misc_feature
<223> OTHER INFORMATION: Incyte ID No: 402456H1
<221> NAME/KEY: unsure
<222> LOCATION: 10, 14, 23-24, 44, 51, 59, 69, 89, 102, 104, 108, 129,
      139-141, 159, 171, 201, 225-226, 239, 265, 268, 273
<223> OTHER INFORMATION: a, t, c, g, or other

<400> SEQUENCE: 22

ggtaacccan ggtnggccta ttnntccccg gcttcttccc aaanttaagg nttttgttna     60

agggcctcng tgggttttta ccattgggng atggtggttt tnanggcngg cccgtaccca    120

attggcctnt agtggtcgnn ntacaattca ttggccgtng ttttaaaagt ngtgacttgg    180

gaaaacctgg ggtaacccaa nttaatggct ttcaagaaca tcccnntttg gccagttgng    240

taatagcgag ggggcccgaa ccgtncgncc ttnccaaaa                           279
```

```
<210> SEQ ID NO 23
<211> LENGTH: 285
<212> TYPE: DNA
<213> ORGANISM: Homo sapiens
<220> FEATURE:
<221> NAME/KEY: misc_feature
<223> OTHER INFORMATION: Incyte ID No: 420765CT1
<221> NAME/KEY: unsure
<222> LOCATION: 148
<223> OTHER INFORMATION: a, t, c, g, or other

<400> SEQUENCE: 23

tctcatttcc aatacaggga actcggatag ccttctctgg cataatagag aaagagtgca     60

tgacactcta cctgagtgat ctctgtgaaa tttagaaacc tgcaggaacc ctaacaaaaa    120

ctggcaagtc ttttcagagg acgatgtnct cattttccac ctttgtcttg aatggccgga    180

gacataattt gtggtggaaa gagctggatg agagaatcct cctgtgatgg cttctgtctc    240

ccatcacaaa cagcttttca gccccttgct cttagcttaa ttaac                    285
```

```
<210> SEQ ID NO 24
<211> LENGTH: 223
<212> TYPE: DNA
<213> ORGANISM: Homo sapiens
```

<220> FEATURE:
<221> NAME/KEY: misc_feature
<223> OTHER INFORMATION: Incyte ID No: 481770H1
<221> NAME/KEY: unsure
<222> LOCATION: 8, 14, 22, 33, 41, 68, 72, 94, 101, 132, 145, 165, 178, 189-190, 196, 203, 211
<223> OTHER INFORMATION: a, t, c, g, or other

<400> SEQUENCE: 24

```
aggttttncg atanccatgg ancctggagg ggnaaaaccc ntacccaaat tggcctattg     60

tgagtggnat tnccaattaa ttgaccatgg tttnccacgg nggtgacttg ggaaaaccct    120

gggtaaccca anttaatggc cttgnagaac atcccctttg gccantgggt atagggaanag    180

acccgaacnn attgcntttc cancattggg nctaaatggg aat                      223
```

<210> SEQ ID NO 25
<211> LENGTH: 672
<212> TYPE: DNA
<213> ORGANISM: Homo sapiens
<220> FEATURE:
<221> NAME/KEY: misc_feature
<223> OTHER INFORMATION: Incyte ID No: 548654CT1

<400> SEQUENCE: 25

```
cccacgcgtc cgccggcggt cgcagagcca ggaggcggag gcgcgcgggc cagcctgggc     60

cccagcccac accttcacca gggcccagga gccaccatgt ggcgatgtcc actggggcta    120

ctgctgttgc tgccgctggc tggccacttg gctctgggtg cccagcaggg tcgtgggcgc    180

cgggagctag caccgggtct gcacctgcgg ggcatccggg acgcgggagg ccggtactgc    240

caggagcagg acctgtgctg ccgcggccgt gccgacgact gtgccctgcc ctacctgggc    300

gccatctgtt actgtgacct cttctgcaac cgcacggtct ccgactgctg ccctgacttc    360

tgggacttct gcctcggcgt gccacccccct tttcccccga tccaaggatg tatgcatgga    420

ggtcgtatct atccagtctt gggaacgtac tgggacaact gtaaccgttg cacctgccag    480

gagaacaggc agtggcagtg tgaccaagaa ccatgcctgg tggatccaga catgatcaaa    540

gccatcaacc aggggcacta tggctggcaa gctgggaaca cagcgcttct ggggcattac    600

accggattag ggcattcgta ccgccctggg accattcggc catcttcctc ggtcaatgac    660

atgcattgaa tt                                                        672
```

<210> SEQ ID NO 26
<211> LENGTH: 2339
<212> TYPE: DNA
<213> ORGANISM: Homo sapiens
<220> FEATURE:
<221> NAME/KEY: misc_feature
<223> OTHER INFORMATION: Incyte ID No: 632097CB1

<400> SEQUENCE: 26

```
aatgactcag atgtttattt tctcaaatac aatatttaaa atattgcaag aagacatctg     60

tttagcattc tcccctcatt tgtcaattac tttattattt gagaattaat accccacatg    120

aagacaatat cacttgccaa agtccttcct ctgacgtggt taagtcgtat caaatccaca    180

ggctgacgtc caaataatac acagtttcat gcttcaggtg agccaagaac aaccttccca    240

ttgagcgcct tgcaggggct gatatcaaag acaagactga acttccttca ttggcatggt    300

gaccaccgtg ggaggtgcag ccctcagcct actcctcggc tgtgccatcc aggatgtgtt    360

taaaggagaa tggagaaaac ttgtaaccat ccccgacata gaacttgttc tggaactcaa    420

cccagtgcag tcgcagggcg tgcaggaaag cagagaggcc ctccatgatc agaaggatgg    480
```

```
ctactgtcag gacagcaaat acggcaaaaa taataaaaac cccgacgatt cctccccagc    540
ctcgcgtctg aaggccgctg ttcatcacca tagtccagag cacttcagac agttgtgcat    600
gagccaggct gagggcccag agccgcaggt aggaggctgt gtttgaaatg cagcccaggc    660
agtactcgat ggtgtggatg gcttggtgga caaagacgtc tccaaagttg aactcttctc    720
catggtcgtc cagagccccg tgggtatctg cagaagtcct ctggccagaa cggctagaag    780
ggctggagct atcaccttca atgttctcag tggcatcttc ttggatcctg gatgcctgca    840
gctgggattt ccgatgactg gctctaagaa taaacggctt aatcagaagc atccacggca    900
cagaaatcaa agccataacc acaaagaaac tttggacttc ttgctgatgt ttgtagaggg    960
gtgcgttgga agagtcactg tagttaaaca gaaacatgtt gatgaagtgg atgaggatgc   1020
tgggggcgtg ctgagatacg tggacgtcaa agcagcacca tttgaaaatg atcatgaaaa   1080
ccaggtatcc aaacagacac aggataaaaa tcatctcagg gataaattgc agaatgatgt   1140
tgagagttct tctgaagtat atgtgattga aaaggctgag gatgacacca aaaaccatct   1200
ggacaattcc caggatcacc gacatcttca ttttatacga gttcagaaat gtgagtttgt   1260
ttgaagccaa gttccaaatc ggatcaatcc caaacgggta tggatttcca aaatacactc   1320
ctggtatggc tgggtccagc tgcagatata gactttcctc cattacatga gtattccatg   1380
tgccgtttct gaacatgggt tggacactcc aagaagagcc aaagatgttc aaggacttgg   1440
agaagcagtc attgtagatc aaacccgtgt agatggagaa gatgcccata agtaggatca   1500
gatagcgccc gtggaagaag gtgttccaaa tctcattgtc tgtcttctgg gagagcaagc   1560
gtctctcatt cagaatcatc caaagtgcag ccaggagcat cacggttcca tgaccacagt   1620
ctccaaacat cacagcgaac aggaagggga aagtgatgat ggtgtagggg gctgggttta   1680
tctcccggta gctgccgaca ccataggcat caacaatatt ctggaagcca gctgtgaatt   1740
tattggtcct gttaaatgtg ggaggggctg ttttagattg cactgtggtc atgatggggg   1800
ccatggagga gccacttagt tccatgcctt gctccagtgc cctcttgata cgtgtggcat   1860
ctgccaccgg gaaccagatc tcggcgatga cacactgctg ggtgacgtcg atgttgcaca   1920
tgttcaggat gtggtagaca gctttcatct tctgcacctt gatgagccag gagtgccagt   1980
tggcagcggc ttcctgcagc aggcgctggc ggtgagactc tgtttgtgtt atgacggtga   2040
ttaaatcttc cagcctcaca ttgacgctct ccaacatctc tctgcgctcc accgcaggct   2100
ctgggcaagg gtagacagtg gctcgaaacc tgtgtttaat atattccaaa ggaaacaggt   2160
gagttcttgc tgcaaagcat tctgcatccc cttttctgct aagacatcgt ttgctgactt   2220
tagttagatg gccagcctat cctagaataa ctgcgtcttt ggccactgga aaaggagtcc   2280
cagcctcgtg ccgaattctt gcctcgaggg ccaaattccc tatagtgagt cgattaaat    2339
```

<210> SEQ ID NO 27
<211> LENGTH: 530
<212> TYPE: DNA
<213> ORGANISM: Homo sapiens
<220> FEATURE:
<221> NAME/KEY: misc_feature
<223> OTHER INFORMATION: Incyte ID No: 647580CT1
<221> NAME/KEY: unsure
<222> LOCATION: 465
<223> OTHER INFORMATION: a, t, c, g, or other

<400> SEQUENCE: 27

```
gggttgggtg ggaacgttcc ccatatatga cagcctctct gctctggtgg agtgcacctt     60
```

-continued

```
tgttttatac caaaggcgtg tctccttctt tgcaaactgc ttgctgaaat gaagtctctt    120

tctcttttaa atgggactcc tttttagtga aagtgttaag agtgtgtagt aggctatacc    180

atctaggttt tgtaagtaca ctttatgatg tttgcacaat gatgacatca cctaatgatg    240

catttctcag tgacacagga ctggaggtaa ttggccccag attacagcta ataattgatg    300

gggctgagaa tcaagcctgc tggtattgga ccctcaagcc ctgggtcttt ccattaaaca    360

catgggctat tagctgctgc cattcccaga gggcacttta aaaacacaag ggaaattgca    420

ttgacgcaca gccagagcag tttcatggca gttcatcact cctancaagc ttttactcct    480

aggaaggctc caaggtctga taaatctttg cacatggtct ttattcgtcc               530
```

<210> SEQ ID NO 28
<211> LENGTH: 948
<212> TYPE: DNA
<213> ORGANISM: Homo sapiens
<220> FEATURE:
<221> NAME/KEY: misc_feature
<223> OTHER INFORMATION: Incyte ID No: 647628CT1

<400> SEQUENCE: 28

```
tttcttttgt cttgtcttag agatgagggg gctacagcag catcatgcaa agagggaaag     60

atgaagggat agaagaagag aaaatccccc tgttctgata ggaacggcct gttccattgt    120

taaatggcaa atggcccaat ttaagggctt tggatctaat ttgcctctga tgtttccttt    180

ggaaacattt aggaatattt ttctccccct accccataaa ttgtgtagca ctttttattc    240

catttgcttt caaatgacta cactaagcct aataatacaa gctccagtgt tatacaataa    300

cccatcagtg attggggaat caaacatttt ggtttaaaaa acatgattat ttaaaactgg    360

aaactaaaaa gaatcaaatt gaattaaagc tatataaaca cagttaaccc ttgtaaatga    420

gtaaacaaat ttttacatgt aagattctct aattgtcata ttttactttt taggattccc    480

taatagtgga ctgtttattt gcagtgtatt tgcttctcat gaactatttc tcgtacaaat    540

cattaaatag ttcattggat gaggctgggt gacatttccc aggacagcat ggtgaacatt    600

accaggcatg ctagctggcc cgtgtaatcc caagacaagg aaaacattcg ttttcctcat    660

gggtcttcca agaaatgagc tattttattg atgccattaa aaagcaagtt gcgatggttt    720

tgtatagcca ggagtttatt gtgattaaac atcaaagaaa caggtagaaa gcctgggttt    780

ctggctgcta gcgttatagc atccatgaca cagaactcat tacggacatt ccacacttcc    840

agggtgcaca tggtaaatct gaagcccaga atttctctca agctgcgtgg gttactggag    900

agaatgagtt ggatagcaca ggctccggta atttggtagg actgtgga                 948
```

<210> SEQ ID NO 29
<211> LENGTH: 249
<212> TYPE: DNA
<213> ORGANISM: Homo sapiens
<220> FEATURE:
<221> NAME/KEY: misc_feature
<223> OTHER INFORMATION: Incyte ID No: 647931H1
<221> NAME/KEY: unsure
<222> LOCATION: 39, 43-44, 61, 115, 153, 213, 217, 221, 225
<223> OTHER INFORMATION: a, t, c, g, or other

<400> SEQUENCE: 29

```
aagatatgcc agataaaaaa atatgaaaca ccctttttna tgnntaaacg ggtttataag     60

naagaaaggg aaacctccag gggtcaaaaa acaagaggca actgaaagta gaggnattgg    120

acatgggcga agtgccctac caagtgtgag ggntggttac tatgagcccc gggaatctac    180
```

-continued aactgttggc ttcatgcaag gggtaagtga cgngggncca ncttnagccc atgagagatg 240
aaaagtcag 249

<210> SEQ ID NO 30
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 648153CT1

<400> SEQUENCE: 30
ggaagatcca gcagggttta tttgatgtcc acaatgaggc aaatggcatc aagattgggc 60
cccaacagtc aatttcaaca tcagtgggac ccagtgcctc ccagcggaac tctcgtgaca 120
tagggtccaa ctctggctgc tgctgaacat ctggcttgaa ctttttttgt ccttcctgga 180
atagcttcag atcaataggc ttaatgaaag aggtctttct tgctttggct gagagcagcc 240
tctttttaaa gtgtgatgtt ttgcctttcc acctaaagac caggagagaa tttgggccct 300
tactgacctg tcctccttca gggacatgag cattccctat agattaaggt tcctcttatc 360
ccccaataca aaattcctta aattgttagg ggtcaaaatg ctgggattaa caggtggttt 420
agcccacccg ttgcccccgg ggcttaaaaa taaaaataaa ttttccggta aaggcattat 480
caccccaatc ccaacttttc ccccaactta aaagaacatc tcagggggtc gcaaacgccc 540
gctccccc 548

<210> SEQ ID NO 31
<211> LENGTH: 612
<212> TYPE: DNA
<213> ORGANISM: Homo sapiens
<220> FEATURE:
<221> NAME/KEY: misc_feature
<223> OTHER INFORMATION: Incyte ID No: 648838CB1

<400> SEQUENCE: 31
ctgacactga ggaggagcaa actgaagggg agagtgggca cattccttgt tggctgctgt 60
ggtgagcagc agctggtcgt tgtcagtcaa gctccggacc actctgatga tgctcactgc 120
attttgatgg agtaagccag ggacattacc actgtgtttg agccatctga agtattcctg 180
ggtgggtctg cagttggcag cccgtgatcc tttttccatt caaggatgat gcaaaggtaa 240
ggggccaagg ctgagctctg tagatgcctg tgagagcctc ctggtctcaa gaggtcatac 300
caagggcctt ggccacgaag gtttcgtgag gaccttgagg tggtttcgcc atcacaatgt 360
cagacgtgtc acacaccatc tggtatgtcc tcactgtata gaggaagaag ggccccagtg 420
gtgaattatc tacaagtttg tagcaagcta atactcagac tccctctaca gccttgctac 480
tcagtgtagt ctgtggtccg gcaatgtcac acaactgggg gtcttaaccg aaatgcaagc 540
tctaagggtc aattcagatc tccttaatta aaggcttgtt tttttggtgg gttggttggt 600
ggtttgaaaa ag 612

<210> SEQ ID NO 32
<211> LENGTH: 61
<212> TYPE: DNA
<213> ORGANISM: Homo sapiens
<220> FEATURE:
<221> NAME/KEY: misc_feature
<223> OTHER INFORMATION: Incyte ID No: 649152H1
<221> NAME/KEY: unsure
<222> LOCATION: 37
<223> OTHER INFORMATION: a, t, c, g, or other

<400> SEQUENCE: 32
tggtaaatgt tatgtatatt ttactacaat taatttnaaa aaccacacac acacaaggac 60
c 61

<210> SEQ ID NO 33
<211> LENGTH: 266
<212> TYPE: DNA
<213> ORGANISM: Homo sapiens
<220> FEATURE:
<221> NAME/KEY: misc_feature
<223> OTHER INFORMATION: Incyte ID No: 649682CT1

<400> SEQUENCE: 33
ccatcatcga gaggccggtc cggcggagcc tcaagacacc ggaagaaata gaaagattga 60
cagtcgatga agacctcagt gatattgaaa gggctgttta tctgctcagt gctggtcaag 120
atgtccaagg aacaagtgtg attgcaaatc tcccattttt gatgcgacag aatcccactg 180
agacgcttcg gagagtgttg ccaaaagtca gatgtcttcc aaggtccatg aggatgcaca 240
cttatttatc cagagagtat ggatct 266

<210> SEQ ID NO 34
<211> LENGTH: 276
<212> TYPE: DNA
<213> ORGANISM: Homo sapiens
<220> FEATURE:
<221> NAME/KEY: misc_feature
<223> OTHER INFORMATION: Incyte ID No: 649917H1
<221> NAME/KEY: unsure
<222> LOCATION: 19, 21, 48, 59, 63, 74, 77, 80, 95, 115, 121, 125-127, 130, 132, 146, 148, 159, 229, 244, 249
<223> OTHER INFORMATION: a, t, c, g, or other

<400> SEQUENCE: 34
ccgacgtcga ggtcatctnc naaacctttg aatctgggaa gccttctncg gctgccgtnt 60
gcncgggtac cccnttnccn cagctcactg taaanatctt ttatttaatg acctntgaga 120
naccnnntan cnttatgctg ggtgcntngg ggcagaggnc agtgaattgt aaacgtccgg 180
agccctggaa tgcggtccaa gcgaaaaggt caccgcggtg ttggggggng gcggtccgag 240
agtncaggnc cgaggggtgg cgactggcgc tgggga 276

<210> SEQ ID NO 35
<211> LENGTH: 167
<212> TYPE: DNA
<213> ORGANISM: Homo sapiens
<220> FEATURE:
<221> NAME/KEY: misc_feature
<223> OTHER INFORMATION: Incyte ID No: 650726H1
<221> NAME/KEY: unsure
<222> LOCATION: 2, 9-10, 15, 19, 33, 41, 44-48, 51, 53, 58
<223> OTHER INFORMATION: a, t, c, g, or other

<400> SEQUENCE: 35
cnctgcgcnn tctcnccgnc atcaccgtcc cgnattcccc ngtnnnnngg ngnggcanca 60
ttcgccttcc attcctgacg gctcaccgcc tggccaccgc gtgcggcgta ttcccattcc 120
acttcggtgg gcaggcgcac aaaacccagg ccgccgtcgt cggccga 167

<210> SEQ ID NO 36
<211> LENGTH: 118
<212> TYPE: DNA
<213> ORGANISM: Homo sapiens
<220> FEATURE:

<221> NAME/KEY: misc_feature
<223> OTHER INFORMATION: Incyte ID No: 652013H1
<221> NAME/KEY: unsure
<222> LOCATION: 61, 81, 92
<223> OTHER INFORMATION: a, t, c, g, or other

<400> SEQUENCE: 36
gagttattaa gcagcggact ttggtttgaa atctatattg aatgatccca ttatccacat 60
ncttactttt atgcattcag ntttacacaa gncacttgat ggaatttctt atactacc 118

<210> SEQ ID NO 37
<211> LENGTH: 57
<212> TYPE: DNA
<213> ORGANISM: Homo sapiens
<220> FEATURE:
<221> NAME/KEY: misc_feature
<223> OTHER INFORMATION: Incyte ID No: 738964H1

<400> SEQUENCE: 37
gttttctgaa aagcttactt tttgatatta atttccattt ttaaagaaat accttga 57

<210> SEQ ID NO 38
<211> LENGTH: 809
<212> TYPE: DNA
<213> ORGANISM: Homo sapiens
<220> FEATURE:
<221> NAME/KEY: misc_feature
<223> OTHER INFORMATION: Incyte ID No: 743323CB1

<400> SEQUENCE: 38
tctgctgcca gggccaggga gggggcact ggctgcttct gtattttggg gtttggggcc 60
ctggagcttc ccatgcggaa ttgccgtccc tcctcctagg cgagtcccag ggccacccca 120
tcccacaggg acccgggcgc cagcttctga aagcatgggg catctgcgga agaactgggt 180
tgtttcccag ctttcgtccc tgcggagggg cgatccggcc cctccatgtc agcagtgttt 240
ggtcgtccac atgcttgtca gccccacgct gtgctcctgc gtctcttccc gtctcatcca 300
tctggatgct tgacacctct gacagcatcc ctttcctgtc atcttagggc agcttcagga 360
aaccgaaaaa caggcttgtg tccttccatt aacccccttta tccacaagtt cagtatcagc 420
atgagccctg gggagctcca aggctgcagc caggagcccc gtagccaggg atggtcctgg 480
ctgtgctgct gcaccagggc cgccttcccc accttttcca gaggaacctg ttctacggcc 540
agaagaacaa gtaccgagca ccccgaggga agccggcccc ggcctcaggg gacacccaga 600
cccctgcaaa ggggtccagt gtccgggagc ctgggcgcag tggtgttgag gggccacatt 660
ccagctgagt ggccttgctc tgtgtgagcc ccgtgcgagg gccctgcttg tagctggacc 720
ctggaacctt ctgtagctaa gagggaatcc tggccccctc cccagaagcc atttgtcaat 780
aaaccatttc taagaaaaaa aaaaaaaaa 809

<210> SEQ ID NO 39
<211> LENGTH: 232
<212> TYPE: DNA
<213> ORGANISM: Homo sapiens
<220> FEATURE:
<221> NAME/KEY: misc_feature
<223> OTHER INFORMATION: Incyte ID No: 753592H1
<221> NAME/KEY: unsure
<222> LOCATION: 45, 48, 57, 66, 69, 89, 97, 99, 101, 112, 120, 156, 168, 208, 224
<223> OTHER INFORMATION: a, t, c, g, or other

<400> SEQUENCE: 39

-continued

```
aaagaggagc gtgtctctga actacggcca tcaacttcca gtctnggnag ccagctncgg     60

ttccgncgnc caacccaccg acaaccccng aaccctntng nggactaacc angggacccn    120

ctgagccccc cgaccgggtt aggtgtgatt ggggtngggt gcatttgntt tataagtgag    180

ggtagggtga gggaggacca agaccatngg gggagggaaa gggngagggg gt            232


<210> SEQ ID NO 40
<211> LENGTH: 847
<212> TYPE: DNA
<213> ORGANISM: Homo sapiens
<220> FEATURE:
<221> NAME/KEY: misc_feature
<223> OTHER INFORMATION: Incyte ID No: 797777CT1

<400> SEQUENCE: 40

tggccagtgc aagctaaaat taaccctcac taaagggaat aagcttgcgg ccgcattcct     60

gcaggggatg actgtgaatg gcttcatcaa cacagtcatc acctccctgg agcgccgcta    120

tgacctgcac agctaccaga gcgggctcat cgccagctcc tacgacattg ccgcctgcct    180

ctgcctcacc ttcgtcagct acttcggggg ctcagggcac aagccgcgct ggctgggctg    240

gggcgtgctg cttatgggca cggggtcgct ggtgttcgcg ctgccccact tcacggctgg    300

ccgctatgag gtggagttgg acgcgggtgt caggacgtgc cctgccaacc ccggcgcggt    360

gtgtgcggac agcacctcgg gcctgtcccg ctaccagctg gtcttcatgc tgggccagtt    420

cctgcatggc gtgggtgcca caccccctcta cacgctgggc gtcacctacc tggatgagaa    480

cgtcaagtcc agctgctcgc ccgtctacat tggcatcttc tacacagcgg ccatcctggg    540

gcccagctgc cggctacctg attggaggtg ccctgctgaa tatctacacg gaaatgggcc    600

gacggacgga gctgaccacc gagagcccac tgtgggtcgg cgcctggtgg gtcggcttcc    660

tgggctcttg ggccgctgct ttcttcaacg ccgttcccat ccttggttaa cctcggcagc    720

tgccaggctc ccaggctacg cggtcatgag agcggcggaa atgcacactt gaaagacagc    780

agccgttggg aagcgagcaa cccgactttg ggaaaacctc cgagacttgc tctctccatt    840

gggtcct                                                              847


<210> SEQ ID NO 41
<211> LENGTH: 313
<212> TYPE: DNA
<213> ORGANISM: Homo sapiens
<220> FEATURE:
<221> NAME/KEY: misc_feature
<223> OTHER INFORMATION: Incyte ID No: 885098H1
<221> NAME/KEY: unsure
<222> LOCATION: 24, 48, 73, 129, 140, 142, 167, 193, 244, 270
<223> OTHER INFORMATION: a, t, c, g, or other

<400> SEQUENCE: 41

attcaccggt aacactgtct cttnaaagtt gattaaatca gagatttnca tataccaagg     60

gaccaagcaa ganaaatctt aggacattag ggcctagaga cccagatttt cttttttaaa    120

tttacaganc attaacctan tnttccttta gagtaaagtg agatcanaat atgcttactc    180

gtgccataag gtnaatggat aaaaatctgt aagatgttgt tacaatatga aaggaaaatt    240

atgntggtgt catgcaaaag ggaatctgan aaacttacag gaaacaaagt agctttgttt    300

ttgtgttgtg tgt                                                       313


<210> SEQ ID NO 42
<211> LENGTH: 359
<212> TYPE: DNA
```

-continued

<213> ORGANISM: Homo sapiens
<220> FEATURE:
<221> NAME/KEY: misc_feature
<223> OTHER INFORMATION: Incyte ID No: 947812CT1

<400> SEQUENCE: 42

```
ctgaccttta gttcttcact gagtgcccac tgggttatat tctgggagcc gaggccacag     60

cagtgaacaa agcacacaaa geccccgac ccatgggggc tccgttctag tgggtccatt    120

tatcatcaaa catctattaa tatctctaga atgtgcccat caggacacca tccagatgct    180

gctgcgcttt tccaggccac acagagggga caccctccag gtgcatcctg catgaatatc    240

aggctcaacc gtgctttcag ggtaggaagc agagggcatt tgaagagtcc tttcccttcc    300

ttcattcatt tgttgtctcc ttgaataaat gctgttgaaa acctaaaaaa aaaaaaaaa     359
```

<210> SEQ ID NO 43
<211> LENGTH: 449
<212> TYPE: DNA
<213> ORGANISM: Homo sapiens
<220> FEATURE:
<221> NAME/KEY: misc_feature
<223> OTHER INFORMATION: Incyte ID No: 948051CB1

<400> SEQUENCE: 43

```
taaatactga atgaatgaat gaagcactaa actgaatgca tataaggcaa agacacaaat     60

aacttaattt tgtgcagcca aatcagtttg taacttcacc aaacagttca catcaacatt    120

taatgagcgt ccctttgccc aaggcactgg gtgaaggatg agggggtatt ggtttgtgtt    180

tatgtagaat tttgcagttt gcaaagtccc ttctcttaca tctcttcatg agggtttcac    240

aacgactctg taaggtaggg gttgtcatta ttcctgcttt cccgataagg atacagaagc    300

tcagagaggg cagacatttg acctggagta gaactagggc aagaatacag gccactgtgt    360

gccccctcct cccacgctct gtttctctct gaagatgacc tggggacagc ataatacaaa    420

gtggatggaa tgggctgaga aaggagagg                                      449
```

<210> SEQ ID NO 44
<211> LENGTH: 571
<212> TYPE: DNA
<213> ORGANISM: Homo sapiens
<220> FEATURE:
<221> NAME/KEY: misc_feature
<223> OTHER INFORMATION: Incyte ID No: 948581CT1

<400> SEQUENCE: 44

```
tttttttttt tttttttttt tgagtcggag tctcgctctg tcgcccagga gaataagggt     60

tagctcgaac tatcattaac ctttattata tattacacat tttagactct ctagcattga    120

aaggaaaact tctctgtcaa tttttacatg atttttgaga acattttaaa taatattaag    180

acaaaaaaca tttcaagaag caaaacacag tggaaagcac acaacagtgg aaagctccac    240

agcaaattgg agcttcctgg tttctgtagg tatttctttt tttttttttt ttttttgaga    300

cagagtctgg ctctgtcgcc caggctggag tgcaatggcg caatctcggc tcactgcaag    360

ctccgcctca cagggtcaca ccattctcct gcctcagcct cccagagtga tgggattaca    420

ggcatgagcc actgtgtgcc actttttttt ctgagacagg tctttgctct attgcccagg    480

cttgagtgca gtggtgcaat ctcaactcac tgaagccttc acctcccaag gtcaaggggt    540

tctcctgcct cagtctccgg gagaactggg a                                   571
```

<210> SEQ ID NO 45

<211> LENGTH: 957
<212> TYPE: DNA
<213> ORGANISM: Homo sapiens
<220> FEATURE:
<221> NAME/KEY: misc_feature
<223> OTHER INFORMATION: Incyte ID No: 948700CT1

<400> SEQUENCE: 45

```
ccaggatgaa actgatatcc ctagttcctc ttccccattt cttctcacac tcccctgcct     60

gagaatcagt tgagttccca atacctcttc cttcagtctc tattcattat atggtctagg    120

ttgagacttc cttggaagca gaacctgagt accaggaact catattttat aaagtatatt    180

tattcctttt agctgcaaac taacccagcc atgttttagt gaatgcttta atctgaagat    240

gactttgagc tcattgacca tattaatctt tcatcaaaca aactggatgt tgtttcatta    300

acaaaaaact cctccacacc aaggagtgtt tagtaacttc tgcacagagg actcatccat    360

ctcttgctta tgtttgggac agaaagacac ttctctggct ttttactggc ttgaacccaa    420

tgggacagag actctctaga aagtttcagg gctcacattc acttgtttgt ccaaaaaata    480

tttttgagtg tctcccaagt gccaaaccct ggctactccc acctttgcct gagcccatga    540

gcggtagtct gggggctgga tgtgaggagt tctgagttgg ctaggaagac acaaggcaca    600

atggacatgg ggcaaagtcc acttgctgga cattggtccc ttccacttcc aagctgtcca    660

tcaggctgag agatctggaa tgcatacccc acactttgaa gatgaggaag ggcgagtttc    720

tcaaagtgtg tgtgtgtgtt tctcttttaa tctgtaatgg tttctgcatt ttgaggtaga    780

aacagaaatc tctttttga gtgggaccac tcgggtgcgg cttcttagtc ttgttgatat    840

aataaagcac atgcccactc ctcatggagt ggagaggaga aaattctaag ggaacgtact    900

ctgaatgcaa atgtttctga gattaaacac tagtcacttg ttaaaaaaaa aaaaaaa       957
```

<210> SEQ ID NO 46
<211> LENGTH: 612
<212> TYPE: DNA
<213> ORGANISM: Homo sapiens
<220> FEATURE:
<221> NAME/KEY: misc_feature
<223> OTHER INFORMATION: Incyte ID No: 948883CT1
<221> NAME/KEY: unsure
<222> LOCATION: 543
<223> OTHER INFORMATION: a, t, c, g, or other

<400> SEQUENCE: 46

```
tgctgtgggt tgtccgccac cagctcctgc aggttgcgca ggtcaccaat gatgcggggc     60

ttggccactt cgtaagggtc gaggaaatgc tcgtcgccag tgatcagaaa gccacgcagg    120

ccggtttcca ggtccaccgt cagcttggat gactcattga ggttattgat aacccggtcg    180

gtgtgctcca cccactggat aaccgacagc aaataagtga tcaggcagac gaaaaacacc    240

gcgctgagca cgccgacgcc caagggtaac gcgacgtttc ggctcaacag ggtacggaag    300

ctcttttcat cgacggacga cgcgggagtc atgggcatgc cttggccaag tgcggaaaaa    360

gggggagttt gcccgaatat cagggggcaa ggctatgttt gtgcgttgtt ttgaagcgct    420

ggcctacagg ctgcgagtga gttacacgcc aattcgggcc ggtttcatca gaccccttac    480

atacgtgcat acagatgcgg cggaacgtag gtgaagggtt gcggcactcc ggacagcgcc    540

tcncgaacac ggaagatctt ttggaaggcg tcttttttgt ctccccaggt acccccaatg    600

agcctaaccg cc                                                         612
```

<210> SEQ ID NO 47

<211> LENGTH: 517
<212> TYPE: DNA
<213> ORGANISM: Homo sapiens
<220> FEATURE:
<221> NAME/KEY: misc_feature
<223> OTHER INFORMATION: Incyte ID No: 948935CT1

<400> SEQUENCE: 47

```
cccacttcca cactaccata tgcctcctgt tttcctctcc ctccactact gccctgccag     60

gtcctgtgtc gcctcttcca aaatttccca aactactcta ggtagaacta gctatataat    120

ttgtgggccc cagtgcaaaa tggcccgttg ttcaaaaatt attcaagaat ttcaattcga    180

ctgaacacgg gataaaaaaa aaaaaagaac ttcaagacag ccacaggaaa tgatgaaacc    240

aagtgcaggg gccttccaag cacaggctgc acaaccacga agccagccct ggccccaggc    300

ttttttcttg tattcccaca gaccctcaat gggaccatat cgactgcctg ctttggatca    360

aaggttttac ctacatgccc attgtctcct ctaggctgcc atcttcatgg ggaaaggagc    420

tcttatctct gcatgtccta aagggtgcat cacaatgcct cgcatgttga gttggtgctc    480

aataaacagt gaattgcatt ataaaaaaaa aaaaaaa                             517
```

<210> SEQ ID NO 48
<211> LENGTH: 533
<212> TYPE: DNA
<213> ORGANISM: Homo sapiens
<220> FEATURE:
<221> NAME/KEY: misc_feature
<223> OTHER INFORMATION: Incyte ID No: 949387CT1

<400> SEQUENCE: 48

```
acataaaatt tcaattagga ggaataggcc atcaaatcca aatttgagca aaaacctctt     60

tcaggaaaaa ttacaactct aaagactgta tcagaaatct attgcacaat atggtggcta    120

cagttaataa caatgtattg tattcttgaa aaatgctaag agagatttta aatatcctca    180

ccacaaaaaa atgataaata tatgatgtaa tacatatgtc aatcagctca atttagccat    240

tccataatgt atgcatgttt caaaacaaca tgtcgtacat aataaatata gataattttt    300

gtcagtggag ataaatagag tgttaaaaaa aagaaaacaa agaaaaaaag gggggggagc    360

tacagagagg tccagtctta gggaggaaaa aaaagggggg gccctccctg ggggtcccgg    420

gctatggatc gggtgaattg cggggtcaaa gcccctccaa ggggcgcccc caaaatttca    480

ttcgcagggg cgggtcgttt aaaaagggcc ggaaatgggg aaaccccccgg gtt          533
```

<210> SEQ ID NO 49
<211> LENGTH: 450
<212> TYPE: DNA
<213> ORGANISM: Homo sapiens
<220> FEATURE:
<221> NAME/KEY: misc_feature
<223> OTHER INFORMATION: Incyte ID No: 951797CT1

<400> SEQUENCE: 49

```
tgagcaccct tgaccgtttc ctgatttgta ctgttggagt atatcattgt tcctacagct     60

tattgaagat tatgattttt ctgcaaacag agtctatgtc ctagttggta agcagctaga    120

atagttcacg tctttgtctc ctgaattctt tatattgttg taattcaaaa tattttgtct    180

attcattcag tgaactaacc aagagcatta tccgtattgt catatttcat gatggtgctt    240

ttgatattca gctattggtt ttacttagtg ggaaataatg aacgtacaag taattgtttc    300

tgtaggtctt aggtatatgt attagtgacg atgttaatat ggtgaattgg tatgaaccat    360
```

-continued

```
gcattctcat ctgtaaatca acaaaaactg gttttcatgg ggattcacta ataaaaggtt    420

ggtcttattt caaagtaaaa aaaaaaaaaa                                     450


<210> SEQ ID NO 50
<211> LENGTH: 658
<212> TYPE: DNA
<213> ORGANISM: Homo sapiens
<220> FEATURE:
<221> NAME/KEY: misc_feature
<223> OTHER INFORMATION: Incyte ID No: 997947CB1      Contig1

<400> SEQUENCE: 50

tgtttacccc tacacatggg gtggattctc tgacatcgac ctaatggctg atgaaatcgg     60

gctgtgggct gtgtatgcaa ctaaccagaa tgcaggcaat attgtcatca gccaacttaa    120

ccaagatacc ttggaggtga tgaagagctg gagcactggc taccccaaga gaagtgcagg    180

ggaatctttc atgatctgtg ggacactgta tgtcaccaac tcccacttaa ctggagccaa    240

ggtgtattat tcctattcca ccaaaacctc cacatatgag tacacagaca ttcccttcca    300

taaccaatac tttcacatat ccatgcttga ctacaatgca agagatcgag ctctctatgc    360

ctggaacaat ggccaccagg tgctgttcaa tgtcaccctt ttccatatca tcaagacaga    420

ggatgacaca taggcaaatg tgacatgttt tcattgattt aaacagtgtg atttgtgata    480

aactctataa gaccccttcc gtttttttct tcactattat ttttcatcat ttctccaaag    540

caaagcattt ttattgtaaa gttggtgttt caaaaacata gctgagcttg tctaacttac    600

catgttggaa acacatctta acttctaaat ttacaaggcc tatcatgtcc ttgtcatg      658


<210> SEQ ID NO 51
<211> LENGTH: 1773
<212> TYPE: DNA
<213> ORGANISM: Homo sapiens
<220> FEATURE:
<221> NAME/KEY: misc_feature
<223> OTHER INFORMATION: Incyte ID No: 1212964CT1

<400> SEQUENCE: 51

ataacagttt ttgaactgat ccctttagca cctgtgaaac tggaaaaaca tctgcacagt     60

gctagatctg aagagggaag actatattat gatggtgaat ggtatatacg tggacaaaca    120

atatgtattg ataaaaaaga tgaatgtcct acaagtgctg taattacaac aattaaccat    180

gatgaagttt ggtttaagag gcctgatgga agcaaatcta agctttacat ttcacagcta    240

cagaaaggaa aatattcaat taaacattca taatcatgat ttaagtgtta tctaaattta    300

ccttattagt gttaccaaat gtaagtgcca tgagagtaaa aaaatgtatt caataactta    360

atattctcac tgaatcatga gagaatgtgt atttgtaggt agtactctaa atagatctca    420

ttgatatgtt attaaaagaa acagtaataa aaattttatc acgatcctta cgttgatttg    480

cctcttaggt ccgatgacca ataggtattc tgtatatggt aggggtttct ttctaaacat    540

ttttctttgg ttttaaaaaa agttatgcaa atttgtctta tctttagtaa actatgacta    600

catttatctg caatttttaa aattttccat atctttgtca ttcattgtgt gtttgtaaat    660

aaggccgata gaatgtttcc tataaatggt ttgtactagt acattagtgt taaaccagaa    720

ctgaaattta aacatatata tatatgagga tgtatatatg gcatcatcag cttatttaga    780

actgatggcc ataccttaca atcttgtttt acccaaaatt aagctattgg ggttgaaagc    840

taaaaggagc acttttgtag aatagcaact tttcttttcc tctttcttga ttgtatggtg    900

gggtggtgac ctatttttac aaattatacc taatgagtaa aattagtgta aagtgataac    960
```

```
atgcttctac ctgtatttct agtgaccctt tagcggcagg tatttatacc tggtatttat   1020

gatgcagtat ataagtggtg aacaataact gacagtattg tgcttgctgt acatgtctgg   1080

tcttttgaaa cagattttag taagcatttt ccagaggtaa aactgtgtcc ttattctaat   1140

tttattccta gggcaaagta gacagggatt atttccttga atctatttcc aaattaatat   1200

ttttttcttt ggtatttcta cactttaagg ccatttggtg caatttagaa agtgttggcc   1260

tcccttccgc tagccacatt caaaattaac ttccaaaacc tcaggaacag tacaaagaat   1320

tgaaaccctc aatatggcag cacagccggc tgtagtgtat atttagggta caccaaatca   1380

ggtattcctg gtggtcttgt gcactttaat ttctgttaca atgagttaag aggatgagga   1440

agaaatctac ttattaacac ttactgcaga aatgtctgca ttattccgtt tgttttctta   1500

ttattttacc tctccaaaca tcttcctgtg cagatcacta cttcatagtt gccaaatttt   1560

aaaacactta actgctgaaa ttcagtgtca gcaaagtgat attacgttgt tctgtttcta   1620

attaacctta gcaaatgtac ataatgtcaa aacccaatag tatttgacag tacttatgta   1680

tacaatgttt gataagcatt tttaataaga tttgtatttt taaatttagt atataataaa   1740

aagatgtgtt tcagtgtgaa aaaaaaaaaa aaa                                1773
```

<210> SEQ ID NO 52
<211> LENGTH: 177
<212> TYPE: DNA
<213> ORGANISM: Homo sapiens
<220> FEATURE:
<221> NAME/KEY: misc_feature
<223> OTHER INFORMATION: Incyte ID No: 1214535H1

<400> SEQUENCE: 52

```
cctttgagta ccgctacctg gaggaccggg acctccagtg acaccccttc ctacacccct     60

tccccgaatg ctgatcccct gcccaggtga ggccccccctg gaagatggag ggaggcccca    120

agccacgggg aatccttttc caggaagaag agggcccagt tttccttta agcccaa        177
```

<210> SEQ ID NO 53
<211> LENGTH: 217
<212> TYPE: DNA
<213> ORGANISM: Homo sapiens
<220> FEATURE:
<221> NAME/KEY: misc_feature
<223> OTHER INFORMATION: Incyte ID No: 1219856H1

<400> SEQUENCE: 53

```
ggagactggt cttctgaggg ctgctccacg gaggtcagac ctgaggggac cgtgtgctgc     60

tgtgaccacc tgaccttttt cgccctgctc ctggtgtctt catctgctgc tggttcacca    120

tcctttacct cccaagtcag agcaccacag tctcctcctc tactgcaaga ttggaccagg    180

cccactccgc atctcaagaa taggaaggca cggccct                            217
```

<210> SEQ ID NO 54
<211> LENGTH: 647
<212> TYPE: DNA
<213> ORGANISM: Homo sapiens
<220> FEATURE:
<221> NAME/KEY: misc_feature
<223> OTHER INFORMATION: Incyte ID No: 1288503CT1

<400> SEQUENCE: 54

```
gtctatcttt cattatgtct tttttttttg attttttttt tttttttttt tttttttttt     60

tttttttttt ttttttttaa caggattcat ctcctttatt cataaaattt gaaagttaaa    120
```

-continued

```
atgtatttaa cagtttgata actaaaagat cataaaagat cagcctcaaa atcacaatga    180

aataactgat tttttttctg agatttgatt gtgttaagtg tctgtgggtc cctcagatta    240

atcctttaaa atggatactt ttaccaattt aatggatatt gtatgaattt tgatgcattt    300

aagcatatga catagaagtc tgtttctgca gattaacctt ataatagcaa tgcttttata    360

gcaggaagtg tgaaggtagg gagtctaggc cccttctatt tttttgctcc atcatcttta    420

taggaaagct tttatcttct tgcttgtcaa atagcagcaa gatgtcttct ctttcatcag    480

ctgtgctgta ggattacatg gccatgcctg gtgccaggga gtccgagaag gtgaatattt    540

tatctggcat aaaatttgag cagcaaggag ctctgtcaca tgtcatcacc atctctcaac    600

tctgcacaga cccagtgctg tccctggctc ttgaagacac tggtttc                  647
```

<210> SEQ ID NO 55
<211> LENGTH: 866
<212> TYPE: DNA
<213> ORGANISM: Homo sapiens
<220> FEATURE:
<221> NAME/KEY: misc_feature
<223> OTHER INFORMATION: Incyte ID No: 1298179CT1

<400> SEQUENCE: 55

```
gacaaggagg ctggaagtca gatgggtgcc atatactcta ttcagatgaa aatatcacta     60

cgattcagtg ctactccctt agtaactatg cagttttaat ggatttgacg ggatctgaac    120

tatacaccca ggcggccagc ctcctgcatc ctgtggttta tactaccgct atcattctcc    180

tcttatgtct cttagccgtc attgtcagtt acatatacca tcacagtttg attagaatca    240

gcctcaagag ctggcacatg cttgtgaact tgtgctttca tattttccta acctgtgtgg    300

tctttgtggg aggaataacc cagactagga atgccagcat ctgccaagca gttgggataa    360

ttcttcacta ttccaccctt gccacagtac tatgggtagg agtgacagct cgaaatatct    420

acaaacaagt cactaaaaaa gctaaaagat gccaggatcc tgatgaacca ccacctccac    480

caagaccaat gctcagattt tacctgattg gtgggtggta tccccatcat tgtttgcggc    540

ataactgcag cagcgaacat taagaattac ggcagtcggc caaacgcacc ctattgctgg    600

atggcatggg aaccctcctt gggagccttc tatgggccag ccagcttcat cacttttgta    660

aactgcatgt actttctgag catatttatt cagttgaaaa gacaccctga gcgcaaatat    720

gagcttaagg agcccacgga ggagcaacag agattggcag ccaatgaaaa tggcgaaata    780

aatcatcagg attcaatgtc tttgtctctg atttctacat cagccttgga aaatgagcac    840

acttttcatt ctcagctctt gggggc                                         866
```

<210> SEQ ID NO 56
<211> LENGTH: 621
<212> TYPE: DNA
<213> ORGANISM: Homo sapiens
<220> FEATURE:
<221> NAME/KEY: misc_feature
<223> OTHER INFORMATION: Incyte ID No: 1305513CT1

<400> SEQUENCE: 56

```
ggcagaagaa ggctattggt cttagacgag ttcaaaatgg agaaaagaat cagcagaatg     60

ttctatataa tgacttttct gtttctaacc ttgtggggcc cctacctggt ggcctgttat    120

tggagagttt ttgcaagagg gcctgtagta ccagggggat ttctaacagc tgctgtctgg    180

atgagttttg cccaagcagg aatcaatcct tttgtctgca ttttctcaaa cagggagctg    240
```

-continued

```
aggcgctgtt tcagcacaac ccttctttac tgcagaaaat ccaggttacc aagggaacct    300

tactgtgtta tatgagggag catctgtaaa tctttagcct tgtgaaaact aaccttctct    360

gctgagcaat tgtggcccat agccatattt tgagaagaaa ttcaagaatg gaatcagcag    420

ttttaaggat ttgggcaaca ttctgcagtc tttgcaatag ttcacctata atcctatttt    480

aaatctcaga gtgatcctgc tgactgccag caaaggtttg taattaagaa gggactgaac    540

cactgcccta agtttcttta tgtggtcaaa aactagataa tgaaagtagc aggtgctaag    600

tatgagtgct aaatgcttct g                                              621
```

<210> SEQ ID NO 57
<211> LENGTH: 222
<212> TYPE: DNA
<213> ORGANISM: Homo sapiens
<220> FEATURE:
<221> NAME/KEY: misc_feature
<223> OTHER INFORMATION: Incyte ID No: 1318926H1

<400> SEQUENCE: 57

```
ggagctccct ggtcctagca gttattttct ggttggcctt tgacactgcc aaattgggtc     60

aacagcagct ggtgtccttc ggtgggctca taatgtacat tgtcctgtta tttctatttt    120

ccaagtaccc aaccagagtt tactggagac ctgtcttatg gggaatcggg ctacagtttc    180

ttcttgggct cttgattcta aggactgacc ctggatttat ag                       222
```

<210> SEQ ID NO 58
<211> LENGTH: 718
<212> TYPE: DNA
<213> ORGANISM: Homo sapiens
<220> FEATURE:
<221> NAME/KEY: misc_feature
<223> OTHER INFORMATION: Incyte ID No: 1328744CT1

<400> SEQUENCE: 58

```
tgactctgcc attttctagc ccttttatgt tgggaaagct actttttcta gtctcaattt     60

cctcataata aaatgaaaat caattataag atcgatttcc atagggttgt catgagtttt    120

gagtaaaaat gtgtatgtaa agttcttacc acaatacctg gcagagagta agtattcaat    180

taatgttagc tattattatc atcataatcg ttgtgttaaa tatattgccc aagataatat    240

gtgggggaat gtttgtttta tatgcatatt gtatcctgac tgtgtgcaga acacattatg    300

tgtattgcat atatgtaaaa gaagtgtaca aggaagtggc catccttgtt caagttacgt    360

atctagttag aacaacttcc cagtccattg gagttctttg agaagcctca gggaagtagc    420

tctgggtcct tctaatcaac ctcccattac tgcgccagta agtttctgtt tcttataaat    480

aaactctttg ctattcagaa aacctcaagg ggcccccaca ttcactaagc atggggctcc    540

taactggggt ccaggtccat agagtgtagg aagaacatat tagaacaata cttgtgctta    600

tttttatcta gctttttat gtttgtgtat gttttataat ggcataatag tacaatggta    660

catgtacata attttaaata aataaatgaa tgaatgaata aataaaaaaa aaaaaaaa      718
```

<210> SEQ ID NO 59
<211> LENGTH: 557
<212> TYPE: DNA
<213> ORGANISM: Homo sapiens
<220> FEATURE:
<221> NAME/KEY: misc_feature
<223> OTHER INFORMATION: Incyte ID No: 1328845CT1

<400> SEQUENCE: 59

-continued

```
gaagcttata atctagttag aaagaaaagg caagctttat acaggacata atcagcaaac     60

tggctagcat ataacgtaac acattgcatg ataggaaata agctaaactg attatcatag    120

ttggcaggat ccaagttata gggcattcag aaacttccct gagtagagat aggatagatg    180

gttcagataa taaggttggt cctcctcccc agagtgggat cactaagccg agggaggaat    240

agaaaaatct tcaccatgca gattatgttt gatattcaag ttgctgcatg agaaatgact    300

gggtgggatt gagagcaggg cttctaggca acagttatta ttggaaacca ttgattgagt    360

cattgttcag aaaatgtatt ccagacaaca aagggtcacc agaagcaggg tctagcatgg    420

tggaatggca ggagctagat tagcaagtaa gaaatcatgt gaatagattg aactgtgggc    480

agcatcctga atatcaatgc aacgtagttc tcatgctgca gctgactgtt ccatggggta    540

atgaaagaga aaaggag                                                   557
```

<210> SEQ ID NO 60
<211> LENGTH: 1340
<212> TYPE: DNA
<213> ORGANISM: Homo sapiens
<220> FEATURE:
<221> NAME/KEY: misc_feature
<223> OTHER INFORMATION: Incyte ID No: 1329044CT1

<400> SEQUENCE: 60

```
cacacatttt gaaatatgtg tcaaatattt aggaatacta atttaatcta aaaatccata     60

attgaaattt aaagagttaa aagtacacaa aatagactga aaaattaatt atccaacaat    120

atgaaaaccc caaatgacct atttctcaga caactagggt atctttcaat ctgctgcttt    180

gtattttctt ctgaagagtc aaaaaattat aaaatatcct taatagtcta cttgacattt    240

ttgactatgg aaaccaagcc caggaatagt atatacagtg tactaaccca gtcaacccac    300

ccagactttg agtccccacg tacaggagtc cccaacccca gggccgaaga ccagtaccag    360

tttgaggcct attaccgggt cacatagcag gaggtgagca gcgggatgag gcagcattac    420

tgcctgaact ctgcctcctg ttagatcagc agcagcatta ggttctcata ggagtgtgaa    480

ccctattgtg aactgtgcag gtgagggatc taggttgcat gctccttatg agaatctaat    540

gcctgatgat ccgagtggga cagtttcatc ccaaaaccat ccaccaccac caccctctcc    600

catgtccatg gaaaaactgt ctttgacaaa actggtccct ggtgccaaaa aggttgggga    660

ccgctgccta agtagaccaa gtctatgagt atctaaaccc agcagacaaa gtacacattc    720

acatccaaaa aatgaagagc aggagtaaga tgagcagagc atcagtgagg ctttgggaag    780

gtcaactatt agcatccatt ttgatatgct ggcatttcat tggatattgg acattcacag    840

catcattctc ttccaggaag ggagaagagc tgtggagtag atctgtgagc aaaagagaaa    900

tggaagacag tggctgatcc caaatacatt tgagtagcag ataattaaga agagttatac    960

aggccagaga caacgaacac aaagaatcta acagtctacc caaaaattat gccctaaaac   1020

agtgacttct caaccagact caatttctct gcaatgtctg gagacattca gtagttgtct   1080

ggagacattc agtagttgtc acaactgagc tggaggtact gtgttgctcc tggcatttag   1140

taggtagaga tcagggatgc tgctaaacac cctacagtgt acaggacagc ccctacaaca   1200

aagaattaac caaaatgtca acaatgctaa ggctgagaaa ctctgaccta aaatgacaat   1260

cattatgact aaccatgtgc atagctgaaa agatccatga aaagccttaa aatagatcgc   1320

aataaacatt atgtagtcaa                                               1340
```

<210> SEQ ID NO 61

<211> LENGTH: 602
<212> TYPE: DNA
<213> ORGANISM: Homo sapiens
<220> FEATURE:
<221> NAME/KEY: misc_feature
<223> OTHER INFORMATION: Incyte ID No: 1329081CT1
<221> NAME/KEY: unsure
<222> LOCATION: 571
<223> OTHER INFORMATION: a, t, c, g, or other

<400> SEQUENCE: 61

```
gtccaggcta ggttgctggg tgctctgcct agggtctcac aaggcagaaa ctgaggtgtc     60

atttggggct gaggcttgtt ggcagaattt gttttttgc agtggtacga tggaggtttc    120

tgggtttttt tttctggcta ttaactgggg gctgctttca tccctggagg tcttctactg    180

ctccctggca tgggggtccc ctctacaaca agcagcttgt ctttttaagg caggagaatc    240

cctctccctt caactctcca acgttaagtg cttgcctcat tatatcagac ctgcccagga    300

aaatctctct tttcatgaac ccaaagtcat ctgattaggg actttaattg cagctgtaaa    360

atgagtcatg ggataatatc ccatcatagt cacaagagcc actcatgatc aaggagaggg    420

attatgcagg gtgcatatac caggggtggg aatcttggag gccactcaga attctttcta    480

ccaccagggc atgaggcaga tacataatta tattataata tgagacatcc tgacaagcat    540

attttttgag acactctcaa aaaaaaaaaa nataaagaaa agaaagaaaa aaggaagata    600

gt                                                                  602
```

<210> SEQ ID NO 62
<211> LENGTH: 99
<212> TYPE: DNA
<213> ORGANISM: Homo sapiens
<220> FEATURE:
<221> NAME/KEY: misc_feature
<223> OTHER INFORMATION: Incyte ID No: 1329095H1

<400> SEQUENCE: 62

```
gcttctgctc taacaaagag agtaaactag gtaggctaca aagtcataat ttattttgag     60

cttgttagaa ctgaagttac aaggtgagca ggtaaactg                           99
```

<210> SEQ ID NO 63
<211> LENGTH: 192
<212> TYPE: DNA
<213> ORGANISM: Homo sapiens
<220> FEATURE:
<221> NAME/KEY: misc_feature
<223> OTHER INFORMATION: Incyte ID No: 1329404CT1

<400> SEQUENCE: 63

```
gttaccacct attgataaaa tggaatagta caagatttgt gcaagacatt cactaagaca     60

gccgggagcg gtggctcacg cctgtagacc cggcacttta ggaggccgag gtgggcagat    120

cacgaggtca ggagatcgag accatcctgg ctcacaccgt taaaccccgt ctctactaaa    180

aaaaaaaaaa aa                                                       192
```

<210> SEQ ID NO 64
<211> LENGTH: 563
<212> TYPE: DNA
<213> ORGANISM: Homo sapiens
<220> FEATURE:
<221> NAME/KEY: misc_feature
<223> OTHER INFORMATION: Incyte ID No: 1329477CT1

<400> SEQUENCE: 64

-continued

```
ggaatggctc accaaatgaa tccctatgga aaaagatgca cttaatccct ccctcacgtt     60

ataaagaaaa tcaaataatg gccttacagt aatattgttt gacttattgt aaacaatgac    120

ttaataagtt gaaaaggata aatatctttt agaccctaag gaaatattaa gacacaagca    180

ttcatatatt tgaccatatt aaaatacttt tgttcattga gaacttttac tcactaaaag    240

gcaatttaaa gaaagtgaaa agacgatgca taaacaaact tggagaaggt aatcataata    300

tctacctaca cttgacagag gattattatc aagaatacag agtattttat catagttaaa    360

aataaaaatt tttaaaagat cacataaaga actttttttt gagatggagt ctcactctgt    420

cgcccagcct ggagtacagt gatgtgatct cgactcattg caacctccgg ctcccgggtt    480

caagcgattc tccctgctca gcctcctgaa gggccgggaa tgccggcgtg gtggcacaca    540

cctgtggtcc cagctactcg gaa                                            563
```

<210> SEQ ID NO 65
<211> LENGTH: 388
<212> TYPE: DNA
<213> ORGANISM: Homo sapiens
<220> FEATURE:
<221> NAME/KEY: misc_feature
<223> OTHER INFORMATION: Incyte ID No: 1329584CT1

<400> SEQUENCE: 65

```
gccacgtgaa cctgaggcat gaaagtcctt gccagcccca cagggtactg ctccagctgc     60

cgcctccagg ggcctgtccc tctgcaggtc cccagctctg tctctccctc cctctcctgc    120

tcaggctgag acttgtgttt tcccggggaa gccaactcca agaccctctc tcctgagtcc    180

ctgcccggat aacaggctct ctccttggaa tgttttccct acaatcctca tgagaacacg    240

ctatgtgacc ttgagcaagt tactcaacct ctccatgcct ctgactcctc taccaagagg    300

ggataataac atacctacct ccctggaact gtgctgtgag gcctcaatgg aaaccaagca    360

aagcacttag aaccctgcct gcctatag                                       388
```

<210> SEQ ID NO 66
<211> LENGTH: 788
<212> TYPE: DNA
<213> ORGANISM: Homo sapiens
<220> FEATURE:
<221> NAME/KEY: misc_feature
<223> OTHER INFORMATION: Incyte ID No: 1329652CT1

<400> SEQUENCE: 66

```
ctttgcatgt tctaatttgc catgacgtgg tcaagtgctg tttccttcct gttgcttgca     60

agcctatgct agagataagg atacatttca gtgcattaaa aaagaagcca ctgaagacag    120

gcttaagcat ggtaattttt aaaacatttt acttatcaga agccttttta aagaacagaa    180

agagtgggct ttaatttctg cttattttta aaagatttaa aaatacttct tactaaactt    240

taaatgtatt tgattttaaa tccttatata aatcctctta aaggtgaaaa tatatacgtt    300

gtgaaattac tcattgggta gcagtttcta tgtatgtgct ttgctgagtt ggtgaaaaga    360

aggaaattgt ttatatatcc tttattgcga ttacaaccct cattattgct ggggtttttt    420

gaccttttttt ttttttttaa tattgagtac ttttaacagt agtttaactg gagagtgggg    480

gagagaggca taattttcag tagtgacaga tgatcttagc aggagcaaac tgttcaaata    540

aaatatgtaa cttttaaaaa agagcgtatg tgcattagtc gtgtcgattt tatttaaaaa    600

cgttaataat aaaaaaatgc tttagcgata ctgccctctg tatcagttat tatatcctaa    660

gtgggtgatt gctttttcat aactaatctg agcttttgtt ttttaggcca agaagcttga    720
```

```
gagaagaaaa atttcagaaa aattgtctca atttgactag aatatcaatg aaccaggaaa    780

actgaagc                                                             788


<210> SEQ ID NO 67
<211> LENGTH: 566
<212> TYPE: DNA
<213> ORGANISM: Homo sapiens
<220> FEATURE:
<221> NAME/KEY: misc_feature
<223> OTHER INFORMATION: Incyte ID No: 1329778CT1

<400> SEQUENCE: 67

acaaagaaaa atatttccct ttggattgaa actagtctta gaatctcata atatattctt     60

caaaacatct aggatttaat ccaaaattac ttatacaaaa attcaaacaa ggcaaaaaat    120

aaaataaaca aacaaaaaag gaaaattcaa ctctcaagga aaagataata acaaatgcca    180

actccaagat gacaaagata ttggaattat ctgtaaaata aagggtaaac gttcttcaaa    240

caaatggaaa agtgaaatat ctcagcaaaa aaaatagaag atagaaagga aaaccaaata    300

gaaatttaaa aactgaaaaa tatactgtcc aaactaaaaa attcactgga tagatccaat    360

agcagaacag agataacaga ataaagagtc agtaaactta aaaatagatt aatggaaatt    420

acacaaaatt tatttataat tattaatatt attaataaat attacccaag agggagacaa    480

catttttta aataagcaga acttagggag ctatgagaaa taccaaagtt cttacatcaa    540

tgtcatgtca tcagttttac aagacc                                         566


<210> SEQ ID NO 68
<211> LENGTH: 553
<212> TYPE: DNA
<213> ORGANISM: Homo sapiens
<220> FEATURE:
<221> NAME/KEY: misc_feature
<223> OTHER INFORMATION: Incyte ID No: 1329830CT1

<400> SEQUENCE: 68

ggggaataaa caatcacttt tcttaagcta agatttagaa agttttttt ccaaaggcat     60

tggaattata cctcaaagct tgtactagta gttctttgac catttctttc agcacatatt    120

tactaatttt taatccttat aaatccttag ggaaatatat attttggtaa ccgtttaaga    180

ggagctgctc tgttacattc ccagctcttt aataagtggg gaatttgttc tctgtggtcc    240

aaaatgttct ctgaaaaaga tctccttgtt ttcccaaatg attctcttag aaaggaaact    300

tgatcattct gctttgttct ggagtgttac acaagtgtta tacctttgtt ctggtgttat    360

accttgttct ggtgttatac ctttgttctg gtaggtagta ctaccaaaag agaacttgag    420

aaattatccc tttgggtgaa gatggtttgt ttcaagtttt tttttttttt tttccctcca    480

gcacactctc tgtcctttta atttgtaact ttctgcatcc tggttaatca agaaatttct    540

aagatggcca cct                                                       553


<210> SEQ ID NO 69
<211> LENGTH: 503
<212> TYPE: DNA
<213> ORGANISM: Homo sapiens
<220> FEATURE:
<221> NAME/KEY: misc_feature
<223> OTHER INFORMATION: Incyte ID No: 1329851CB1

<400> SEQUENCE: 69

gtgaaaacca gtagcaccta atcattaatt aaggcaaact gtactagtaa tcattgtaca     60
```

```
gttttccatt gaacaacata ggtctgacct ttgtgggtcc atgtatacat gaattttctt    120

ccatacacag caagaccacc aactccctaa gttttgggag ggtcaaaaat tatatgcagg    180

tttttgattg tgtgatgggt tggtgcctgt aacacctgtg ttattcaaaa gtcaactgta    240

tttttaatgc cacacaccca cagttaaaaa aaaaaatcag ttttacctaa tgtgcacatt    300

aaaagcagta aaaaaaaaaa agaaaagaaa agaaaagaaa aattgattct ggtgtggtag    360

ctcacacctg taatcccaac acttttggag gctgaggtgg ttggattgct tgagcccagg    420

agtttgagac cagcctgggc agcatggtaa accttgcttc tcaaaaaaaa aaataggggg    480

ggccccccat ttgttgtcct gtc                                            503
```

<210> SEQ ID NO 70
<211> LENGTH: 704
<212> TYPE: DNA
<213> ORGANISM: Homo sapiens
<220> FEATURE:
<221> NAME/KEY: misc_feature
<223> OTHER INFORMATION: Incyte ID No: 1329862CT1

<400> SEQUENCE: 70

```
cagttccttc ccagggtctc ttcagcttgc tggttggacc tcttagcctg cttatgaagc     60

ctgaattgac atcatgccaa ctggtctcct gctgataagt gattccttaa cttcctcggg    120

agcagcagaa acttgttttg aaaaaaatca gattctaaat ctttacagct gtttacttct    180

gcaagcacaa tggccgtagt aaggaattca agtcacagcg cacgcgtggc agggaaggct    240

ctgcatggag tcacaggaca aagcctgtcc tggaaacgtg ctggaaggaa gtcggcctca    300

ttctttacga cgggcagcag ctccaaatga gaaaccaagg ggcttggctc tgggtcagta    360

gcatctgcct ggcatgcggt gccagctgtg gagaccagtg aggtggcagc agctgcactg    420

ggctcctggg gtgtgcgtgg ggacctcagg ggtttaggag ctgatatact tttggttctc    480

atcatcttgt gtgttccttg cagacacaga atgttcagct taacaaagaa atgacacttg    540

ccagcaaccg gagcctggca gaaggaaacc ttttgtacca gccccagctg gacacgttga    600

aagcacgctt gacccagaaa taccaggaac tccaggttct ctttgaagcc tatcagataa    660

agaagaccaa attaggtaac tttttaaggg tgatcattcg agaa                     704
```

<210> SEQ ID NO 71
<211> LENGTH: 573
<212> TYPE: DNA
<213> ORGANISM: Homo sapiens
<220> FEATURE:
<221> NAME/KEY: misc_feature
<223> OTHER INFORMATION: Incyte ID No: 1329971CT1

<400> SEQUENCE: 71

```
tttttagtag agacgcgttt caccatgtta gccaggctgg tcttgaactc ctgaattcaa     60

atgatctgcc cacctcaacc tcccaaaatg ctgcgattac attttaaaac tctacctttt    120

aaaaattaga acctggacaa agaggtatta aagaatgtgt ctcttattaa tttattatgg    180

taatgagaag agtttggatt tggacctacc taggtttttc tttcctccag ctccgccacc    240

ccaactcctt actcatgctt cctctgtaaa atgatcactc cccagtttga cagggaatgc    300

ccctggaatc ccatctggtg ttctaattgt taccaaatcc aggcaaatct tgcctgtgat    360

acaggtggtg aagctactgg atagaactgg agcatctaac tggtgtgaga tgggatctca    420

ttgtgggttt gaatttgcat ttctcctgat gggccaatgg atgattgagc aattgtttca    480
```

-continued

```
atgtggcctg ttgggctcgc ataaaagggc cgtctttttg aagaagtggt ccggattcat    540

aacccttccg gcccaacttt ggggtggaga tga                                 573


<210> SEQ ID NO 72
<211> LENGTH: 597
<212> TYPE: DNA
<213> ORGANISM: Homo sapiens
<220> FEATURE:
<221> NAME/KEY: misc_feature
<223> OTHER INFORMATION: Incyte ID No: 1329994CT1

<400> SEQUENCE: 72

gtctgggaga aattggaaat aagattccgg agtttggcaa gatgcctggg cctgagatgt     60

agctccaggt gccaggtgga agacaggcac atggataaag aggcccattg agaagattta    120

gcaagaaaac cagcaaggct gaccagcagc agaactctgt ggagcatcaa catttaagta    180

ctttggctca tgaattatag tttatcaaac caaccaaact atgctgaagg tttacttaat    240

gaacacccat tttgctaaga tattacttgt gaaatagtat ctgagtgctt gctgtatgcc    300

agggactgtt tcaccagatt gtttaccgtc ttccaaattg gcaccaaaat gtttgataat    360

gaagttagaa gaaagaacag aacacaaaag gctttgaaaa gtaatgtttg cattggtggt    420

aacagtggtt tcttcgaagt ttgatgatac aatgtgctgt gtgaaggttt atgcctaatg    480

cgggggtaaa aagaacagat ggacctactc aaaacctgca gtgaggggtc ttcactgaac    540

ttagatagag caagaaaact cttttacatt catttgcttt gtggagtctc tcacaga       597


<210> SEQ ID NO 73
<211> LENGTH: 823
<212> TYPE: DNA
<213> ORGANISM: Homo sapiens
<220> FEATURE:
<221> NAME/KEY: misc_feature
<223> OTHER INFORMATION: Incyte ID No: 1329995CT1

<400> SEQUENCE: 73

attaatacga gcactatagg gaatttggcc ctcgaggaag taattcggca cgagtgaaat     60

gacagataaa gccataccat ataacaactt attgaagata tattaaaact ggcaggttaa    120

cccacatcta gagccagaaa gcataaatat ttttgacatt gattgtcaca aagaaataat    180

gtgaaagtat agggtatttt ggcatacaaa ttttgtgtaa atgtcaagaa ttcaaaggct    240

tttatatctt tgtttttggt gaggaattac taatactaaa caactttgta ttatcagata    300

ttaagactcc ttttcattct cactaatgtt catcttaatg ttttccaaac tacactttaa    360

aaccagagct gcaatttcta ccacactaat gggaaaattt ctggcaataa cttttttgct    420

tttataagat aaaatattgg tgaatgatca atatgtgatc aacagtcttc tgcatgctat    480

ttagtataaa actgcctgtt tggtttttaa actggaacca ctatttacaa aggatgactt    540

taattggcta attcagaaaa atgcagaatt acaaaataat caacaaatat ctgtcaagta    600

ccacctcgtt gtgtcatttg ccatgggata tataaaatca agtgttaaga tatggtcctt    660

gctctcacaa aacttaccaa ggaactacct aagcaacaaa ataattactt catgaactaa    720

attgcagcaa ttaaagccag gtgctgtggt acatgccact gcttaggaag ctgaggctca    780

ggagtttgag gccagcctgg acaacgtaac aagacttcat gtc                      823


<210> SEQ ID NO 74
<211> LENGTH: 627
<212> TYPE: DNA
<213> ORGANISM: Homo sapiens
```

```
<220> FEATURE:
<221> NAME/KEY: misc_feature
<223> OTHER INFORMATION: Incyte ID No: 1330007CT1

<400> SEQUENCE: 74

tgatgtttgg ttttgcgtca cgcttttaat tttttttttt tttttttttt gagacggagt     60

cttgctctgt cacccaggct gagattgtgc cactgtactt tagcatgggc aacggagcaa    120

gactctctca aaaaaataaa taaataagag agaaagatag tggtggggtt ggagaaagta    180

agattttttt ttaatgaggt ggaaaaatag acaaatagca atgattatga gaaggagttg    240

tgtgagactt agagtacagt ggaacttaaa tggcatgagt tgccctccaa accagtaatt    300

ctctatagcc aagaaaaaga gaaataggtt taatcaaaag ttaggaatta gtggaagact    360

gcagttgtaa ggtgttcaac atgtaaataa atgtgttcaa catgtaatgt gttcaacatg    420

taaataaaaa gcaaagttag aaaaaagaga ttgtcatata aaattccaaa taacttaaag    480

tcagtttaca agaggttgat ttccaaagtt aattaaacac attggacttc acagtttctt    540

ggaaatgtgc ataaactaag atctctgagc catggtagat actaaaccag cactaggtga    600

gacctgttag cctgggcaac agagatg                                        627


<210> SEQ ID NO 75
<211> LENGTH: 554
<212> TYPE: DNA
<213> ORGANISM: Homo sapiens
<220> FEATURE:
<221> NAME/KEY: misc_feature
<223> OTHER INFORMATION: Incyte ID No: 1330016CT1

<400> SEQUENCE: 75

cggctcgagg ttttatagcc ttacatgttt ctaacaacaa aagaagtatc ttctaactga     60

aggagaaaat acacagatat gcatacataa taaaatccgt aagtcatgtg agctctacct    120

gaaacctgtg cccaaattca ttcactcttc tgcatcacac accacacctt aggtcaagcc    180

actgtctgtt ctcacctgca ccattgcaac agtctcttcg ctgtctgctg ccttaccctt    240

ttagcttcat tatacaaatt gtagccaaag tagtcttcaa aatgtcaaat cgctccacct    300

cttcacaaag gatttcccat tggtttcctg ttgcatctgg aatacaatct aaagtcctca    360

ctaagtcctg taaaatgcat tattaggtgt tttcattgag ggctccttct gttcatcttt    420

gtatcagctc agatgtcacc tgtttagaaa gacctccttc acccaatcag tccatttagc    480

ataatagtcg tatataaaca gcacattggt ttttattcct tataactgtg catctttcac    540

attcttaaca tgtt                                                      554


<210> SEQ ID NO 76
<211> LENGTH: 490
<212> TYPE: DNA
<213> ORGANISM: Homo sapiens
<220> FEATURE:
<221> NAME/KEY: misc_feature
<223> OTHER INFORMATION: Incyte ID No: 1330023CB1

<400> SEQUENCE: 76

ggctgatgtt tgtattttta ctatagacat ggtttcacca tgttggccag gctggttttg     60

aactcctgac ctcagatgat ccacccacct cagcttccca aagttctggg attataggca    120

ggagccacca tgcccggcca gttttttttt aaaagaaaga aaaagataaa ggaaataacc    180

ctgttgatat ttagctgggg cgaggataag gtgggagggg aaaagcagta gaagtgtttt    240

cctgagtacc acaactgtga ggaaaattga gctcactcca gttcacaaca agctaaacat    300
```

```
tttcaaaatt atgctagaaa cagtagggga aacgaggagg atatacattt gcagtgcgag    360

tagcgaggtt catagaagat attccctctg atactgggaa atgaaaaata gaacattaca    420

gctggggaag ttctttatag tttacttggt ctgatatctt ccctttccct agggggaaat    480

tgggactgca                                                           490


<210> SEQ ID NO 77
<211> LENGTH: 399
<212> TYPE: DNA
<213> ORGANISM: Homo sapiens
<220> FEATURE:
<221> NAME/KEY: misc_feature
<223> OTHER INFORMATION: Incyte ID No: 1330061CT1

<400> SEQUENCE: 77

ggccttgctg cttttttaa acatacatca ggagatacag aggaagcttt gtgttttcgg      60

tggcaaatcc agcaagttca gcttgcaaca tgagttgcag gcaattggaa gaggataaac    120

ctctgtctgt ccccagctca cgtgtcattg ggagcctcca gagcagaagg agtgccccag    180

agtcattggt gtatgccatg ctgcactgca gtgggcagca gagattcgac tcttcattcc    240

aaatggctgc cggtccagat gttaacccag gtttacggaa agtgctgctt gagagattgc    300

cgctgtgcct gtgctgcaga tcccctgttt gcttacatac ttgggttatc tgtttgaggg    360

gaaataaaaa gggtaaaaca ctccaaaaaa aaaaaaaaa                           399


<210> SEQ ID NO 78
<211> LENGTH: 512
<212> TYPE: DNA
<213> ORGANISM: Homo sapiens
<220> FEATURE:
<221> NAME/KEY: misc_feature
<223> OTHER INFORMATION: Incyte ID No: 1330108CB1

<400> SEQUENCE: 78

ctccatccca aaaataaaat aaaaataaat aaaatcagac aaaatagact ttaaaaacaa     60

accatgttat tagagatact gagaagcatt ttacaatgac aaaagggaaa atttaacagg    120

aagaaataga aatcataaac agaagtcata aagaaataaa aatttataac agctaaaaac    180

acagccctga agtatatgaa ataaaactgt cagaaatgaa gagagaaaca gacaattgaa    240

caataataga caactcaaca ataatagtac taactcttgt tgattttctg tcttgttgtt    300

ctatcaatta ttcagagtga gttattgaac tattacccaa ctactattct tggatgaaat    360

ggtgggaggt gaggctggca ctctgcttaa taccctcccc tgttctggtg tcagggagac    420

aaatgtggag ctgacttttc gtcagaaaca gtggtaccca gaaagtagtg ggtaacaga     480

tcccaagtgc tcaaagtaaa aaaaaaaaaa aa                                  512


<210> SEQ ID NO 79
<211> LENGTH: 259
<212> TYPE: DNA
<213> ORGANISM: Homo sapiens
<220> FEATURE:
<221> NAME/KEY: misc_feature
<223> OTHER INFORMATION: Incyte ID No: 1330215CT1

<400> SEQUENCE: 79

aaatcattca tgtttatttt ctctcagctt ttaaaaaatg tgtttagaat tgctctctct     60

accttttac caaccagtta tagtttttt acaatctgat gttttcctca taccattcta      120

cttgtggtgt ttcataataa tatccagtgg cctttctca gttcttaccc ctctacccca     180
```

```
gtttatttat agccagattg ggggaacaga aagcataaat acggaaagat gctccgtggt    240

gttaggtaaa atctctgag                                                 259


<210> SEQ ID NO 80
<211> LENGTH: 830
<212> TYPE: DNA
<213> ORGANISM: Homo sapiens
<220> FEATURE:
<221> NAME/KEY: misc_feature
<223> OTHER INFORMATION: Incyte ID No: 1330424CT1

<400> SEQUENCE: 80

ggtagcctta gacagccatc aagaagtatc cagtgaaaga aaaataaata aaaaataaaa     60

taaaataaaa taaaataaaa acaatgaaaa agaggcatcc agtgaaggcg attgcctcac    120

tgagaaaatg atcacctttt atgttgtcaa cactttaaaa cttaacggaa atgttcattt    180

gacctgagta gataatcctg gaaagagagt aaaagatgca gactagtttt gaaaggagtc    240

tgccatcatg attgtcagca tcttcccttc atttattgaa cacctattat gtgttctctg    300

aaaaacactt tccatactgt acatttaatc taaataacaa tactttaatt aaaagttcca    360

tgaagaaaca atgtcttaca gaggagaaag aacttgttta ggtcatacaa caagatttta    420

taaatgcagg ctaatacctg tctgtctctt tatggtgccc tgaattcttt ccattatatt    480

aaaaataact tctccccatc ttcctctccc tgcacccatt ttgaacatta ctaatcaata    540

atttccacgg agcatagttt cagaatcctt ttcagcatat tatagaacac cactaccaac    600

tgatcaatga atatttctgg agaaaacaat ttccccaaca tggtgaaacc ctgtctgtac    660

caaaaataca aaaattaatt gggcatggtg gtggacacct gtaatcccag ctactaggga    720

ggctgaggca ggagaattgc ttgaacctgg gaggcggagg ttgcagtgag ccactgcact    780

ccagcctgat gacagagcaa gactcagtct caaaaataaa tacagccata               830


<210> SEQ ID NO 81
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 1330429CT1

<400> SEQUENCE: 81

tatcaatgct cgggccaggc cacaccaaca gaagacacag taagagacag acacttaggt     60

ctatccacgg cgacagctac aaatacaagg aaaagggtca agttcaggca ctgatgatgt    120

tggcatggga ttttccagaa tggcaactga ctctcagtga agcgctgaac caaagaacaa    180

tcttctctag agtcacacag atgggatatt cttgtattag aacaacattt taaacacttg    240

ttaatgcttt catttaaaag cataaaaatc tagaccaggc acagagtggc tcacacctgt    300

aaacccagca ccttgggagg ctgagttggg aagatcacct gaggtcagga gtttgagacc    360

agcctggcta acatggtgaa accctgtctc tactaaaaat acaaaaatta gctgggcgca    420

gtgacacatg cctgtattcc cagctactcg ggaggctgag gtgggagaat tccttgaacc    480

cggggagatg gaggttgcag tgagccaaag tcacaccact gcactccaac ctggcgacag    540

agtgattc                                                             548


<210> SEQ ID NO 82
<211> LENGTH: 745
<212> TYPE: DNA
```

<213> ORGANISM: Homo sapiens
<220> FEATURE:
<221> NAME/KEY: misc_feature
<223> OTHER INFORMATION: Incyte ID No: 1330478CT1

<400> SEQUENCE: 82

```
attaataata tagcatgact aggtaaggtt tattctagga tgtaaggata ttttaccacc     60

aggatatttc agtatacttc attgctgaat gaatgaaagg ttaaaatcat gtgattttat    120

tatatgataa agtggacatt tgatagaatt tagtctttcc cagtaaaagt tctaagtaaa    180

atacagatag gaagaaattg cctaaatctg ataaaaatta gttactaaaa tttaaagtaa    240

atattgcatt aaatattgga gtactgaagc tacttgcgtt taaataggaa acaagacagt    300

cccataacta ctttgagact tatgcaggag agactttgtg cagtgtctta agaaaatgaa    360

taattgatac taatgttaga agaaaacaaa tacactattg gaccacagag gacttgggct    420

attctggtta aaacttaacc acagaggacc tgggctattc tggttaaaac ttaaccacag    480

aggacctggg ctattctggt taaaacttaa gttgaataga gcagttggga aaaaaacttt    540

gttctcaaaa ctgttggatc agtgtgaatg gtgggctctc atagttgata atgttttaac    600

ttttatgagc actacagcag cctttcccaa atagatttcc aggctgtgta aattagaagt    660

ttgacaaaag gcattctgtg gtcaaataaa tttgagaagc tttgaatgtt atattccaag    720

accagtgata cacaataaac attga                                          745
```

<210> SEQ ID NO 83
<211> LENGTH: 500
<212> TYPE: DNA
<213> ORGANISM: Homo sapiens
<220> FEATURE:
<221> NAME/KEY: misc_feature
<223> OTHER INFORMATION: Incyte ID No: 1330641CT1

<400> SEQUENCE: 83

```
gaaggaatgt catttgtatt tgctcttata gatgttaagg tagacaagaa actcagttgg     60

aatgacagag tataatttct acatttaaaa tgttgtgttg actaatgcaa ttaatttgta    120

ctcagttata agtagaggcg atgagtacca aggcatatga tcagtgcaag tatacccctg    180

agacaatata attttcaggg aatcaaaata atcagcaaga gagcatatat ttccttaatg    240

gagtactgag agtttattag cttctactgg agtgctgatt aagaaaaagg agaaaagagg    300

ttcagttgag tttttaaact gcagttaaat aaaaagattt tgcctatgtt atttgcatgg    360

ttaatgtatc tagaagggtt aattttatat tgaagaaaca agtgtagtaa ttatagacat    420

gaatataaat attaccagtg gatttgagga attaaaatgt cacagtttca tttattactt    480

tactatatca gacctgtgtt                                                500
```

<210> SEQ ID NO 84
<211> LENGTH: 494
<212> TYPE: DNA
<213> ORGANISM: Homo sapiens
<220> FEATURE:
<221> NAME/KEY: misc_feature
<223> OTHER INFORMATION: Incyte ID No: 1330656CT1

<400> SEQUENCE: 84

```
ttacaactga taattaactt ggtctaaaaa gaatcttaat agatttcaaa agtagaaaac     60

ttccaggctt ccttcataaa acaataagat atattgaaaa ttagcctcta aaagacaatc    120

gcatagaaat ttaaacaatc gaaactcttc taagtaattc ttagatcaat gaatagatta    180
```

-continued

```
aatttgacat ttcagattat atattgatta gcgaaaatga aaatacttca tatcaaaact    240

tgagataagg ttaaaactgt gcccagagga aaactggtag tctattttaa aagcacttta    300

ggttttgaca ttaaatatga aagagtaaaa taattaaaat aaaagtccat taaaaaaata    360

attgaggctg ggatggtctc gaactccttg gtctgaagcc accctcctgc cttggcctct    420

caaagttttg ggattatagg tgtgagccat ggtgccaggc ctgagaccct gttactaaca    480

aaaaaaaaaa aaaa                                                      494
```

<210> SEQ ID NO 85
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 1330683CT1
<221> NAME/KEY: unsure
<222> LOCATION: 461
<223> OTHER INFORMATION: a, t, c, g, or other

<400> SEQUENCE: 85

```
gaaaaaaaaa tttgtgaaat tcagtgtata gaattttcta agattcaatg aaatcactaa     60

agaacatact gacagatttg agttaaactc atatacttca taaaaggtaa tcaaaatgta    120

aagatcatta acctttagag gaatttgcag aaaagaatta acatcttcag tataaggaaa    180

ataaacaaat tttaaaactg atactataat cgagttctca tattctggcc caagaatagg    240

ttgcatcaga tttagtttca agtgtagatt cctgtcctct gtcaaactct tctgccaagt    300

cttcagcctc caaaggttgg gatcctttct cttctctggc agaaggcatt cattcatgtg    360

agggtacaaa agaggaagga atggtatatg gttaacagga aaatggaagt caataatgtg    420

caaagaaaaa ggacgagatc attttgtatc aaggtatcca ngagaaaatt tgtaaagacc    480

ggtccatata ggagattaag attttcctct agcttagtcg gaaaaaaggg ggggcccccg    540

gctttgta                                                             548
```

<210> SEQ ID NO 86
<211> LENGTH: 563
<212> TYPE: DNA
<213> ORGANISM: Homo sapiens
<220> FEATURE:
<221> NAME/KEY: misc_feature
<223> OTHER INFORMATION: Incyte ID No: 1330740CB1     Contig1 1

<400> SEQUENCE: 86

```
tgtggtccag cgtactttgg gagtccgagc atttccttgg gcctgggagg tcgaggcaca     60

ggcgaaccaa gatccagtga accaagatcc agccactgca ctccagcatg ggcaaccaag    120

caagactccg tcccaaaaat aagtaaataa ataaaaaata aaaaagacgg tggtcatgtc    180

tctaccaggc tctcttcccc ttcctgttgg cttgaacttg tggacaccta gctgcagcct    240

tgtaggcaca acagtgccct agtgtgtggt gagggatcaa gacagaagga atccgggtct    300

caggatgtct gtgttgaatg gagcttcctg ctgacttgga aagttcacca ggcagttaca    360

tgggagacaa ataaacttcc atcttctttc atccacagaa tgattgctag gcctctttgt    420

tatagaggct gagccttacc cttccttacc aagcacaggg gagaagagca tggcagaacc    480

aaaggcttcc caggctaaca cagcagtcca gcccccaggc ctgcatggct gccatggaac    540

atcgccagga ttgcatccca agg                                            563
```

<210> SEQ ID NO 87

<211> LENGTH: 1329
<212> TYPE: DNA
<213> ORGANISM: Homo sapiens
<220> FEATURE:
<221> NAME/KEY: misc_feature
<223> OTHER INFORMATION: Incyte ID No: 1330847CT1

<400> SEQUENCE: 87

```
aaaacctact aggagagaaa acaaacaaga agttttgatg tactatgaac ctaatttaca     60

gaaggcacta tttgagaatt ttcctttcca ttcacgcaaa tacagaggtt caagagtgtg    120

taacctcagc aattaattgt tatttcctgt atgttaatta cgccatgaag caacatccat    180

tctgtatgat gcctccatta agtattatgc ccactccttt tcattttctc tgtttataca    240

aatataattt cttgattatc ccatgtaggt aagcctgcct cacagttggc ccatacttct    300

ccatgtctta atatggccca aagatagcta gatttaattc tttttcatgg aatgatttag    360

tggttttttt gaatgaccaa atacctgtta ttatttctgt atgcctaagg aaataaatgt    420

tccccttctc tacctgaagc tgctctgctg tgtgtacatg agcattcttg tgtgtatggg    480

tgtacgtgtg tctgtgtgtc tgtctcacct ccagggaaac ctaacactat cgttttatac    540

cataactgaa taaatcacag cagtcagaga gatgtgaacc caaggaaaat tattataatt    600

aatggaaact tcagggaaag atgaataatc caaggagctc agaactaacc caaaatgaaa    660

ataataatag taaatgcagc atcctctctg ataaaatctt gggcccaaaa ctgcaacaaa    720

atgagaaact ccatttaggt ggaacatggg tgttttatct tacctctttg aatgttgaag    780

gaaatctgct ccagtagaat gagttacttt gtatgagata gaaggtgaaa aagagagaag    840

aaattggcaa cactcttagc ccactgaaag cagcctgctt cagaacctaa ggccttgtgg    900

ttatttttac tcgcttgcaa aagtgaggaa ggatgttata ggtctctttg agcctctttg    960

cttttaccct ttatttctat atgatctaca tttatattaa taaattatta catgccatat   1020

aagttccaga atcattcctt ttgacagtcc catgggattt aatcccctcc taaatcccaa   1080

aatatagaaa gagaaaatgt ttgggtacag cactggggca tcatgcatac tgaatattca   1140

acaataacca tttgaatgag tggatgattt gggggtcatt ccttactatg tgactgctct   1200

tctctcaggc agtcttagtc cctgtgtcac tctcctagtg tgtagccggg ctgctgcctg   1260

agtgtaatcc tagcctttca agataaccat ttattatatg gtgctgaccc ctaacaacac   1320

aagccaggg                                                           1329
```

<210> SEQ ID NO 88
<211> LENGTH: 546
<212> TYPE: DNA
<213> ORGANISM: Homo sapiens
<220> FEATURE:
<221> NAME/KEY: misc_feature
<223> OTHER INFORMATION: Incyte ID No: 1330861CT1

<400> SEQUENCE: 88

```
gaggtgggga agacggagga acagcagacg caaaggtctt agccagaaac acttgtcaaa     60

ttcaaggcag ctagaggctg aacatagcaa aagggagggg agtatgacgt gggccagggg    120

acggggggtg gtcagaaaag taggaggcag ctggatgatt taatacettt ttaggtatgg    180

taaggagaat tctaaatgat tggtatgaag tgtgatgaga caatagatgt ttaagcagcg    240

tgacatctga tttgtctttg aaaaggatca ctcaggctgt tctgtggatc agattaaggc    300

agagcaagag tggaagtagg gagaccagtt aagaggctat tccaggaatc caataaagat    360

gtcatagttc tttgaaccaa ggtggagact gtggagacag aagtggatgg ttttggtttt    420
```

ggttttggtt ttagaggtat aatcagtcat acttgcatgg aatggaataa aagtgggcaa 480
gtaaagaaca aacaacaaac aaaaaaaaag gcaagggaaa ttgatccacc atggtataac 540
cacctt 546

<210> SEQ ID NO 89
<211> LENGTH: 593
<212> TYPE: DNA
<213> ORGANISM: Homo sapiens
<220> FEATURE:
<221> NAME/KEY: misc_feature
<223> OTHER INFORMATION: Incyte ID No: 1330882CT1

<400> SEQUENCE: 89
ggtaaaatga agttggttca gcatcctttt ctgaatcttc caattccaat cttgcctcct 60
ggatggttct ttggtttcat tttacagatg gctaatctcc actatgtgca gatttttcta 120
gtttaatttt tagatggaaa tcttattaac tgaccttaac tttttttttg agggttttga 180
ggccccctca tgtattctgt ctcccaataa aattttaagc tcctggatag ttccctgcat 240
agataagaaa tgaatgacta tcaaatacat tagatattct atcataacaa agcttttccc 300
cattaaaatt gagtaacagc tatatatcct tgatttgcac ttaaaaatta tgcttgattc 360
aattttaaat ttcaaaaagt tggtatgaaa tagtttttga caatcaaaag gcataaagaa 420 atgtttttc tcttggaact acaggtgaga agaggagttg ctgttgtgat tgggggagtc 480
aattttggga gcagaaaggt agagcgggcc cgggtgtggt ggcttatgcc tgtaaaccta 540
gcattttggg agggtgagtc gggaggatga cttaaggtca gagtttaagt cca 593

<210> SEQ ID NO 90
<211> LENGTH: 762
<212> TYPE: DNA
<213> ORGANISM: Homo sapiens
<220> FEATURE:
<221> NAME/KEY: misc_feature
<223> OTHER INFORMATION: Incyte ID No: 1330907CT1

<400> SEQUENCE: 90
tttgctaatg aatatgagtt accttcataa ctgaggaaga ggccataata caaatttatt 60
ctttgtttaa cccttcatga aaaatttaag tatatcttgt attttattga cttcatatga 120
attataattg tgcatttacg aataaaacta atattgagag attaattcag gtggagagaa 180
aatgagtttg agattctggc gggacatctg gcatagctgt ctagtggata tataccaata 240
gatatattgg tatcaggttt tctgaagtca agatcagact tacaaatgtt ggaagcagca 300
gtggatttgt ggtggttaat cctgtaaggg tgtaagaaat cattcaagta agtatagtgt 360
aagaagaggg caagaccaag gatggggaac accagcatta agcgatgggt agagacagcc 420
aaggagtctg aggaagagca tcaggaaagg aggaaatcta gggggcagtg gtctcataga 480
agccaggaga ggagagtttt aacaaggaga gaagtctatc tgggagtcaa gaactgatta 540
cgtgcctatt gtctttggaa gttaggatgg gggctttaac ctcagcagac ataatttaag 600
tacagtgtaa gggtagaagc caagtttgaa tgaatctgag gagagaatag tgattctgca 660
ctcacaagta aatgtgagtt tagaatccgt attttgagaa acaaaggtta gaaggagagg 720
cgatccattg attagggaga tgattaacaa aaaaaaaaaa ag 762

<210> SEQ ID NO 91
<211> LENGTH: 548
<212> TYPE: DNA

```
<213> ORGANISM: Homo sapiens
<220> FEATURE:
<221> NAME/KEY: misc_feature
<223> OTHER INFORMATION: Incyte ID No: 1330918CT1
<221> NAME/KEY: unsure
<222> LOCATION: 481
<223> OTHER INFORMATION: a, t, c, g, or other

<400> SEQUENCE: 91

tgccaccatg cccggctaga tacgattctt gttcagtaac ttagaataac ttttttttta     60

aaaagggtgt ttgtgggtga attatgtttg agagacggag tcttacttgt tatccaggct    120

gttctccaac tcctggactc aggtgattct cctgccgcag ctacttggga gactgaggca    180

tgagaactgc ttgaacctgg gaggcggagg ctgtagtgag ctgaggttgt gccactgtac    240

tccagcctgg gcaacagagc gagactgtct caaaaacaaa aaaaacaaaa aaaacaaaaa    300

aacccaaaat gtattctgtt ttacttagga agtgaatatc tatttgaaat aaaaagtaga    360

ataaataaat tgaataaata aacatctttc tgaactatga aagatttttg tcagcagtgt    420

tcaagtataa aaatattgtg gccaggtgca gtggttcatg cctgtaatcc cagcagttcg    480

ngaaggctga gacaagagga tcgcttgagg ccaggagttt gagaccagcc tgggcaacaa    540

agtgagac                                                             548


<210> SEQ ID NO 92
<211> LENGTH: 422
<212> TYPE: DNA
<213> ORGANISM: Homo sapiens
<220> FEATURE:
<221> NAME/KEY: misc_feature
<223> OTHER INFORMATION: Incyte ID No: 1330930CT1

<400> SEQUENCE: 92

caagaaaaaa taaaaataaa cacacaagat aaacgttctt atgctgtcta aagctgcaag     60

aagtatacag tgtgaacaaa gaattctcat caaaataaaa taaaaataca gaccaggtgc    120

agtggctcac tcctttggga tcccaacact ttgggaggct gaggtgggag aatcacttga    180

gcccagaagt ttgagaccag cctgagcaac ataggaagac ctcatctcta caaataataa    240

taataaaaaa aatagctgga tgtggtagtg tgtgcctgta gtaccagcta ctctggaggc    300

tgaggtggga ggattacttg agcctgggag ttcaaggctg cagtcagctg tgagccatga    360

ttgcactact gcactccagc ctggacaaca gagggagacc ttgtctcaaa aaaaaaaaaa    420

aa                                                                   422


<210> SEQ ID NO 93
<211> LENGTH: 386
<212> TYPE: DNA
<213> ORGANISM: Homo sapiens
<220> FEATURE:
<221> NAME/KEY: misc_feature
<223> OTHER INFORMATION: Incyte ID No: 1330957CT1
<221> NAME/KEY: unsure
<222> LOCATION: 371
<223> OTHER INFORMATION: a, t, c, g, or other

<400> SEQUENCE: 93

tcaagcataa tcattgtcct cagagacctt ataatataat tgataagtta acatttactg     60

ataaatagtt aagtgttaac ttgtacgcta cctgcccagt aagcttttaa aaagaataaa    120

attgttatgg attggaatga ttaggtcata aaatctttat gaccaagttt gggcattagc    180

tagacctcta agtggcatag cttttcaagg ctggagggga ggaggaacag atcagggatg    240
```

-continued

```
gatgatcatg cagtcagtgg tgggactgtg tggacatact tgatttggga agtaggtagt    300

aatctaggtt gcaagagaaa tttcctgcaa gagactactg agagataaaa ccaggaaaaa    360

aaaaaaaaaa naaaaaaaaa aaaaaa                                         386


<210> SEQ ID NO 94
<211> LENGTH: 736
<212> TYPE: DNA
<213> ORGANISM: Homo sapiens
<220> FEATURE:
<221> NAME/KEY: misc_feature
<223> OTHER INFORMATION: Incyte ID No: 1330969CT1

<400> SEQUENCE: 94

tgaaatattt agctgttgac ttaattgggg ggtggcagaa attcaattac attatttagc     60

ttcacatcac aagaagtgga ttactctttc ttttacattt ttagattaaa agtaataaag    120

ttctctaaca gcttaaagtg attcatttca gaagtcttta tcctcaaggt aggcttctta    180

attattctca gaggaaatca aatcattcgt ctaataatta tagggaacct ccatggtatc    240

tcttacatct gtccatttct aaccatcttt actcctattt tagttcttgg tttactacat    300

caggcaccta aagagagatt tctagcatta atctcagttg tctcaagtga ttatctccac    360

tttgttctca acgatctttc agtggccgtc atttttctaa agtgtaagag ctttggtact    420

ataatctcat tcccttgaga atgaaaccct gactccttaa ttgtgcaaaa ttatctggtc    480

agcctcactg cttatttctt cgtgcctgcc ctatagcaag cccctccaat tatgttctag    540

cgatattaaa tcaatttgca gatgcccaag tgttttgtac tccctctgac ctgcctgttc    600

ttcaggtctc acttcagatg ttgtcttttt ctagaaatcc taaaactatt agtcgctcct    660

aacatctgga aacttggata ttgtttcatc atttaatgta atttaatatc aataaatcat    720

ttatgtattt gtaaaa                                                    736


<210> SEQ ID NO 95
<211> LENGTH: 555
<212> TYPE: DNA
<213> ORGANISM: Homo sapiens
<220> FEATURE:
<221> NAME/KEY: misc_feature
<223> OTHER INFORMATION: Incyte ID No: 1331030CT1

<400> SEQUENCE: 95

aagtatgact ctgtatgtaa aaaaacagac catgtgtcaa aaagaaacca gaatcattaa     60

aaacacttga ttaatttaaa aaggcagaaa agggatgaag ggaattaaat aacagatgtg    120

gtatagaaaa caaatagtaa gatgatagac tcagatgtac tgtatcagta atcacattga    180

atataaatgg tctgaataac catttaaaaa acagagattg tcagattgga tgaaagaatc    240

cctactatat ggtgcctatt aaaaaatgta ctttacagtt agcaacttaa aataggttaa    300

aagtaagaag aatggaaaaa gataaacttt gttaacactc ataaaaagaa agctggaggg    360

gctgtactaa tagcagacaa aatagacttc agagcaaaga atattaccaa gggtaaagaa    420

agtcatttta tgataaagta ggggtgaaat gttccaacag atataataat tctaaacatt    480

tatgcactta gtaacagagt ttcaaattag agcaaataaa acctgataga actgccagag    540

gtagtcaatt acaca                                                     555


<210> SEQ ID NO 96
<211> LENGTH: 555
<212> TYPE: DNA
<213> ORGANISM: Homo sapiens
```

-continued

<220> FEATURE:
<221> NAME/KEY: misc_feature
<223> OTHER INFORMATION: Incyte ID No: 1331172CT1
<221> NAME/KEY: unsure
<222> LOCATION: 211-260, 278, 449
<223> OTHER INFORMATION: a, t, c, g, or other

<400> SEQUENCE: 96
agcaactatc agcttctctt ctacttcagg aaatgaagaa gctgcataca ctacagttat 60
ttttaaaaga ctaataactt ataggtcatg gtagtttttt tctatagtgt tattaccatt 120
attatcttct acagcagtaa aaattgattg ttgagatgag cagtgtgaga gaccctcaaa 180
ttcaggcacc aggactaaat ctcccatcta nnnnnnnnnn nnnnnnnnnn nnnnnnnnnn 240
nnnnnnnnnn nnnnnnnnnn agagtatatt aagctgcnaa ccatcttcct tctttgtaag 300
tttccgacaa attttctgaa tgtccatgga tgtaccacaa tacatccttc aaagtgaagc 360
tgcattttta agttataagt cttaagtctg tgaccatctg tcacctgttt tggtcctctt 420
taccatattt gcattactgc tataattana ataccttcac acatagctcc acatgtaaga 480
tttgtgtttg tagtaaactg gctaaatact gtttgggata catactggga tccaggtaaa 540
tggtggaaaa gggcc 555

<210> SEQ ID NO 97
<211> LENGTH: 400
<212> TYPE: DNA
<213> ORGANISM: Homo sapiens
<220> FEATURE:
<221> NAME/KEY: misc_feature
<223> OTHER INFORMATION: Incyte ID No: 1331278CT1

<400> SEQUENCE: 97
cttgaaccca ggaggtggag gttgcagata gccgagatcg caccattgta ctccagcctg 60
gtgacaagag caaaactccg tctcaaaaaa aaagttaaca ggttccaaaa aggttgttta 120
gaagcagcat aggtgtaggg gactggggag aggagaaact ggaaagtgta taagtaggat 180
gggaggagga aatgaacagg aaataaaaac aaaacacgga cagcaaatag cccatttcat 240
cagttcatga agccactaaa tattttattc actttagcaa attctctgct atatgaaata 300
aacataaaaa agaagtcaag tcttcaaagc ataatctgag gctttaggtt gacagtaata 360
aggaaatagt tttgactttg gagtcaaaaa agactaataa 400

<210> SEQ ID NO 98
<211> LENGTH: 396
<212> TYPE: DNA
<213> ORGANISM: Homo sapiens
<220> FEATURE:
<221> NAME/KEY: misc_feature
<223> OTHER INFORMATION: Incyte ID No: 1331316CB1

<400> SEQUENCE: 98
gaaaccatta attctaagag tgtttctgga ataaaagtgc tatatcattt attagattct 60
acttctttga acaagatttg ttgacataaa agtaaaacat ggccaggtaa ggtggctcat 120
gcttataatt cccgtgcttt gggaggcaaa agtaggagga atccttcttg ccaggagttc 180
aagaccagcc tgggcaatat agcaagacct tgtctcttaa aaaaaaaaaa aaaaaaaagt 240
attagctgga tgtggtggca cacacttaca ctcctagcta ctcgggatgc tgaggcagga 300
ggagtctttg agcccagaag ttcaggctgt agtgagctat ggtcatgctg cagcctggac 360
aatacaggga aacctcatct caaaaaaaaa aaaaaa 396

<210> SEQ ID NO 99
<211> LENGTH: 578
<212> TYPE: DNA
<213> ORGANISM: Homo sapiens
<220> FEATURE:
<221> NAME/KEY: misc_feature
<223> OTHER INFORMATION: Incyte ID No: 1331330CT1

<400> SEQUENCE: 99
aaccacccat aagaatgttt atatttaagc tacagtagaa aggagcatgt gagtgactat 60
ttagattata gttactgctt aagaaatact tctcctttcc ctcttttgtg tatatctagt 120
ttagaattga ggccaataag atatcatctc aaaatactcg agtgcttccc attatttatt 180
atctgtaata tactagatat ataattttgg acatcatcct gcagttgaat gttagctaaa 240
ataatcatat tactttgtct aaatgtagta tgagatcctt taaatatttt agtaataaaa 300
cttcctttgg ggccgggcgc ggtggctcac gcctgtagtc ccagcacttt gggaggctga 360
ggcgggcgga tcacgaggtc aggagatcga gaccatcccg gctaaaacgg tgaaaccccg 420
tctctactaa aaatacaaaa aattagccgg gcatagtggc gggcgcctgt agtcccagct 480
actcgggagg ctgaggcagg agaatggcgt gaacccggga ggcggagctt gcagtgagcc 540
gagatcccgc cactgcactc caacctggca gacagagc 578

<210> SEQ ID NO 100
<211> LENGTH: 562
<212> TYPE: DNA
<213> ORGANISM: Homo sapiens
<220> FEATURE:
<221> NAME/KEY: misc_feature
<223> OTHER INFORMATION: Incyte ID No: 1331371CT1

<400> SEQUENCE: 100
gttatttttt tatttgcaca tggtaaaatt tgctttttct ggtgtacagt tttgtgagtt 60
tgtacacatg cacagatttt tgtgaccacc aacacaaaca ggatacagaa taactccagc 120
tccccgaagg ccactcttga gctgcccctt tattcagacc ctgccttcaa cccttactcc 180
ctgaactgtg gaaggagtct tcgagccaca cacagccatg gtcaagggtg aaactccgca 240
gctacggggg cttcagcaca acctctggcc actaagtggc ttgtgctgtc ccacaagtga 300
tccctagcga gttagactaa aatataaaaa caaggggaaa atctgagtgg ggctggcagc 360
tgcgcactgt aggggaatag acttcagaga atcattaata gttcaaccaa gtacccacac 420
aattaagtga cagctgcagg cctctgggaa gtgggagtat cagtgagcag attgttacag 480
ttattaatta gaagatccag ttttcaatga aaaattataa gacatgtaaa gaaactagct 540
cgtgtgaaca cacatgggcc cc 562

<210> SEQ ID NO 101
<211> LENGTH: 428
<212> TYPE: DNA
<213> ORGANISM: Homo sapiens
<220> FEATURE:
<221> NAME/KEY: misc_feature
<223> OTHER INFORMATION: Incyte ID No: 1331411CT1

<400> SEQUENCE: 101
gcgggtgtga gccaccatgc ctggcctaaa tcctgttagt tttgaatgga aattttcttt 60
ctttcttttt tttttttctg ggacagattc ttgcttcgag acaatgacaa atacaaacta 120
ggtttactgt aaatatgaga aagggaaaaa atacttttat tgtattagaa gacttgaaat 180

```
cacatgaagt gataccaatc ttttgttgtt gttggtcaga tgttttagct attttaggtg    240

tttgggtttt ttgtctttct acataactgc taaccttgtt agtatctgca gaatgcctta    300

attaggaaag gtattaaccc tatgtgtcag atttgtataa ttcatattgc tttacatgga    360

gtcttccaat aaatgtatat ggtataaaaa aaaaaaaata gaaaggtgtt taggagaaaa    420

aaaaaagg                                                              428


<210> SEQ ID NO 102
<211> LENGTH: 769
<212> TYPE: DNA
<213> ORGANISM: Homo sapiens
<220> FEATURE:
<221> NAME/KEY: misc_feature
<223> OTHER INFORMATION: Incyte ID No: 1331481CB1

<400> SEQUENCE: 102

tgagagtcat cgtaaacaaa tactgttgga agaatgagaa ggaggtgtgt gtggcaggag     60

tgttgagagc cagcaggtgt gtctccatat gacattgcac aggtaggtag gagccagatc    120

tcatgttgag ccttgtagag catgatagct tctcacttat cctttggaag ggttttcagt    180

agagaaatga cattatgaga tttatgtttg aaatgttcac tcactacatt tgtgatgaga    240

caagaatgga tgcagataga tcattaggaa agtagtatag tagctcagaa aagaaatgat    300

ggtaattcac tctactgcta gtgtggtagc agtagagaga agtgggttga ttagagaacc    360

ctgtagatca gaaagaaaaa tgaactatgg agttgggtga gatataggaa ggagtaaatg    420

atacaataat gtatcttaca tatgactaga aacggatatt acataaaact ttctagtggg    480

ccaggcatgg tggctcatgc ttgtaatccc agcatttagc taggctgagg taggaggatc    540

acttgagccc aggagtttga gaccaacctg ggcaacatag tgaaactgta tctctacaaa    600

aaaaaaattt ttttttagc tagctaggtg tggtgttgtg cccctggagt cccagctaca    660

tgggtggctt tggcgggcag atggcccgag cccaggagtt tgaggctgca gtgagctata    720

atcacaccac tgcactccaa cctgggtgat agcgtgagac ccagactca                 769


<210> SEQ ID NO 103
<211> LENGTH: 836
<212> TYPE: DNA
<213> ORGANISM: Homo sapiens
<220> FEATURE:
<221> NAME/KEY: misc_feature
<223> OTHER INFORMATION: Incyte ID No: 1331917CT1

<400> SEQUENCE: 103

ctgacttaag ggtcctgcat aaccctgtta atgatatcca cgaataaaga attttctgtc     60

ccctaattgc tgtggtgcag tgagcagtgg ggaataattg ttatcaaaat gaaactaaac    120

cctataagga ttcacagagt cacaatactt ttgaccagca ttcatgaaga agcccttact    180

tatgggtccg aggggcagtg tggaaataat tggccagtag atatggggcc catgaacctc    240

acctcattag tgtccacctg gcactgactg atcagcacac tataacatca tgagaaagat    300

ggcgggaaga tccctggtaa ttatacattt ttacttacgt agcaacaaag gagagagcgg    360

gaagctagaa ggcagcagga acgtgaacag cgaaggagag aacaagaaga aaagaggcgt    420

ctagaggagt tggagagaag gcgcaaagaa gaagaggaga ggagacgggc agaagaagaa    480

aagaggagag ttgaaagaga acaggttagt tcacagataa catagcaggc atacacttgt    540

gaagtttgtt actttgcaga gctgggggat ttttagaaag tatacacaca tgtgatgcat    600

acacacatgt acacacatac acatatactt agaacttcag atgtatgaac gtggtgaaac    660
```

acagttggaa tgacaccaat aaattcagtc tcttgtctta aaaagggttt ataaatcatt 720
acactttagg aacctgttga aaccagttaa gtggtctcta aatagtataa tacctgaaag 780
atgtctgcat gtatcttctc aggcttggct taaatgctgt agaccccaaa tatatg 836

<210> SEQ ID NO 104
<211> LENGTH: 591
<212> TYPE: DNA
<213> ORGANISM: Homo sapiens
<220> FEATURE:
<221> NAME/KEY: misc_feature
<223> OTHER INFORMATION: Incyte ID No: 1332023CT1

<400> SEQUENCE: 104
gaaagaaaga aagaaaagaa agagaaagaa aagaaaaaga gaaagggaaa gaaagaaaag 60
gaaggaagga aagaaagaaa aagaaagaaa ggaaaaaaga gagagaaagg gaaagaaaaa 120
gaaaaggaag gaaggaagga aaataaagaa aaaagaaaga agaaagaaga aagaagaaat 180
cagctagctc aacaagcttt cttaacgcta agtgagagaa cttaagggca ctgtccaagc 240
tgaggggaca agtgaacccc agagcctagg attagtatcc agttcggtct aacgcagaag 300
cccacgcgcc atgctggctc cctacactgg tggccaccat gagaagcttc ggcctcgtcc 360
ccttgggtct cctcccaggc ctctccctgc cccaaggagg cgaacagggc tctgcttaac 420
gacagctctt gctggaccat catcggcacc gagtcggtgg aattttcctt cagcaccagc 480
ctgggcgtgt acccttggaa cccggtcact acgggtgcct ctacatcagg cacctaagag 540
ctgagccaac agggggcgac gtaggccacg cttggagctc aacgggagag a 591

<210> SEQ ID NO 105
<211> LENGTH: 538
<212> TYPE: DNA
<213> ORGANISM: Homo sapiens
<220> FEATURE:
<221> NAME/KEY: misc_feature
<223> OTHER INFORMATION: Incyte ID No: 1332138CT1

<400> SEQUENCE: 105
ctaatataaa gggtagaatg tggaaagact tagcacaatc attgtctaga tagactgagg 60
aataatcaaa aagattgtag tattttgctc tcccctatca tatggtgcta caaatattaa 120
tagatacatg aaagttttac agcaaatact acctgttcac ttctgtcacc tggcgttctg 180
ccttcccctc aaggaagcaa aacacacaca cacacacaca cacacacaca cacacacaca 240
cacacacaca cacacacaca cacacaccaa acacagagcg tgtcttattt gtggcaacaa 300
ggtaactttg tttccacaat agctagggca acaggagata tattgcagac gcaggaaata 360
taaagctaat aaaatggaat tttcatgctc tgtgtcccat ttgccccatt ttccctgctc 420
ttggaaaaat atgggcttct aaagaattta cagaatgttt ttcaaatgac attttattta 480
gaatatgtgt gctgtctggt tatcttctag cacaatgctt ggcacttagg tgcatgct 538

<210> SEQ ID NO 106
<211> LENGTH: 568
<212> TYPE: DNA
<213> ORGANISM: Homo sapiens
<220> FEATURE:
<221> NAME/KEY: misc_feature
<223> OTHER INFORMATION: Incyte ID No: 1332171CT1

<400> SEQUENCE: 106
gcccagcctg agtagttctg aagagcgtgt aggagtcttc caggtcgact gaatcaggca 60

```
gagggcctgg caagggtgac agagagaaag gtctagagga tttgggggaa gaggctgagt    120

gtgactcagg gcaaggtgcc tttcacctag aagtttctcc aggcagacct gccccagata    180

tctccatctg tgccatatgt ggctatactg gaggggggagg ggagttgaat gtgagaccca    240

gagctcagct gtttcctgtt tccagcctct tctagcacgg gtctgggccc caattcagct    300

aacatttatt gaacagatat gccctgcctc tcctgctcac actctatggc tggcattcac    360

ctgtggggcc aggtcgaaac tcctggcttg gccgtcaatg ccttactgga gctgctctgc    420

taacctcctg ctgcttcctc tcggacctcg attcagccat catgaattta ccagcataga    480

gcttgtgatt tcagcactcc aagcttttgc acatgctggt ccctgcccag aaagggctcc    540

tttaagccat gtccaagtcc ttttttct                                       568
```

<210> SEQ ID NO 107
<211> LENGTH: 1307
<212> TYPE: DNA
<213> ORGANISM: Homo sapiens
<220> FEATURE:
<221> NAME/KEY: misc_feature
<223> OTHER INFORMATION: Incyte ID No: 1332391CT1

<400> SEQUENCE: 107

```
gctcaaagta gatcagggag tcctgtaggc ctctgtaatg tagatgtctt atttatctgt     60

ggagatgttt ttaaccttca ctaactggag ttattctgaa cactagccag agaccttagg    120

gaaactgttt tagagcagag ttacacacag agccgggtgg ccctcacggc ctaaggcacg    180

atgacctttg tagacttatc aaatggagaa tatgatacat gagtcttagc ttcagcatct    240

ccccagccaa agacctttga gcccaaagaa accagacata ccagtgggtg aaacaaggcc    300

gtcttaagat cgtttaaata agagcagtca gcctgggcag aagcccagtc ttcacatttc    360

tcatcttaac caacgctccc aatgcctatg gtctgaatag gctttacagt gtatgaaggt    420

cttttcaagc acattctctg gattttaata gcttccagga ggtggtttgg ttgttgccac    480

tgcgtaggaa gcctgcttag agtctcacag ctgatggaag cctccatcac ctcccagaaa    540

gtcagttgta ggcctggtgc agaggccagc agcagcaaga tagtcacatt ctagcagagt    600

gtctccatcc actggctgct aagccacgga attcactcac cagcatgctg gccagatatt    660

gtgaagcgct cctgatttct tttcagaaac tcacgggatc aacttgatag caggatggaa    720

ttttggactc ttaggaggtc tcccagtgta gcccatctca ctagtcacat tgctttgaga    780

gtctgtaact aacccacccc cacggaaata agagcctgtc gcatcatttc aggtgcctga    840

tctgtgtaga cagtggaatg ggatggctct tgtcttgcaa agtttgctct ctacataggt    900

gtttaagtgg gccctcaagc acgttaaatc ttccaagttt gcccaggccc atctctatca    960

ctaagtcttc ctggtcctct ttcattcgag ttgaggccgt cttcacctct gggctagtct   1020

aagagggtgg ggtgcttgcc ttgtggcgtt ctctggctgg tggtgcagga agtgaacctt   1080

cagagtttgg atgaactctg tcttatttga aaaggaccag cctggccaac atggtgaaac   1140

cccgtctcta ctgaaaaatg cagaacaatc ggctgggcac ggtggcggat gcctgtggtc   1200

ccagctattc aggaggctga agcaggagaa tcacttgaac ctgggagatg gaggttgcag   1260

cgagccgaga tcgcgccatt gcattccagc ctggatgaca agaaggt                  1307
```

<210> SEQ ID NO 108
<211> LENGTH: 500
<212> TYPE: DNA
<213> ORGANISM: Homo sapiens

```
<220> FEATURE:
<221> NAME/KEY: misc_feature
<223> OTHER INFORMATION: Incyte ID No: 1332480CT1
<221> NAME/KEY: unsure
<222> LOCATION: 482
<223> OTHER INFORMATION: a, t, c, g, or other

<400> SEQUENCE: 108

ggaaggtctc ccaggaccca aacccggcat aacctgcctt ttccaccctg agtctgcccc     60

agcctactgg ggtctcacag tgccaagacc aggggtccta cttggggaga attctcccct    120

ctgctaatgt ctggttgtat tggctgtcac aactgcaggg gatcgggga gaagagtctt    180

attggcgtgg agagggtgga ggccagggac gctgttcagc accctgcagt gtccaggacg    240

gcccccacaa tcaggaattg tttatcctga atgtcaacag taccaagggg gctgagcatg    300

gtggctcatt cctgtaatcc caggactttg ggaggccatg gctggaggat cacttgagac    360

caggagtttg agacaagcct gggcaacact gtgagacccc catctctaca aaaaaaaaaa    420

aaagaaaaaa agaaaaactg gccgggcacg gtgactcaca cccagcccag cactttgggg    480

gngcaaggca agcggatcca                                                500


<210> SEQ ID NO 109
<211> LENGTH: 481
<212> TYPE: DNA
<213> ORGANISM: Homo sapiens
<220> FEATURE:
<221> NAME/KEY: misc_feature
<223> OTHER INFORMATION: Incyte ID No: 1332803CT1

<400> SEQUENCE: 109

cctatttgct tttctcctaa caagagcata ggtgttttac tgtgtgatcc ctgggattta     60

tctcacctta gccatttccc tgtacccttt tttaaggggc tcataatttc gttattcagt    120

aatccttagc tgttttcttg cctgtagtct catctcaaac tagcctaacc tacttgtctt    180

tagacttctt ctttacatgt tgctcttttc tggttagtcc cttctgttga aaaactggat    240

gttcatatct gtgagtgcca ttgatgtact tagctgattt tggtaataaa aatcaagtat    300

tttagagttg atctagtctt ttccctaatc acataaagca acagttttct tctgaaatgg    360

gctgtatttt ggattacttg acttggttat ttcaattagt ttgcatttta gctaccaggc    420

atttttcttt gtaattatct tttttaaagc attccccctc aaacctaaaa aaaaaaaaaa    480

a                                                                    481


<210> SEQ ID NO 110
<211> LENGTH: 134
<212> TYPE: DNA
<213> ORGANISM: Homo sapiens
<220> FEATURE:
<221> NAME/KEY: misc_feature
<223> OTHER INFORMATION: Incyte ID No: 1332830CT1

<400> SEQUENCE: 110

ctggctagca gttgagccag atttaagccc aggcccttga attcctgaag cctgaagtct     60

ttctacaaca ctgctggtcc caaccctggc catgcagcag gataatctgg tgaattacca    120

aaaaaaaaaa aaaa                                                      134


<210> SEQ ID NO 111
<211> LENGTH: 563
<212> TYPE: DNA
<213> ORGANISM: Homo sapiens
<220> FEATURE:
```

<221> NAME/KEY: misc_feature
<223> OTHER INFORMATION: Incyte ID No: 1332955CT1
<221> NAME/KEY: unsure
<222> LOCATION: 488
<223> OTHER INFORMATION: a, t, c, g, or other

<400> SEQUENCE: 111

```
gctccctctg taggtttgca gggaggaaaa aagaatcact agccagatag gaattaaatg     60
caaacaaacc ctgaactgta aataattggg tcacatatga gctcatgatg tcttcatatt    120
agtatctgtc acagcaagtt ggacagtttc ttatgaaaat tggagtctcg gctgggcgca    180
gtggctcatg cctgtaatcc cagcactttg ggaggacaag gtgggtggat catgaggtca    240
ggagttcgag accagcctga ccaacatgga gaaaccccgt ctctgctaaa aatacaaaat    300
tagctgggca tggtggcgca tgcctgtaac cccagctact cgggaggctg agacaggaga    360
atcacttgaa cctgggaggc agaggttgcg gtgagccaag atcacaccat tgcactccag    420
cctaggcaaa aagagtgaaa ctccatctca aaaaaaaact aaaaaaaaaa aaagaaagaa    480
aatggcgnaa aaaaggggga gaaagatctc ttgaagaatg tggagggaga gaggagtggg    540
gggcatagta ggagactgga ggt                                            563
```

<210> SEQ ID NO 112
<211> LENGTH: 632
<212> TYPE: DNA
<213> ORGANISM: Homo sapiens
<220> FEATURE:
<221> NAME/KEY: misc_feature
<223> OTHER INFORMATION: Incyte ID No: 1332966CB1

<400> SEQUENCE: 112

```
caagtactcc atagccacac gtggctagtg gctagcccat ctctgcttgc tggttagggc     60
cttgcgaggc tgaaatgttg gctcttattt tctcatttgc ctcagaatcc aaagctgggc    120
tttaggctgt cagctgttaa ggcatctaga gaaaggtgtg ctggagtgca gcgtggttgg    180
gcaccagtaa ccaaatctgg ccgttgctga gaaccaggct tgtggggtgt ctcctggaaa    240
gggaggtggg gtgtgtggct gataaggatc ttatctttag agattctctt aggcatcctg    300
tgttggatga gtgcttccca gatctttaaa caaaataaaa caaaacaccc acacaaacat    360
tttacaaaga aaaagaacaa atccatactt agaagtagaa tgtccactag gtcaaagtaa    420
gaacaagaga tgtgccaggc cccaggactc atggaaatta gatcatgtgg tcagagttga    480
tatcaaatag ggggaacata gcaaaagatc ttcttcttat cccacaggac tctagttagg    540
caaattctta tgttttaaag ccagctagga aatgcgtaaa taggggtgaa tgcccatggc    600
aagaaacagg aatcaggaaa aaaaaaaaaa aa                                  632
```

<210> SEQ ID NO 113
<211> LENGTH: 977
<212> TYPE: DNA
<213> ORGANISM: Homo sapiens
<220> FEATURE:
<221> NAME/KEY: misc_feature
<223> OTHER INFORMATION: Incyte ID No: 1332981CB1 Contig6
<221> NAME/KEY: unsure
<222> LOCATION: 972
<223> OTHER INFORMATION: a, t, c, g, or other

<400> SEQUENCE: 113

```
gcaagaaaaa aatcctggat catttaacat tcaatggata tttattgagg agcacttctt     60
aaacaccaga tactgtgctg ggtactagag cttcagtctt ttgatcatat tgcatcaaat    120
```

-continued

```
gttattaatg gaacattaac atttgattct atttcatgtt aagctctttt agccccaaac    180

gttatacagc ttggtccata aaccttcagt tggttcagcc tgttcactta tgtttgtgtt    240

cagttgttga atgtttatgt gtaacaggca acatatgttg ggtgctcaga cagttttgaa    300

gatgaacaag aattggagag agttctccaa ttctctagct ggttgactgg aatttaccag    360

gtagatctgg cagctgtcta gtttgctggg attcctccca gaggagagta tagtcagcag    420

caatgtatcc cctttcctta ttctgtttgg attgggccct tccctttgcc ctttacacct    480

tctccctaat ccctgtcttt aaatttgaga caaatgaaaa ttagctcctt tgtattaagt    540

ttgggcagct ccatcaggac agcacttccc tgatgatgcc ctaaagttag aaacccttcc    600

aggagaatct ctgttgccat gtaatcccag cactttggga ggccaaggca ggaggattgc    660

ttgaggccag gacttcaata ccagcctagg caacaaagtg agaccccaat ctctttattt    720

tttgtttttc gacatagagt ctcactcttg tcatccaggc tggagtgcag tgccgtgatc    780

tcagctcatt gcactccgcc tcccgggttc aagcaattct gcttcagcct cccaagtagc    840

tgggatgaca ggcatgtgtc accatgcccg gctaattttt tttttttttt cttgtatttt    900

tagtagagac aaggtttcac catgttggcc agctggtctt gaactcctga gtgcaggcct    960

gtgccgaatc tnccttc                                                   977
```

<210> SEQ ID NO 114
<211> LENGTH: 482
<212> TYPE: DNA
<213> ORGANISM: Homo sapiens
<220> FEATURE:
<221> NAME/KEY: misc_feature
<223> OTHER INFORMATION: Incyte ID No: 1333006CT1

<400> SEQUENCE: 114

```
caggaaagaa gtggcagact gtcatctgag cccggcctgt cctgctgtct gctctctcca     60

gagagcatcc ttcatcctga taaacaggct gcgagctgga catgtgactg agctccttaa    120

gacatgagtc ttcagtctcc tgccctcagc ttagctggaa gctggatgac agccacatta    180

agaggctttc tgcaagtggc ttttggatga aaagggggcc tctcaggtac tccactctca    240

cgttgcaggc tctgcagcag ctggtctatc tggtggcact gggagtaagt agtatgggag    300

acccctccat gccggggtcc cctggagtgt cctcctcata gcgtgagggt tcttctcagg    360

gatactgagg ataattcaca atggctttgt agttgcaata ttcttttttt atttcttaag    420

tttctgtgtc ccaaatttta gtacaaataa acatttatat acatggcaaa aaaaaaaaaa    480

aa                                                                   482
```

<210> SEQ ID NO 115
<211> LENGTH: 417
<212> TYPE: DNA
<213> ORGANISM: Homo sapiens
<220> FEATURE:
<221> NAME/KEY: misc_feature
<223> OTHER INFORMATION: Incyte ID No: 1333107CT1

<400> SEQUENCE: 115

```
gtgccactga agtcatctgt gtagtacata aaaaattgaa agtgctccaa ggtcctctga     60

gacaggagaa ttagattttt attctgtaag cttataaatt ttcgttgatt ccaactggtt    120

atctgaggca catgcaagtg ggggggggtt tctgcaaatg aacactaaat tttaattttc    180

ctcttttccc tcgatttagc ttgggacatc tgggtctggc ttttcttatt gtagttaagc    240

tgaatatatg gtgttgagtg tttctgtagt atataacaga gtctttcctt caactgaatc    300
```

```
tgaaaccctt ccaaagtcag aaggagaaaa aaaaactaac cctgaaagaa atcacttgtt    360

tgactgtaat aatctgcaga aactggttaa agcattaaac aaaaaaaaaa aaaaagg       417


<210> SEQ ID NO 116
<211> LENGTH: 603
<212> TYPE: DNA
<213> ORGANISM: Homo sapiens
<220> FEATURE:
<221> NAME/KEY: misc_feature
<223> OTHER INFORMATION: Incyte ID No: 1333116CT1

<400> SEQUENCE: 116

gtgcgggccg ggcgttggcg ttggattgag ttctgtgagt tgactgggca ttctgcatca     60

caaggtgtgg ctgggcactg gaacagccga agtcacctgg gagctgactg ggttggactg    120

tccaggatgg ttcactccta cgacagtgga tgctcaactg ggctgtcaa ctggagcccc     180

catagtgcct ttgtgaacat gggggtcccc aagttttcag cgggtgaagc cagcaggcaa    240

cagctcacac tggcattttg tcagtcgggc accttcatct tggcatttgg gcttccatcc    300

aggctgcctc agctcttttg aatgaacatg gcctgcaaat agttcatcca cagagctggc    360

ttggcaggcg aaggcttctc agcccaagca gggggctcga tctgcctgct ctcctttctg    420

tggcctcgga tccagccctc acttcttacc tccaccagat ttggagtttt cagagctaac    480

tgaggcttcg ggaaaagttc tgtgtttgga caaagctttg caataaggca gatctgggtt    540

tgaatcatca atttatttaa tcctgaaaac ctcaatttta tctgtaaaat aaagatgatg    600

att                                                                  603


<210> SEQ ID NO 117
<211> LENGTH: 409
<212> TYPE: DNA
<213> ORGANISM: Homo sapiens
<220> FEATURE:
<221> NAME/KEY: misc_feature
<223> OTHER INFORMATION: Incyte ID No: 1333133CT1

<400> SEQUENCE: 117

ggaaagtcaa agaatgaaca aatagacact tcttatctag tgagcaaagc ttgagctctc     60

cctccatttc ttggagatct gaggcatgtt ttacataact agtgtgaaaa tctttctggg    120

ctggcatagg agttacacag ttaattagat cataccctaa atatttaatg acaacaatat    180

gttctaacaa tattgtagaa atatttaatt ggagagaggt atatcagggg atctaaaacc    240

gattgcagaa aagatatagt tatctgagac ttgccaacac agcaaggcat ttctcctggg    300

cagttcctat ggttttagat attgaatatt gcttgtattc ttacacttgg tttaagaaac    360

tactaatgat ctcatcatgg taaacaccca aaggagaaga aaaaaaagg                409


<210> SEQ ID NO 118
<211> LENGTH: 455
<212> TYPE: DNA
<213> ORGANISM: Homo sapiens
<220> FEATURE:
<221> NAME/KEY: misc_feature
<223> OTHER INFORMATION: Incyte ID No: 1352448CT1

<400> SEQUENCE: 118

tttcataacg actgccccct cttcggctct tttgtccaag gttacggcat tttcctcttc     60

tgccgcctac tttctggggt tgggattgga gggtccatcc ccattgtctt ctcctatttc    120

tccgagtttc tggcccagga gaaacgaggg gagcatttga gctggctctg catgttttgg    180
```

-continued atgattggtg gcgtgtacgc agctgctatg gcctgggcca tcatccccca ctatgggtgg 240
agttttcaga tgggttctgc ctaccagttc cacagctgga gggtcttcgt cctcgtctgc 300
gcctttcctt ctgtgtttgc cattggggct ctgaccacgc agcctgagag cccccgtttc 360
ttcctagaga atggaaagca tgatgaggcc tggatggtgc tgaagcaggt ccatgatacc 420
aacatgcgag ccaaaggaca tcctgagcga gtgtt 455

<210> SEQ ID NO 119
<211> LENGTH: 471
<212> TYPE: DNA
<213> ORGANISM: Homo sapiens
<220> FEATURE:
<221> NAME/KEY: misc_feature
<223> OTHER INFORMATION: Incyte ID No: 1385827CT1

<400> SEQUENCE: 119
caaatattta acagaactaa tggaactatt ttagtatgct ttcccctggg ctggagtgta 60
ggctaagact ttatttaaat acaggatgga tggtgttttg actgaagatg cctccaactt 120
ttgctcttct gtttttatt tgatgtgctc aagcttctaa ttccctttt tgttgttgtt 180 gttgtggatt tttggttttt gagactccgg cctgggtgat ggagcaagac ctcgtctcag 240
aaaattggaa actattgact aagagaagtt tctaggtttg cactgaattg tcttttgtac 300
atacagtgaa ttgttttgct gttctcccca ctccatatta atgcaggagc caggttggtc 360
tgttaggatg aacaaaggtt gaggggaggg caggattcgt gcatctgggg gccaaacaca 420
tgttccgtct tgattgcctt aagagttact agcgaggtca gtgttaggct t 471

<210> SEQ ID NO 120
<211> LENGTH: 242
<212> TYPE: DNA
<213> ORGANISM: Homo sapiens
<220> FEATURE:
<221> NAME/KEY: misc_feature
<223> OTHER INFORMATION: Incyte ID No: 1385922CT1

<400> SEQUENCE: 120
tggtcatgtg agttaaattc gaatcctcta cttgtatgac cctaggaata gattggaata 60
ctgcagagga ccaaagctga ggcatgctaa acagctgctt ggaggtggaa gcaagttcag 120
tcacctactc agcttcctct ctccaccacc cagttcctcc ctcagtatca cattattttt 180
ttcttctgct tttcattaac ctaactcatc tcatcagtac aaccattttc ttattctcta 240
ag 242

<210> SEQ ID NO 121
<211> LENGTH: 234
<212> TYPE: DNA
<213> ORGANISM: Homo sapiens
<220> FEATURE:
<221> NAME/KEY: misc_feature
<223> OTHER INFORMATION: Incyte ID No: 1386485CT1

<400> SEQUENCE: 121
cataaaccta ctttatcatc ctctcctaaa gaagagaaga tttagctaga ataattatta 60
acagaagatg tggagataca gaagaaacta gaaaatatct cacaatcaat acatctttca 120
agcagtcaat catttgtcac tcatattgct tttttaaacc cagctttaca tggaaggaat 180
aaatggaact ccagtttggt ttttcttctt tttttttttt tctgttaagg caga 234

-continued

<210> SEQ ID NO 122
<211> LENGTH: 486
<212> TYPE: DNA
<213> ORGANISM: Homo sapiens
<220> FEATURE:
<221> NAME/KEY: misc_feature
<223> OTHER INFORMATION: Incyte ID No: 1386553CT1

<400> SEQUENCE: 122

```
gtattatatg gttaagtcag cctatcaata gggctttgag aaattgaaaa atagccccag     60

ttaaataaca acattaagcc agtctcagtc tcccaaagtg ttgggattac aggtgtgaac    120

cactgcacct ggcccaaaat ctcttgattg atacagtcct ctttattttt caagatcaag    180

ttatgatacc tttaccaaca gtcatacatt cttttggaac tttgcacaat agtcatatgt    240

tcttttagaa ctttacactt ctattcttta ttgccctgta ttataattgc ttgtatgcct    300

gactcctcta catgactgta tggtttgaac caaagtgtac gggatgtcgc acagtgtcta    360

gtagtgtcac acaacaagta ataggtattc agtaagtgag ttaagatgaa atagtaacat    420

gaaagagtgc tttgaaagca gtttttttaaa gagtttctgt tctgctaatt gtaagccatt    480

tttaaa                                                               486
```

<210> SEQ ID NO 123
<211> LENGTH: 250
<212> TYPE: DNA
<213> ORGANISM: Homo sapiens
<220> FEATURE:
<221> NAME/KEY: misc_feature
<223> OTHER INFORMATION: Incyte ID No: 1386660CT1

<400> SEQUENCE: 123

```
gtctgtgtac catcttacct ggaatagaga ttgtgttaaa ttaacagatc atctgactga     60

gaggtttttt tcccccaaaa cagaagcaaa taaacattat tttgttcctt tggtataact    120

ttcattgaac agttatatag tgctttggaa gtatcaagtc ctgtgctaaa taaatgctgg    180

agatacaaaa gcccctgacc tcagaatgtc atagtcttgg ggtaagaaaa aattcattct    240

gtgcccgagg                                                           250
```

<210> SEQ ID NO 124
<211> LENGTH: 270
<212> TYPE: DNA
<213> ORGANISM: Homo sapiens
<220> FEATURE:
<221> NAME/KEY: misc_feature
<223> OTHER INFORMATION: Incyte ID No: 1386859CT1

<400> SEQUENCE: 124

```
ggaaactcca ggctcctggt ttttccctgg gcggggaaag agaagactga aacatctgtg     60

tgacattcag atttttcaga ggtctgccca agggtctggt ttttattttg cttgaatata    120

agttctgaca ggaaagggca ccaggttgcg gggtcattga aaacaaagtt gacagtttag    180

attagcaggc actcaccatg gtccctcccc ctccctcagc atgaaaccag caggagaaaa    240

tcttcagctc tgggcttccc ctggggaaga                                     270
```

<210> SEQ ID NO 125
<211> LENGTH: 238
<212> TYPE: DNA
<213> ORGANISM: Homo sapiens
<220> FEATURE:
<221> NAME/KEY: misc_feature
<223> OTHER INFORMATION: Incyte ID No: 1387302CT1

<400> SEQUENCE: 125
agcgatcaaa tcggaaaggt aaagatgaaa tgcttttcct gtttcttgat ttttatctac 60
cagcaataat atgaggcaca ctcgtaaagt aaaggtttgc attatattta caattaaact 120
ctagaaaagc ataattctga gctaaatatt ctgcctaaag aatctctttc acataatcct 180
tcctggtcac ttgctccttg cactcacaat ttgtttctta attcctatgc tttttatc 238

<210> SEQ ID NO 126
<211> LENGTH: 457
<212> TYPE: DNA
<213> ORGANISM: Homo sapiens
<220> FEATURE:
<221> NAME/KEY: misc_feature
<223> OTHER INFORMATION: Incyte ID No: 1388063CT1

<400> SEQUENCE: 126
cacaagttaa aacttcccat gtataaaaac acttacattt taaaacatca ctgccaactg 60
tgtgctcatg tgggagtaca gatgtgtata tacagacatg tacattttta aagacttggt 120
tgtctctgca gtgaagacaa tatgttttat tttttattcc atatacttct ctgtattttc 180
tatatttgct tcaataagct ggtgtaactt ttaatttttt taattaaaaa aaatttagcg 240
taaaattaca cttaaacatt agcagctgct gctgggaaaa catggacaaa ttgcccaggc 300
agccacatta gaagaagaca gtcatttgaa tacagttata tacttatttt tattgagaca 360
catcttgctg tttcacccag ggttttgctc tgttgccaca gcttaactgc gccgtgaacc 420
gggctcaagt gatccctccc aactcaggcc cccttcc 457

<210> SEQ ID NO 127
<211> LENGTH: 694
<212> TYPE: DNA
<213> ORGANISM: Homo sapiens
<220> FEATURE:
<221> NAME/KEY: misc_feature
<223> OTHER INFORMATION: Incyte ID No: 1422814CT1

<400> SEQUENCE: 127
tttccctaat atttaaatta ttccttataa accagtagaa aagctttaac aacataacag 60
aaaaatggga aaagactatg aatagacggg acccagaaaa gcacatacaa ataagtggct 120
attttactac acctttactt tggaaaactt caaacctgta ctaaaataga atagggcagt 180
gaacctccct gcctgcaccc atcactcagc gtcaacattg atcaactcat gggcaatctt 240
gttttatcta ttaccactcc cccctgcccc ccgctccctg acagctccct cagaaatacc 300
atttccacct accagattga caaagattta aaaaattgac agactttgtt aaagaaaaag 360
ttaaaaaaac aggaagtctc atacattgct agaaggaatg taaattaatt acaatcccta 420
tagagagcaa tttgttctta cccatcaaaa ctctaaacac ttctatccag aaattctgct 480
tcaatgattt tattatgcag ctgtacttgc acgtgtgcaa acagcacatc cacagttatt 540
aattataata gccaattatt ggaaatacct aaaatgtgaa aactttgcag ctctgaacaa 600
aaataaggaa actatattga tatggagtgt tctccaaggt gtattggggt gaaatgcaag 660
gtgcagaaca gtgcaagcaa tgtaagtccg caga 694

<210> SEQ ID NO 128
<211> LENGTH: 80
<212> TYPE: DNA
<213> ORGANISM: Homo sapiens
<220> FEATURE:
<221> NAME/KEY: misc_feature
<223> OTHER INFORMATION: Incyte ID No: 1423820H1

<400> SEQUENCE: 128

```
atgacattgg ttgcctcagc cctgaaaagc tatgtctctg cattcttagt tttctttgtt     60

tttctttttt ctttttcttt                                                 80
```

<210> SEQ ID NO 129
<211> LENGTH: 521
<212> TYPE: DNA
<213> ORGANISM: Homo sapiens
<220> FEATURE:
<221> NAME/KEY: misc_feature
<223> OTHER INFORMATION: Incyte ID No: 1429651CB1

<400> SEQUENCE: 129

```
gagaacttta cgcctggatc tcatctaact gacacagaaa ccctgtaagg atccagaggt     60

ctcgttcagg accatggaga gcggcaccag cagccctcag cctccacagt tagatcccct    120

ggatgcgttt ccccagaagg gcttggagcc tggggacatc gcggtgctag ttctgtactt    180

cctctttgtc ctggctgttg gactatggtc cacagtgaag accaaaagag acacagtgaa    240

aggctacttc ctggctggag gggacatggt gtggtggcca gtgggtgcat ccttgtttgc    300

cagcaatgtt ggaagtggac atttcattgg cctggcaggg tcaggtgctg ctacgggcat    360

ttctgtatca gcttatgaac ttaatggctt gttttctgtg ctgatgttgg cctggatctt    420

cctacccatc tacattgctg gtcaggtcac cacgatgcca gaatacctac ggaagcgctt    480

cggtggcatc agaatcccca tcatcctggc tgtactctac t                        521
```

<210> SEQ ID NO 130
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 1436525CT1
<221> NAME/KEY: unsure
<222> LOCATION: 462, 477, 493, 496, 499, 520, 528
<223> OTHER INFORMATION: a, t, c, g, or other

<400> SEQUENCE: 130

```
cttctagcta aagcttcgga tcattttggc aaattccaaa aaatgtcttg ttggacagct     60

tttggttgtg attgcattgg atttataatt taatctagag gactaatgac aaaacaactt    120

tcagccattg tggctaacat tttatcatgt cctggaacgt cttggacata gtctaatgct    180

ccacctcatg tacgcccatc tgaatgacac aatgcccagg ctttggctta ctttggctcc    240

ctttgtgcag gtgacatctg agtgcatagc acctacaact tgccagccct gaaacagctg    300

tcataagaat ctcacttgta ctcacaacag ttcttcagct tagatcattg tcctgtgtta    360

cctaatcagg ctcagaaaga tgaattagtg accacaaagt taaagaacta gtacatggtg    420

gctgagattt aagccagatc ctttgtgact ccaaaagctt antttcccct ttcaatncac    480

ttggtgttat ttnccnaanc cccctttggt aattaaaaan cccttctnac ctgggataca    540

ggttactt                                                             548
```

<210> SEQ ID NO 131
<211> LENGTH: 567
<212> TYPE: DNA
<213> ORGANISM: Homo sapiens
<220> FEATURE:
<221> NAME/KEY: misc_feature
<223> OTHER INFORMATION: Incyte ID No: 1453124CT1

<400> SEQUENCE: 131

```
tgactctggg gaacattcta cccgtttcca aaaatggaaa tgctcaggtc aatggacctg     60
tgatatccac ggttattcaa aactattcca taaatgaagt tttcctattt ttttccaaga    120
tagagtcaaa cctgagccag cctcattgtg tgttttggga tttcagtcat ttgcagtgga    180
acgatgcagg ctgccaccta gtgaatgaaa ctcaagacat cgtgacgtgc caatgtactc    240
acttgacctc cttctccata ttgatgtcac cttttgtccc ctctacaatc ttccccgttg    300
taaaatggat cacctatgtg ggactgggta tctccattgg aagtctcatt ttatgcctga    360
tcatcgaggc tttgttttgg aagcagatta aaaaaagcca aacctctcac acacgtcgta    420
tttgcatggt gaacatagcc ctgtccctct tgattgctga tgtctggttt attgttggtg    480
ccacagtgga caccacggtg aacccttctg gagtctgcac agctgctgtg ttctttacac    540
acttcttcta cctctctttg ttcttcg                                        567
```

<210> SEQ ID NO 132
<211> LENGTH: 566
<212> TYPE: DNA
<213> ORGANISM: Homo sapiens
<220> FEATURE:
<221> NAME/KEY: misc_feature
<223> OTHER INFORMATION: Incyte ID No: 1460891CT1

<400> SEQUENCE: 132

```
aaaagacaat ctttacatat taggtaactt tatgcaatta aaatgcttct cttcacaaaa     60
attaaaatgc ctttccatgt ttccgcacta catctgcaca ctgaagcaac cacatttgct    120
gttagaaaag tactcctact acctaatttc tggttaaacc aaggcctgat gttttctgct    180
tccatttgta gtgagggtac tttgtatcct ataagcgagg gactataggg gtttctttgt    240
tcaaattttt cccacatccc tgagaggctg acatgtgttg ctgtgaccac ttaattgatc    300
ccagcacttt gggaggccaa ggtggatgga tcacctgagg tcaggagttc gagaccagcc    360
tggcgaacat ggtgaaaccc tatctctact aatgatacaa aaatcagcct gttgtggtgg    420
caggctcttg tagtcccagc tacttgggag gctgaggcag gaaaattgct tgaacccagg    480
aggcaaaggt tgcaatgagc caatattgtg ccactacact ccagcctggg caacagagtg    540
agactccatc tcaaaaaaaa aaaaaa                                         566
```

<210> SEQ ID NO 133
<211> LENGTH: 632
<212> TYPE: DNA
<213> ORGANISM: Homo sapiens
<220> FEATURE:
<221> NAME/KEY: misc_feature
<223> OTHER INFORMATION: Incyte ID No: 1465590CT1
<221> NAME/KEY: unsure
<222> LOCATION: 559
<223> OTHER INFORMATION: a, t, c, g, or other

<400> SEQUENCE: 133

```
cccacgcgtc cgtattacta atatgtatac tagtgttatc ctacaatacg tttctatttt     60
tttttttagc ttcaataata tagaaaaatt gtatgtgttg gtgttcttaa ctggatactc    120
ttttaaggtc acttgtttcc attttacttt tgatttttag agtttgcgtt tttaaaatga    180
gttttataat tggtatgtat tatttatatt tgtatgtttc ataattaact ctttttaaaa    240
aaatagaggt ttagtcattc tttcagaaaa tgttgagatt agcaaatcat gctcaaagat    300
aggaattaaa ggttgtaaaa caaaaaaaag aaaagaaagc gcagaagaag aggaaaggaa    360
```

```
cggtagacag aagaagagaa cagtagattg cgagagaagg gagaggaagg cgagagtcac    420

cggaagagaa agaacagagg ggcgccgcgc cctctggggg gtcccagggt gtttgtaggg    480

ggtcgcttat ggggggcat agggcctctc ccagagaggg ccccgccaga atttcagtgc    540

ccgggggcgg ggtcggttnt caaaagggcc gggaactgtg gaaaaccctc gggggtgtcc    600

ccacacttta aaggcccttg gggggggca ga                                   632
```

<210> SEQ ID NO 134
<211> LENGTH: 395
<212> TYPE: DNA
<213> ORGANISM: Homo sapiens
<220> FEATURE:
<221> NAME/KEY: misc_feature
<223> OTHER INFORMATION: Incyte ID No: 1466523CT1

<400> SEQUENCE: 134

```
gactggctca tggcctctgt aaatggctgc tggcgggact gtctgcctag cgggtgccct     60

tggaacctag cccttggtgg gttttgagga aatgattcct gaatgaggag tcgattgccg    120

tgtgaagggc tggtggcacg gcacccgcgt gagctacgcg tgccctcagt gcgcttctgg    180

attgactggc catgggtgct cacagacatg cacattgtgc caccacattg cagtaacccc    240

catgcttttg taggctgaag atgaggaggg gtacgcaagc tcatcgacca gaagaaggac    300

aagcgcctgg cctaccatct tgcagcagac agacgagtac gtggctaacc tcacggagct    360

ggtgcggcac acaaggctgc ccaggtcgcc aagga                               395
```

<210> SEQ ID NO 135
<211> LENGTH: 480
<212> TYPE: DNA
<213> ORGANISM: Homo sapiens
<220> FEATURE:
<221> NAME/KEY: misc_feature
<223> OTHER INFORMATION: Incyte ID No: 1466902CT1

<400> SEQUENCE: 135

```
caaggataca gccgttgtat ttaaggggtt gagggacaaa gtagtgaaga actgtaagat     60

attcaatata gtgtattgat gaattagaat tgtatggaaa gataaaccgc agaaggtgag    120

agtcctgtat aagtaaatcc ttacacatat aactttgctc ccaagtaaca tggaacacga    180

ggaattctgt gtgaatcagt gaggaccata tctcataagg ctaaatactc ttactaaccg    240

atagcgcata gtaccgtgag ggaaaggtga aaagaacccc tggaggggag tgaaatagaa    300

cctgaaattg tgtgcttaca agcggtcaga gcccattagg gtgatggcgt gccttttgga    360

gaatgatcct gcgagttacg ttaaacggcg aggttaagta taacggagcc gaagggaaac    420

caagtcttaa tagggcgata tagtcgtttg gcgtagacgc gaaacctggt gatctaaacc    480
```

<210> SEQ ID NO 136
<211> LENGTH: 502
<212> TYPE: DNA
<213> ORGANISM: Homo sapiens
<220> FEATURE:
<221> NAME/KEY: misc_feature
<223> OTHER INFORMATION: Incyte ID No: 1468040CT1

<400> SEQUENCE: 136

```
atcaccttac aacccatttc tcagaacatg tttctattgt taaacaacac acaactattt     60

tatttatgtg ttttatttat gcctgatcac caatatcaat aactgaaaca cagcagttta    120

gtaataattt aatacacacc ataacctgcc tattgagaat ggcattatat ttgttttcat    180
```

```
tgtagtggct ccatccaaaa taaaatgatt tttttccttc cttcaggatg aaggcaagca    240

tttattccta cggtctggat tcctcatatc acctacaagt taactgcttt tgtgttctaa    300

gagaggaaaa atgaagtcaa ccttattgaa aaacaaggag ggaaactaag gaacatgctt    360

ttgcttttga ggttctaggc cagaagtcat aagctgtaac ttgtccaagt tatggccaag    420

cagatatgtt ttgtttggcc cacatggagt atattttttc taattgaatc aacattttaa    480

aatatgatga tttaatattt at                                              502


<210> SEQ ID NO 137
<211> LENGTH: 978
<212> TYPE: DNA
<213> ORGANISM: Homo sapiens
<220> FEATURE:
<221> NAME/KEY: misc_feature
<223> OTHER INFORMATION: Incyte ID No: 1480833CB1

<400> SEQUENCE: 137

aaaaaattga aaaggcaaat gtgattgaat atctgaaaag ctttaaaagt ggcctttctg     60

ttacgtctgt ggcacaaatg gctcatgagc gcaggacact tatggtcttg tgtcctatac    120

ttcatgtgtg atgccaccag aaatgttatg gattccgtat tgaacacact gagagtggta    180

tgagccctca ggactgcacc acagagtaaa cacaaccttg atatggtggc gaatatgtgt    240

gtctttcttg tttcatttgt ggttggggac aaaatcgatg tatttgtcta aatagtcgat    300

attcatctta acatggttgg ttgtgtaatc accagctata ttgtgaactg tgcaataaaa    360

cagaagcgtt tgtgtatata attacctttg gatacctgaa attcccaagc ttggttacaa    420

tgtaatgctc agtataaggc tgtgcaaaca tgtaagggaa taatggtggt cgatgggata    480

tatgaaatgg gatctagagg gcttcgagtg aagccaatca tgttgaacga acactggttc    540

agtgtagatg aagtagagtg aggcgtatgc agtcataaaa tgaagggtgg acaggagatt    600

acatttgaag aaaggataag cactcagact tggtctcttt taaattaaaa tatttctttt    660

ctcatgtgca aatgtatatc aaagacttga acaggtattc tcttgaaatt tgaggatttt    720

tagtttttaa tgctgtcttt gcttaatatt aaatatgtgt tgcctattgg ctcccaaatt    780

gtgtgggagt ctctaaatgt ttcctcttga aggttcatta ttgaaagtgg ttaagtgcac    840

aatgctattt ttgtttgata gtttgagttt tatgacccta tgagtttaaa tgaaatctgt    900

taaatgtttc agagttaaca cttttttttt gataatttgg aataaagttt gttttttaag    960

cccaaaaaaa aaaaaaaa                                                  978


<210> SEQ ID NO 138
<211> LENGTH: 851
<212> TYPE: DNA
<213> ORGANISM: Homo sapiens
<220> FEATURE:
<221> NAME/KEY: misc_feature
<223> OTHER INFORMATION: Incyte ID No: 1516908CB1

<400> SEQUENCE: 138

gtggcatcca ccattaaggt taagtgtggt gtgccctgtg agtctgaatg tctacttaag     60

aaccttaagt agacattaag aaccttaaga aggtttttg tttgttttg ttttttttgtt    120

gttgagatgg agccttgctc cgttgcccag gctggagagc agtggcgcaa tctcagctca    180

ctgcaacctc tgcctcccag gttcaagcaa ttctcctgtc tcagcctccc gagtagctgg    240

gactgcaggc gcctgccccc aagcccggct aatttttgtg tttttagtag aaatggggtt    300
```

-continued

```
tcaccttgtt ggtcaggctt gtctcaaact cctgacctca ggtgatccac ccacctcggc    360
ctcccaaagt gctgggatta caggcatgag ccactgtgcc tggccaacca gtgtttttttg    420
ttgttgtttt gttttgtttt gttttggaga tggagtctct ctctgtcgcc aggttggagt    480
gcagtgacgc catctcagct cactgcaacc tccacctccc aggtgcaagc gattctcctg    540
catcagcttc ctgtgtagca cctgggatta ccggcgcgca ccaccatgcc caagtaattt    600
ttatattttt agtagagaca gggtttcacc atgttagcca ggatggtctc gatctcttga    660
ccttgtgatc cacccacctc agcctcccaa agtgctggga ttacaggagt gagtcactac    720
acctggctgg ccgccagtgt tatttttttt acctccatgt ggtccctccc tgggaggcct    780
cctttgagaa acataactga caagtccatt ttgtccagcc agggctcctt ttattcattc    840
aggggtgggt t                                                          851
```

<210> SEQ ID NO 139
<211> LENGTH: 1760
<212> TYPE: DNA
<213> ORGANISM: Homo sapiens
<220> FEATURE:
<221> NAME/KEY: misc_feature
<223> OTHER INFORMATION: Incyte ID No: 1518320CT1

<400> SEQUENCE: 139

```
cccagttcca aatgaggccc gggtgaactg ctcccacccc ttcggtgcct ttaggtacca     60
gtcagtctgc agcttcacct gcaatgaagg cttgctcctg gtgggagcaa gtgtgctaca    120
gtgcttggct actggaaact ggaattctgt tcctccagaa tgccaagcca ttccctgcac    180
acctttgcta agccctcaga atggaacaat gacctgtgtt caacctcttg gaagttccag    240
ttataaatcc acatgtcaat tcatctgtga cgagggatat tctttgtctg gaccagaaag    300
attggattgt actcgatcgg gacgctggac agactcccca ccaatgtgtg aagccatcaa    360
gtgcccagaa ctctttgccc cagagcaggg cagcctggat tgttctgaca ctcgtggaga    420
attcaatgtt ggctccacct gccatttctc ttgtgacaac ggctttaagc tggaggggcc    480
caataatgtg gaatgcacaa cttctggaag atggtcagct actccaccaa cctgcaaagg    540
catagcatca cttcctactc caggggtgca atgtccagcc ctcaccactc ctgggcaggg    600
aaccatgtac tgtaggcatc atccgggaac ctttggtttt aataccactt gttactttgg    660
ctgcaacgct ggattcacac tcataggaga cagcactctc agctgcagac cttcaggaca    720
atggacagca gtaactccag catgcagagc tgtgaaatgc tcagaactac atgttaataa    780
gccaatagcg atgaactgct ccaacctctg ggaaacttc agttatggat caatctgctc     840
tttccattgt ctagagggcc agttacttaa tggctctgca caaacagcat gccaagagaa    900
tggccactgg tcaactaccg tgccaacctg ccaagcagga ccattgacta tccaggaagc    960
cctgacttac tttggtggag cggtggcttc tacgataggt ctgataatgg gtgggacgct   1020
cctggctttg ctaagaaagc gtttcagaca aaaagatgat gggaaatgcc ccttgaatcc   1080
tcacagccac ctaggaacat atggagtttt tacaaacgct gcatttgacc cgagtcctta   1140
aggtttccat aaacacccat gaatcaaaga catggaatta ccttagatta gctctggacc   1200
agcctgttgg acccgctctg gaccaaccct gtttcctgag tttgggattg tggtacaatc   1260
tcaaattctc aacctaccac cccttcctgt cccacctctt ctcttcctgt aacacaagcc   1320
acagaagcca ggagcaaatg tttctgcagt agtctctgtg ctttgactca cctgttactt   1380
gaaataccag tgaaccaaag agactggagc atctgactca caagaagacc agactgtgga   1440
```

-continued

```
gaaataaaaa tacctcttta ttttttgatt gaaggaaggt tttctccact ttgttggaaa   1500

gcaggtggca tctctaattg gaagaaattc ctgtagcatc ttctggagtc tccagtggtt   1560

gctgttgatg aggcctcttg gacctctgct ctgaggcttc cagagagtcc tctggatggc   1620

accagaggct gcagaaggcc aagaatcaag ctagaaggcc acatgtcacc gtggaccttc   1680

ctgccaccag tcactgtccc tcaaatgacc caaagaccaa tattcaaatg cgtaattaaa   1740

agaattttcc ccaaaaaaaa                                               1760
```

<210> SEQ ID NO 140
<211> LENGTH: 600
<212> TYPE: DNA
<213> ORGANISM: Homo sapiens
<220> FEATURE:
<221> NAME/KEY: misc_feature
<223> OTHER INFORMATION: Incyte ID No: 1529624CT1

<400> SEQUENCE: 140

```
ctagttctag atcgcgagct gccgcccttt tttttttttt ttggttgttt gcttgtttga     60

agtttaaata ataattgatt tctgtttaca aaaataaaac tggaaaaaat taaataatta    120

ccattgatct gaagcacccg gcaaagccca acgcccgatt ctgagattct ggactcaaaa    180

gagttgtgag ttgggggctg ccggctggcc gcgggaggac gaagtattgg atcaccgcca    240

gtgccttctc agcaggctac tatcgctgtt catgcgactc cgggccgggc tccggtggac    300

tcccagatcc gtaaccctct cccccccttt ttttctcccc ccccccgacg gggcccattt    360

cccccccgc gggccccgag cggaccctct tgcctggcct gcgttgcccc gctgtgcgcc    420

catgccctct ccgcctgtca ctcacgtcgc cgctcccgcg aggccggctc ctatcttctc    480

gtcatccctg ccccccggc gctctcggtg gccctgctct ctcccccccc tctctcctgg    540

cggcctgccc cgaacgccag ctcgcgtcgt tccgctcccg tcgggtccgc cgcttgggcc    600
```

<210> SEQ ID NO 141
<211> LENGTH: 203
<212> TYPE: DNA
<213> ORGANISM: Homo sapiens
<220> FEATURE:
<221> NAME/KEY: misc_feature
<223> OTHER INFORMATION: Incyte ID No: 1590311CT1

<400> SEQUENCE: 141

```
ggcccttgga accaggtggc tgatctccct ggtaacagtt gctaggacaa ctaggactct     60

catcagggag cccaagatgg agggggctgg ccgaagtcca aagtcggggt gaagtatcag    120

actgagcccc aacccagaca aacttctcac cttctcctcc cctactcggg cagggcggac    180

cccggaggcc tgagcggcac ctg                                            203
```

<210> SEQ ID NO 142
<211> LENGTH: 219
<212> TYPE: DNA
<213> ORGANISM: Homo sapiens
<220> FEATURE:
<221> NAME/KEY: misc_feature
<223> OTHER INFORMATION: Incyte ID No: 1590335CT1

<400> SEQUENCE: 142

```
cttccagact ggagccaagg tgacctttct gctagagttt gagtttagct gctcctctct     60

cctggagcca ggtcttcgtg aagctgactg ccagcagtga cagcctggag agaaatggga    120

cccttcaaga taacacagcc cagacctcag cctacatcca atatgagccc cacctcctgt    180
```

-continued

```
tctctagtga gtctaccctg caccgctatg aggttcacc                          219


<210> SEQ ID NO 143
<211> LENGTH: 209
<212> TYPE: DNA
<213> ORGANISM: Homo sapiens
<220> FEATURE:
<221> NAME/KEY: misc_feature
<223> OTHER INFORMATION: Incyte ID No: 1590422CT1

<400> SEQUENCE: 143

tgcgtgggga tccagcagag agcctcggtg gggtggggtg gccctgggca ggcggcaagg     60

actccaggcc cagccttgtc tccccctgca ggtgacctgg tggctgaggc gcccagtgcc    120

aaacccccgc cagacagcct gatgtgcagt gggtgagccc ccatccctta cctctgtatt    180

ttaggggaga gaaactgtgg ccttggaag                                      209


<210> SEQ ID NO 144
<211> LENGTH: 148
<212> TYPE: DNA
<213> ORGANISM: Homo sapiens
<220> FEATURE:
<221> NAME/KEY: misc_feature
<223> OTHER INFORMATION: Incyte ID No: 1590455CT1

<400> SEQUENCE: 144

ttcactcttc aaatgtttgc ttcctgttcc tgctaccctg aaccctgctg ttgaggggtt     60

ctagtgtcta caagggaacc gctgccacca cgaggaataa cacagtgctc ttacagcctg    120

ttccaagtgt ggcttaatcc gtctccac                                       148


<210> SEQ ID NO 145
<211> LENGTH: 723
<212> TYPE: DNA
<213> ORGANISM: Homo sapiens
<220> FEATURE:
<221> NAME/KEY: misc_feature
<223> OTHER INFORMATION: Incyte ID No: 1590464CT1

<400> SEQUENCE: 145

catgtcctaa atgaacacag ctctgttgct gaccgtccta gccactctgc tttccttccc     60

tctcccgtgc ttggtcagcc cttttcccac ttggtgttca agttctgacc cagggctgag    120

cacccaaggg ctctcaaggt ggggcatcac ctacagtcac catggaacac agtggaatgg    180

tgcctaaagc cctggtgtgg aggatgtacg gcagcttgat aggaccagag gcagccagtt    240

tgtctgggag gtctttgcca ccacttttcc ctgtcccgct agccccccttg gtgcatggga    300

ctctctgcaa agcccctgga gaggagccat cccaacatgc taggcccttg acttctatcc    360

tccagtgtcc agctaactta gctgagggat gggctgcccc agcccctgag tccctggaac    420

cctaagccac ttgccccctt gcatggcgct gctcagatgc ccagagccag cagtctgctg    480

tgatcccttt gacgtgagca taggctctcc tgtctggtga tgcaccaggc tgatgctgag    540

tctctgtgca acctcagatg agcagctggg gtttggaggc atgtagcaat gcagttgccg    600

agtgcagtgg ctcgatctca gctcactgca ccctctgctg cctgagttca agcgattttt    660

gtttctcagc ctcctgagta gctgggatta caggcatgca ccaccgacat gcaaaaaaaa    720

cag                                                                  723


<210> SEQ ID NO 146
<211> LENGTH: 200
<212> TYPE: DNA
```

<213> ORGANISM: Homo sapiens
<220> FEATURE:
<221> NAME/KEY: misc_feature
<223> OTHER INFORMATION: Incyte ID No: 1590496CT1

<400> SEQUENCE: 146
gaataataga aaatgactat aaataggaga ttgtataata tagtataata gtcttttgag 60
cagttaccta ttttgtagaa attttttaag gtcttgggat tttatttttc tttacaagga 120
atattttggg ttactttagg tgcagaaaag actgactcat tttatcattc ttctggtggg 180
ctggagttat atggagaacc 200

<210> SEQ ID NO 147
<211> LENGTH: 201
<212> TYPE: DNA
<213> ORGANISM: Homo sapiens
<220> FEATURE:
<221> NAME/KEY: misc_feature
<223> OTHER INFORMATION: Incyte ID No: 1590713H1

<400> SEQUENCE: 147
ccagtatccc atccatcaga gcaagaaaat gtcagtccct ctggggcaga gccagctctg 60
aaaccagcac aacgcaggct ttgaccccaa ggcaaggtca tccttctaaa gttccccaga 120
gacaagtaga gataaataag aacttgagct ggtatttatg tctactagaa atgaagcaga 180
cctgaatttg agttatggct c 201

<210> SEQ ID NO 148
<211> LENGTH: 89
<212> TYPE: DNA
<213> ORGANISM: Homo sapiens
<220> FEATURE:
<221> NAME/KEY: misc_feature
<223> OTHER INFORMATION: Incyte ID No: 1590769H1

<400> SEQUENCE: 148
gaaataaggt ctcttgtgtc acccaggctg gagccttcct attgtcatga tcccgcgccc 60
tctgcagcaa ggcatgaagg acctcaact 89

<210> SEQ ID NO 149
<211> LENGTH: 114
<212> TYPE: DNA
<213> ORGANISM: Homo sapiens
<220> FEATURE:
<221> NAME/KEY: misc_feature
<223> OTHER INFORMATION: Incyte ID No: 1590779H1

<400> SEQUENCE: 149
tttttatatg tacattgaaa gacataaaac ttgatacaga gaaagtcaaa ttttaaattg 60
ttaaggatta tcaaattgaa tttgccatgt agttcacagt ttccaacaaa atgt 114

<210> SEQ ID NO 150
<211> LENGTH: 203
<212> TYPE: DNA
<213> ORGANISM: Homo sapiens
<220> FEATURE:
<221> NAME/KEY: misc_feature
<223> OTHER INFORMATION: Incyte ID No: 1590931CT1

<400> SEQUENCE: 150
ctctgccccc tcgattgtaa actcctcagg ggcagaggta acagctttgc agccctggga 60
gttaggtttg cttaagggac cagaacaggt gtgactggca gggagcgaag tctggagctt 120

```
tgtctgaggc gctgataggt ggatcggcgg aaggacgcgg aacctggaca ggtcggaaat    180

aaagccgggc gagcagctct gtg                                            203


<210> SEQ ID NO 151
<211> LENGTH: 225
<212> TYPE: DNA
<213> ORGANISM: Homo sapiens
<220> FEATURE:
<221> NAME/KEY: misc_feature
<223> OTHER INFORMATION: Incyte ID No: 1590958CT1

<400> SEQUENCE: 151

ggagaatgtg acatagattt gctggcacat gggtttccta tgagcaaacc ccagaattgg     60

acacacgtat ctggtgctgc attggaatca tccgaaaaaa ccaaggcttg cattgcatat    120

ctatctgctg tctgctgaag gagccctgtc tgtgtgccca aggaagtgac atccttgcca    180

agggctgtcc ctgttgcagg agatgaagga gccctgtcta tgtgc                    225


<210> SEQ ID NO 152
<211> LENGTH: 200
<212> TYPE: DNA
<213> ORGANISM: Homo sapiens
<220> FEATURE:
<221> NAME/KEY: misc_feature
<223> OTHER INFORMATION: Incyte ID No: 1590973CT1

<400> SEQUENCE: 152

ggggactgct gattttcata acaaaatctt cagaagtatt tgctttaaac tactaatatc     60

agttggccaa aaatatccag agttttgtgg tacgctgcta ccagtggtat gctgataaat    120

tgttgacaac cagccctcca aaggaaaaaa taagcgacat aattcgaaac atttgctaat    180

ttctgtggtg taaattattc                                                200


<210> SEQ ID NO 153
<211> LENGTH: 200
<212> TYPE: DNA
<213> ORGANISM: Homo sapiens
<220> FEATURE:
<221> NAME/KEY: misc_feature
<223> OTHER INFORMATION: Incyte ID No: 1591090H1

<400> SEQUENCE: 153

ctggaagcct ctgaatggct caacttcccc ctccaggcct gtccttccat cagctgggag     60

gccctgaggt ggaaggctga gaggggacgg gaatgccacg gacagaagat tttgtggagc    120

tgggtccagt gagagccggg acagaacctc acgtgtgcca gaaccccgt aatccaacag     180

tgacacttca cagactcacc                                                200


<210> SEQ ID NO 154
<211> LENGTH: 1340
<212> TYPE: DNA
<213> ORGANISM: Homo sapiens
<220> FEATURE:
<221> NAME/KEY: misc_feature
<223> OTHER INFORMATION: Incyte ID No: 1591713CB1

<400> SEQUENCE: 154

ggccagacgg tgctgggaag gcagttgttc attgggaggg tgagggttcc ggttcggccg     60

tgggatggct tccttccctg gggttttctg cctgtgtcac cttggtgccc gtcttggggc    120

ctctccacac atgccctttg ttgggccgaa gccgtccctg gcagagccct cgtgcattga    180

cttgacagcc tctccggcag cacaggccta gctggttctg ggttggagtt ggctctggat    240
```

```
agggttagtc accaggcctg gactgaaggc agttattttt attattatta ttatttgcaa    300
tgagagagat ggttggcccc gaatgaggct catgggaggt ttggacgggt gctgtgccgc    360
atgtcgaggc cgattgtgtg ccaggcggtg cgggacgtgc ctcccgtgtg ttatttaatc    420
ccttcaggag cccacaagat gggtgttatt ctcattttac agaggaggga ggggagacgc    480
gaagggattg cctggtctaa gggcacccag cagcagagct aggacttccg ccctaaggct    540
gtgcctcact gccaccaggc acagccgcct ccggaatgca caggcgagtc cctgccctcc    600
ctcccaggcc gcacaggtcc tgccaagcct cacggagcac gggggagtct gtggtggcca    660
gtttacctgg gcatctggct gagaggaaga aaggccaacc tgatcctgag gggacccaga    720
catatccttt gcactgtccc tagaggggcg atgagctttg cagcattaaa aaatggtgaa    780
ggggggaaat attttgaacc aaagaccaaa tgttaggccg ccgttatatt tgcagaagct    840
ttgagaacca tgcgtatagc ctcctgcatt ctcccctctc ctaggagctc ttttgtctct    900
gtccttacga ggcgtcatac agaggcagtg gggtgggcac agatgagcag agtggatggt    960
tcggtgggtc cccacgaggc gagtggtggt catatgtgat ggcacgtgtt cacacaccct   1020
cctgtgtacc cccccagggt caccgaagtc cccacacgct ggctctccac acccctcctg   1080
ttccagaaag catgtccgaa agcagtccag gagattatta aggggtcgcc atgaatccac   1140
tttggtttta aaaccattcc cgaatgtcct agtggattgt gttgtgctgc ctaagctgcc   1200
ggctgcagga gccagagaag tgacccccgc gggagcagcg gcaggtggat ctccacggtg   1260
gctcgctttg tttttgtttt gttttttctt ttaagacgga gtctcgctct gtcgccgagt   1320
ttggagtgta ttggcgcgat                                               1340
```

<210> SEQ ID NO 155
<211> LENGTH: 2277
<212> TYPE: DNA
<213> ORGANISM: Homo sapiens
<220> FEATURE:
<221> NAME/KEY: misc_feature
<223> OTHER INFORMATION: Incyte ID No: 1642794CB1

<400> SEQUENCE: 155

```
agtgagtggt gctggcttta gcccttctag caagatggaa ggtggtcact ttgtgcctcc     60
tgggaagacc acagctggct cggtggactg gactgaccag ctgggtctca ggaacttgga    120
agtgtccagc tgtgtgggtt ctgggggctc gagcgaggcc agggagagtg ccgtgggaca    180
gatgggctgg tcaggtggcc tgagcttgag agacatgaac ctgaccggct gtttggaaag    240
tggagggtct gaagagccgg ggggaatcgg agttggggag aaggactgga cttctgatgt    300
taatgtgaag agcaaagatt tggctgaggt cggggaggga ggaggccaca gccaggccag    360
agagagtggc gtggggcaga ctgactggtc aggtgtggag gccggagagt tccttaaatc    420
aagggagcgt ggagttggac aggcagactg gacacctgac cttgggctga gaaacatggc    480
cccaggggca gtctgcagtc ctggagagtc caaagagctt ggggtgggcc agatggactg    540
gggtaacaat ctgggcctga gggatttgga ggtgacctgt gacccagact ctggaggttc    600
tcaggggcta cggggatgtg gagtggggca gatggactgg acccaggact tggcgcccca    660
gaatgtggag ctctttgggg ctccaagtga agccagggag catggggtgg gcggggtgag    720
ccagtgccca gagcccggcc tgaggcacaa tggcagcttg tctcctggcc tggaggccag    780
agaccccttg gaggccaggg agctggggt tggtgagaca agtgggccag agacccaggg    840
tgaagattac tcctcgtctt ccttggagcc acaccctgca gaccctggaa tggagacagg    900
```

```
agaagccctc agcttcggag caagccctgg caggtgcccg gcccgccccc caccctccgg    960
ctcccagggc ctgctggagg agatgctggc agccagcagc tccaaggcgg tggctcggag   1020
ggagtcagcg gcctcgggcc ttgggggcct gttggaggag gaaggagccg gggcaggtgc   1080
tgcccaagag gaggtgctgg agcctggcag ggactctcca ccctcctgga ggccgcagcc   1140
tgatggtgag gccagccaga cagaagacgt ggatggcacc tggggctctt cagcagccag   1200
gtggagcgat caggggccag cacagacttc tcggcgaccc tcccaaggcc ctcctgccag   1260
atcccccagt caggacttct ccttcattga ggacaccgag atcctcgaca gtgccatgta   1320
tcggagccgt gccaacttgg ggcgcaagcg tgggcaccgg gccccggtca ttcggcctgg   1380
gggtaccttg ggcctgtcgg aggcagcaga ctcggatgca cacctgttcc aggactctac   1440
agagccacgg gcatctcggg tgccatcttc agatgaagag gtagtggagg aacctcagag   1500
ccgccggaca cggatgtcgt tgggcaccaa ggggctgaaa gtcaacctct ttcctggcct   1560
gagcccctca gccctgaagg ccaagctgcg cccccggaat cgctcagctg aggagggaga   1620
gctggctgag agcaagtcga gccagaagga gtccgcggtc cagcgttcga aatcctgcaa   1680
ggtcccagga ctgggaaagc ccctcacgtt acctcccaag ccagagaaat cctcagggtc   1740
agaaggatcg tcgcccaact ggcttcaagc cctgaaactg aagaagaaga aggtctgaga   1800
agtcactgag gttcttccca cctggcagtc tcaggcagtg cccattcctg tggggtccct   1860
gggtgaggag acggctggag ccccaccatg ccccaggctg cagcctctgt cccctccacc   1920
tctgaggagc gtctggggag gcacatttat gcactttgta tcaccctccg aactcccccc   1980
acaccttccc ttccctggat ttcatcacta gtggttgaag gttttgtccc ttcctctcct   2040
ccttccctct ccctctctgc ttcctcctcc agcctccctt gggtttctt ttgataccaa    2100
tttatagcat tttttataaa agcctttgat ttttataatg ggtgggactg tatccctgcc   2160
tcaccccagg tctccgtctg ccccgccagg taccccacag agaccaatga cattttgcca   2220
cttgaaacaa taaataaagt tttttgggaa ttggtgctgt ccaaaaaaaa aaaaaaa      2277
```

<210> SEQ ID NO 156
<211> LENGTH: 2312
<212> TYPE: DNA
<213> ORGANISM: Homo sapiens
<220> FEATURE:
<221> NAME/KEY: misc_feature
<223> OTHER INFORMATION: Incyte ID No: 1687080CT1

<400> SEQUENCE: 156

```
tgtataatat tgtattatta atttattttt actttctata ccatttcaaa acacattaca     60
ctaaggggga accaagacta gtttcttcag ggcagtggac gtagtagttt gtaaaaacgt    120
tttctatgac gcataagcta gcatgcctat gatttatttc cttcatgaat ttgtcactgg    180
atcagcagct gtggaaataa agcttgtgag ccctctgctg gccacagtga ggaaagtagc    240
acaaatagga tacagttgta tgtagtcatt ggcaacaatt gcatacaatt ttactaccaa    300
gagaaggtat agtatggaaa gtccaaatga cttccttgat tggatgttaa cagctgactg    360
gtgtgagact tgaggtttca tctagtcctt caaaactata tggttgccta gattctctct    420
ggaaactgac tttgtcaaat aaatagcaga ttgtagtgtc tggtttggtt tggacagtag    480
tgctttctat catattgttg tgtgcaatgg taatttgttc tactggccaa agcctctttc    540
agcagtgcct tgccatcatg cttaaaagtt tggctagtat atcttgctgg atggagcctt    600
gaactccggc aaggattgaa ccatctgact tccaaatttg ccttcccctc tggacctcac    660
```

```
tattaacaag caaacctttc agggccctct tagctctcag aagctatgta tgggctttcc    720

cagattttaa agctgctgcc tcgagaacta ctcatttctc tcctggtcag cagacagaaa    780

tagccatact aatctcatag ggctcaaatg catcttcagg cagcagggaa ccaagcagcg    840

tggcacaggc cttcttgact ggaggaagag cttgctggca tggtgggcag tattccagga    900

gaggccatgt ccgtgttcac ttcttggcac atttcagttc cgttttcctc ttgtttaaaa    960

ctgcctcttt agatgtggat gccttaatgc tgtaacacat ttgaaaacat tggcaatact   1020

taagttgctg ccatgattac agatggaatt attggctacc aaagagacgc aattgatgat   1080

gagaagcatg attcttgctt ccatataacc aaagttaatc ttaattgcaa tttgactccg   1140

tttccttggt agggatagac tttcttcaga ttccaagtgc tctcttaaat ggcaaattaa   1200

gttaaagaat actactgctc cattcccctc acttattctc cagttaattg cttgtcagtt   1260

ccatttcaag aaagcagtga tgttccaggt ttgattcagt tttcctgtgc acactattgc   1320

caaatttttt tttagcaaag attctgcact ggaacgtaga cagttggaaa cagtactacc   1380

tacctagagg ttatgtgttt tctctttctc cccgctttca cctctttctt tcccaattca   1440

aaacagccaa gtgagccctg ttctggtatt ttgaatcatt agagaaaaga aagggagtgg   1500

ctgttttgag ttgtcctttc tttgcagaaa ggagaaaatg tgattgtgtt ttttttttac   1560

cagcctactt ctaagtgtca ctgcctggtt tttctctttt tcaaggatta gaactaagag   1620

gacacaccag catcggagtg tattaagccc ctgaaacaca tggtagctag ggactgaaca   1680

caggaaccgt atgacagcag cacaaacccc caaaggatgt tcctgccttg tgggcccctg   1740

agccccttgg gagactgaga atcatgacca gattcatcca gaactgctgc agtgttaagt   1800

gaaaatcctc tgtagttgtt ctgcagagga accttccttc cattagaaaa tttctgctca   1860

atacagaatg gtccacatca cccaaagtgc actgttggag atgctgtgaa attaaaacct   1920

ctttgtacct gagacatcta gattcacctc aggaggcctg aaggaaatgt gtaacttgtg   1980

ggaaagaact agacaaccat ttaggaattc tctagatata ctcagcctaa cccagtggct   2040

taacacaagg agattggctt tgatcttttt ttcttgtggc atcttccagc aagttagaag   2100

tctcatggga taagactgca gttcccctgg ttcaatagct ggaacagtga ttttaaatgt   2160

cccttttct ggatcccttg taaacatgaa atcattccat ggatggctgc cttataattt    2220

tgtctctttc cactttaatt gtgaatggtt aaaaaaatgc tgttttctga tattaaattt   2280

ttattagtgc ataccttaaa aaaaaaaaaa aa                                 2312
```

```
<210> SEQ ID NO 157
<211> LENGTH: 2547
<212> TYPE: DNA
<213> ORGANISM: Homo sapiens
<220> FEATURE:
<221> NAME/KEY: misc_feature
<223> OTHER INFORMATION: Incyte ID No: 1722845CB1     Contig3
<221> NAME/KEY: unsure
<222> LOCATION: 2303, 2357, 2379, 2410, 2450, 2477, 2482, 2487-2488,
      2496, 2503, 2512, 2515, 2521, 2523, 2527-2528
<223> OTHER INFORMATION: a, t, c, g, or other

<400> SEQUENCE: 157

ccgctggcct atgatgccat ctgggacttg gcactggctc tgaacaagtc atctggagga     60

cgcggtcgtt ccggcagtgc gctggaggac ttcaactaca acaagcagac cattaccgac    120

caaatctacc gggcaatgaa ctcttcgacc tttgagggtg tctctggcca tgtggtgttt    180

gatgccagcg gctctcggat ggcatggacg cttatcgagc agcttcaggg tggcagctac    240
```

-continued

```
aagaagattg gctactatga cagcaccaag gatgatcttt cctggtccaa aacagataaa    300
tggattgtta tatccagaac tcacagccca acctgaacaa cctgactgct gtgggctgct    360
cactggcttt agctgctgtc ttccccctgg ggctcgatgg ttaccacatt gggaggaacc    420
agtttccttt cgtctgccag gcccgcctct ggctcctggg cctgggcttt agtctgggct    480
acggttccat gttcaccaag atttggtggg tccacacggt cttcacaaag aaggaagaaa    540
agaaggagtg gaggaagact ctggaaccct ggaagctgta tgccacagtg ggcctgctgg    600
tgggcatgga tgtcctcact ctcgccatct ggcagatcgt ggaccctctg caccggacca    660
ttgagacatt tgccaaggag gaacctaagg aagatattga cgtctctatt ctgccccagc    720
tggagcattg cagctccagg aagatgaata catggcttgg cattttctat ggttacaagg    780
ggctgctgct gctgctggga atcttccttg cttatgagac caagagtgtg tccactgaga    840
agatcaatga tcaccgggct gtgggcatgg ctatctacaa tgtggcagtc ctgtgcctca    900
tcactgctcc tgtcaccatg attctgtcca gccagcagga tgcagccttt gcctttgcct    960
ctcttgccat agttttctcc tcctatatca ctcttgttgt gctctttgtg cccaagatgc   1020
gcaggctgat cacccgaggg gaatggcagt cggaggcgca ggacaccatg aagacagggt   1080
catcgaccaa caacaacgag gaggagaagt cccggctgtt ggagaaggag aaccgtgaac   1140
tggaaaagat cattgctgag aaagaggagc gtgtctctga actgcgccat caactccagt   1200
ctcggcagca gctccgctcc cggcgccacc caccgacacc cccagaaccc tctgggggcc   1260
tgcccagggg accccctgag ccccccgacc ggcttagctg tgatgggagt cgagtgcatt   1320
tgctttataa gtgagggtag ggtgagggag gacaggccag taggggggagg gaaagggaga   1380
ggggaagggc aggggactca ggaagcaggg ggtccccatc cccagctggg aagaacatgc   1440
tatccaatct catctcttgt aaatacatgt ccccctgtga gttctgggct gatttgggtc   1500
tctcatacct ctgggaaaca gacctttttc tctcttactg cttcatgtaa ttttgtatca   1560
cctcttcaca atttagttcg tacctggctt gaagctgctc actgctcaca cgctgcctcc   1620
tcagcagcct cactgcatct ttctcttccc atgcaacacc ctcttctagt taccacggca   1680
acccctgcag ctcctctgcc tttgtgctct gttcctgtcc agcaggggtc tcccaacaag   1740
tgctctttcc accccaaagg ggcctctcct tttctccact gtcataatct ctttccatct   1800
tacttgccct tctatacttt ctcacatgtg gctccccctg aattttgctt cctttgggag   1860
ctcattcttt tcgccaaggc tcacatgctc cttgcctctg ctctgtgcac tcacgctcag   1920
cacacatgca tcctcccctc tcctgcgtgt gcccactgaa catgctcatg tgtacacacg   1980
cttttcccgt atgctttctt catgttcagt cacatgtgct ctcgggtgcc ctgcattcac   2040
agctacgtgt gcccctctca tggtcatggg tctgcccttg agcgtgtttg ggtaggcatg   2100
tgcaatttgt ctagcatgct gagtcatgtc tttcctattt gcacacgtcc atgtttatcc   2160
atgtactttc cctgtgtacc ctccatgtac cttgtgtact ttcttccctt aaatcatggt   2220
attcttctga cagagccata tgtaccctac cctgcacatt gttatgcact tttccccaaa   2280
ttcatgtttg gtgggggcaa tcnacacctc tccttgtcac agaatctcca tttctggctc   2340
agaattcccc cccatcntcc aattggcatt caatgtacna accctcaagt ctaacaattc   2400
acaaatcaan cttcgtccca aagactggtt cccctttttg gttttggggn tttttttgaa   2460
gggggaattt aaagggnaaa tnaagtnngg ggggangggtt ttngaagaag cnggnttcca   2520
ngngggnnaa ttggatggga atccccg                                        2547
```

<210> SEQ ID NO 158
<211> LENGTH: 658
<212> TYPE: DNA
<213> ORGANISM: Homo sapiens
<220> FEATURE:
<221> NAME/KEY: misc_feature
<223> OTHER INFORMATION: Incyte ID No: 1732911CT1

<400> SEQUENCE: 158
ctctcactct ctacccgctg ggcggtaccc cgcatctcgc tctggccgcc ccagaggttc 60
gcggcttctg gacctgctgt gcccctctcc agcctggatc aggacggaga acacccccga 120
aacccacctc accagcacag ccggcggacc cttccggagg tggccgcaga gactagccaa 180
cttgcgcgcc cgccgacccg gaccacagct cccagcacac ctcaagggcc cacgcccgcc 240
aggactacaa ttcccggcgt cctccggaag ctcaagtgta cccaggcgcg gtgcctgctg 300
ggaattgtag ttgacgttgg tcagcacgga ggccacagga tcccagcccg gcctttgtgg 360
gactgaggtg gcgctgagtg ggagagcagc aggcgatgcg cgaaaggcgg gacttggagg 420
ttctggatgt tcctgtggat aacctcaagg agcacgggac ctgggacatg actgccccca 480
gcattccttc tggcggcaga cagagtttgt cagttcgcca acatcctgct ttcatgagaa 540
cagtttgctg tttgctcaca gagcctccac tggtatactg agttggtccg accctcattc 600
ttcgcctcca acatctcccc ttttgttttt gcattaattg aataaatgta atttcatg 658

<210> SEQ ID NO 159
<211> LENGTH: 135
<212> TYPE: DNA
<213> ORGANISM: Homo sapiens
<220> FEATURE:
<221> NAME/KEY: misc_feature
<223> OTHER INFORMATION: Incyte ID No: 1785913H1

<400> SEQUENCE: 159
agatctaaac agagagaaac aaagatctac atagaaaaca aagatctaaa tccatgtata 60
tggattgtaa aactcaacat agtaaagata ccagttatcc tcacatagat aaagaagtct 120
aacaattcct atcat 135

<210> SEQ ID NO 160
<211> LENGTH: 1200
<212> TYPE: DNA
<213> ORGANISM: Homo sapiens
<220> FEATURE:
<221> NAME/KEY: misc_feature
<223> OTHER INFORMATION: Incyte ID No: 1809069CT1

<400> SEQUENCE: 160
tatttaatac gctcactata gggaatttgg ccctcgaggc aagaattcgg cacgaggggt 60
ggcttccacg ctatgaaaac cgagataaca acaactccaa caacagaggc agctacaacc 120
gggctcccca gcaacagccg ccaccacagc agcctccgcc accacagcca ccaccccagc 180
agccaccgcc accacccagc tacagccctg ctcggaaccc cccagggcca gcacctacaa 240
taagaacagc aacatccctg gctcaagcgc caataccagc acccccaccg tcagcagcta 300
cagccctcca cagagctttg gctttttttcc ctccactttc cagccgagtt acagccagcc 360
accctacaac cagggaggtt acagccaggg ctacacagcc ccaccgcctc cacctccacc 420
accacctgcc tacaactatg ggagctacgg cggttacaac ccggcccccct ataccccacc 480 gccacccccc accgcacaga cctaccctca gcccagctat aaccagtatc agcagtatgc 540

-continued

```
ccagcagtgg aaccagtact atcagaacca gggccagtgg ccgccatact acgggaacta    600

cgactacggg agctactccg ggaacacaca gggtggcaca agtacacagt agccagtgtg    660

acccagaggc tcccggaggc ccctgccggc ttcctccacc agcgcctgcc tcggcccctc    720

ctctgccccc gccagatccc gtggtgctgg ggatggggtc atcccagggc tgcctccctc    780

cagcccactg cctcccctct gaggggcttc cttcccctcc atagggccag gcattttttt    840

ctggattcaa acaggcaaca atgacctttt attttctgtt tgtccccacc tccccagcct    900

tccacctcct gttcttccta ccttcttcct ttttgactaa ataatcccca cctcccttga    960

tcatacagtg aggctacagt gactgagggg agaatcccct cctgttcact ctcccaaccc   1020

tgctccagcc cctcagcttc ccagaccctc atgcagttgg ttgtaaattc tcccaggagc   1080

tgttttactg tctacttttc aggattaaaa aaaaaatcaa aacttaaaaa aaaaaaagtt   1140

taaaaagcaa aatggggagg gggaggaagc agtgactttt ttttggtaat tatgcgcttt   1200
```

<210> SEQ ID NO 161
<211> LENGTH: 442
<212> TYPE: DNA
<213> ORGANISM: Homo sapiens
<220> FEATURE:
<221> NAME/KEY: misc_feature
<223> OTHER INFORMATION: Incyte ID No: 1867626CB1 Contig1

<400> SEQUENCE: 161

```
gacgtagccc ctaccttggt ctcagtaaat tatttctgaa caaccaggag tcctttaggt     60

aagctagctg actctgaagt ctgacttagc tatatcatga tgttttgaat aagatttgtc    120

aaaatacttc atagtgcaca gacaactgtt tggaattagg tttcatttcc tgtcattttc    180

atattagaag ctataattgg tttggaggct atattgcttg tgtagagtca gttattcaga    240

aaatgaataa ctttactaag gtaaaagtgg gcactgtgac ctatttttat ttggttaatg    300

tatgtagtct ctatacattc agtttgcaga aaagtttcag gaatttaaag aagctgctcg    360

actagcaaag gaaaaatcac aagagaagat ggaacttacc agtacacctt cacaggtggg    420

tatatcattt ctattcttaa tt                                             442
```

<210> SEQ ID NO 162
<211> LENGTH: 360
<212> TYPE: DNA
<213> ORGANISM: Homo sapiens
<220> FEATURE:
<221> NAME/KEY: misc_feature
<223> OTHER INFORMATION: Incyte ID No: 1880501CT1

<400> SEQUENCE: 162

```
gcgacctgct ctgcgccctg acgctgcccc cgctggccgc ctacctctat ccccccaagc     60

actggcgcta tggggaggcc gcgtgccgcc tggagcgctt cctcttcacc tgcaacctgc    120

tgggcagcgt catcttcatc acctgcatca gcctcaaccg ctacctgggc atcgtgcacc    180

ccttcttcgc ccgaagccac ctgcgaccca agcacgcctg ggccgtgagc gctgccggct    240

gggtcctggc cgccctgctg gccatgccca cactcagctt ctcccacctg aagaggccgc    300

agcagggggc gggcaactgc agcgtggcca ggcccgaggc ctgcatcaag tgtctgggga    360
```

<210> SEQ ID NO 163
<211> LENGTH: 2412
<212> TYPE: DNA
<213> ORGANISM: Homo sapiens
<220> FEATURE:
<221> NAME/KEY: misc_feature -continued
<223> OTHER INFORMATION: Incyte ID No: 1881009CB1 Contig3

<400> SEQUENCE: 163

```
cttggaacgt ggtggggccc ctgcagctgc gccaggccct gcgtggctcc ctctactacc     60
tgctcagtgc cctgccccag cccaaggccc caggatacat ctgccatggc ctcagtcctg    120
ggggcctctc caatgggagc cgtgaggaat gctactgggg ccacgtcttc tgggaccagg    180
acctctggat gttcccgagt atcctgatgt tccacccaga agccgccagg gccatcctgg    240
agtaccgcat ccgcacgctg gacggggccc tggagaacgc ccagaacctg ggctaccagg    300
gagccaagtt tgcctgggag agtgcagact ccggcctaga ggtttgccct gaggacattt    360
acggagtcca ggaggtccac gtcaacgggg ccgtggtgtt ggccttcgag ctgtactacc    420
ataccaccca ggacctgcag ctatttcgag aggctggtgg ctgggacgtg gtcagggctg    480
tggccgagtt ttggtgcagt cgtgttgagt ggagccccag ggaggaaaag taccacctga    540
ggggagtcat gtcccccgac gagtaccatt caggggtcaa caactctgtg tacaccaacg    600
tcctggtcca gaacagcctg cgctttgctg ctgccctggc ccaggacctg ggtcttccca    660
tccccagcca gtggctggcg gtggctgaca agatcaaggt accctttgac gtggagcaga    720
acttccaccc ggagttcgat gggtatgagc ctggagaggt ggtgaagcag gcagacgtcg    780
tgctcctggg atacccagtc cccttctccc tgagtcctga tgttcgcagg aaaaatctgg    840
agatttacga ggctgtgacg tccccccagg gccccgccat gacctggagc atgtttgctg    900
tgggctggat ggagctgaag gacgcagtgc gggcccgggg cctcctggac aggagctttg    960
ccaacatggc tgaacccttc aaggtgtgga cggagaatgc agacgggtca ggcgctgtga   1020
acttcctgac aggcatgggg ggcttcctgc aggcggtggt cttcgggtgc acggggttca   1080
gggtcacccg agcgggtgtg acctttgacc ctgtgtgtct gtcggggatc tccagagtga   1140
gcgtctccgg catcttctac caggggaaca agctcaactt ctctttttcc gaggactccg   1200
tgaccgtgga ggtcacagct cgagcagggc cctgggctcc tcacctggag gctgagctgt   1260
ggccatccca gtcccggctc tccctgttgc caggacacaa ggtctccttt ccccgctcgg   1320
ctggccggat acaaatgtca cccccgaagc tgcctggaag ttccagctcc gagttccctg   1380
ggaggacttt ttcagatgtt agggacccgc tccagagccc cctctgggtc accctgggtt   1440
cctccagccc caccgagtca ctcactgtgg accctgcctc tgaataatca ggaacggtgg   1500
cttcagagac gtctcttggg ccttccctct ggccacgtct gcacccaccc ctcctgggca   1560
ccctcctagc ctgccatccc tcacctgcag ccaggctctc agggaaggtc catgctgctt   1620
ggcctgagtt caaggctttc tgcctgtagc ctggactccc gtggaccccc gtgggcaggt   1680
ggcttccccg tggcatctcc acaccgcctc tgcctgcccc tgtggactga tgctatcgcg   1740
cacggtccca cgaccccacc ccgagctcct gaagccgggg tctgagcctg catcacctct   1800
ggcctctcat cccccactct cctgagagca gtggtcacag cggccggccg ctctgctgag   1860
aaggcagaga ggcaggctca ggcctcagcg tggacagcag ggataagggg cacgaaggac   1920
ggggactcgg ccccttcaga attcctcagg actctcaggt gcagctttgc caaaaaggaa   1980
cttttcatgt catgcagttg aggggactta gtctcaatcc caggctcctc ttgactctgg   2040
gcagctttaa tcaggttggg cagcctctgc tacagcgtgg agtgggatgg ctctcttccc   2100
tcagccacgc cgcttgtgag gacagaggtg gggggagtggg aagtgggaag tcaccagaga   2160
acaggagagg gatttgaggg cgcgacccca gcgctctcca cggaccagcc agagggactg   2220
gagccaggtg tgcatgggtt caaggccctg gccctgccca gcctctgtct tgggagctca   2280
```

gccccagggt tcggtcgtca gcagtttccc aagaacaaga tgtgatggca tctgctgctg 2340
aaaccctgat gaggaccagg ccccctgcac cgctgtcagc ctgaggaatt aaagctttgg 2400
tgctgggaag ac 2412

<210> SEQ ID NO 164
<211> LENGTH: 291
<212> TYPE: DNA
<213> ORGANISM: Homo sapiens
<220> FEATURE:
<221> NAME/KEY: misc_feature
<223> OTHER INFORMATION: Incyte ID No: 1909132CT1

<400> SEQUENCE: 164
cgccatccca tctccaaaat cctcagtcct gtgatgacct ttccctactt tataggccta 60
agcatgctga gcgccatcag caccgagcgc tgcctgtcca tcctgtggcc catctggtac 120
cactgccgcc gccccagata cctgtcatcg gtcatgtgtg tcctgctctg ggccctgtcc 180
ctgctgcgga gtatcctgga gtggatgttc tgtgacttcc tgtttagtgg tgctgattct 240
gtttggtgtg aaacgtcaga tttcattaca atcgcgtggc tggttttttt a 291

<210> SEQ ID NO 165
<211> LENGTH: 145
<212> TYPE: DNA
<213> ORGANISM: Homo sapiens
<220> FEATURE:
<221> NAME/KEY: misc_feature
<223> OTHER INFORMATION: Incyte ID No: 1955094H1
<221> NAME/KEY: unsure
<222> LOCATION: 17
<223> OTHER INFORMATION: a, t, c, g, or other

<400> SEQUENCE: 165
gacaccatct gcaaaangg aaaatgttac caccgactcc cagaaactgt aactcccccct 60 gagcacactg cccagaggta gtgaatttgc agcagttaat ttcttaggca ccacagtaat 120
gtgatggttg ttaagaccat gatga 145

<210> SEQ ID NO 166
<211> LENGTH: 516
<212> TYPE: DNA
<213> ORGANISM: Homo sapiens
<220> FEATURE:
<221> NAME/KEY: misc_feature
<223> OTHER INFORMATION: Incyte ID No: 1955688CT1

<400> SEQUENCE: 166
ccttgacctc atgaaatagc ttatcatcac accttttcta aagattaaaa aaaaactaaa 60
gcactgagag gttaaataac ttgcccaaga ttacacagcc aataagtgtc agggctgggt 120
tttgaactct gtccttgcct ctggacaagg gttttgtctg catcatgtgg ctcagtggtc 180
ctctagaccg aagctcacct agatggcccc acatatcaca agagatacgt gcacaaaata 240
gagaccccca cactgcacac ggggctaatt ctgcaagata attttgggga ggaatcttaa 300
ctattacttt ttgttttatg ttaatgaatg aatcattctg aatgtgggag gtaaagactc 360
agttcctttc ttgcttccaa ataacagagt gaaaaatatt gtcagtagca tctttgagga 420
ggaagggaga atatttacta agaaatgcag ggaaagaaat aaaactggat tgtcactgaa 480
aatcatatgg tagctcgatt cttctgataa aagttt 516

<210> SEQ ID NO 167

<211> LENGTH: 403
<212> TYPE: DNA
<213> ORGANISM: Homo sapiens
<220> FEATURE:
<221> NAME/KEY: misc_feature
<223> OTHER INFORMATION: Incyte ID No: 1956694CT1

<400> SEQUENCE: 167
cggctcgagg aggatggcgt tggcctgggg tgggggtgct cgctttgtct tctgtccttt 60
ggttctcctt ccataatgct cctgtaccca gtttatttac ggggacatgc actggaatag 120
gaaatgtccc ccatctccct tcctgcaccc tgctgtgctc cctccaaacc caccttgctc 180
tgtgttctca ggccccccctg cttttgtctc accaggaccc atacctttca ccttgttccc 240
ttccacccct ccagttagtc cctatctggg taagggtctt cccttgagct ccagggggtg 300
gaacccaatg tttacattct cttctgtctc tgcccccacc ccatgcagcg ctttgaggaa 360
ttggaaaaga acctgctgtt gtacctggaa aaaaaaaaaa aaa 403

<210> SEQ ID NO 168
<211> LENGTH: 339
<212> TYPE: DNA
<213> ORGANISM: Homo sapiens
<220> FEATURE:
<221> NAME/KEY: misc_feature
<223> OTHER INFORMATION: Incyte ID No: 1957189CB1

<400> SEQUENCE: 168
cttagtttta ttaatcctct actgttaact tttttgtttc attaatttat cctattattt 60
ctctgtcaaa accacaagct gaactccaat gccttctctt ttttttggaa ataaggtctc 120
actctgtcac ccaggctgga gtacagtggc acgatcacag ctcactgctg tgatcagttt 180
actgaaaaca gcccagtctc cctgcctggc acacactaac cagtgggtgc caactgatgt 240
cagtgtgact ccccccatct gattaatata cccaaagatg gtatttgttt gttgctgttt 300
gagacaaggt ctcactctat cacccaggct tcagtgcag 339

<210> SEQ ID NO 169
<211> LENGTH: 178
<212> TYPE: DNA
<213> ORGANISM: Homo sapiens
<220> FEATURE:
<221> NAME/KEY: misc_feature
<223> OTHER INFORMATION: Incyte ID No: 1957920CT1

<400> SEQUENCE: 169
ggtggcaggc acctgtaatc ccagctactc tcaggaggct acggcagaag aaccgcttga 60
ggccgaggca gaggttgcag tgagctaaga tagtgtcact gcactccagc ctggccaaca 120
cagcaaaact ccgtctcaaa aaaaaaaaaa agaaaacaac aacaaaaaaa aaaaaaaa 178

<210> SEQ ID NO 170
<211> LENGTH: 143
<212> TYPE: DNA
<213> ORGANISM: Homo sapiens
<220> FEATURE:
<221> NAME/KEY: misc_feature
<223> OTHER INFORMATION: Incyte ID No: 1957977CT1

<400> SEQUENCE: 170
atatacttgc tgtgtcagtg agttgacctg ttagcctgtt caacaacaag gcttgccaac 60
tgcagaatga gcccatcttc ccgggtgcag caggaaagcc ataagaacaa gtttcttgaa 120
atgctcaaga gaccgcctcg agc 143

<210> SEQ ID NO 171
<211> LENGTH: 244
<212> TYPE: DNA
<213> ORGANISM: Homo sapiens
<220> FEATURE:
<221> NAME/KEY: misc_feature
<223> OTHER INFORMATION: Incyte ID No: 1958505CT1

<400> SEQUENCE: 171

```
tggggattcc ctacctatgt cttcacccca gattagtaaa ggtagaaagc ctcatccctg     60

cccacatgga actcatcatc atcttgggtc aagataaatt aattctgtat tttattgatt    120

tgttcacaac cccttatttt atttagcgcc ataaatttta tgagaggaat ataaaaatga    180

attaagcaag gattcggccc ttacaaagtt tatagcccag tagggaagat gtgtaaatat    240

aaag                                                                 244
```

<210> SEQ ID NO 172
<211> LENGTH: 1108
<212> TYPE: DNA
<213> ORGANISM: Homo sapiens
<220> FEATURE:
<221> NAME/KEY: misc_feature
<223> OTHER INFORMATION: Incyte ID No: 1972687CT1

<400> SEQUENCE: 172

```
ctcggaattc ggctcctgct tcctagaagg taatgtacga actcgtctcc aaaggatact     60

taggttgcac cagtgtattt gtaaaacagg agcaaatttg gaccttgccg ggccaaagtc    120

gtgtcacgtg gaacctctta atctcagcat ccggagctcc aggaagggaa aatttcaagt    180

cagatagaat tctatatata ccatttcttt ggaaccttca gccctcaaga ttccaacatc    240

atgacctcag tttcaacaca gttgtcctta gtcctcatgt cactgctttt ggtgctgcct    300

gttgtggaag cagtagaagc cggtgatgca atcgcccttt tgttaggtgt ggttctcagc    360

attacaggca tttgtgcctg cttgggggta tatgcacgaa aaagaaatgg acagatgtga    420

ctttgaaagg cctactgagt caaacctcac cctgaaaacc tttgcgcttt agaggctaaa    480

cctgagattt ggtgtgtgaa aggttccaag aatcagtaaa taagggagtt tcacattttt    540

cattgtttcc atgaaatggc aacaaacata catttataaa ttgaaaaaaa aatgttttct    600

ttacaacaaa taatgcacag aaaaatgcag cctataattt gctagttagg tagtcaaaga    660

agtaagatgg ctgaaattta cataagtaat atttcataat cttagaattc tctcaaagca    720

tgtgaaatag gaagaaggaa gttcttgccc agaatcttag gaaatcacca ctgttcggtt    780

ataatcactg cctcctgaat cgttgaggag tcttttaaat tagatttttg ttttgttgtc    840

tcccaagtta atattatatt tagatatcag agagtcaggc aaaaaggaaa acttttatct    900

ctagggaaaa aacatttaga aaaatgtatt cagtgtatct aatactgaaa tgcggaaaaa    960

aatttaatgt taaaaaaaaa ctatagacat tgacatggaa aagagattta atgttttgaa   1020

aaaaaacttt atattaactg agtaacatcc tcctgatgag aagtactata ttaaatataa   1080

acccattatg ttataaaaaa aaaaaacaa                                     1108
```

<210> SEQ ID NO 173
<211> LENGTH: 435
<212> TYPE: DNA
<213> ORGANISM: Homo sapiens
<220> FEATURE:
<221> NAME/KEY: misc_feature
<223> OTHER INFORMATION: Incyte ID No: 1975013CB1

<400> SEQUENCE: 173

```
taaagaggta agaaaaagta aagaagagaa aattcagttt gtaatcaaaa aatcgagtct     60
taatcgtttt tatataattg attgcggact gcaatttcac aggcaaaacg agttcaaggg    120
ttttttggaa gaatatttca aggaccctga aaaaacaaga tggataagat gtgttgcatc    180
gtgaagatgt tcatgtcgaa gttcatcaga ttcacaagag aaaggaaata agagcgaacg    240
gaggatgcct aggcttctgg aggcgaagaa ggacgcggca agctgcgaaa agtcacgggt    300
atctgcaagc atgaaatgat ccgtgaatat ccgaatgggg caacccgtgc aggtgaagcc    360
tgcacacctg aataaatcag gggcagacgc agggaactga aacatcttag tacctgcagg    420
aaaaaaaaaa aaaaa                                                     435
```

<210> SEQ ID NO 174
<211> LENGTH: 1314
<212> TYPE: DNA
<213> ORGANISM: Homo sapiens
<220> FEATURE:
<221> NAME/KEY: misc_feature
<223> OTHER INFORMATION: Incyte ID No: 2010369CT1

<400> SEQUENCE: 174

```
tggggcgaga ttcggacctc gccgcatccg ggaagaatca gtgatgcttg ggacagtcaa     60
tcctagcacg gggggccctcc ccttccagtc cctcatggtt gcagacctag gcgatgtgaa    120
tgtcaatctt tacaaccttc aggacagctg ccggcgaatt caagaggcct atgagaaaat    180
tgtagcagct ggctgtattc ctctgacctt gggtggagat cacacaatca catatcccat    240
attgcaagcg atggcaaaaa agcatggccc agtggggctg ctgcacgtgg atgcgcacac    300
ggacacgacc gacaaggccc taggagagaa gctctaccac ggggcgccct tccgccggtg    360
tgtggatgag ggtctcctgg actgtaagcg tgtggtgcag attggcatcc ggggctcttc    420
cacgaccttg gatccctaca gatacaaccg gagccagggc ttccgggtag tcctggctga    480
agactgctgg atgaagtcgc tggttcctct gatgggggaa gtcaggcagc agatgggagg    540
caaacccatt tatatcagct ttgatattga cgctctggat cctgcctatg cgccagggac    600
agggacacct gaaattgctg gtctcactcc tagtcaggct ctggagatca tcaggggttg    660
tcaaggcctg aacgtgatgg gctgtgatct tgtcgaagtt tcaccaccgt atgatctttc    720
tgggaacaca gccctgctgg cggctaacct gctgtttgag atgctatgtg ctctccccaa    780
agtgacaacc gtctgagtct tgtgctcttc aagacaaaac agattgcgtc gctgacaagt    840
tctcaagaag aacttatgag taagcagtct gagaactaaa gagtttatgc caagaaaact    900
ttctgctgaa agtgtcattg ctggctgtga agtcgggata atcagtagaa ttctcaccca    960
aacagcaaca tttctaagga acttggatta attgggggaa aaaaaaagga gtacttgtac   1020
tgctttgatt ttttttcctt tgatgaaaga tggaggataa aggggaagtg aggagaattt   1080
ctttcaagat tatctaaaca ttagaaacat gacatttaaa aaaactaaaa aaaaaaaaaa   1140
agggggggg taccgacctc gaattcgtaa ccaggtaaaa gctgttcccc gggtaaaaat   1200
tttaaccggc ccacaaattt ccaccccaaa atttcggggc ccgggaagcc ctaaaagtgt   1260
gtaaaacccc tgggggggcg ccccaatggg ggtttacgcc caacctccca cttt         1314
```

<210> SEQ ID NO 175
<211> LENGTH: 264
<212> TYPE: DNA
<213> ORGANISM: Homo sapiens
<220> FEATURE:
<221> NAME/KEY: misc_feature
<223> OTHER INFORMATION: Incyte ID No: 2019581CT1

<400> SEQUENCE: 175

```
gtaagacacc accccactcc cttggcctca tttccttttc tgcacaataa gaacagtaga     60

ctagatgagc cccttccaac tccaacatta catgatttgt ctatgtaagc cactaagaat    120

ttggttcaca gtagtgactt ttcttttctc ccattgtttc actggtagac aatatgtctt    180

cttgcaatac aagtctcccc taaaggcctg gaatcaggcc tagcacttag taactttttc    240

cttacaacca tctgtacctt gctg                                           264
```

<210> SEQ ID NO 176
<211> LENGTH: 586
<212> TYPE: DNA
<213> ORGANISM: Homo sapiens
<220> FEATURE:
<221> NAME/KEY: misc_feature
<223> OTHER INFORMATION: Incyte ID No: 2022460CT1

<400> SEQUENCE: 176

```
aagatatagc ccattacccc acagttacag ttaggtcacc atctccactt gcttccccca     60

ccaccccccct tgtctagggt aagagtggct ttcctcctgg taaaggttag tctctgtatc    120

tctctccaga ttcttaccct gtctcttcag ggatctgact tcagaagaat ctatttcctg    180

cctcttgtcc tgtagcctat cagtatgctt ggttttctcc agtttaaaaa aaatgacgac    240

cttttcttat accatacaca aaaattgact ccaaatggat cacagaccta actataagag    300

ctaaaactat aaaattctta gaataaaaca tgggagtaaa tcttcatgat ctcaggttag    360

atgaagcctt cttaagtgtt acaccaaaag cacaagtagc aaaagacaaa acaaaacaac    420

aggaaaaaag cacaagcaac caaaatcaca aacaacaaaa gaagacaagc tgggctgcaa    480

tcccagcact ttgggaggcc ccgcaggcag attacttgag cccagaagtt cgagatcagc    540

ctggtcacca tggtgaaacc ctgtctctac aaaaaaaaaa aaaaag                   586
```

<210> SEQ ID NO 177
<211> LENGTH: 594
<212> TYPE: DNA
<213> ORGANISM: Homo sapiens
<220> FEATURE:
<221> NAME/KEY: misc_feature
<223> OTHER INFORMATION: Incyte ID No: 2022624CT1

<400> SEQUENCE: 177

```
ctaaaagaaa aaaaaaattc aaagttgttg ggagtgagag gtagagttcc agcatcataa     60

gattacatct ggcaaacacc tgaaatccga aagcgatgca ccaggacttc caaggcatca    120

atatattact aaataacttt ggtaaaatat agtactggcc aggcacagtg gctcatgcct    180

gtaatttcag cactttagga ggccagagca ggaggagcac ttgagcccag gaactgaaga    240

ccagcctggg caacatagtg agatcccatc tctaccaaaa caataaataa attagccagg    300

cgtggtggtg cgcatgtgta gttcagctat ttgggaggct gaggttggag atttgcttga    360

gcctaggaag ttgaagctgc agctattgtg ccactgccct ctaacctagg tgacacagcg    420

agactctgtc tcaaaataaa ataaaatgta gtactttaca acctgtatgg tgggaaattt    480

ggttaagaca actacatgtg tgcttactct ttcacttagc tttcatattt cttgggattt    540

atcttgtaga tacatcttca atagtatcga tttacataga cattgaggtg ttgt          594
```

-continued

<210> SEQ ID NO 178
<211> LENGTH: 506
<212> TYPE: DNA
<213> ORGANISM: Homo sapiens
<220> FEATURE:
<221> NAME/KEY: misc_feature
<223> OTHER INFORMATION: Incyte ID No: 2022628CT1

<400> SEQUENCE: 178

```
cttaattttc ccagcaatga tatgtgacaa cacgtactaa atattaccag ccagaaagct     60

caccctagcc ttggggtcta ggtttttatt gcatgtcagt cacatagggc aatcacatga    120

ccgactttag ttacttaatc accagctgct ccagaggtca aaatgataca gcatggccca    180

aggtccccac cataaatcac attattagca caaactatct ggcctggtat ggcccaaggc    240

ctgaggtata caaagacacc cctacttggg aggatattcc aaggacttag aggttatctc    300

ccaggagccc attaaggcca gtttttttctt tgagatgtgc tgggtttgga cacttcaagc    360

ctgctgagtt aacccttata gcacagtccc caaatgctga gggaccaact gggcctacaa    420

taagtttgta tctttaaggg ttaaggtgtt ttacccatac ctccttgcct tatatctcat    480

gataatatga ggcttttgga aggcag                                         506
```

<210> SEQ ID NO 179
<211> LENGTH: 614
<212> TYPE: DNA
<213> ORGANISM: Homo sapiens
<220> FEATURE:
<221> NAME/KEY: misc_feature
<223> OTHER INFORMATION: Incyte ID No: 2022630CB1

<400> SEQUENCE: 179

```
gagggtcttg tctggacctc cagagccccc agccttgctc acttggctct gcttctgggc     60

agggtgcctg gcattgctgt tgctggcacc tgccgtgcct tggaggggtc tccagtggga    120

cctctgagca cggctcttcc tgtacttctc agaggtgagc agagggcatt tgtgggagaa    180

ctggaacctg gggaggaaaa accccaaggc tggcaaagac tccctgcagt ctgtccagtg    240

atccactgag gctgagtggt ggaggacatg gaggccggcc cgggaccagg acatggaggc    300

cggccaggga cctggggaag agagggcctc agtctggtga gaccagcctg gtgggtgcct    360

ggggaagaga gggcctcagt cctgtgagac cagcctggtg ggtgcctggg gaagagaggc    420

cctcagtccg gtgaggagac cagcctggtg ggtgcaggcc acccttgcct gctgtcaggg    480

cctgcccttc tctccggcct ccagctgctt tgccccagcg atcaggcgcc tgagcttcct    540

cccccgagcc tgagtccagc tgagctccgt gtggctttcc cggtggagca gactctgtct    600

gatttcccaa cggg                                                      614
```

<210> SEQ ID NO 180
<211> LENGTH: 1750
<212> TYPE: DNA
<213> ORGANISM: Homo sapiens
<220> FEATURE:
<221> NAME/KEY: misc_feature
<223> OTHER INFORMATION: Incyte ID No: 2022631CB1

<400> SEQUENCE: 180

```
agctggggaa gggtgcaggc gggaagagtg ggctgtcttt cccagggtga tgcaagcatg     60

ccgcagccct ggaggctggg aatgtggagg ctctgtgagc cctgcagccc tcagaatcag    120

ggccagggat gcagaagatt gagaggatat ggagatggat agagggcagg agacccttag    180

gatagattgt gggacccagg caggaacagg tgtccacaag aactcaggat ggcatcagtt    240
```

```
agctcagaag ccacctggaa gacccagtgt ttccatctct ggaatctctg ttttatgcta    300
aatggattta ggaagactgt tttctttta agggggaaac aaggtagaga aaaggacgaa    360
gaagtgtaag tcccgctgat tctcgggggt aaggctcgga tggcaaggac gcgttctgcc    420
tgggcatgta ggggaggtgt ttttgccatc accagtttct caggctgggg agcacagagg    480
ggaggaggag gactaaatga aaagttgttc ccagcctgca catgaacaca ttcatgacac    540
acaaaactgg ctggaaggag ataagagcac tgggtttgag attccctcca ttaaaacaac    600
caagacaaag aaaggagggg aaaaaaagat aaaaagcaag ccagggttcc ctgccctatt    660
gaaactcaaa cccagactgc cttgggtttt atctttccct taccccctggc acctccagag   720
aactgggacc tgaaatagtc cctccgttct cccctttgac catgtaataa atgaaccaga    780
agcactgaga ttaacctatc aacgccctga gaagccttcc agcctgcggt gctgtctgct    840
gggaggtcag ctggtcaagg cagaggagga gaggaggaaa ggatgggggc tgaagagcag    900
aagggagggg agacagaggg gattaaagag gggaggagag agtgcagagc tccaggaaag    960
ggtatcagag ctgcagccag ctctgccctc taccctaggg aggccagaaa gacacaaaca   1020
gccctccggg cctttacgct ggactctggc ttggcaggct ccaggcaggg tcctctggga   1080
agttactcta gaaaacgaag ggaggaggag cacaagatcc tcagcaacga acacctgcac   1140
ttagaaaaag tggacagctt ctgccaacca caccctaccc atggtactgt atgctattaa   1200
ctcctggaaa cgccccgtaa atgcgagttg tttttgtatt tgtgtgttga gatgggcctt   1260
gtggtttctc tgtactcaga gcacatttct tgtaattact attgttattt ttattgtcat   1320
gactgcccct gagctctggt gagaaaagct gaatttacaa ggaaagggat gaagttaata   1380
tttgcatcac ataattatat cattactgtg tatctgtgta ttgtactaaa tggactgatg   1440
ctgcgcacat gagctgaaaa tgaagagccc tcccatccat tctatgagaa agaaggtcac   1500
cctgagtgac ttctgtttca tgatttccca aacaggtttt agagctggaa aaggacttaa   1560
agaaagagac tgggtggtgc tttctagaaa ggaggaagat gggtatcagg ggaaggaagg   1620
agttagaggg ctttgtacaa agccgagatt gctcattaaa tgaggaacat cctggcctgt   1680
gggcttgtaa gactgacctt cttgggactt caggaggatc ttgaactaaa agaaaaacaa   1740
aaaaaaaagg                                                          1750
```

<210> SEQ ID NO 181
<211> LENGTH: 364
<212> TYPE: DNA
<213> ORGANISM: Homo sapiens
<220> FEATURE:
<221> NAME/KEY: misc_feature
<223> OTHER INFORMATION: Incyte ID No: 2023275CT1
<221> NAME/KEY: unsure
<222> LOCATION: 306
<223> OTHER INFORMATION: a, t, c, g, or other

<400> SEQUENCE: 181

```
ttggtcaagt cttcctgtgt gagtgacacc tacccatgtt ttatgcattg ccagtactca     60
atactgaatt acaccaaatc cctctcctta aaatatccct gttattttat ttagtcagat    120
caaggaaata cattaaaaca gtgttctcaa agtgtagtct aatatggtaa atactgaact    180
cgagccccac ctaaagaaaa gctctctggg gtacaatttt taagacggtc aaaggaattc    240
ttgagtccaa agagtctgcg agtcgccgca ttaaataaat gggaagtttc agtttcaggg    300
acttgnatgt ctgctcaatt gtttgaaggc acagggattt ttaaaaatga caacccaggg    360
```

-continued

```
cttt                                                                364

<210> SEQ ID NO 182
<211> LENGTH: 296
<212> TYPE: DNA
<213> ORGANISM: Homo sapiens
<220> FEATURE:
<221> NAME/KEY: misc_feature
<223> OTHER INFORMATION: Incyte ID No: 2023747CT1

<400> SEQUENCE: 182

gtgcatctgt atagttgaga atcagcccaa aactgtacat gaataaacta cataaacaag    60

aatattgaga taaatactct ttggcattag tgaaacttaa acagaacaat tagaggattg   120

aatcgttttg tgttaatgca gatgtactca ggaaggaaaa atatcttttt ctcttttttt   180

ttttgagatg gagttttgct cttgttgccc aagctggagt gcagtgagct gagattgcac   240

cgctgggctc cagcttgggt gacagaacga gacttcatct caaaaaaaaa aaaaaa       296

<210> SEQ ID NO 183
<211> LENGTH: 745
<212> TYPE: DNA
<213> ORGANISM: Homo sapiens
<220> FEATURE:
<221> NAME/KEY: misc_feature
<223> OTHER INFORMATION: Incyte ID No: 2044305CT1

<400> SEQUENCE: 183

atggtttgac tttcttgtga attaaagaga aagtaacata atctgtattt agcagaacca    60

tacctggagt cacttggcca tttcacagtg attttggctt gtatttgcac ctttctgagc   120

atttactcca gcagtttaaa ttccttcatt ctttcaatat cttgagccct ccttgccact   180

gattttgtta tttattccaa gagatggcat ggattttgtt agtgtttatg gctttatcac   240

ttggctgtcc ttgcttcaag ccacttagag ctcccactca ttttattcat tccagaaata   300

aattactagt atttacaatg ggcagcactg tgctagggac acagccttgc actcacagac   360

ttacgtcctg cgtgcataca tctttctgtc tacaggcaat ggcagaatta gagttagagt   420

gtagtgtgtt gagtgtgtgc gtcctggcct ccttaatact agccgttaca aaataattta   480

aaaatcatgt tagattagga gcttatttta caaaatgctt aactctgtca tcatcctacg   540

catgtcatca aaaaagcaga actggcagat tcactgtgtt tggatgttta ctttgccttc   600

acttcacatc tttattctta ggcacctgtt tcttgtccac caccacgttc ccactggcag   660

ttaacaccaa gcttgattag aaaaatacat ttcccaggtt tgtcaaagta acctgcacaa   720

tgtgcacatt accctaagag ttaag                                         745

<210> SEQ ID NO 184
<211> LENGTH: 1432
<212> TYPE: DNA
<213> ORGANISM: Homo sapiens
<220> FEATURE:
<221> NAME/KEY: misc_feature
<223> OTHER INFORMATION: Incyte ID No: 2069971CB1
<221> NAME/KEY: unsure
<222> LOCATION: 1203, 1232, 1235, 1238, 1263, 1273-1275, 1290, 1304,
      1345, 1355, 1359, 1365, 1396, 1406, 1409, 1415, 1418, 1425
<223> OTHER INFORMATION: a, t, c, g, or other

<400> SEQUENCE: 184

gaaagacata cacacttcat gtaatgctac ctgcaagtct ccctagaaaa gcagtttttg    60

taggtgaaaa caatgaagcc aggtaatatt gcaaggaggc tgtaatttta gcagacctac   120
```

-continued

```
caacaacact gatgtaggaa gctcattatt ttaatttctg gagcctttta atttttttctt    180

tagaaagtgt ataaataatt gcagtgctgc tttgcttcca aaactgggca gtgagttcaa    240

caacaacgac aacaacagcc gcagctcatc ctggccgtca tggagtttct tgaaagaacg    300

tatcttgtga atgataaagc tgccaagatg tatgctttca cactagaaag aaggagctgc    360

aaatgaacac ttcatagcaa tgtggaactc caacagaaac cggtgaataa agatcagtgt    420

cccagagaga gaccagagga gctggagtca ggaggcatgt accactgcca cagtggctcc    480

aagcccacag aaaagggggc gaatgagtac gcctatgcca agtggaaact ctgttctgct    540

tcagcaatat gcttcatttt catgattgca gaggtcgtgg gtgggcacat tgctgggagt    600

cttgctgttg tcacagatgc tgcccacctc ttaattgacc tgaccagttt cctgctcagt    660

ctcttctccc tgtggttgtc atcgaagcct ccctctaagc ggctgacatt tggatggcac    720

cgagcagaga tccttggtgc cctgctctcc atcctgtgca tctgggtggt gactggcgtg    780

ctagtgtacc tggcatgtga gcgcctgctg tatcctgatt accagatcca ggcgactgtg    840

atgatcatcg tttccagctg cgcagtggcg gccaacattg tactaactgt ggttttgcac    900

cagagatgcc ttggccacaa tcacaaggaa gtacaagcca atgccagcgt cagagctgct    960

tttgtgcatg cccttggaga tctatttcag agtatcagtg tgctaattag tgcacttatt   1020

atctacttta agccagagta taaaatagcc gacccaatct gcacattcat cttttccatc   1080

tggtcttggc cagcaaccat cactatctta aaggacttct ccatcttact catggaaggt   1140

gtgccaaaga gcctgaatta cagtggtgtg aaagagctta ttttaggcag tcggacgggg   1200

gtnctgtcct gtggcaacag ccctgcaaca anctnggnct tctaaccaat gggaatcaaa   1260

ggnaaattcc tcnnnaagct tcaaaggttn gcttaaaagg aagnccaaac ccggggccca   1320

agcccaaggt ggggttccgg gaggngggaa aattncctna aaggncccct taaggcaaaa   1380

aggcttttaa cgggtngcaa cttaanttna cccanttnaa gggangggat tc           1432
```

<210> SEQ ID NO 185
<211> LENGTH: 821
<212> TYPE: DNA
<213> ORGANISM: Homo sapiens
<220> FEATURE:
<221> NAME/KEY: misc_feature
<223> OTHER INFORMATION: Incyte ID No: 2070872CT1

<400> SEQUENCE: 185

```
ttttttttt ttttttctc tctttcttga ttttatttta aacaacacac attaacattt     60

taaaatagaa tttaaacagg tgcccagtaa cagaatgaca gacgttaagt gtgaaatcag    120

aaagttaaaa aactaaaccg cagatggtca cctttttatt ttttttaaca tccgcctgcg    180

ctggactgtt aagtggcctc atcactgtca agccaggcag gatttgtaaa gcttgggatg    240

tgtgtattca gagatgacat ttgcttggtg cctttaatga tttctgtaat tagtcattta    300

aacagattgc cctgtgatcc aaaacaggga atacagagag atgagctgag aaaatcattt    360

cctggaggca ctttagagct aattgtggaa aatgaggctt gtctctttgc aagactctct    420

ggatcatatt tcattgggtg gggatggagc tggagagcaa cattctccag gaatctataa    480

aatgtatatg cctgggaggt gtttttcttt ttgacaccac agtgctaaaa gactttgttg    540

ggtcacaaaa tttaacagat attaagtaag tgatccaaat ttgccactgg caatttagaa    600

accagagaaa gaaatgcacc cggtcagaga aagttgaggc tacatgacag agaaaagcca    660

agaacttgat atttcacagg aatggggtaa gacttgggag acctatgact ttgccttcat    720
```

-continued

```
tgcactggac agttgttctt tttattaata aatgtccttg gagtgacaat tctgctcttc    780

aaagataaaa gcggaagctt tcagagacag tcagaaaggg a                        821


<210> SEQ ID NO 186
<211> LENGTH: 832
<212> TYPE: DNA
<213> ORGANISM: Homo sapiens
<220> FEATURE:
<221> NAME/KEY: misc_feature
<223> OTHER INFORMATION: Incyte ID No: 2072228CT1

<400> SEQUENCE: 186

gatagattga ctatagggaa tttggcctcg acatagtaat ttggcagagt aaattcttaa     60

aatcatcacc acgattctga ccttatggac tttgaagggc agatgttgtg tctcattgct    120

ttcgtgtcca caagacctgg cacatagacg atgctcaata aatattattt gaaggagtga    180

atgatggtga catggttctt aggagttaaa atgagaaaac ccaaggagcc gaaagcatgt    240

ctctacgggg aaaggttaga gagcactgac tcaaaccatc gtctccaatt atgcagtttt    300

aatgaggaag caagcccaac cttgaacatt atttaagcca gagttatccc aataagcatt    360

ttcctaccat gagtggtaga ttaagtagca ttgagtcatg tagtgaaagt aatgtccctt    420

cttcatacca tttcaatgcc tctggtaagt caagagaaag tctttgataa tagcctattt    480

ttaacacctc tcacccttgt ttgtcagaaa gagcagacct cagattcaga gactttagca    540

agcaaagata tccagtaaag aaatgaaata atggccgggc acagtggctc acgcctgtaa    600

tcccagcact ttgggagtcc taggcaggcg gatcacgagg ttgggagttc gagaccagcc    660

tgaccaacat ggtgaaaccc cgtctctact aaaaatacag aaaaaaaaaa aattagccgg    720

gcgtggtggt ggcacatgcc tgtaaaccca gctactcagg aggctgaggc aggagaattg    780

cttgaacccg ggaggcggag gttgcagtga gagccgagat tatgccactg ca            832


<210> SEQ ID NO 187
<211> LENGTH: 1249
<212> TYPE: DNA
<213> ORGANISM: Homo sapiens
<220> FEATURE:
<221> NAME/KEY: misc_feature
<223> OTHER INFORMATION: Incyte ID No: 2085633CB1

<400> SEQUENCE: 187

tgagatgtcc catgggtagg gatgtcatag acaaacaagc actaagccct ggacagggga     60

tggatgagcc tcccactgag attatttccc tccatcactg aactctaaca agggcctttg    120

atcttgcctt tggcacaagc atgccttcct ctgagcacac tacaagtccc tatggaagag    180

agagtgttct aggcagcagg acaagaagga gcatgacaca tttggaaaac ggagccacag    240

tgtgaacagg gcgatgctta gatgtgccca gcagaagcac cctgggaaat gaggggtagg    300

gaacaaccaa caaccttgat ctccttgaag actctttctg ctcattgagt ggataaggcc    360

ccagagattc agtgtggttt tctggggttt gggcccatca cagagtcaga ttttgggctt    420

taaggaggcc ctccctgtac ctggatgggc tccaaggaca gtctcagctg actgagtgag    480

caggtggcct gcctcaagtc ttcatcagtg gccagcacaa tgatgagtgt ccagtgggcc    540

ccattgcttg cagacacatc cctctgtgct ctgactttca cttccatctc cttctcccac    600

accctgctct cattttaggt tcctgcgcct ctgaactctg aaattccaca aatgcaccat    660

tccctctatc ccatctccat gcttttgcct ctcctgttcc cttagcctgg gatgcgttca    720

cttgctttac tgacttgcaa aactcctacc cacgtttcaa atttcatacc actgtgaatc    780
```

```
cttccctgac ttcaccaaga gactcagata gaccttcttc tctgctcccc ctgcatctgt    840

acatacttct gtctgtatct ttatcatatt gaagtataat aaactgttga tatgttggtg    900

tttacacaag accaagaaat cctcatgggc caagtccatg ccttatttac ttcatgttga    960

atgcacctag catttgagaa ggtggttggt aaagtggctc atgcctgtaa tcccaacagt   1020

ttgggaggct gaggccggca gatcgcttga ggtcaggagt ttgaaaccag cctggccaat   1080

atggcaaaac cccatcttta taaaaataca gaaattagcc aggtgtggtg gctcatgcct   1140

gtaatcccgt gcctgtaatc ccagccttgg gaggctgagg caggagaatc acttgaatcc   1200

aggaggcaga ggttgcagtg aactgagatt ggaccactgc actccaggg               1249
```

<210> SEQ ID NO 188
<211> LENGTH: 347
<212> TYPE: DNA
<213> ORGANISM: Homo sapiens
<220> FEATURE:
<221> NAME/KEY: misc_feature
<223> OTHER INFORMATION: Incyte ID No: 2088104CT1

<400> SEQUENCE: 188

```
cagaagagaa aaagtcaaag tcataactac atactaatga gttaattaaa ataaaaaaat     60

tacaaaacac attaagggta gcaataacat atatatatcc agtttgcttc aatatcaact    120

agttttagac ataactacta aaagactaac actaaagaat aaagtttaaa gtgttcctgg    180

aagctgagct accaaagttt tcttattcaa tacattttct tattggagga ataagtttaa    240

gcccttttag tgatgagaca gctttgttgc cactagttgt atacaataac aaccagaacc    300

tgggctactc taaaagtctc caaatcattc ttaaaaaaaa aaaaaaa                  347
```

<210> SEQ ID NO 189
<211> LENGTH: 483
<212> TYPE: DNA
<213> ORGANISM: Homo sapiens
<220> FEATURE:
<221> NAME/KEY: misc_feature
<223> OTHER INFORMATION: Incyte ID No: 2091133CT1

<400> SEQUENCE: 189

```
tgtagcgtct gcatctgaaa ttgtttttac atctgtccca cctgcaccct tcaccccagg     60

ctgttagttt cttgaggaca aggacttcat cattttcaaa cattattggt caaataaatg    120

aagaaatagg ctgcatcctt tctctttatc ctttgacctc ctctatcatc ctgctgttat    180

cttccagaag gagaagaaac agcttcacag gaaaagtaga ggagattttc ccattatggt    240

gaaagtgcca aatcagaatg tgaaatagga attctgggct ctgtaccagg catttactcc    300

tatgctgtta gctgatgtta aagagggtgg atttcttttc ccttaggtct caccttctgt    360

gccttcaggg gaagttggtt ggaagtttga atggtttgtt gttgtcgtca ttgttttgta    420

ttaaggaggg ctgtaatgga acgaatacaa tggttattga tggagagtaa aaaaaaaaaa    480

aaa                                                                  483
```

<210> SEQ ID NO 190
<211> LENGTH: 1935
<212> TYPE: DNA
<213> ORGANISM: Homo sapiens
<220> FEATURE:
<221> NAME/KEY: misc_feature
<223> OTHER INFORMATION: Incyte ID No: 2123514CB1 Contig1

<400> SEQUENCE: 190

-continued

```
agcttccctg gggccggctt ttgcgtccgg cctcctgctg tccagtgctg gcttctgtgc    60
ccctcacagg tctcagccca acctctccgc cctctccatg cccaacctct ttggccagat   120
gcccatgggc acccacacga gccccctaca gccgctgggt cccccagcag ttgccccgtc   180
gaggatccga acgttgcccc tggcccgctc aagtgccagg gctgctgaga ccaagcaggg   240
gctggccctg aggcctggag accccccgct tctgcctccc aggccccctc aaggcctgga   300
gccaacactg cagccctctg ctcctcaaca ggccagagac ccctttgagg atttgttaca   360
gaaaaccaag caagacgtga gcccgagtcc ggccctggcc ccggccccag actcggtgga   420
gcagctcagg aagcagtggg agaccttcga gtgagccggg ccctgagggt gggggatgca   480
ccgaggcccg agggtccgtc cactgctgcg gttccgaggc tcccccgcca ctctctctct   540
gcccaggttc tgctggtggg aagggatggg acccctctct gctgccccct cctcccctcc   600
acactgccca tctctgatgt ctggccctgg ggaatggcac cagttccagc ctgggaatca   660
acccagttcc tgagtgccca tcccaccccg cggttgcctc tcctcggcac ccttgattgg   720
gttttgcact aaagaaagag gtcagctggg ccaatgatat tgctccagac cgagtcctac   780
ccaccttccc ccggaagtgt cccaagaggc tccgaaggcc tcccctccga gcccagctct   840
cctgtctcct ccacagccag gccctgcacg cccacctcct cggacacagg tgacagggtt   900
accctccagt ttgagctcat ctgcacgaga cacaggtagc ttggggttga agttaggact   960
cctcctgggc tggaggattt acctggtggg gcacttccag actgtttcta gcaatataca  1020
cacacgttct ttcctgtgtc ttcaccccaa aacttcagtt gattctgacc tgggaggatc  1080
tggggaccag gggtcttggg gctgccttgt gatacacagc cccagccacc ctgcacgggg  1140
gctgcgagca ccagcaactt tgatttatag aaggaaaatg gaaacccccca tctgagtatt  1200
ttgggaggag cccccagccc tcatccagct ctggcacgct gatacctcca ggtactcccc  1260
tcactgtcaa agctggggct cagcctcttg tcatctggag ctttgtgggc aaagctgaga  1320
agctgcaacc cagatttcaa cccaaaaagg tcaagctgaa tgcctcagac tgatgtggaa  1380
ggcagctggc cttcctgggt tggaacgagg cagtggccct gagccccttc tccagggcca  1440
ggtagaaagg acaaacttgg tctctgcctc ggggaagcag gaggagggct agaagccagt  1500
ccctccccac ctgcccagag ctccaggcca gcacagaaat tcctgaggcc aacgtcacca  1560
aagttagatt gaatgtttat tatctttctt tttccttttt accttattga tttgatgaat  1620
cttgaaatgg attcatttcc ataaaccaag ttaaagtatg gcccgaccat ttaagaaaac  1680
aaccatctga gacacgcagg aaattgtgag catttcgacc cgagctctca tttcctattt  1740
gtgaagggtc agacacagtc tacccagggg tgtctggggg acaaggggggt ctctggagat  1800
gtcacccagg gagcccccctc tatgtctgag aggctgccac tgctgcacat gctcagtgag  1860
gcttggcggc catcctggca catggctctt cctgggtcaa ccgtgacctg tctggctcag  1920
gaatgggctc tgggg                                                   1935
```

<210> SEQ ID NO 191
<211> LENGTH: 2657
<212> TYPE: DNA
<213> ORGANISM: Homo sapiens
<220> FEATURE:
<221> NAME/KEY: misc_feature
<223> OTHER INFORMATION: Incyte ID No: 2150261CB1 Contig1

<400> SEQUENCE: 191

```
ctggctgtgg ggcagcgcat gcggcagggc agcatcggcg cctggaggac catcagcccg    60
```

-continued

```
tacctcagtg gtgtcggggt cgccagcgtg gtggtctctt tcttcctctc catgtactac     120
aacgtcatca acgcctgggc cttctggtac ctcttccact ccttccagga tcccctgccg     180
tggtctgtct gcccactgaa tggtaaccac acgggctacg atgaggagtg cgagaaggcg     240
tcctccacac agtacttctg gtacaggaaa accctcaata tctcgccgtc cctccaggag     300
aacgggggtg tgcagtggga gccggcgctg tgcctcctcc tggcctggct ggtggtgtac     360
ctgtgcatcc tgcgtggcac cgagtccact ggcaaggtgg tgtatttcac ggcgtcactg     420
ccctattgcg tgctcatcat ctacctcatc aggggcctca cgctccacgg agccaccaat     480
ggcctcatgt acatgttcac tcccaagata gagcagctgg ccaaccccaa ggcctggatc     540
aatgcagcca cccagatctt cttctcactt ggcctgggct tcggcagcct gatcgccttc     600
gccagctaca atgagccatc caacaactgc cagaagcacg ccatcatcgt gtccctcatc     660
aacagcttca cctccatatt tgccagcatt gtcaccttct ccatctatgg cttcaaggcc     720
accttcaatt atgaaaactg cttgaagaag gtgagtctgc tgctgaccaa cacttttgac     780
cttgaagatg gctttttgac agccagcaac ctggagcagg tgaagggcta cctcgcatct     840
gcctacccaa gcaaatacag cgagatgttc ccgcaaatca aaaactgcag cttggaatcg     900
gagctagaca cggccgtcca gggcactggc ctggcattca tcgtctacac agaggccatt     960
aaaaacatgg aggtgtccca gctgtggtcg gtgctctact tcttcatgct gctgatgctg    1020
ggcattggga gcatgctggg gaacacagcg gccatcctca cccctctgac agacagcaag    1080
atcatctcca gccacctgcc caaggaggcc atctcaggtc tggtgtgcct tgtcaactgt    1140
gccattggca tggtgttcac gatggaggct gggaactact ggtttgacat attcaacgac    1200
tacgcagcca cactgtccct gctgctcatc gtgctggtgg agacgattgc cgtgtgctac    1260
gtgtacgggc tgaggagatt tgaaagtgac cttaaggcca tgaccggccg agctgtgagc    1320
tggtactgga aggtgatgtg ggctggcgta agcccactgc tgattgtcag cctctttgtc    1380
ttctacctga gcgactacat cctcacgggg accctgaagt atcaagcctg ggacgcctcc    1440
cagggccagc tcgtgaccaa agattacccg gcctatgcac tggctgtcat cgggctgctt    1500
gtggcctcct ccaccatgtg catccccctg gcggccctgg ggacttttgt tcagcgtcgc    1560
ctcaagaggg gagacgcaga ccccgtggcc tgagatgtgg gcttcccagc cgctcacggt    1620
tttacagata ctatttacag gcggaaactc ctcggctgct tttcaaatg cttaagccag     1680
gagtgctcag cccatcaact tcctgagtgt ctaaagaaga tgaggaaggt gtgcaggaag    1740
aaaactccct tgggagaacg cacaccctcc cgtggtggct gttcctccct gtcacctgcc    1800
tcctcatcat ggaaggaggt gggctatgaa agccggtctc aaagataact gcatccttca    1860
ttccaggaaa gccctagaat tagggcacat tgcaaactga aatatgacta taattcttat    1920
gggaccaaat ttaagcaatt tttgtttttg gctgaagaga caccaaaata ttagaggaca    1980
aatattttta gatccattta aggagttttg aagtgcctaa gatgacctat ttgtcagtgg    2040
tgcaaaatta attctcttct tttttgagtt gtagtgaata tgcaatttct gtgttcccct    2100
tccacccttt aaatcttagg atgacaagtt ataaagaaag aagatctttg tctgggaccc    2160
ccaaagggat cctttctcta aggtctctga cagtgggtcc aggaccagac ctctctacaa    2220
aaaattgccc caactacagt ttgcaacccc aaaccacatt agaagtctgt gcagacatcc    2280
ctccgtggtg tgtgtcttgg tgcattggaa aaggagtcag gagccactgt gaggtgagaa    2340
tgaaagtgga tctcagctgg gcacggtggc tcacgcctgt aatcctagca ccttggggt     2400
```

```
caaggtgggt ggatcacttg aggtcaggag tttgaggcca gcctggccaa catggcgaaa   2460

ccccatttct actaaaaata caaaaaaatt agctgggagt ggtggcatag gcctgtaatt   2520

ccagctactc tggctgctga ggcacaagaa tcatttgaac ctaggaggtg gcggttgctg   2580

tgagccaaga tcatgccact ccactccagt ctgggcgaca gagcaagact ctgactcaaa   2640

aaaaaaaaaa aaaaaaa                                                  2657
```

<210> SEQ ID NO 192
<211> LENGTH: 1171
<212> TYPE: DNA
<213> ORGANISM: Homo sapiens
<220> FEATURE:
<221> NAME/KEY: misc_feature
<223> OTHER INFORMATION: Incyte ID No: 2170670CT1
<221> NAME/KEY: unsure
<222> LOCATION: 1115, 1121
<223> OTHER INFORMATION: a, t, c, g, or other

<400> SEQUENCE: 192

```
gtaatttccc taacctgaaa taccctatag aatctcaatc tccagaacat tacttccaaa     60

aaccaaaact tcaccaacga accctgaaca aatgtaaaat accacaaaga aatactgtcc    120

gaatcaacct tgaccatttt caccagaata agacagcaaa aatgctctgt tgtgcatacg    180

agtacaacat gtatggtaat aaatcaccag tggatcattc cgggctggta cgagccttct    240

tggtggaagt aggtgcacac ggaagcaaac tcatcccgct gcttccggaa gaatctgctt    300

gctgccatgg agggctaaat tgccgtggat ttcgagcccc tgagctccaa gcagatcaag    360

accatctcag gaaagactcc acagcagtat gagagagagt acaacaacaa gcggtcagac    420

gtggggccca gcaagttcca cgggtacgcc tacgatggca tctgggtcat cgccaagaca    480

ctgcagaggg ccatggagac actgcatgcc agcagccggc accagcggat ccaggacttc    540

aactacacgg accacacgct gggcaggatc atcctcaatg ccatgaacga gaccaacttc    600

ttcggggtca cgggtcaagt tgtattccgg aatggggaga gaatggggac cattaaattt    660

actcaatttc aagacagcag ggaggtgaag gtgggagagt acaacgctgt ggccgacaca    720

ctggagatca tcaatgacac catcaggttc caaggatccg aaccaccaaa agacaagacc    780

atcatcctgg agcagctgcg gaagatctcc ctacctctct acagcatcct ctctgccctc    840

accatcctcg ggatgatcat ggccagtgct tttctcttct tcaacatcaa gaaccggaat    900

cagaagctca taaagatgtc gagtccatac atgaacaacc ttatcatcct tggagggatg    960

ctctcctatg cttccatatt tctctttggc cttgatggat ccttgtctct gaaaagacct   1020

ttgaaacact ttgcaccgtc aggacctggg attctcaccg tgggcttaca cggaccgctt   1080

tttgggggcc atgtttgcaa agacctggga gagtncacgg ncatctttca aaaaatgtgg   1140

aaaatggaag gaaggaagga tccatcaagg g                                  1171
```

<210> SEQ ID NO 193
<211> LENGTH: 555
<212> TYPE: DNA
<213> ORGANISM: Homo sapiens
<220> FEATURE:
<221> NAME/KEY: misc_feature
<223> OTHER INFORMATION: Incyte ID No: 2199484CB1

<400> SEQUENCE: 193

```
gccacccttg caacaaatac aggcgcctgc acagcctggc ccacctgttc attaatgcac     60

tcaatttagt actgaatggt ctttctccca gcccattccc agcccttcct atttcctttc    120
```

-continued

```
ctattttttt tttctcccca cactttcttg ggactcccac cttggaagga ggaagggctg    180

acctgggttc tcttcagccc ccaggtgcgc cgggtcaccc gtgccccttc attatggacc    240

tgggccctac tggaacccct gccccagtta ccacaactca ggccggctgg cccgggccac    300

gggctgcgca aatcaccagc cccaacccca gggaggaact ggcccctcct agggagcctc    360

ttcgactttt ttagaaaaat gatctccatt tctttccagc catgatgttt agtaaatatt    420

tttagtaccg cacttagcag acagctttcc aagtgtgctt tcttgccaca aaagtgtcct    480

ggcaagagcc ccttattttt taagacatca ggaaagcaga ccgctttgag tttgggagat    540

tttggagctc aacaa                                                     555
```

<210> SEQ ID NO 194
<211> LENGTH: 100
<212> TYPE: DNA
<213> ORGANISM: Homo sapiens
<220> FEATURE:
<221> NAME/KEY: misc_feature
<223> OTHER INFORMATION: Incyte ID No: 2204242H1
<221> NAME/KEY: unsure
<222> LOCATION: 49-50
<223> OTHER INFORMATION: a, t, c, g, or other

<400> SEQUENCE: 194

```
gtcttgctag tctgaattca tgtcttgacc cagtcatata ctacttttnn actaatgagt     60

tccgaagacg gctttcaaga ccagattttg caatgacagc                          100
```

<210> SEQ ID NO 195
<211> LENGTH: 510
<212> TYPE: DNA
<213> ORGANISM: Homo sapiens
<220> FEATURE:
<221> NAME/KEY: misc_feature
<223> OTHER INFORMATION: Incyte ID No: 2236316CT1

<400> SEQUENCE: 195

```
agactcccat tcttaacttg gcatttttgt agcttacagg aaccagcttg gtgtaccttc     60

tcttatgaga tgcagctgga aagccattta tgcaagaggt ggtttcactt ttgtcgctcc    120

tccattcatt gacccttcag cctttaaaaa attagaatgt gaaaattagt agcaaagagt    180

gcagagatat tagcttaagg gataaataaa tgaaagtagc aagtagctca ttatttatga    240

agagtaataa ttaatactca tttattcatc aagtatcacc gtgcctggcc agcaattaga    300

attttaacac tggcagttat gaataatatg aaggagaggt agatttctga gtgattctgg    360

tttaaccagc tgggtggatg gtggttccac gtattcaggt ggcaaacagg aaaaacatgt    420

gttcgaagaa gaatggaggt aggtggtctc ttaagaatgg ttaagaggct tgggagtcag    480

actgcttggg gttgcatccc agctttgacg                                     510
```

<210> SEQ ID NO 196
<211> LENGTH: 512
<212> TYPE: DNA
<213> ORGANISM: Homo sapiens
<220> FEATURE:
<221> NAME/KEY: misc_feature
<223> OTHER INFORMATION: Incyte ID No: 2237722CT1

<400> SEQUENCE: 196

```
gaaccctccg gcctagaagt tcagatgtct tgccaatata tctgtgcttc acaacttgcc     60

tactctctct gacccctaac attttcacat acttttccaa ttctgcctgt cataaatttg    120

ctgcttcccc ctaagtagaa tgttgattcc tgtcaaacac acagcctagc cctgattcct    180
```

```
cctcttctct caagcagtga tattgtcaac aatgataaac aactactatg tactgagtgt    240

ttttttatgt gctgctcaca ctttatacac atgtatagat tcattcttca tcatagattt    300

ttcagctagc tggcatttat tagccccact ttgcatatgt aggaacacag gctcaaggaa    360

agaaagcaac ttcccacaat ttcccaggct agtaaaagtc agagatggaa ttcaagccca    420

gatcattcca agtttgtgct cttcctgtga cacgacactg cctcagtcaa ggcatcagag    480

aggaagttag aaagcagatg gtgagaggga gt                                  512


<210> SEQ ID NO 197
<211> LENGTH: 534
<212> TYPE: DNA
<213> ORGANISM: Homo sapiens
<220> FEATURE:
<221> NAME/KEY: misc_feature
<223> OTHER INFORMATION: Incyte ID No: 2238625CT1

<400> SEQUENCE: 197

gccttcagca ctttagtagt ggatgtcagc ggtaaattct tcgaatacac tctgaaaaga     60

gaaatcagcc ctggcaagat caacagcgta aagcagaatg acatgctagg gaaggtaaca    120

ttcgacccat aggtattttt caacattctt ctgcctccag ttattttcca tgctggatac    180

agcttaaaga gacacttttt tagaaatctg gggtcactcc ttcttgggga ctgctgtttc    240

gtgcttccgt attggaaatc tcaggtatgg tatggtgaag ctcatgaaga ttatgagaca    300

gctctcagat aaattttact acacacattg tctctttttt agagcaatca tctctgccac    360

tgacccagtg actgtgctgg cgatatttat gaattgcatg caagacgtgg atctttatgt    420

acttctgttt gggagagcga tcctaaatgc ccgtggtaat gttggacctt ccctcaccaa    480

ttgctcgggt atcaggcagc cgggcctgaa cttcaactca cgccttttct ggtg          534


<210> SEQ ID NO 198
<211> LENGTH: 454
<212> TYPE: DNA
<213> ORGANISM: Homo sapiens
<220> FEATURE:
<221> NAME/KEY: misc_feature
<223> OTHER INFORMATION: Incyte ID No: 2242277CT1

<400> SEQUENCE: 198

gtccttttct taaaagatac atcccgcccc aaatctccgg gggcattata tatttatata     60

ttcctaccgc agagaatata tataggaggg gtatatatat gatgtgttat atatatatat    120

atttgtgtgt gtatatatat atatatatat acatttcttt gtctatttat agaacaggtt    180

aagtgacttg tccaaagtaa cacagctaaa aagtgacagc aggggttcaa acccattctc    240

tttaactcca caaatgagta tggttctcca attcatgctt ccttcagcta acagagtgtt    300

caaaaatgca gattgtaaag gccaagtgag gtggcttatg cctgtaattt cagcactttg    360

gggagccaga gtgtgaagat ggctggcctg agcccaggaa ttcaagacca gcctgggcaa    420

tatagtgaga ccttgtctca aaaaaaaaaa aaaa                                454


<210> SEQ ID NO 199
<211> LENGTH: 507
<212> TYPE: DNA
<213> ORGANISM: Homo sapiens
<220> FEATURE:
<221> NAME/KEY: misc_feature
<223> OTHER INFORMATION: Incyte ID No: 2244782CT1

<400> SEQUENCE: 199
```

-continued

```
aatgagcaaa atgttgtttt ttgtattgtt aatcaaatca gaaactggtt taaaagattt     60
acaaaattca caagggtatg aaaaacagag gttgtattta ctgattggtc tgtttaatgg    120
aaattgtcta atggaattgt ctcatatttt caaatgggat tttgttttca tggaatttaa    180
ttagtctgat tataatttac aagttctttt aaaaagtaca ggagcagctt tttaaagttt    240
gagaaacaga aaaaagtaat tgactaaaga aatttacaac taacatgcct ggtccactat    300
tttcctcata gcagtgcctg tatcacaagc atacttatcc accatgaatc tgtgtgtgct    360
tttgcaagtt gacattattg cttcctgagt gaagctgtag aaaccatttc tatctagcaa    420
tgccgaattc ttgatcttgg ttccttctgt ttgactctca ttagttttag cataaacagg    480
taaatgtgct tttttacaag tatattt                                        507
```

<210> SEQ ID NO 200
<211> LENGTH: 807
<212> TYPE: DNA
<213> ORGANISM: Homo sapiens
<220> FEATURE:
<221> NAME/KEY: misc_feature
<223> OTHER INFORMATION: Incyte ID No: 2272244CT1

<400> SEQUENCE: 200

```
gagcagcaaa ttcggcacga ggaatcgctt gaacccggga gcagaggtta cagtgagcca     60
agatcgcgcc atcgcactcc agcctgggca acaagagcaa aactccatct caaaaaaaaa    120
aaagaatatg tgcagctctg gctattcttt aatcatgtct ttctgaaatg tgtatttgag    180
attagaaatt gaggttgaga ggaactcagg agattttttt tttaaatcat atgacagtat    240
aagccatcag tactaaatgg acagctccca gtatactgtg gactgtgata aactgaatgt    300
atgtttttta atggtttatt gctgcaggtt ttttgtgtat ttgattttta gtttttaact    360
tatttttcaa taggtaataa ttgcacatgg ttcaaagcta aaaggtatga agtattatgt    420
agggatacgt ccctcccatt ctgtcccaca gccaccacct ctctcctcag ccagcaatga    480
catcagcgtc gacttgcctt tcccggggtt gtgcagagtt agatatgcac atacatgtgg    540
tataagcaca tgtacagagg agtacacata gcatataaac atgtctgtag cacatatata    600
ttctttcccc tcttttaaaa caaatggtag caaaccaacc acacactgtt ctgtatcttg    660
ctctgtttgc ttgatacatc ttgtaagtgg ctcctaatta ctatgtaaag attgacctta    720
tttaaatttt tttatgttga aatcatcaat attcccatca ttatggtgtg ttctttgatt    780
gacaaatcag ctctcaataa accactt                                        807
```

<210> SEQ ID NO 201
<211> LENGTH: 1137
<212> TYPE: DNA
<213> ORGANISM: Homo sapiens
<220> FEATURE:
<221> NAME/KEY: misc_feature
<223> OTHER INFORMATION: Incyte ID No: 2284108CT1

<400> SEQUENCE: 201

```
gacaatctct gattgtgaag ccctcttttt ctctccttct atttctctct agagcactca     60
agacttcact gacgaaaact caggaaatcc tctatcacaa agaggtttgg caactaaact    120
aagacattaa aaggaaaata ccagatgcca ctctgcaggc tgcaataact actacttact    180
ggatacattc aaaccctcca gaatcaacag ttatcaggta accaacaaga aatgcaagcc    240
gtcgacaatc tcacctctgc gcctgggaac accagtctgt gcaccagaga ctacaaaatc    300
```

-continued

```
acccaggtcc tcttcccact gctctacact gtcctgtttt ttgttggact tatcacaaat    360

ggcctggcga tgaggatttt ctttcaaatc cggagtaaat caaactttat tatttttctt    420

aagaacacag tcatttctga tcttctcatg attctgactt ttccattcaa aattcttagt    480

gatgccaaac tgggaacagg accactgaga acttttgtgt gtcaagttac ctccgtcata    540

ttttatttca caatgtatat cagtatttca ttcctgggac tgataactat cgatcgctac    600

cagaagacca ccaggccatt taaaacatcc aaccccaaaa atctcttggg ggctaagatt    660

ctctctgttg tcatctgggc attcatgttc ttactctctt tgcctaacat gattctgacc    720

aacaggcagc cgagagacaa gaatgtgaag aaatgctctt tccttaaatc agagttcggt    780

ctagtctggc atgaaatagt aaattacatc tgtcaagtca ttttctggat taatttctta    840

attgttattg tatgttatac actcattaca aaagaactgt accggtcata cgtaagaacg    900

aggggtgtag gtaaagtccc caggaaaaag gtgaacgtca aagttttcat tatcattgct    960

gtattcttta tttgttttgt tcctttccat tttgcccgaa ttccttacac cctgagccaa   1020

acccgggatg tctttgactg cactgctgaa aatactctgt tctatgtgaa agagagcact   1080

ctgtggttaa cttccttaaa tgcatgcctg gatccgttca tctatttttt cctttgc      1137
```

<210> SEQ ID NO 202
<211> LENGTH: 609
<212> TYPE: DNA
<213> ORGANISM: Homo sapiens
<220> FEATURE:
<221> NAME/KEY: misc_feature
<223> OTHER INFORMATION: Incyte ID No: 2287109CT1

<400> SEQUENCE: 202

```
cgtgccagta tgtctattgt tttggtctaa ctttagctta gttagaaaga ggtaaaaaaa     60

aacttgaccc cttttctatt cctctggggc tcagtcaaga atttttagaa cagctttgaa    120

atttctgagt tctgagaata ttttctcctt tcagtttcct tcaaatggca aaagatgaaa    180

agagaaaatt attccaaaat gtcccaagat aatgtttgct gaagaagaaa aaacctgtcc    240

tgatatgcca aattctgctc ctggggggttt ccaaattgac tgcttcaaga ctttcacctt    300

accttttgat ctaaaaagtc accttcaaat ctcaagtttt caatgacttt tgaaggtgtg    360

actgcaatta tgttgcagct atggttgcta aaggggttaa tttttttttt agtctctaaa    420

caggatagta gaatattaaa tgtacatcag ctgtgaagca catgatcgtt gatagattgc    480

aactaagcca tataggaagt cttctctttg atttcaaatt attttattgt aatatattaa    540

attcgatact taatagaaag atttttagtg tccgcagtgg ccaaatactc tttcaaaaaa    600

aaaaaaaaa                                                            609
```

<210> SEQ ID NO 203
<211> LENGTH: 514
<212> TYPE: DNA
<213> ORGANISM: Homo sapiens
<220> FEATURE:
<221> NAME/KEY: misc_feature
<223> OTHER INFORMATION: Incyte ID No: 2289873CT1

<400> SEQUENCE: 203

```
ggaaattact ttgttacaat gtttgatgat tattctgcta cactgcctct gctaattgta     60

gtcattttgg agaatattgc tgtatgcttt gtttatggca tagataagtt tatggaagac    120

ctaaaagata tgctgggctt tgctcccagc agatattact actatatgtg gaaatatatt    180

tctcctctaa tgctattatc attgctaata gctagtgttg tgaatatggg attaagtcct    240
```

-continued

```
cctggctata acgcatggat tgaagataag gcatctgaag aatttctgag ctatccaaca    300

tggggactgg ttgattgtgt ctctctggtt gtctttgcaa tactcccagt ccctgtagtt    360

ttcattgttc gtcgcttcaa ccttatagat gatagttctg gtaatttagc atctgtgacc    420

tataagagag gaagggtcct gaaagagcct gtgaacttag agggcgatga tacaagcctc    480

attcacggaa aaataccgag cgagatgcca tctc                                514
```

<210> SEQ ID NO 204
<211> LENGTH: 478
<212> TYPE: DNA
<213> ORGANISM: Homo sapiens
<220> FEATURE:
<221> NAME/KEY: misc_feature
<223> OTHER INFORMATION: Incyte ID No: 2375491CT1

<400> SEQUENCE: 204

```
tcctgatttt taaaataata agaatgatgt atatttctta acatgatgat ttcagtccta     60

acatcagcat agctaacacg tcttgcatat ggggaaacac tagaggaatt ctcacttagg    120

tcaggaacca agacaaggat acccactatc tgcattaact gttggatata ctacccagca    180

cagtcaaata agaaaaaaac aactatccag tgtgatggct ctgatttaaa aaaaaaaaca    240

gagaaaaaaa tagctagagc cctaaaattt tattttactt ttttgagtat aaatttaagg    300

ggaacaagtg cagttttgtt acatggatat attgcctagt ggtgaagcct gggcctttaa    360

tgggaccatc gcccggatag tgtgcattgt accccatatg aaattactca acccttactc    420

acctaccacc cttctattat tttggagaca gtctcaacta tattgcccaa actggggt      478
```

<210> SEQ ID NO 205
<211> LENGTH: 502
<212> TYPE: DNA
<213> ORGANISM: Homo sapiens
<220> FEATURE:
<221> NAME/KEY: misc_feature
<223> OTHER INFORMATION: Incyte ID No: 2376547CT1
<221> NAME/KEY: unsure
<222> LOCATION: 407
<223> OTHER INFORMATION: a, t, c, g, or other

<400> SEQUENCE: 205

```
aacttgtaac tttctagttt tttactccat ttacaattat ctgtgctttt gaggttgttt     60

acatcttgta aataaactgc tcatttcttc ccatctctgg gctccatatc aaacattgga    120

agcttgaaat cagcttccaa acgtgcaaat acttttgttt gtatttaccc cagggaaatc    180

agcaaacact acaaatcagt gcttgattga ttattttatt agctgtcaag acttcagaaa    240

gtgatggaga aaatgttaac attgcaaata taaacttaaa agtgcattaa tgcctttcac    300

tattacatat tactttacat aatagtaaac acatatatta ttctgtatct gaaaactatt    360

aaatgatctg attcagcaac aaaaaagtgg ctcacatcat tgataanaca atggaatttt    420

gacattcatc ttctgaaaaa ttgaacgaaa ggggacactt ctaaactcag tttatgaggc    480

cagcattaac cgattacaaa ga                                             502
```

<210> SEQ ID NO 206
<211> LENGTH: 562
<212> TYPE: DNA
<213> ORGANISM: Homo sapiens
<220> FEATURE:
<221> NAME/KEY: misc_feature
<223> OTHER INFORMATION: Incyte ID No: 2377774CT1

<400> SEQUENCE: 206
gatcttctgg ctttattcat atcacaaaca aaaattctga aagacagcct gtttattgtc 60
atagaaatgg atataacctc acaaggagtg ttattaaagt tacttttgta agtgttttaa 120
aaacatgggc atgcagtttg tattaatagt gatactcctc tactgagtta ctgctaattt 180
gccattttcg cagtaatttc agaaaataag aaatcgttaa cattattgta ttatttaaat 240
actcccatgg atttctatta aggatgaata gcatcattac agtatttgtt agaaagtcat 300
atacatcacg atgcctgtaa tcccagcact ttgggaggcc gaggcgggtg gatcacgagg 360
tcaggagttt gagaccagcc tggccagcac agtgaaacct cgtccctact aaaaatacaa 420
aaaatcaacc ggccatggtg gcacacaact gtaatcccag ctactcagga ggctgaggca 480
ggagaaatgc ttgaacccag gaggcggaag ttgcagtgag ccgagatcgc gccactgcac 540
tccagcctgg caacagacaa gt 562

<210> SEQ ID NO 207
<211> LENGTH: 719
<212> TYPE: DNA
<213> ORGANISM: Homo sapiens
<220> FEATURE:
<221> NAME/KEY: misc_feature
<223> OTHER INFORMATION: Incyte ID No: 2378093CB1

<400> SEQUENCE: 207
ctcagaggtc tgtacctcga gggctcccat ggatagcctt gacagatcct gccaggactg 60
gtgcgacagg aagcaacact ggttggagat cggaccaccg gacttggtgg agcgcaaggg 120
ctccctgacc ctccgctccc atcacaagaa atactcgaag ccggtgttgg tgtattcctg 180
atttggacat cagaaacaca tgaaaagttg tcacaaatgt gtttaaacac agaatgggtt 240
gaaatgaaga gcaaggcttt attgaatgag gaaacagtga gctccgggat tatcgaaagg 300
gtcaccggat tgcctgccac aggttttgga gctgtctttc ctagacatcc accggattgg 360
agcaaaatgt gtgcattgac aacgtactca gaagattatg ttccaccata tgattatcag 420
ccacatgctt atccctgtca agatgattat tccatagtcc acagaaaatg ccgttctcag 480
ttcacggatc taaatggttc taaaagattt ggcatcaaca cttggcatga tgagagtggg 540
atttatgcta attcagatgt aaaacagaaa ctctatccct tgactagtgg gcctattgtg 600
ccaatttaaa aataatgtat agaatcagca tctctgacta atgaaaaatg gatgtagcag 660
ttgatgattt tctatcttaa taaatgcaat ggaagtgtta ctataaaaaa aaaaaaaaa 719

<210> SEQ ID NO 208
<211> LENGTH: 892
<212> TYPE: DNA
<213> ORGANISM: Homo sapiens
<220> FEATURE:
<221> NAME/KEY: misc_feature
<223> OTHER INFORMATION: Incyte ID No: 2378367CT1

<400> SEQUENCE: 208
actcttttgg cctgagacag aaaaacctaa aataaccctc aagaatgcca tgaaaatgga 60
aagtggaagc tgcaacacag ggagcatcct cctccatctc cctggtggcc aacatcgctg 120
tgaatctgat tgccttcctg gccctgctgt cttttatgaa ttcagccctg tcctggtttg 180
gaaacatgtt tgactaccca cagctgagtt ttgagctaat ctgctcctac atcttcatgc 240
ccttttcctt catgatggga gtggaatggc aggacagctt tatggttgcc agactcatag 300
gttataagac cttcttcaat gaatttgtgg cttatgagca cctctcaaaa tggatccact 360

-continued

```
tgaggaaaga aggtggaccc aaatttgtaa acggtgtgca gcaatatata tcaattcgtt    420

ctgagataat cgccacttac gctctctgtg gttttgccaa tatcgggtcc ctaggaatcg    480

tgatcggcgg actcacatcc atggctcctt ccagaaagcg tgatatcgcc tcgggggcag    540

tgagagctct gattgcgggg accgtggcct gcttcatgac agcctgcatc gcaggcatac    600

tctccagcac tcctgtggac atcaactgcc atcacgtttt agagaatgcc ttcaactcca    660

ctttccctgg aaacacaacc aaggtgatag cttgttgcca aagtctgttg agcagcactg    720

ttgccaaggg tcctggtgaa gtcatcccag gaggaaacca cagtctgtat tctttgaagg    780

gctgctgcac attgttgaat ccatcgacct ttaactgcaa tgggatctct aatacatttt    840

gaggtcagcc acttctccag tggaactctg aagtacagat gctgagattt tt            892
```

<210> SEQ ID NO 209
<211> LENGTH: 350
<212> TYPE: DNA
<213> ORGANISM: Homo sapiens
<220> FEATURE:
<221> NAME/KEY: misc_feature
<223> OTHER INFORMATION: Incyte ID No: 2378405CT1

<400> SEQUENCE: 209

```
ctcgggaggc tgaggcacaa gaatcgcttg aacctgggag gcaaaggttg cagtgagctg     60

agatcgtgcc actgcacgat ctctctctct ctatatgtat atgtatacta aaggtcacca    120

ataatttctt agtaaatata atgacatttt cttcaggact ttttatcctt cagaatcacg    180

ttaccttttt cttccttcaa tttctatgta tggttcaatt ctcagcattt actattttga    240

gaaagtacac ttactcactc tctttcctgt ttattcaaac aactcccaga tctgtgtctt    300

tattcctgac ctcttttcct catcaccagt attagagcac cgcctgccca               350
```

<210> SEQ ID NO 210
<211> LENGTH: 563
<212> TYPE: DNA
<213> ORGANISM: Homo sapiens
<220> FEATURE:
<221> NAME/KEY: misc_feature
<223> OTHER INFORMATION: Incyte ID No: 2378406CT1

<400> SEQUENCE: 210

```
ctctgaatta agagggtttt taatggtgaa ggtaatttcc tgttttctct gactcaagta     60

gaggaagcaa catcaagttc agaattagtc cttgaagttg acaacatttt agtaaggaat    120

ggttaatgtt attgagaaat ttaagtccta ggaaaaacca tccagaaata cttctgtgtt    180

agacatcatg tatgtgaaac atcatcttta ttttcaacaa aactagtagg gtaaatgtgc    240

taaaagtatc aaacactgaa ttgaaaaaat gtgtattatt acctgataaa acctgtagtg    300

gctaaaatct ctaaaagtaa cattagtctt ctagctaatg actaatgcta aagcagaaga    360

aagtttttaa gattcataaa atttaaatta ttccttaggt tgttgattct ttctatgttt    420

tactaaaatg gactggaaaa cattttgtgt gaaaggctag aaagtagaca ttttaggttt    480

gtagattctc tgtcaaatct actccattat gctattgtag cacaaaacca accatataca    540

acacataaac aaataaatag ata                                            563
```

<210> SEQ ID NO 211
<211> LENGTH: 371
<212> TYPE: DNA
<213> ORGANISM: Homo sapiens
<220> FEATURE:

```
<221> NAME/KEY: misc_feature
<223> OTHER INFORMATION: Incyte ID No: 2381364CT1

<400> SEQUENCE: 211

caggcccatt gttgtaggtg aggtggtttc ttttgtttga tatataacgt tttgctgact     60

ttcgacttgg gaattgcaaa ggcttaccca aaaccctgaa ggaaaagcta agaattcata    120

cttattaagc acttggtagg tgtctgacac tgtagtagat atatgcgaga gcccagaaca    180

agctgatgtc catgtacata tctttaaaaa atataatgat ctagtcttat ctgtggaaac    240

tgcttcagat actgatctta ctctttcctg ttacatcaga aattctggaa ggtaatatcc    300

tgaaagattt atcctcaaga ataacaatac attaaaatct tctgctttga aaatgcaaaa    360

aaaaaaaaaa a                                                         371


<210> SEQ ID NO 212
<211> LENGTH: 591
<212> TYPE: DNA
<213> ORGANISM: Homo sapiens
<220> FEATURE:
<221> NAME/KEY: misc_feature
<223> OTHER INFORMATION: Incyte ID No: 2381732CT1

<400> SEQUENCE: 212

gaaggacttt tactccaggg ctgttgggag ggaggccgga ccatttggca gtttgggctg     60

cagagattgg aaggccttct atgctgctgg cttgcgggga agctgttgga tctgtaggtt    120

gagctattcc tcttgacctg gagttcctaa acagagggat attctttttc tgtttcctta    180

gaaatcaaag gaaaaaaagc ttacaggctt ttaacttgct agttttatta ttatacttaa    240

gttctagggt acatgtgcag aacatgcagt tttgttactt aggtatacat ttgccatggt    300

ggtttgctgc acccatcaac ccgtcatcta cattaggtat ttctcctaac ttgctagttt    360

taaccctacc tgctagcctt ttcaaacaac ttccttcttc ctcccaccaa gagctaaaaa    420

tagaagtcag tactctttgt ttataatgac gtagagggtg catctgttct tttgggctgt    480

gcgtcctcct aacgcatgag tcctcaaact ttgggtgggg caattaacgg tccccttggg    540

taagcaagtt taaaatggcg gaactcctaa ggccccccttc cccaagaatt t            591


<210> SEQ ID NO 213
<211> LENGTH: 405
<212> TYPE: DNA
<213> ORGANISM: Homo sapiens
<220> FEATURE:
<221> NAME/KEY: misc_feature
<223> OTHER INFORMATION: Incyte ID No: 2383045CT1

<400> SEQUENCE: 213

aggttctggt taaacactgt aatgttgcca aatttttgag gatatattaa aatttgaagg     60

aatcttgatt tctaaagcta atacattttt tatattggct tgggaagaga cctaaggtca    120

taagtattat gagaacatat ttagcttgaa taagttacta tatgattttt atcaaaggaa    180

tgacatgaga cagatatgat gtagaactct gttatgaatc aaagtccact taaggaataa    240

aaaattacca ttacttattt aaggttcttc ttggccataa tttagaggat gaaaaaaaag    300

tgggcttgat actttcaaaa taacagggca gctgttgctg tctaatttgt tgaccaaatg    360

gagatttctg ccttcttggg atttccatgg aaaaaaaaaa aaaaa                    405


<210> SEQ ID NO 214
<211> LENGTH: 2612
<212> TYPE: DNA
```

-continued

<213> ORGANISM: Homo sapiens
<220> FEATURE:
<221> NAME/KEY: misc_feature
<223> OTHER INFORMATION: Incyte ID No: 2470285CT1

<400> SEQUENCE: 214

```
cccagacaag gcctttgggt gggttgaaag aactcaaagt cctaacgctc cagaataatc     60
agttgaaaac agtacccagt gaagccattc gagggctgag tgctttgagg acagttttga    120
aggacttgtt cagttacggc atctgtggct ggatgacaac agcttgacgg aggtgcctgt    180
gcaccccctc agcaatctgc ccaccctaca ggcgctgacc ctggctctca acaagatctc    240
aagcatccct gactttgcat ttaccaacct ttcaagcctg gtagttctgc atcttcataa    300
caataaaatt agaagcctga gtcaacactg ttttggtgga ctagataacc tggagacctt    360
agacttgaat tataataact tgggggaatt tcctcaggct attaaagccc ttcctagcct    420
taaagagcta ggatttcata gtaattctat ttctgttatc cctgatggag catttgatgg    480
taatccactc ttaagaacta tacatttgta tgataatcct ctgtcttttg tggggaactc    540
agcatttcac aatttatctg atcttcattc cctagtcatt cgtggtgcaa gcatggtgca    600
gcagttcccc aatcttacag gaactgtcca cctggaaagt ctgactttga caggtacaaa    660
gataagcagc atacctaata atttgtgcca agaacaaaag atgcttagga ctttggactt    720
gtcttacaat aatataagag accttccaag ttttaatggt tgccatgctc tggaagaaat    780
ttctttacag cgtaatcaaa tctaccaaat aaaggaaggc acctttcaag gcctgatatc    840
tctaaggatt ctagatctga gtagaaacct gatacatgaa attcacagta gagcttttgc    900
cacacttggg ccaataacta acctagatgt aagtttcaat gaattaactt cctttcctac    960
ggaaggcctg aatgggctaa atcaactgaa acttgtgggc aacttcaagc tgaaagaagc   1020
cttagcagca aaagactttg ttaacctcag gtctttatca gtaccatatg cttatcagtg   1080
ctgtgcattt tggggttgtg actcttatgc aaatttaaac acagaagata acagcctcca   1140
ggaccacagt gtggcacagg agaaaggtac tgctgatgca gcaaatgtca caagcactct   1200
tgaaaatgaa gaacatagtc aaataattat ccattgtaca ccttcaacag gtgcttttaa   1260
gccctgtgaa tatttactgg gaagctggat gattcgtctt actgtgtggt tcattttctt   1320
ggttgcatta tttttcaacc tgcttgttat tttaacaaca tttgcatctt gtacatcact   1380
gccttcgtcc aaattgttta taggcttgat ttctgtgtct aacttattca tgggaatcta   1440
tactggcatc ctaacttttc ttgatgctgt gtcctggggc agattcgctg aatttggcat   1500
ttggtgggaa actggcagtg gctgcaaagt agctgggttt cttgcagttt tctcctcaga   1560
aagtgccata tttttattaa tgctagcaac tgtcgaaaga agcttatctg caaaagatat   1620
aatgaaaaat gggaagagca atcatctcaa acagttccgg gttgctgccc ttttggcttt   1680
cctaggtgct acagtagcag gctgttttcc cctttttcat agaggggaat attctgcatc   1740
accccttttgt ttgccatttc ctacaggtga aacgccatca ttaggattca ctgtaacgtt   1800
agtgctatta aactcactag cattttttatt aatggccgtt atctacacta agctatactg   1860
caacttggaa aaagaggacc tctcagaaaa ctcacaatct agcatgatta agcatgtcgc   1920
ttggctaatc ttcaccaatt gcatcttttt ctgccctgtg gcgttttttt catttgcacc   1980
attgatcact gcaatctcta tcagccccga aataatgaag tctgttactc tgatattttt   2040
tccattgcct gcttgcctga atccagtcct gtatgttttc ttcaacccaa agtttaaaga   2100
agactggaag ttactgaagc gacgtgttac caagaaaagt ggatcagttt cagtttccat   2160
```

-continued

```
cagtagccaa ggtggttgtc tggaacagga tttctactac gactgtggca tgtactcaca   2220

tttgcagggc aacctgactg tttgcgactg ctgcgaatcg tttcttttaa caaagccagt   2280

atcatgcaaa cacttgataa aatcacacag ctgtcctgca ttggcggtgg cttcttgcca   2340

aagacctgag ggctactggt ccgactgtgg cacacagtcg gcccactctg attatgcaga   2400

tgaagaagat tcctttggct cagacagttc tgaccaggtg caggcctgtg gacgagcctg   2460

cctctaccag agtagaggat tccctttggt gcgctatgct tacaatctac caagagttaa   2520

agactgaact actgtgtgtg taaccgtttc ccccgtcaac caaaatcagt gtttatagag   2580

tgaaccctat tctcatcttt catctgggaa gc                                 2612
```

```
<210> SEQ ID NO 215
<211> LENGTH: 2340
<212> TYPE: DNA
<213> ORGANISM: Homo sapiens
<220> FEATURE:
<221> NAME/KEY: misc_feature
<223> OTHER INFORMATION: Incyte ID No: 2488060CT1
<221> NAME/KEY: unsure
<222> LOCATION: 2094
<223> OTHER INFORMATION: a, t, c, g, or other

<400> SEQUENCE: 215

gctttaatgt tccaaactcc tttaaaaaaa tggcattcta taggttcaag tggcaagttg     60

aaaggaaagg cttggccttc aaaattatct tggatccaaa aaaggttgga ccaatggtaa    120

aaggctcaag ttgtgggcaa gacgagtttt ttgaaagtat actggttaag gcatttacca    180

tatcctaaat ttgcactctt tggcagactt gtgcacatat attccgcttt cagaatagtt    240

ttgcaaattg tacacaaaca aaccaaaagg tggaagctct ccaataaaga aattgcattt    300

ataaatgatc tgtattagaa tataataaat ctccagttat agtcaattac tacccatgtt    360

gtacaacaga taccttctat tttagttgct aataaagggc tcggaattcg gctcgagcgc    420

tgctctgtga gactggaggt ttccccaaca ttcacccacc ccttggtatt ctcccaattc    480

tgttgccttt tgattcatac ttcacctcaa gaatccactt gctaaacacc caacaaaagg    540

ctgggaatag agcaaggaag gtaaaaggtg tctaggagag ttttctggca atgttggaag    600

tttctgctat attgagattt tgggtaagca tgagaaccgc agtacatacc ccgtcttcat    660

ccaagcgatc tgtgcacttc aaattagtat caagaatgac cttcatggtc tgagtgtacc    720

cgcccatgga cgcatgatgc aaagctgtcc agccattgtg gtcactggta aagagttaag    780

aaaaggtgtg tgcatacact taacagatga aatgcgggat gggatgccac ttggcttatt    840

ctaggtaaat ctgatgacaa caaaaagcat tattgagatc tggcaactaa atatttataa    900

aacatttata ataaatgagc taattccaag ctcaatgatc ttaaatgacc tatttctaat    960

gtgattcata cacgtttttt acttagtggt ttaaaatatg aaagtatata aacacattac   1020

caaacacttt ggggtaggag aagtacgctt agcatgtctg tgtcatacct aatttttttta   1080

aagctataat gaactgatac acatcaattt aaatcttgtt ttattctttc aatgaacact   1140

gtatcaaaat ttttttatga agtaatgtta gtctttgtgg tcaatagtta ttggtaatac   1200

tactagtaat atggtacatg gctataagat gcttagctta gtgtcagtta ttattctaag   1260

agtttaaatc taaaaagctt ccctcttgtg ctctgaaaaa tgcttactca attgctttga   1320

aaaatgttta tccttttcca cagaaattca agatgtaaat acaacaaagc cttgtcatat   1380

tagctatctt ttttcaaatt agacagaaaa aaattcgtga cactatttaa tttcagtgct   1440

agtgagcaga tgttttaggg tgcaagagcc atgttgctat ttcagttatg atgtaattaa   1500
```

```
gcaacaactg tctggcctgg gtctacttcg gtcccctttg caggtcagtt gcttggtgtt   1560

tctttgtaaa ccagaaaaaa actgagcaaa acattcattc atgtagctgt agcaccaatt   1620

tgctggcatc aatattatgg taaggaaatg tgtttttgaa cattagccta ataagctctt   1680

tgctactgct atggtaagat atcaaatgaa aaacctctgt aaaacatttc caggtttttt   1740

ctttcttatc acaatatcat ttaattatgc cacatatttt attatactta catattttaa   1800

ctttgtttct tgtacttgag ttcatttaag tataataaaa ttcagaaatt tttaccatca   1860

aaaaaaaaaa aaaggggggg gggtcccgac ctcgatttcg aaatcatgta aaagattttc   1920

ccggtgtaaa attgttaccc gcccaaattt ccacaaaact tggggccggg aggcttaagg   1980

tttaaaccct ggggtcccta atgggtggcc aaccccactt tatttgggtg gcgcaaattg   2040

ccggtttcca agtgggaaac cttgtggtcc aaacggttta atgaatcctc aaangcccgg   2100

ggaaaggggg ttttcctttt tgggggcttt tccggttcct cggccaattg acctcgtggc   2160

cccgggtttt cgggtttggg gggaggggtt ttaccccccc tcccaaaggg gggggaaaag   2220

ggggtttttc ccaaggttat ccgggggggta aaccccgcgg aaagaaacat tgttttccca   2280

aaaagggccc ccccaaaagg cgccagggcc ccttaaaaag aggccccttt ttttttgggt   2340
```

<210> SEQ ID NO 216
<211> LENGTH: 242
<212> TYPE: DNA
<213> ORGANISM: Homo sapiens
<220> FEATURE:
<221> NAME/KEY: misc_feature
<223> OTHER INFORMATION: Incyte ID No: 2503084H1
<221> NAME/KEY: unsure
<222> LOCATION: 229
<223> OTHER INFORMATION: a, t, c, g, or other

<400> SEQUENCE: 216

```
tgtgagttta tggtgaatca tgggtatgcc ctttatcaga ttgagttttg ctatactcga     60

caatttgcca gatcttccag aatgcaatta agttgttagg gtgaactcta catatctata    120

catattactt ctttatttcc tttgcttttt aattcttagc actgatgcat ctgagattaa    180

ggaagtgttt ttcaagattg gcattttggg ccagataatt acaattttna tttttttttt    240

aa                                                                   242
```

<210> SEQ ID NO 217
<211> LENGTH: 1153
<212> TYPE: DNA
<213> ORGANISM: Homo sapiens
<220> FEATURE:
<221> NAME/KEY: misc_feature
<223> OTHER INFORMATION: Incyte ID No: 2511221CT1

<400> SEQUENCE: 217

```
gtgcgccgga ggagcggcgg cgtggcgcac ggcgacatgg ccgttgtctc agaggacgac     60

tttcagcaca gttcaaactc cacctacaga accacaagca gcagtctccg agctgaccag    120

gaggcactgc ttgagaagct gctggaccgc ccgccccctg gcctgcagag gcccgaggac    180

cgcttctgtg gcacatacat catcttcttc agcctgggca ttggcagtct actgccatgg    240

aacttcttta tcactgccaa ggagtactgg atgttcaaac tccgcaactc ctccagccca    300

gccaccgggg aggaccctga gggctcagac atcctgaact actttgagag ctaccttgcc    360

gttgcctcca ccgtgccctc catgctgtgc ctggtggcca acttcctgct tgtcaacagg    420

gttgcagtcc acatccgtgt cctggcctca ctgacggtca tcctggccat cttcatggtg    480
```

```
ataactgcac tggtgaaggt ggacactttc tcctggaccc gtggcttttt tgcggtcacc    540

attgtctgca tggtgatcct cagcggtgcc tccactgtct tcagcagcag catctacggc    600

atgaccggct cctttcctat gaggaactcc caggcactga tatcaggagg agccatgggc    660

gggacggtca gcgccgtggc ctcattggtg gacttggctg catccagtga tgtgaggaac    720

agcgccctgg ccttcttcct gacggccacc atcttcctcg tgctctgcat gggactctac    780

ctgctgctgt ccaggctgga gtatgccagg tgtctagaag gctcccaaaa gcctattcct    840

tggaaaaacag catggcacgg gaatcagaga gagaaaggaa ccagatcaga cgaggagctc    900

tctctcaaga gtcctgcaga aagaacagaa cttacccccca agatgtggca acccttggag    960

ccgtgaatca gccctttgct tctctgcaga aacgcactgg ctcattggtg ccctgcagag   1020

gctgatgaaa cagaagcagt cagtaatcca gccggtggca gcagttcatg ctccccaccg   1080

tctcagccta gtacacattc cctctccttg gccgaagaat taaagaggac accttgaaag   1140

gtttctaggt cgt                                                       1153
```

```
<210> SEQ ID NO 218
<211> LENGTH: 430
<212> TYPE: DNA
<213> ORGANISM: Homo sapiens
<220> FEATURE:
<221> NAME/KEY: misc_feature
<223> OTHER INFORMATION: Incyte ID No: 2512109CT1

<400> SEQUENCE: 218

tgagactcca gggagtggga agtggccacc cctgccccaa ctgtattgct ggatagctcc     60

cattctcaaa cagtccttat ctacattgag agtgaatctg tctttttgta atgcaagcct    120

tttcatcttt gttctggtgt ctcatgtcat acggaatcta cctataactg cttttctaga    180

acatctttta agggtctgga ggtcactgtt atggcactgt ctaagctttc ttcatcccag    240

gtaaaacaac ttcaattcct tcaaccaggc ttcctaatgc caagtttcca ggccattccc    300

actctggttg tcctctacca caggtgcagg gcacaaatgg acccattcct gtctttataa    360

gaatgtccca ggacaggcgt gagccaccgc acctggccag taggagcctt ttctacgata    420

agtaagaata                                                           430
```

```
<210> SEQ ID NO 219
<211> LENGTH: 490
<212> TYPE: DNA
<213> ORGANISM: Homo sapiens
<220> FEATURE:
<221> NAME/KEY: misc_feature
<223> OTHER INFORMATION: Incyte ID No: 2553280CT1

<400> SEQUENCE: 219

gaaaaaaaaa tctgtcaagt cataaaaagg ctataggaat gatcatggtc gtgaccgctg     60

cctttttagt cagtttcatg ccatatcata ttcaacgtac cattcacctt catttttac     120

acaatgaaac taaaccctgt gattctgtcc ttagaatgca gaagtccgtg gtcataacct    180

tgtctctggc tgcatccaat tgttgctttg accctctcct atatttcttt tctgggggta    240

actttaggaa aaggctgtct acatttagaa agcattcttt gtccagcgtg acttatgtac    300

ccagaaagaa ggcctctttg ccagaaaaag gagaagaaat atgtaaagta tagtttaaac    360

ccatttccag tccaaaccaa tgaaaatagt ttcccaaata agtattttgt caaatcattt    420

acaaaaaaaa taaaaatttt acttaatatt ttacaaatac ttaactattt gggcctacaa    480
```

ctctatctta 490

<210> SEQ ID NO 220
<211> LENGTH: 723
<212> TYPE: DNA
<213> ORGANISM: Homo sapiens
<220> FEATURE:
<221> NAME/KEY: misc_feature
<223> OTHER INFORMATION: Incyte ID No: 2603450CT1

<400> SEQUENCE: 220
ttggagtgtg gaccatagca gttctggcac ttacttgtaa tgctttggtg acttcaacag 60
ttttcagatc ccctctgtac atttccccca ttaaactgtt aattggggtc atcgcagcag 120
tgaacatgct cacgggagtc tccagtgccg tgctggctgg tgtggatgcg ttcacttttg 180
gcagctttgc acgacatggt gcctggtggg agaatggggt tggttgccat gtcattggtt 240
ttttgtccat ttttgcttca gaatcatctg ttttcctgct tactctggca gccctggagc 300
gtgggttctc tgtgaaatat tctgcaaaat ttgaaacgaa agctccattt tctagcctga 360
aagtaatcat tttgctctgt gccctgctgg ccttgaccat ggccgcagtt cccctgctgg 420
gtggcagcaa gtatggcgcc tcccctctct gcctgccttt gccttttggg gagcccagca 480
ccatgggcta catggtcgct ctcatcttgc tcaattccct ttgcttcctc atgatgacca 540
ttgcctacac caagctctac tgcaatttgg acaagggaga cctggagaat atttgggact 600
gctctatggt aaaacacatt gccctgttgc tcttcaccaa ctgcatccta aactgccctg 660
tggctttctt gtccttctcc tctttaataa accttacatc atcagtcctg aagtaattaa 720
gtt 723

<210> SEQ ID NO 221
<211> LENGTH: 520
<212> TYPE: DNA
<213> ORGANISM: Homo sapiens
<220> FEATURE:
<221> NAME/KEY: misc_feature
<223> OTHER INFORMATION: Incyte ID No: 2605934CT1
<221> NAME/KEY: unsure
<222> LOCATION: 401
<223> OTHER INFORMATION: a, t, c, g, or other

<400> SEQUENCE: 221
cgcagaatga ccgcagtgcc cgtggcgctg tccctcaccg ctagcttcat gtcagccgtc 60
actgtcctgg gcaccccctc cgaggtctac cgttttgggg ccatttttag catctttgcc 120
ttcacctact tctttgtggt ggtcatcagc gcggaggtct tcctcccggt gttctacaaa 180
ctgggaatta ccagcaccta cgagtattta gaacttcgat ttaacaaatg tgttcgtctc 240
tgtggaacag tcctcttcat tgttcaaaca attctgtata ctggaattgt tatatatgcc 300
cctgccctgg ctttgaatca agtcacagga tttgatctgt ggggcgcggt agtggcaacg 360
ggggtggtct gcacattcta ctgcacactg ggtggtctta nagccagtat ctggacagat 420
gttttcaagt tgggatcatg gtgggctgat ttgcatcggt gaatatacag gctgtggtga 480
tgcaaggtga atcagcacta tttaaatgat gctatgatgg 520

<210> SEQ ID NO 222
<211> LENGTH: 532
<212> TYPE: DNA
<213> ORGANISM: Homo sapiens
<220> FEATURE:
<221> NAME/KEY: misc_feature
<223> OTHER INFORMATION: Incyte ID No: 2674641CT1

<400> SEQUENCE: 222

```
gctcatggca gctacccatg ctgtctacgg caagctgctc ctcttcgagt atcgtcaccg      60
caagatgaag ccagtgcaga tggtgccagc catcagccag aactggacat tccatggtcc     120
cggggccacc ggccaggctg ctgccaactg gatcgccggc tttggccgtg ggcccatgcc     180
accaaccctg ctgggtatcc ggcagaatgg gcatgcagcc agccggcggc tactgggcat     240
ggacgaggtc aagggtgaaa agcagctggg ccgcatgttc tacgcgatca cactgctctt     300
tctgctcctc tggtcaccct acatcgtggc ctgctactgg cgagtgtttg tgaaagcctg     360
tgctgtgccc caccgctacc tggccactgc tgtttggatg agcttcgccc aggctgccgt     420
caacccaatt gtctgcttcc tgctcaacaa ggacctcaag aagtgcctca ggactcatgc     480
cccctgctgg ggcacacgag gtgcccggct cccagagaac cctactgtgt ct             532
```

<210> SEQ ID NO 223
<211> LENGTH: 1228
<212> TYPE: DNA
<213> ORGANISM: Homo sapiens
<220> FEATURE:
<221> NAME/KEY: misc_feature
<223> OTHER INFORMATION: Incyte ID No: 2681738CT1

<400> SEQUENCE: 223

```
ccaacgtcaa tgtcttttct gagctttccg ctcctcgtcg caatgaagac tttgtcctcc      60
tgctcaccta cgtcctcttc ttgatggcgc tgaccttcct catgtcctcc ttcaccttct     120
gtggttcctt cacgggctgg aagagacatg ggcccacat ctacctcacg atgctcctct      180
ccattgccat ctgggtggcc tggatcaccc tgctcatgct tcctgacttt gaccgcaggt     240
gaggatgaca ccatcctcag ctccgccttg gctgccaatg gctgggtgtt cctgttggct     300
tatgttagtc ccgagttttg gctgctcaca aagcaacgaa accccatgga ttatcctgtt     360
gaggatgctt tctgtaaacc tcaactcgtg aagaagagct atggtgtgga gaacagagcc     420
tactctcaag aggaaatcac tcaaggtttt gaagagacag gggacacgct ctatgccccc     480
tattccacac attttcagct gcagaaccag cctccccaaa aggaattctc catcccacgg     540
gcccacgctt ggccgagccc ttacaaagac tatgaagtaa agaaagaggg cagctaactc     600
tgtcctgaag agtgggacaa atgcagccgg gcggcagatc tagcgggagc tcaaagggat     660
gtgggcgaaa tcttgagtct tctgagaaaa ctgtacaaga cactacggga acagtttgcc     720
tccctcccag cctcaaccac aattcttcca tgctggggct gatgtgggct agtaagactc     780
cagttcttag aggcgctgta gtattttttt tttttttgg ctcatcctta ggatacttct      840
tttaagtggg agtctcaggc aactcaagtt tagaccctta ctctttttgt ttgtttttg      900
aaacaggatc ttgctctgtc acccaggctt gagtgcagtg gtgcgatcac agcccagtgc     960
agcctcgacc acctgtgctc aagcaatcct cccatctcca tctcccaaag tgctgggatg    1020
acaggcgtga cgacagctcc cagcctaggc ccttaatctt gctgttattt ccatggccta    1080
aggtctggtc actgagctca cgctggtcaa aagtctagtg tgctgtccct aactccagtg    1140
ggtttgtaag cctgtgccaa acagactgca tactgacaaa atagcaacgc tcttagccca    1200
ttgctaattc actgaagcat tgttgttc                                       1228
```

<210> SEQ ID NO 224
<211> LENGTH: 441
<212> TYPE: DNA
<213> ORGANISM: Homo sapiens -continued
<220> FEATURE:
<221> NAME/KEY: misc_feature
<223> OTHER INFORMATION: Incyte ID No: 2723293CT1

<400> SEQUENCE: 224
caacggatgt gtgtgtttgt atgtttgtta acagttacat atgtttgtat gagtgtatat 60
atatatctgt gtgtgtgtat ctctaacgtc agtgtataag taagttgggt ttatggtggg 120
ctttgactat gtcattaggt gggtacaaaa cccaactgat gtggagaaaa attgatgttt 180
gatgttgata gatatgctta tacctaattt ttagttttta aactatttta aaatatacta 240
tgattttata tgtatatttc ctatagactc tttaagatgt atttataatg tttctaatat 300
gaaatcacta aactctagta cattatagca ggtgctttgt aatctggaat ggagaagagg 360
taggggcatt tggggattcc tgtttacttg ctgctgccac accttttccg actgatctgt 420
cctggtaggt gtttattagc a 441

<210> SEQ ID NO 225
<211> LENGTH: 648
<212> TYPE: DNA
<213> ORGANISM: Homo sapiens
<220> FEATURE:
<221> NAME/KEY: misc_feature
<223> OTHER INFORMATION: Incyte ID No: 2762348CB1

<400> SEQUENCE: 225
cttctttccc ttgtaaaagt aactgaagct taaaggtgaa aatgacttaa ataatagaaa 60
ccatgttagc cttactcccc ttcccgatta gccacaaatt ggtggcgatc accattttgt 120
gcaccgagcc tgggtctcac gcttgcaagt ccttgggctc atctggagtc agcttcatca 180
gtttgtccac acagagcagg atgagggtga ggaaccagag gctccagcca acagctgccg 240
cgatccagcc gtactcgtcc actcctgtgc ggcagcaccg ggctgcttgt gggcagaagt 300
ccacgttgag gcactgctcc agggtcccag ggtctgggtg gtgagcggtc aaggttgagc 360
tgttgctgct gcttgctgcc gagcaagccg agtggaggga ggcaaaggcc aggctgagga 420
tcagggtggc ccgggtggca gcggggaggc gctgcatgct ggaggctgtg ctgagtgccc 480
ggtgcaggtg agccggtcct gcggagttgt gccgagtgcc tgctgcagac cgaggctggg 540
ccaagatggc gtctgtgttt cgaagcgagg agatgtgttt gtcacaactg tttctccagg 600
tggaagctgc atattgctgt gtggctgagc tcggagactc ggattggt 648

<210> SEQ ID NO 226
<211> LENGTH: 611
<212> TYPE: DNA
<213> ORGANISM: Homo sapiens
<220> FEATURE:
<221> NAME/KEY: misc_feature
<223> OTHER INFORMATION: Incyte ID No: 2773609CT1

<400> SEQUENCE: 226
gggaggtgga ggttgcagtg agccaagagc acgccactgt actccagcct gggcgacaca 60
gcgagactcc atgtcaaaaa aacaaaaaca aaaaccactt ctcctccagt gcccctcaat 120
tagacaatag gcctgattta ttcctcactt acttattcat gcagtgcccc tgagaggagc 180
attactgaat caaaatggaa ttaactcaac aaatgtttat tgaacaccta ctatacacca 240
ggccctgttt catgtacttg ggatatagcc atgaatgaaa taagcaaaga tcagggaact 300
ttctagccag ggagaccaac aatgaacata aataagtaaa tgatacagta tgtgaggtga 360
cgaatgctgg ggaggaaaac taaaactaga ccaggtgagg tgaatcggga acactggggg 420

```
tggaggtggg gcaggtgggt tgaagggtgg gcctcattga cagagtgaca tttgggcaac    480

tattgaagga agtgggtgga ggaggtggca gccaggaggc tatccagcta ggaagagcct    540

tccaggcaga agaacattct agagcaaggc tctacagtgt ggtctggccg gggatgttgc    600

ttgcacaaca a                                                         611


<210> SEQ ID NO 227
<211> LENGTH: 611
<212> TYPE: DNA
<213> ORGANISM: Homo sapiens
<220> FEATURE:
<221> NAME/KEY: misc_feature
<223> OTHER INFORMATION: Incyte ID No: 2776266CT1

<400> SEQUENCE: 227

gggaggtgga ggttgcagtg agccaagagc acgccactgt actccagcct gggcgacaca     60

gcgagactcc atgtcaaaaa aacaaaaaca aaaaccactt ctcctccagt gcccctcaat    120

tagacaatag gcctgattta ttcctcactt acttattcat gcagtgcccc tgagaggagc    180

attactgaat caaaatggaa ttaactcaac aaatgtttat tgaacaccta ctatacacca    240

ggccctgttt catgtacttg ggatatagcc atgaatgaaa taagcaaaga tcagggaact    300

ttctagccag ggagaccaac aatgaacata aataagtaaa tgatacagta tgtgaggtga    360

cgaatgctgg ggaggaaaac taaaactaga ccaggtgagg tgaatcggga acactggggg    420

tggaggtggg gcaggtgggt tgaagggtgg gcctcattga cagagtgaca tttgggcaac    480

tattgaagga agtgggtgga ggaggtggca gccaggaggc tatccagcta ggaagagcct    540

tccaggcaga agaacattct agagcaaggc tctacagtgt ggtctggccg gggatgttgc    600

ttgcacaaca a                                                         611


<210> SEQ ID NO 228
<211> LENGTH: 681
<212> TYPE: DNA
<213> ORGANISM: Homo sapiens
<220> FEATURE:
<221> NAME/KEY: misc_feature
<223> OTHER INFORMATION: Incyte ID No: 2777115CB1

<400> SEQUENCE: 228

ccttacacat acaggaagac aagacctgag tggtgctgtc ttggtgtccg tcgtgtatgc     60

tcctccctgt cttcatttct tctcactctg tctctaaacc tctctctctc tccttgaccc    120

atcagtactt agtctacaga cctatgtgcg tgtccctatc cttctgtcct tttctctctt    180

cagctctccc tgcctctcac acacaatttt acatgccccg aggagccaag tttgggacat    240

ttaccctcca ggcatctgtg tcccctcttg aagagaaaac acacagcttc acacatccag    300

gcataggggg caagctcttg gggcatcagg accctggagc accaggtcct tcctggaata    360

ttagatccac ctggagcacc gggtctctct aagtctcacc tggggaattc ggtcccacct    420

ggggcaccag ttcccaccta gagcactgtg tcctgcccta gagcacaaag acctgctcct    480

cccgagactc tctctgactg cagccaggca tagtaccctt gcctgtgttt gctccctggt    540

ccacagattt ggtggctggg caggtgcctg gacagtgatg aggtcttgcc gccttaactg    600

tccccccag tcacttctcc cacaggccca gcaggacgca gtcctgagga tcagggattc     660

tacagctgca ttaaaatcaa c                                              681


<210> SEQ ID NO 229
```

<211> LENGTH: 1776
<212> TYPE: DNA
<213> ORGANISM: Homo sapiens
<220> FEATURE:
<221> NAME/KEY: misc_feature
<223> OTHER INFORMATION: Incyte ID No: 2812882CT1

<400> SEQUENCE: 229

```
ggaaaggagt ccagggggcc actcagatgg cgccagtcct cggagccctg tgcccaccac     60

acttcctggc ctccgccacg ccccctggca aggccctcga ggcccccccg acagcccaga    120

tgggtctccc ctcactcctg tgccttccca gatgccctgg cttgtggcca gcccagagcc    180

gcctcagagc tcacctacac ctgctttccc cctggctgcc tcctatgaca ccaatggcct    240

tagccagccc ccacttcctg agaaacgcca cctgcccggg ccggggcaac agccaggacc    300

ctggggccca gagcaggcat catcgccagc cagaggcatc agtcaccatg tcaccttcgc    360

acctctgctc tcagataatg tcccccaaac cccagagcct cctacacaag agagccaaag    420

caatgtcaag tttgtccagg atacatccaa gttctggtac aagccacacc tgtcccgtga    480

ccaagccatt gccctgctga aggacaagga ccctggggcc ttcctgatca gggacagtca    540

ttcattccaa ggagcttatg ggctggccct caaggtggcc acaccgccac ccagtgccca    600

gccctggaaa ggggaccccg tggaacagct ggtccgccat ttcctcatcg agactgggcc    660

caaaggggtg aagatcaagg gctgccccag tgagccctac tttggcagcc tgtccgcctt    720

ggtctcccag cactccatct cccccatctc cctgccctgc tgcctgcgca ttcccagcaa    780

agatcctctg gaagagaccc cagaggctcc agtgcccacc aacatgagca cagcggcaga    840

cctcctgcgt cagggtgctg cctgcagcgt gctctacttg acctcagtgg agacagagtc    900

actgacgggc ccccaagctg tggcccgggc cagctctgca gctctgagct gtagcccccg    960

cccgacacca gctgttgtcc acttcaaggt gtcagcccag ggcattacac tgacggacaa   1020

ccaaaggaag ctcttctttc gccgccatta tccagtgaac agcatcacct tctccagcac   1080

tgaccctcaa gaccggagat ggaccaaccc agacgggacc acctccaaga tctttggttt   1140

cgtggccaag aagccgggaa gcccctggga gaatgtgtgt cacctctttg cagagcttga   1200

cccagatcag cctgctggcg ccattgtcac cttcatcacc aaagttctac tgggccagag   1260

aaaatgaagg aaggccacaa gctcagagcc cacatcaaca ctgcccccct cccagcaccc   1320

cacagccctc acatcccctg gcctggaccc aggagaccca ggagaaagca ccctccctta   1380

ggaatgagga gtgggcatca ggcctgggac actgctctcc ttccccgccc ccagcctgct   1440

aagttaagtg gacaggccca caagatgacc ttgcatgtga gcagatggca gagatgggtg   1500

tgtgaggggt gaggaggcat cagcagttga gccccgaagg agatcaggca gccccacctg   1560

caggagaacg tcagccctcc aggggatcag cccctgccag ttccacccag ctgcaggtgc   1620

cagcacggca gggatgggag aggggtgggg agcgagtcac tgcctcctct gagcagagat   1680

tcagagtagg atcacatgaa taggggaaaa aagagagtct atttttgtct aataataaag   1740

aatttctata aactttagcc gaaaaaaaaa aaaaaa                             1776
```

<210> SEQ ID NO 230
<211> LENGTH: 624
<212> TYPE: DNA
<213> ORGANISM: Homo sapiens
<220> FEATURE:
<221> NAME/KEY: misc_feature
<223> OTHER INFORMATION: Incyte ID No: 2821121CT1

<400> SEQUENCE: 230

```
ttggactgtg gaccgctttc ctgtgtattg tccttgtggc aactgatgcc agttcccttg     60

tctgctacat tacccgtttc actgaagaag catttgcctc cctaatttgc attattttca    120

tctatgaagc aatagaaaaa ctgattcacc tggcagagac ctaccccatc cacatgcaca    180

gccagctgga ccaccttagc ctctattact gcaggtgtac tctgccagag aatccaaaca    240

atcacaccct ccagtactgg aaggaccaca acatcgtgac agcagaagtc cactgggcta    300

acctgactgt cagtgaatgc caggagatgc atggagagtt catgggatct gcgtgcggcc    360

atcatggacc ctacactcct gatgtcctct tttggtcctg tattctcttt ttcaccacct    420

tcatcctctc aagcacctta aagacgttta agacgagccg ttatttccca accagaatgg    480

agtcttgctc tgtcgcctgg ctggagtgcg gtggtgtgat cttggctcac tgcaacctcc    540

gcctcctccc gagtagctgg gactacaggc acgcaccacc acagccagct aatttttgta    600

tttttagtag agacggggtt tccc                                            624
```

<210> SEQ ID NO 231
<211> LENGTH: 769
<212> TYPE: DNA
<213> ORGANISM: Homo sapiens
<220> FEATURE:
<221> NAME/KEY: misc_feature
<223> OTHER INFORMATION: Incyte ID No: 2848989CT1

<400> SEQUENCE: 231

```
cggctcgagg ctgccccagc cgtgggcggg cacgggccac gtggtgtaca acggctccct     60

gttctataac aagtaccaga gcaacgtggt ggtcaaatac cacttccgct cgcgctctgt    120

gctggtgcag aggagcctcc cgggcgccgg ttacaacaac accttcccct actcctgggg    180

cggcttctcc gacatggact tcatggtgga cgagagcggg ctctgggctg tgtacaccac    240

caaccagaac gcgggcaaca tcgtggtcag ccggctggac ccgcacaccc tcgaggtcat    300

gcggtcctgg gacaccggct accccaagcg cagcgctggc gaggccttca tgatctgcgg    360

tgtgctctac gtgaccaact cccacctggc tggggccaag gtctacttcg cctattttac    420

caacacgtcc agttacgagt acacggacgt gcccttccac aaccagtatt cccacatctc    480

gatgctggat tacaaccccc gggagcgcgc cctctatacc tggaacaacg gccaccaggt    540

gctctacaat gtcaccctgt ttcacgtcat cagcacctct ggggacccct gagccaatgc    600

tgtggctcgg gctgctgcct ggggggcctc cgggggctgg gggccctttt cattctgcct    660

gtgtccctca agggtgatct ctctgtctct gtcacgccct ttctccccgc ctttttgctg    720

ggcttttgtt ctctgcctat gtatttctgt ctattttttc aatttcccc                 769
```

<210> SEQ ID NO 232
<211> LENGTH: 51
<212> TYPE: DNA
<213> ORGANISM: Homo sapiens
<220> FEATURE:
<221> NAME/KEY: misc_feature
<223> OTHER INFORMATION: Incyte ID No: 2854471H1

<400> SEQUENCE: 232

```
gtcagagaat gtttttttac atgaatgaac agattaaaaa tggaataata t              51
```

<210> SEQ ID NO 233
<211> LENGTH: 528
<212> TYPE: DNA
<213> ORGANISM: Homo sapiens
<220> FEATURE:

<221> NAME/KEY: misc_feature
<223> OTHER INFORMATION: Incyte ID No: 2854670CT1

<400> SEQUENCE: 233

```
aaaggtggca ctctcagccc tccctggagt ccacgccggc aggtgaagga tcagagcccc     60

atgccccatc cttggggcca ggggctggga cccaggtcac caggagcctc cagttgaagt    120

ggggaggtga ctggggtggt gcagtagtga gccatcccct cacacactgc cagccttgcc    180

cactgtgtcc tccctggccg cccggagctg tgtccgcctc ctgcctggct gcctgtgctc    240

ggcccctcca caagcccaaa acagccctag ggtactcagt gttttcagag ccgcctagat    300

gcagggctgt ttgtgttttg gttttaaatt tttttaatta atttattttt tatagagacc    360

aggtctcacc atgttgccca ggctggtttc aaacccctgg gctcaaatga cctgcccgcc    420

gcagcctccc caaagtgctg ggattataa gttttgagcc ccccgcatgc ccactggttt     480

taaattttta aaacggaaaa caatatttta taattcctcc gggctttt                 528
```

<210> SEQ ID NO 234
<211> LENGTH: 770
<212> TYPE: DNA
<213> ORGANISM: Homo sapiens
<220> FEATURE:
<221> NAME/KEY: misc_feature
<223> OTHER INFORMATION: Incyte ID No: 2855520CT1

<400> SEQUENCE: 234

```
gcgtcgcgct caccctgcgc gtgcccccgc ggcgcctggg cgtcttcctg gactacgagg     60

ccggagagct gtccttcttc aacgtgtccg acggctccca catcttcacc ttccacgaca    120

ccttctcggg cgcgctctgt gcgtacttca ggcccagggc ccacgacggc ggcgaacatc    180

cggatcccct gaccatctgc ccgctgccgg ttagagggac gcgcgtcccc gaagagaacg    240

acagtgacac ctggctacag ccctatgagc ccgcggatcc cgccctggac tggtggtgag    300

gcgccctcgt ggccgcggga ctggccccgg gggggccccc tggatcccag gccagcgctt    360

tgctctcctg ctccgtctga agggagcagg tgcaccagcc aaaatgtcag cgagggggac    420

aaagagaggg acctttgcct acgtagatgt gtatgtgtag tgcgattttc ttcaaggaaa    480

ggagacaagt ccaaagctcg tttgtggatt gtgggactga gcaaaggagt acaaatatat    540

ccacgtcgct cagagctggg gtgctcacgg tgggtggtgg gaaagaagcc agcatggaag    600

aaagaaggga gaaaactttg gtgactgcct tagagggatc agttaatttg tatagtttta    660

tattttttgt atatgtttgc tagctctaaa aaggtcgaga tgcaataaca cttcgtaagc    720

aacgagttca cctaagtaag gctcagatcc tagttttaaa aaccatttcc               770
```

<210> SEQ ID NO 235
<211> LENGTH: 260
<212> TYPE: DNA
<213> ORGANISM: Homo sapiens
<220> FEATURE:
<221> NAME/KEY: misc_feature
<223> OTHER INFORMATION: Incyte ID No: 2855815CT1

<400> SEQUENCE: 235

```
catcagtgtg tgcatgcgtg tgtgtgtgtg cgtgtcttta ttagtaacat ggatccagcc     60

tctactccag aagagtgtgt gcgtgtgtgt gtgtgtgtgt gtgtgtgtgt ctttattagt    120

aacatggatc cagcctctac tccaggtacc tgtatcaata gaattgcatt gtccttttta    180

gagtcccctc ctgaagaatt tttgcatctt gccttatttt cttactaaag gagttgtgtg    240
```

cagacgccct ctttcttttc 260

<210> SEQ ID NO 236
<211> LENGTH: 599
<212> TYPE: DNA
<213> ORGANISM: Homo sapiens
<220> FEATURE:
<221> NAME/KEY: misc_feature
<223> OTHER INFORMATION: Incyte ID No: 2857653CT1

<400> SEQUENCE: 236
tgcagtgagc caagatcgag ccattccact ccagcctgtg caaaagagcg agattccatc 60
tcaaaaaaaa aaaaaaaaaa aagagagaga gagagaaagt ctataagcaa gaggcacatc 120
acaatcctgt gtaacctaat catggaaggg atattccatc accttagtca tattctgttt 180
gttagaagaa agtcactggg ccatccccaca ctcaagggga ggtaattgca cacgtatgag 240
aatgccggga ggcagtatca atggggccac cttagagtct gcctgccaca gcctccagca 300
ctccagtgtc accaatttct ggcaacctct tatcaatgac aagttcactc aacccttcag 360
taccctcact gatgagtaat aaaaaaattg atcgagacca tggtgaaact ccgtctctac 420
taaaaataca aaaaattagc tgggtgtggt ggcgggcacc tgtagtccca gctactcagg 480
aggctgaggc aggagactgg cgtgaacctg ggaggcggag cttgcagtta gccgagatca 540
caccactgca ctccagcctg ggcaacacag tgagactctg tctcaaaaaa aaaaaaaaa 599

<210> SEQ ID NO 237
<211> LENGTH: 313
<212> TYPE: DNA
<213> ORGANISM: Homo sapiens
<220> FEATURE:
<221> NAME/KEY: misc_feature
<223> OTHER INFORMATION: Incyte ID No: 2866122H1
<221> NAME/KEY: unsure
<222> LOCATION: 10, 42, 49-50, 219, 246
<223> OTHER INFORMATION: a, t, c, g, or other

<400> SEQUENCE: 237
tggcacgcan ggtagctgca cctgtcgctg gctgcctgca cnaaccagnn ccacattgtc 60
aactacctga cggagaaccc ccacaagaag gcggacatgc ggcgccagga ctcgcgaggc 120
aacacagtgc tgcatgcgct ggtggccatt gctgacaaca cccgtgagaa caccaagttt 180
gttaccaaga tgtacgacct gctgctgctc aagtgtgcnc gcctcttccc cgacagcaac 240
ctggangccg tgctcaacaa cgacggcctc tcgcccctca tgatggctgc caagacgggc 300
aagattggga acc 313

<210> SEQ ID NO 238
<211> LENGTH: 547
<212> TYPE: DNA
<213> ORGANISM: Homo sapiens
<220> FEATURE:
<221> NAME/KEY: misc_feature
<223> OTHER INFORMATION: Incyte ID No: 2925464CT1

<400> SEQUENCE: 238
tgatcttggc tcacagggga cgatgtcaag ctcttcctgg ctccttctca gccttgttgc 60
tgtaactgct gctcagtcca ccattgagga acaggccaag acatttttgg acaagtttaa 120
ccacgaagcc gaagacctgt tctatcaaag ttcacttgct tcttggaatt ataacaccaa 180
tattactgaa gagaatgtcc aaaacatgaa taatgctggg gacaaatggt ctgccttttt 240
aaaggaacag tccacacttg cccaaatgta tccactacaa gaaattcaga atctcacagt 300

```
caagcttcag ctgcaggctc ttcagcaaaa tgggtcttca gtgctctcag aagacaagag    360

caaacggttg aacacaattc taaatacaat gagcaccatc tacagtactg gaaaagtttg    420

taacccagat aatccacaag aatgcttatt acttgaacca ggtttgaatg aaataatggc    480

aaacagttta gactacaatg agaggctgga agggaatttg atttcataaa atcggggggt    540

acgagct                                                              547


<210> SEQ ID NO 239
<211> LENGTH: 537
<212> TYPE: DNA
<213> ORGANISM: Homo sapiens
<220> FEATURE:
<221> NAME/KEY: misc_feature
<223> OTHER INFORMATION: Incyte ID No: 2954714CT1

<400> SEQUENCE: 239

atgttctttt tgttgtctac cgtaatagtc acaaaaatct atctagtata gtttgattgt     60

ccccctccc cagccattct gagtgtaatt tgaatatcac ctaggggaca ccttggttta    120

gagagcacag tcttaaccat tgatctcttt ttcctcacat aattgacatt ggttttataa    180

agaagaaaat atacaatgag tacatttata tctctgttta acataatttg catttatata    240

ttaaaataaa ttttgaaagt agatttcaaa atatccaggt acaaattagt gcctttatag    300

tttaagcaaa ttattatgct gtatagtaat gatacatcta gtatacttct ctgattaatt    360

tccaagttta gtatcttgac atttgttcaa tgtcagactt ttaatttaaa acctggacat    420

agacatttaa agatagctaa tgcatgaggg gcttaaaacc cagatgacag gttgatgggt    480

gcagcaaacc accgtggcac atgtatacct atgtaacaaa cctgcatgtt ctccaca       537


<210> SEQ ID NO 240
<211> LENGTH: 289
<212> TYPE: DNA
<213> ORGANISM: Homo sapiens
<220> FEATURE:
<221> NAME/KEY: misc_feature
<223> OTHER INFORMATION: Incyte ID No: 2986560CT1

<400> SEQUENCE: 240

gtgcaggagg tgtatagttt ttccagaaaa tgctaaaatt caaaaattat caccattcac     60

caatttgctt tttaatagta ggtgtgcttg caccaaaata ctcaatgcat cttagcatgc    120

agatagacca aagcactggc acaccctcct gccagaacac gtactccacg ggttctggta    180

ggagaagtaa gagaaccttg aggcgtggcg tctcttactt cctctgccaa ttgacaaacc    240

tgctgaggcc ctgacttgcc aagagcacct ggaatatgag aaatgtgag                289


<210> SEQ ID NO 241
<211> LENGTH: 787
<212> TYPE: DNA
<213> ORGANISM: Homo sapiens
<220> FEATURE:
<221> NAME/KEY: misc_feature
<223> OTHER INFORMATION: Incyte ID No: 3068234CB1

<400> SEQUENCE: 241

agagggactg cattctaata cggagctccg aggatgttca cttcttctcc acaatgaatg     60

agtgtcacta tgacaagcac atggactttt tttataatag gagcaacact gatactgtcg    120

atgactggac aggaacaaag cttgtgattg ttttgtgtgt tgggacgttt ttctgcctgt    180

ttattttttt ttctaattct ctggtcatcg cggcagtgat caaaaacaga aaatttcatt    240
```

```
tccccttcta ctacctgttg gctaatttag ctgctgccga tttcttcgct ggaattgcct    300

atgtattcct gatgtttaac acaggcccag tttcaaaaac tttgactgtc aaccgctggt    360

ttctccgtca ggggcttctg gacagtagct tgactgcttc cctcaccaac ttgctggtta    420

tcgccgtgga gaggcacatg tcaatcatga ggatgcgggt ccatagcaac ctgaccaaaa    480

agagggtgac actgctcatt ttgcttgtct gggccatcgc catttttatg gggcggtcc     540

ccacactggg ctggaattgc ctctgcaaca tctctgcctg ctcttccctg gcccccattt    600

acagcaggag ttaccttgtt ttctggacag tgtccaacct catggccttc ctcatcatgg    660

ttgtggtgta cctgcggatc tacgtgtacg tcaagaggaa aaccaacgtc ttgtctccgc    720

atacaagtgg gtccatcagc cgccggaaga cacccatgaa gctaatgaag acggtgatga    780

ctgtctt                                                              787


<210> SEQ ID NO 242
<211> LENGTH: 283
<212> TYPE: DNA
<213> ORGANISM: Homo sapiens
<220> FEATURE:
<221> NAME/KEY: misc_feature
<223> OTHER INFORMATION: Incyte ID No: 3077943CT1

<400> SEQUENCE: 242

ctctgtccca cctggctcat cagggaggtg cagaaggctg aagagagcaa agtccctgag     60

gactcactgg aggaatgtgc catcacttgt tcaaatagcc acggcccttg tgactccaac    120

cagcctcaca agaacatcaa aatcacattt gaggaagaca aagtcaactc atctctggtt    180

gtagacagag aatcctctca tgatgaatgt caggatgctc taaacattct cccaggtagc    240

ctctattttc cttgtgtctc atacctctgt ctaggctatg gaa                      283


<210> SEQ ID NO 243
<211> LENGTH: 203
<212> TYPE: DNA
<213> ORGANISM: Homo sapiens
<220> FEATURE:
<221> NAME/KEY: misc_feature
<223> OTHER INFORMATION: Incyte ID No: 3144006CT1

<400> SEQUENCE: 243

ccccgccaag gcccgtgcga gaggttagac ttgtttctta tatgtgatgc cattccagca     60

ctggactcca tctcaaaaaa aaaaaaaaga ttcacttatt tgaataagat acctcttatc    120

tttggtgtcg gtaactattt gtaaatagct ttcaaaataa ttgaactttt tttttaatat    180

tccctaaaaa ggagttcatg gtc                                            203


<210> SEQ ID NO 244
<211> LENGTH: 202
<212> TYPE: DNA
<213> ORGANISM: Homo sapiens
<220> FEATURE:
<221> NAME/KEY: misc_feature
<223> OTHER INFORMATION: Incyte ID No: 3226980H1
<221> NAME/KEY: unsure
<222> LOCATION: 44
<223> OTHER INFORMATION: a, t, c, g, or other

<400> SEQUENCE: 244

ctttgaccac gccctctttg gggaggtggc ctgccgcctc tacntgtttc tgagcgtgtg     60

ctttgtcagc ctggccatcc tctcggtgtc agccatcaat gtggagcgct actattacgt    120
```

-continued agtccacccc atgcgctacg aggtgcgcat gacgctgggg ctggtggcct ctgtgctggt 180
gggtgtgtgg gtgaaggcct tg 202

<210> SEQ ID NO 245
<211> LENGTH: 721
<212> TYPE: DNA
<213> ORGANISM: Homo sapiens
<220> FEATURE:
<221> NAME/KEY: misc_feature
<223> OTHER INFORMATION: Incyte ID No: 3290614CT1

<400> SEQUENCE: 245
gcaagtgacc cagggagaca aacacttgga gatacttggg gctgagtttg agcaagactc 60
cctaacctgt gtctggacaa gtctgatgtc ctgtgtggcc caagaagaac tgaccccgtg 120
tctggagctc ccaccgttat tgcatccctg ctgtggctca cctgctgctg tctccaggag 180
cccctgagaa gatttgcctc ctctcccctg ctaagctcca ggtcctgaga ttgaattagg 240
ggctggagct cactgcactc cagcagtcat gggacccagg atagggccag cgggtgaggt 300
accccaggta ccagacaagg aaaccaaagc cacaatgggc acagaaaaca cacctggagg 360
caaagccagc ccagaccctc aggacgtgcg gccaagtgtg ttccataaca tcaagctgtt 420
cgttctgtgc cacagcctgc tgcagctggc gcagctcatg atctccggct acctaaagag 480
ctccatctcc acagtggaga agcgcttcgg cctctccagc cagacgtcgg ggctgctggc 540
ctccttcaac gaggtgggga acacagcctt gattgtgttt gtgagctatt ttggcagccg 600
ggtgcaccga ccccgaatga ttggctatgg ggctggagct cactgcactc cagcagtcat 660
gggacccagg atagggccag cgggtgaggt accccaggta ccagacaagg aaacaaaggc 720
t 721

<210> SEQ ID NO 246
<211> LENGTH: 496
<212> TYPE: DNA
<213> ORGANISM: Homo sapiens
<220> FEATURE:
<221> NAME/KEY: misc_feature
<223> OTHER INFORMATION: Incyte ID No: 3291235CT1

<400> SEQUENCE: 246
gcctggcagt gcagtgggct ggctggtatg tgggggcctc tccctgctgg ccaatgcctg 60
gggcatcctc agcgttggcg ccaagcagaa gaagtggaag cccttggagt tcctgctgtg 120
tacgctcgcg gccacccaca tgctaaatgt ggccgtgccc atcgccacct actccgtggt 180
gcagctgcgg cggcagcgcc ccgacttcga gtggaatgag ggtctctgca aggtcttcgt 240
gtccaccttc tacaccctca ccctggccac ctgtttctct gtcacctccc tctcctacca 300
ccgcatgtgg atggtctgct ggcctgtcaa ctaccggctg agcaatgcca agaagcaggc 360
ggtgcacaca gtcatgggta tctggatggt gtccttcatc ctgtcggccc tgcctgccgt 420
tggctggcac gacaccagcg agcgcttcta cacccatggc tgccgcttca tcgtggctga 480
gatcggcctg ggcttt 496

<210> SEQ ID NO 247
<211> LENGTH: 282
<212> TYPE: DNA
<213> ORGANISM: Homo sapiens
<220> FEATURE:
<221> NAME/KEY: misc_feature
<223> OTHER INFORMATION: Incyte ID No: 3324775H1

<400> SEQUENCE: 247

```
ggctgccaag acgggcaaga ttgggatctt tcagcacatc atccggcggg aggtgacgga     60

tgaggacaca cggcacctgt cccgcaagtt caaggactgg gcctatgggc cagtgtattc    120

ctcgctttat gacctctcct ccctggacac gtgtggggaa gaggcctccg tgctggagat    180

cctggtgtac aacagcaaga ttgagaaccg ccacgagatg ctggctgtgg agcccatcaa    240

tgaactgctg cgggacaagt ggcgcaattc ggggccgtct cc                       282
```

<210> SEQ ID NO 248
<211> LENGTH: 287
<212> TYPE: DNA
<213> ORGANISM: Homo sapiens
<220> FEATURE:
<221> NAME/KEY: misc_feature
<223> OTHER INFORMATION: Incyte ID No: 3333159H1
<221> NAME/KEY: unsure
<222> LOCATION: 32
<223> OTHER INFORMATION: a, t, c, g, or other

<400> SEQUENCE: 248

```
gctgatcttt tcgttggagt tagctgcttg gntcctactc tgtcacttct ccactactcc     60

acaggtgtcc acgagtcatt gacttgccag gtttttggat atatcatctc agttctaaaa    120

agtgtttcta tggcatgtct tgcttgcatc agtgtggatc gttatcttgc aataaccaag    180

cctctttcct acaatcaact ggtcacccct gtcgcttgag aattgcatat tttgatctgg    240

atctactcct gcctaatttt ctgcctcctt ttttggcggg ggaaacc                  287
```

<210> SEQ ID NO 249
<211> LENGTH: 1491
<212> TYPE: DNA
<213> ORGANISM: Homo sapiens
<220> FEATURE:
<221> NAME/KEY: misc_feature
<223> OTHER INFORMATION: Incyte ID No: 3393404CT1

<400> SEQUENCE: 249

```
cagcagagtc acagaggaga tggccaactg ccaaatagcc atcttgtacc agagattcca     60

gagagtggtc tttggaattt ccccaactcct ttgcttcagt gccctgatct ctgaactaac   120

aaaccagaaa gaagtggcag catggactta tcattacagc acaaaagcat actcatggaa    180

tatttcccgt aaatactgcc agaatcgcta cacagactta gtggccatcc agaataaaaa    240

tgaaattgat tacctcaata aggtcctacc ctactacagc tcctactact ggattgggat    300

ccgaaagaac aataagacat ggacatgggt gggaaccaaa aaggctctca ccaacgaggc    360

tgagaactgg gctgataatg aacctaacaa caaaaggaac aacgaggact gcgtggagat    420

atacatcaag agtccgtcag cccctggcaa gtggaatgat gagcactgct tgaagaaaaa    480

gcacgcattg tgttacacag cctcctgcca ggacatgtcc tgcagcaaac aaggagagtg    540

cctcgagacc atcgggaact acacctgctc ctgttaccct ggattctatg ggccagaatg    600

tgaatacgtg agatagtgtg gagaacttga gctccctcaa cacgtgctca tgaactgcag    660

ccaccctctg ggaaacttct cttttaactc gcagtgcagc ttccactgca ctgacgggta    720

ccaagtaaat gggcccagca agctggaatg cttggcttct ggaatctgga caaataagcc    780

tccacagtgt ttagctgccc agtgcccacc cctgaagatt cctgaacgag gaaacatgac    840

ctgccttcat tctgcaaaag cattccagca tcagtctagc tgcagcttca gttgtgaaga    900

gggatttgca ttagttggac cggaagtggt gcaatgcaca gcctcggggg tatggacagc    960
```

-continued

```
cccagcccca gtgtgtaaag ctgtgcagtg tcagcacctg gaagccccca gtgaaggaac   1020

catggactgt gttcatccgc tcactgcttt tgcctatggc tccagctgta aatttgagtg   1080

ccagcccggc tacagagtga ggggcttgga catgctccgc tgcattgact ctggacactg   1140

gtctgcaccc ttgccaacct gtgaggctat ttcgtgtgag ccgctggaga gtcctgtcca   1200

cggaagcatg gattgctctc catccttgag agcgtttcag tatgacacca actgtagctt   1260

ccgctgtgct gaaggtttca tgctgagagg agccgatata gttcggtgtg ataacttggg   1320

acagtggaca gcaccagccc cagtctgtca agctttgcag tgccaggatc tcccagttcc   1380

aaatgaggcc cgggtgaact gctcccaccc cttcggtgcc tttaggtacc agtcagtctg   1440

cagcttcacc tgcaatgaag gcttgctcct ggtgggagta agtgtgctac a            1491
```

<210> SEQ ID NO 250
<211> LENGTH: 224
<212> TYPE: DNA
<213> ORGANISM: Homo sapiens
<220> FEATURE:
<221> NAME/KEY: misc_feature
<223> OTHER INFORMATION: Incyte ID No: 3429408H1
<221> NAME/KEY: unsure
<222> LOCATION: 103, 164, 166, 182, 207, 212
<223> OTHER INFORMATION: a, t, c, g, or other

<400> SEQUENCE: 250

```
gccgaacctg tggccgcttg gtggagccag gaggggcccg gggaggctgg gggctggacc     60

tcggagggct gccagctccg ctccagccag cccaatgtca gcnccctgca ctgccagcac    120

ttgggcaatg tggccgtgct catggagctg agcgcctttc ccangnaggt ggggggcgcc    180

gnggcagggc tgcaccccgt ggtatanccc tncacggcct tgct                     224
```

<210> SEQ ID NO 251
<211> LENGTH: 499
<212> TYPE: DNA
<213> ORGANISM: Homo sapiens
<220> FEATURE:
<221> NAME/KEY: misc_feature
<223> OTHER INFORMATION: Incyte ID No: 3447545CB1     Contig1

<400> SEQUENCE: 251

```
ccatccgagg ccagagccca ggtagcagcc acagctctga cctattgtct gtctgtctgt     60

ctgtcttctc tgcagttctg aaagccccat ggccccagca ggcctctgag ccccaccatg    120

ggcagcttgt actcggagta cctgaacccc aacaaggtcc aggaacacta taattatacc    180

aaggagacgc tggaaacgca ggagacgacc tcccgccagg tggcctcggc cttcatcgtc    240

atcctctgtt gcgccattgt ggtggaaaac cttctggtgc tcattgcggt ggcccgaaac    300

agcaagttcc actcggcaat gtacctgttt ctgggcaacc tggccgcctc cgatctactg    360

gcaggcgtgg ccttcgtagc caataccttg ctctctggct ctgtcacgct gaggctgacg    420

cctgtgcagt ggtttgcccg ggacggtctg ccttcatcac gctctcggcc tctgtcttca    480

gcctcctggc catcgccat                                                 499
```

<210> SEQ ID NO 252
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 3486012CT1

<400> SEQUENCE: 252

```
tgttaataag ccaatagcga tgaactgctc caacctctgg ggaaacttca gttatggatc     60

aatctgctct ttccattgtc tagagggcca gttacttaat ggctctgcac aaacagcatg    120

ccaagagaat ggccactggt cacctaccgt gccaacctgc caagcaggac cattgactat    180

ccaggaagcc ctgacttact ttggtggagc ggtggcttct acgataggtc tgataatggg    240

tgggacgctc ctggctttgc taagaaagcg tttcagacaa aaagatgatg ggaaatgccc    300

cttgaatcct cacagccacc taggaacata tggagttttt acaaacgctg catttgaccc    360

gagtccttaa gagacctgtc cttttcctgg tctcctcatt cagcctccat atgatcctgt    420

tgtgaacatc aagtttcctg ctacactgga cttaactata atgcatttgc tgcaggtttc    480

cataacaccc atgaatcaaa gacatggaat taccttagat tagctctgga ccagcctgtt    540

ggacccgc                                                             548


<210> SEQ ID NO 253
<211> LENGTH: 560
<212> TYPE: DNA
<213> ORGANISM: Homo sapiens
<220> FEATURE:
<221> NAME/KEY: misc_feature
<223> OTHER INFORMATION: Incyte ID No: 3513925CT1

<400> SEQUENCE: 253

ggagaaagga atacaggagt gatggaggag gaaaggaggg acagggaagg agagaaggaa     60

ggaagcagga tgaagagacg gaacgagata ggtaggtgta tggatgggag ggagggaaaa    120

acgaacaata aatagataga ctctagatct cctaaaggcc catatctaag caatttttgt    180

gtccccagga ggcagatttg ataaagaaat ctgtctacta gattccattg gcatctttta    240

aatgattata atcatagatg actttttag tgcttgcact ttgtcaagca ctatgctaaa     300

acttctgcat acatttttta atgtaagtct cagaacaacc ctgtaagtag attattttgc    360

ctactccact gtgaggttca gagaagtcct tgcccacagg gccacacaca attagaaaat    420

atcagagcca gggtgtgccc cagccgagag gtggctccag tgcccctgct cttgcctgca    480

tttggaactg cctgtgaata gttggcattt tccgagtgct tactttgtgc ccatgtgttg    540

cagacacatc tcattttcat                                                560


<210> SEQ ID NO 254
<211> LENGTH: 712
<212> TYPE: DNA
<213> ORGANISM: Homo sapiens
<220> FEATURE:
<221> NAME/KEY: misc_feature
<223> OTHER INFORMATION: Incyte ID No: 3542591CT1

<400> SEQUENCE: 254

gcttcctaga aggtaatgta cgaactcgtc tccaaaggat acttaggttg caccagtgta     60

tttgtaaaac aggagcaaat ttggaccttg ccgggccaaa gtacgaattc tttttcaaat    120

cttaatatca agtcctgaaa tgaaattatc tctgttctgt ttctttttac cttttcttgt    180

gtgggtgaac tgaccaactt ttaagtctag ttccctgttg gacagacttt tctcaactca    240

ttacctatcc ccctaccgtc catatgggcc tccaggctct ctcacggact cctaactgcc    300

tcctttaaaa atgtaataat agtaagtaag aaattaaatt ttttctaaat tccctcccac    360

tacgggcccc ccttacaccg aaactccccc caatggccta gaaataaatt aggggtccgg    420

tgggcccacg cgtgggagaa acccttctcc ttaaaaagcc tcccaaggct ttttccgcgg    480
```

```
gaaaaggctt tccccgggga aaatgggggg agaaaaattt ttcccacagg ggttccccag    540

attaggagaa ttttccccac ggattaatct caccacatat tgccccctgt tgggggaaaa    600

gagtccctct aagttaaatt tttcccccca aaaaaatatt tttgggaaga ggctcttaaa    660

aaaatggtct cgggtggaga catcttttgt ccccaaatat ttgtgggccg cg            712


<210> SEQ ID NO 255
<211> LENGTH: 1126
<212> TYPE: DNA
<213> ORGANISM: Homo sapiens
<220> FEATURE:
<221> NAME/KEY: misc_feature
<223> OTHER INFORMATION: Incyte ID No: 3556218CT1

<400> SEQUENCE: 255

actggtctat agctggcttt cattccattg agcaataagg aatttttcaa aactactatg     60

cacccaatgg agtatgcttc cctcttcatt cagaagatac agaaagtatt ggagcccaga    120

tttattcagt ggcaattttt cttggtatta atttggccgc atttatcatc acagtttttt    180

cctatggaag catgttttat agtgttcatc aaagtgccat aacagcaact gaaatacgga    240

atcaagttaa aaaagagatg atccttgcca aacgtttttt ctttatagta tttactgatg    300

cattatgctg gatacccatt tttgtagtga aatttctttc actgcttcag gtagaaatac    360

caggtaccat aacctcttgg gtagtgattt ttattctgcc cattaacagt gctttgaacc    420

caattctcta tactctgacc acaagaccat ttaaagaaat gattcatcgg ttttggtata    480

actacagaca aagaaaatct atggacagca aaggtcagaa aacatatgct ccatcattca    540

tctgggtgga aatgtggcca ctgcaggaga tgccacctga gttaatgaag ccggaccttt    600

tcacataccc ctgtgaaatg tcactgattt ctcaatcaac gagactcaat tcctattcat    660

gactgactct gaaattcatt tcttcgcaga gaatactgtg ggggtgcttc atgagggatt    720

tactggtatg aaatgaatac cacaaaatta atttataata atagctaaga taaatatttt    780

acaaggacat gaggaaaaat aaaaatgact aatgctctta caaagggaag taattatatc    840

aataatgtat atatattagt agacattttg cataagaaat taagagaaat ctacttcagt    900

aacattcatt catttttcta acatgcattt attgagtacc cactactatg tgcatagcat    960

tgcaatatag tcctggaagt agacagtgca gaacctttca atctgtagat ggtgtttaat   1020

gacaaaagac tatacaaagt ccatctgcag ttcctagttt aaagtagagc tttacctgtc   1080

atgtgcatca gcaagaatca tagcgatttt aaatagaggt gtggac                  1126


<210> SEQ ID NO 256
<211> LENGTH: 456
<212> TYPE: DNA
<213> ORGANISM: Homo sapiens
<220> FEATURE:
<221> NAME/KEY: misc_feature
<223> OTHER INFORMATION: Incyte ID No: 3665056CT1
<221> NAME/KEY: unsure
<222> LOCATION: 450
<223> OTHER INFORMATION: a, t, c, g, or other

<400> SEQUENCE: 256

gaatttaatc tttaggaaga cagatcacat actatatagc aactagtgag gtgttttaga     60

gaaataattc tttcttcttt tatagaattg gaatgttatg tgctgtgcaa ttatgcatac    120

tagatttatg gcaagaacaa aagaagaaag aatttaatct ttaggaagac agatcacata    180

ctatatagca actagtgagg tgttttagag aaataattac acatctattt ttgaaatgat    240
```

```
caggaattaa agaactctga tatgtatata ttaatgtatt tttctattag gataatagag    300

aatttttaac aacaacaaaa aaaaaacaga caaaagcctg ggtgctcaca cctgtaatcc    360

cagcactttg ggagatggag gcaggaggat catctgaggt caggagttca agaccagcct    420

gggcaatatg gtgaaccccca ttatggttgn attcgt                             456


<210> SEQ ID NO 257
<211> LENGTH: 202
<212> TYPE: DNA
<213> ORGANISM: Homo sapiens
<220> FEATURE:
<221> NAME/KEY: misc_feature
<223> OTHER INFORMATION: Incyte ID No: 4043152H1
<221> NAME/KEY: unsure
<222> LOCATION: 9, 56
<223> OTHER INFORMATION: a, t, c, g, or other

<400> SEQUENCE: 257

gggaaagana gggagttcct aacctctagg ggaaccccca ttaaatatta caaggnaacc     60

atggagttat tgcacacagt acaaaaacca aggaggtggc agtcttatac agatgaagcc    120

atcaaaaagg gaaggagagg ggagaacggc agcataagca gctggcagaa gcagcagaaa    180

ggaaatagag aaagagacag aa                                             202


<210> SEQ ID NO 258
<211> LENGTH: 65
<212> TYPE: DNA
<213> ORGANISM: Homo sapiens
<220> FEATURE:
<221> NAME/KEY: misc_feature
<223> OTHER INFORMATION: Incyte ID No: 4080842H1
<221> NAME/KEY: unsure
<222> LOCATION: 2, 5, 23
<223> OTHER INFORMATION: a, t, c, g, or other

<400> SEQUENCE: 258

anganttact ttaggtaaga ggnaaccagg agtgcacaga ttgaaaaata gcagcaatag     60

ctatc                                                                 65


<210> SEQ ID NO 259
<211> LENGTH: 562
<212> TYPE: DNA
<213> ORGANISM: Homo sapiens
<220> FEATURE:
<221> NAME/KEY: misc_feature
<223> OTHER INFORMATION: Incyte ID No: 4081268CT1
<221> NAME/KEY: unsure
<222> LOCATION: 540
<223> OTHER INFORMATION: a, t, c, g, or other

<400> SEQUENCE: 259

ttgaacacaa agcacacagc ccattgccca gcacatagta agaattcaac aaatttagtt     60

ttgtttttta tctatttttt tgcacctcat aaatttttcc tgttttgaag aacaaaatac    120

taaagtggag cctatctgag gcacatcttc ataagtgtct ccaaccagcc tttattcatt    180

ggcattaaga tattgaacat gcagacttta ggaggcttaa ttttttctgc tctggcctgc    240

aggttggagg tttcactaca ttttaataaa aacccttgca aagcaactta cagatctaaa    300

taaaaacaat gttttgctta tttagctggt ttcatagttg tgccttttaa aagaatgtta    360

gtcccatgta ctttgcaagg gttttcctgc ccatttagaa tggtggcaac aagtgaccca    420

gctggcggag gccccagggt taccatctat aggccccagc atgggtacgg ggagaccttg    480

ctggggtgtt gggggaagaa gggagagcca ttttcccaca ggtagcctga acacccctgn    540
```

```
aacacagggg ctttcttggg gg                                         562


<210> SEQ ID NO 260
<211> LENGTH: 234
<212> TYPE: DNA
<213> ORGANISM: Homo sapiens
<220> FEATURE:
<221> NAME/KEY: misc_feature
<223> OTHER INFORMATION: Incyte ID No: 4082591CT1

<400> SEQUENCE: 260

ggaatccata actgacctaa gcaatgtgag aaaacatgaa aatgaaactc taggtcagtc    60

tctttttcaa atatgaataa aggaatcctc catgagaaat taacaataag acttagtaat   120

gcatttaaaa aatagtactt cctgaccaag tagggtttat ctcaatattg aaaggttagt   180

ttacttttag aatttatcag taaatgtgtc atattggcat attaaaaaag aaaa         234


<210> SEQ ID NO 261
<211> LENGTH: 541
<212> TYPE: DNA
<213> ORGANISM: Homo sapiens
<220> FEATURE:
<221> NAME/KEY: misc_feature
<223> OTHER INFORMATION: Incyte ID No: 4084463CB1

<400> SEQUENCE: 261

gccagttact gaaagcagat ataacgcgga tcctgtaaag agtgctttag atgctaacat    60

tgaagatgca caaccatgag gatgtaggag actggatccc tgaatcactg cttggatgat   120

agcagcaagc ttctttggcg ttaaacaact tagatattct gataaagcat ctactgttgc   180

cttaattaag gagagatgga taatattttc ttggatgaaa gtgatagagg tgaggatgaa   240

gagaagtggt cagattctac atacaattat cagagaaaca ggaattcctg agaatatgga   300

tatgatgaga agaaaggaag tcttgccatg ttgtccagat tggtcccaaa ttcctgggct   360

caagcgatca gccacctcgg cctcccaaag tattgggatt acaggcatga gccactgccc   420

gcagccaggt ttttgtgact caggggaagg atgatgtcaa gctgttgtca agccaattgc   480

atggaaagag aagaattaac gtgttctccc ttcaaaatga tggattccat ggctccacat   540

t                                                                   541


<210> SEQ ID NO 262
<211> LENGTH: 708
<212> TYPE: DNA
<213> ORGANISM: Homo sapiens
<220> FEATURE:
<221> NAME/KEY: misc_feature
<223> OTHER INFORMATION: Incyte ID No: 4085069CT1

<400> SEQUENCE: 262

caggaagacc tccaggagta aaagttaagg cttcaaaagc atggcaaaga tgtagatttg    60

gagaaattcc atccatgtgc atttggtaag caccttgggc tggtgggtaa attcttaaaa   120

tttaaaatat agcacttctc cctggagcag tagttctcaa agtggtcctt ggaccaacag   180

caggtaagtt ccctgggaac ttatcaaaaa tgcaaggtct caagccctac ccccagaccc   240

tctgaatcag aaactctgag ggtggagcca ggaagctgtg tttgaacaag ccctccaaaa   300

gacactgatg catgctgaag ttagctgctg ctttagagaa actgttaatg agtttgggga   360

aataagagat acatacatga aatggctgga ggagactcaa gcattatgca tgacatttag   420

tgaacgtaaa agacggagtc tagacaactt tatttccata atattaacaa aggacaatcc   480
```

```
tctcttaaaa ttcctggggt cagatgaatt tctaaattca gattttgttt ttcaatttag    540

aaaggtaaaa tgtgcatgta ccatatatta cataatacct ttggtaaggt ctggggtgac    600

actctaatat actaattttc tgcaagggaa atcatgaatg acataagtgt atgcttggat    660

tatctactgc aatgtaataa atgttcacaa aataaaaaaa aaaaaaaa                708


<210> SEQ ID NO 263
<211> LENGTH: 255
<212> TYPE: DNA
<213> ORGANISM: Homo sapiens
<220> FEATURE:
<221> NAME/KEY: misc_feature
<223> OTHER INFORMATION: Incyte ID No: 4129226CT1

<400> SEQUENCE: 263

aaaagtcagc ataaaatatg atccaactaa aagggattaa tttttggcat ttttgtatat     60

ttatgcatta ggtgatggga cttttaaagg tttgaattta ttaggacacg aactaaaaat    120

aaaagtgcac taggggacag ttgatttcaa tctaagaaaa gttaacactt gggaattaca    180

agaagtaaaa caagtgcaac taaatcattt attagttgtt ttttgaaagc agttttatgt    240

ataaataaca aatgt                                                    255


<210> SEQ ID NO 264
<211> LENGTH: 223
<212> TYPE: DNA
<213> ORGANISM: Homo sapiens
<220> FEATURE:
<221> NAME/KEY: misc_feature
<223> OTHER INFORMATION: Incyte ID No: 4129407CT1
<221> NAME/KEY: unsure
<222> LOCATION: 71, 86
<223> OTHER INFORMATION: a, t, c, g, or other

<400> SEQUENCE: 264

gattttgaaa gaatccttga ggcaatgaag cagagttgtg aaatgaaaaa catttttcac     60

tctttgcagc nactaccttt catagnctga cttcttaaag tgagacttat atttagtaat    120

tctgcttcat aacctcattt attctcattc actgcaaatt cacatctatt gccatcactc    180

cactgaaact agttttccat gccaaaagct gctcctctcc caa                     223


<210> SEQ ID NO 265
<211> LENGTH: 332
<212> TYPE: DNA
<213> ORGANISM: Homo sapiens
<220> FEATURE:
<221> NAME/KEY: misc_feature
<223> OTHER INFORMATION: Incyte ID No: 4130289CT1
<221> NAME/KEY: unsure
<222> LOCATION: 19, 217
<223> OTHER INFORMATION: a, t, c, g, or other

<400> SEQUENCE: 265

caggaataaa aagttaganc tcaccccacc atctgcggtg agaaaaccag agggtacttt     60

tcaattgcca tcgagccagc agtggggaag tgctgctttg ttcagaatga gcttggccag    120

aatggccaga gcttcatctt tgactacagc atcatcaatt aagaagcaat tcacaatata    180

tgacagaaag cttggtagaa aaagctaaag ttaaganaaa aaaaatcaca cttattaaca    240

gatataataa agagaagatg ctaacattca aaactagacc aaaaacaaag gatcaagaat    300

cacatggctt agacctctac ataggaacat gg                                 332
```

-continued

<210> SEQ ID NO 266
<211> LENGTH: 649
<212> TYPE: DNA
<213> ORGANISM: Homo sapiens
<220> FEATURE:
<221> NAME/KEY: misc_feature
<223> OTHER INFORMATION: Incyte ID No: 4130748CT1

<400> SEQUENCE: 266

```
cggggggctt ccccgcgcgg agccgaccct tcgccccatt gggacccatc ccaatcatcc     60

gaaggccacg gccttaataa gcccctgtgt aaaccccggg tcgaatcgat gccaacccgt    120

gtgcctggtc caagtttcct ggtggttgac ctgggcgaat aaaaataaga catgttctgc    180

agagttctcc ttttaaattc cttgtgtaat attccgtttg ttttgctcct ttgcaattaa    240

ctacaaactt ctaagtccta gaaaagattt caagtattta tagagtgagc aacgatcatt    300

ttcctagtca aatagtatgg caaaaatcac tgttttaaaa agttgtggca ttaaactata    360

aatcctccct cccctcgctt cccaccccca attatgaaag aaaagcatat gacaatgcct    420

actgggctca gcttttgggc taattgagtc tgactgagcc ttcttagcag gttcctgtct    480

tttgaaacct caaatcccaa aaagctgtct aataatttta cttttttagg gactaagacc    540

aggtattttc agcagaggtt cttacttttc tgtaattgag gcgcaactat aatgttccag    600

aacacaatct taaatctgaa agtgagagga agaaaaaaaa aaaaaaggg               649
```

<210> SEQ ID NO 267
<211> LENGTH: 786
<212> TYPE: DNA
<213> ORGANISM: Homo sapiens
<220> FEATURE:
<221> NAME/KEY: misc_feature
<223> OTHER INFORMATION: Incyte ID No: 4131249CB1

<400> SEQUENCE: 267

```
tttgaaatag gcatgaaaat ttgaaatgat tatgttgctg atttcttttg ataataaaat     60

ggtaatttgt aaaaactatc ctacaactac cctttaggat aaaaatttat gtaaaaacat    120

tacagtttag agacaggtaa tctagaataa actcaataaa atatttcttc ctttgttata    180

aaacaaagta aaagacaaaa atattcaata cagagaacat attcagttga ttttgtttac    240

atgctgttat tgttcggcag gtattttctt tggagggata agaaaaaatt tggggggggg    300

gaaaaaaaaa accccccggg gggaaaacta aagggggggg gggtcaattt tgttgtagag    360

gaagcacgag gctttccttt ttactcctcc agcttgagat agtgtgtgtg ttttctgtgt    420

gtgtcttctc gtgtgctgat cgttccaacg tgtgaaggtg ggtcgacgtc agcgcgttgc    480

ttaccggtgg tactcggcgt cgtagcgacg ttcgcacgcg gtgttggctc cggtggactt    540

gccgcgacgc tcctcgcccc actccttcac tgggagtttg cgctatttca acacgtatct    600

cacgctctcg tgttgagtga gttgtgcgtc tcactggtac gcgttgtgat gtagttgaac    660

ggagcggaac gttgcgcggc ttcatcggcg gtagtgtgtg ttcggctcaa gacctgccgc    720

agtgcgttgc gtctctgggc tcttgttcgt ggtgagctgc gctgcgacgt agctactctc    780

ctcttg                                                               786
```

<210> SEQ ID NO 268
<211> LENGTH: 59
<212> TYPE: DNA
<213> ORGANISM: Homo sapiens
<220> FEATURE:
<221> NAME/KEY: misc_feature
<223> OTHER INFORMATION: Incyte ID No: 4132125H2

<400> SEQUENCE: 268
aaaaggagga gggaagagct ctgcgcgctc ccgccctcag cgccgcgagg ccggcggat 59

<210> SEQ ID NO 269
<211> LENGTH: 237
<212> TYPE: DNA
<213> ORGANISM: Homo sapiens
<220> FEATURE:
<221> NAME/KEY: misc_feature
<223> OTHER INFORMATION: Incyte ID No: 4132371CT1
<221> NAME/KEY: unsure
<222> LOCATION: 205
<223> OTHER INFORMATION: a, t, c, g, or other

<400> SEQUENCE: 269
acttgttcca tgttgcagaa aaattgcaaa gttgaaagtc agaatatcag acacaagtaa 60
tagtattcat cttaaagggg gaacatacct cgtttagagt ggactacact cccagtagtt 120
aggagacaac agagtaatga tgagattgca tgcggtctgg gcttaagtct tggcctgcac 180
acttgggaac aaagtgactc ttganccagt tacataacct tttgatatgt ccatttc 237

<210> SEQ ID NO 270
<211> LENGTH: 209
<212> TYPE: DNA
<213> ORGANISM: Homo sapiens
<220> FEATURE:
<221> NAME/KEY: misc_feature
<223> OTHER INFORMATION: Incyte ID No: 4132403CT1

<400> SEQUENCE: 270
taacttctta ttttccatgt tatttattca tttttaaaca agcattcatt gagtacctac 60
tatgccacag ctctatactt ggtagaaact gaggctgcca aaatgttaaa tctgtttccc 120
tgctcttaga acttaggaaa caatggagaa acagtcatgt tcaagagata gagtgaaatg 180
caaggtgata ggtgcctaat agagatgga 209

<210> SEQ ID NO 271
<211> LENGTH: 320
<212> TYPE: DNA
<213> ORGANISM: Homo sapiens
<220> FEATURE:
<221> NAME/KEY: misc_feature
<223> OTHER INFORMATION: Incyte ID No: 4132547CT1

<400> SEQUENCE: 271
tgatggtaag ttgtttcagg cataaaattt gaaataaatt atgaggctcc atgatatgct 60
atattggttt taccttcaga agaatattta gtttcactca ggtttttcaa agctacgctg 120
tcccccaaaa aacgaaacaa aacaaaaaaa caaccttttt aagagttgat ggctactcat 180
ttgatctgcc tcctctgctg aatcaattag gaattttttt ttttttggcc tgcaaataac 240
agaaaactga ttaccggtgt aggagataaa gtgattacaa atagggattt ttcctcccac 300
acacactaca atatttctgg 320

<210> SEQ ID NO 272
<211> LENGTH: 723
<212> TYPE: DNA
<213> ORGANISM: Homo sapiens
<220> FEATURE:
<221> NAME/KEY: misc_feature
<223> OTHER INFORMATION: Incyte ID No: 4133631CT1

<400> SEQUENCE: 272

-continued

```
ctcaggggtc ccaccgagtc tgccttctga agacagctga tactgtgatc ttgaacaagt     60

tgtaccccac agctaattga gatgtgctga gtttttcccc tgcttgagtt gctttcattt    120

aaatttcccc aaccaccagc ctgctgcccc agggaaaagc cactcagctt caccactctg    180

gcctgcttgg actttcttcc ttggattttc ctaggctgcc ttagccacac tggaattttg    240

tagcaactaa gagctgtagt ttttcaccca ccatggtttt gttaaatgtg gttttaaggt    300

aatgtggctt aatatttcca tatcaaaaaa tttaaatcca ctctctttta aaaatctagg    360

tcctaactcc taaatctggg tctagatgcc ataaaagaac aaaacaatga tggtttctct    420

ctcggggact atatgggcag cctgtggggt agagagagaa gctgtctgtt gccctaagac    480

ccaatttagc ccggcgagat ttcccatggg agaatgccca gggaatacat tccttttaag    540

ccgggaaggg caattttgaa aacccaattt gtgaggaaac cctgaactta aatcctggca    600

aaatctcttt ttccggaaaa ggcagtttgc tccactccaa attggacacc ctgaagcagc    660

ttgagtccga gggaaagtac aactttccgg acagggttct ctaatacccg aggaatcttc    720

gtt                                                                  723
```

<210> SEQ ID NO 273
<211> LENGTH: 742
<212> TYPE: DNA
<213> ORGANISM: Homo sapiens
<220> FEATURE:
<221> NAME/KEY: misc_feature
<223> OTHER INFORMATION: Incyte ID No: 4166159CT1

<400> SEQUENCE: 273

```
aagtccactg ctctcctcaa gaatttgagt ataatgcaag attataacta aagataaacg     60

taaaaatcag agggaagaaa tattgtgatt agaaggcaga cagttgcagg gccatgcaca    120

cacccatgca catcactcat cacagctgta ccatgtccct gcctaatagc aagagtagca    180

agccacaatt ctgcttccag gcaggcttag gtgaacaggg ctttaggcac aaaacatctg    240

ctgcaggaat tgtctccaac tttatactct catttaaaag acaaaaattt taaatgacaa    300

actcagaatt catttaataa actagtcatt tattcaccat tatgctcttt aagtgacttc    360

ttggcctgat aaaattctcc taccaggctt gctcagtaca tggcttatca atcatcgaaa    420

atttcatggc caagcctggt ggctcatgcc tgtaatccca gctctttggg aggccgaggc    480

aggaggatca ctatggtcag gagtttgaga ccagcctggc caacatggtg aaacctcttc    540

cctactaaaa atacaaaaat ttggctggat gtggtggcac acgcctgtag tcccagctcc    600

tcgggaggct gaggcatgag aatccatttg aacccaggag gcagaggttg cagtgagcca    660

agatcatgcc actgcactcc agcaatgggt gacagagcaa gaccctgtct ccggaaaata    720

attggaaggc ggggatgggg ag                                             742
```

<210> SEQ ID NO 274
<211> LENGTH: 493
<212> TYPE: DNA
<213> ORGANISM: Homo sapiens
<220> FEATURE:
<221> NAME/KEY: misc_feature
<223> OTHER INFORMATION: Incyte ID No: 4167883CT1

<400> SEQUENCE: 274

```
tcatgggaga aagggaagaa tatggctttg gccccagaaa ggctcagatt cccccaggcc     60

atcccccatc ctgaggacaa ggttttgggc ccttttctgt ttgcaggcag gaggctagag    120
```

-continued

```
agcgctccag gccaggagcc caggaaaggc tctcccttcc cctccctcct cacccccac    180

cctgccttcc ccagggtggg gaagcttcat ctctaccaat tccatcagcc ctaaaatact   240

cttctccatc ccaaggccag tataagtgca gcctttgtgt cacagccacg tgtccctatg   300

gccctgggct ccaatgggca tgatgccaga cccacagagt ggaacctggg tggtcccatg   360

ggttccatgc aggcttcgtt gagcaccttg cagcctaaat atttagccta caatttgcag   420

ccaagtctcc tccttaccta atgcttcctc ttcctgagcc cacaggggca ggatatagag   480

cagtcccacc ccc                                                      493


<210> SEQ ID NO 275
<211> LENGTH: 281
<212> TYPE: DNA
<213> ORGANISM: Homo sapiens
<220> FEATURE:
<221> NAME/KEY: misc_feature
<223> OTHER INFORMATION: Incyte ID No: 4220523CT1

<400> SEQUENCE: 275

tttgtggaaa atgactggag catgaaggtc atttctagcc gtaacagcag ggcaagactg    60

gaaatcatgg tgtggtggaa agagaagcgg cctcatagga gcaatcaagg tcatgaccca   120

gcaactatgt gcttactagt tgtgaggctt ggggcaaatc acctcattcc tggggacctt   180

caattcttct ctagcaaatg ggaatttgga ttataaaaac gtagccagac caggcgcagg   240

ggctcacacc tgtaatccca gcactttggg aagccaagcg g                       281


<210> SEQ ID NO 276
<211> LENGTH: 522
<212> TYPE: DNA
<213> ORGANISM: Homo sapiens
<220> FEATURE:
<221> NAME/KEY: misc_feature
<223> OTHER INFORMATION: Incyte ID No: 4220713CT1

<400> SEQUENCE: 276

tacttttaca tttaattaat cttctaaaga ttaatttaga agagatagat ataaaatgcc    60

agatttttc tggggaaaag ctacaaaatg tatttttggt attccagata ttctacacca   120

aaaagtgtat taatttcaga aaaatataga tggcctattt tgtacgtttg aaatgaatcc   180

ctttttcgtt tattattcaa aatacttcat tttaaaaagg atacctttag gccaggtgtg   240

gtggcttact cctgtaatcc catcactttg ggaggcctag gtgggaggga ctgcttgagg   300

ccaggagttc aagaccatct tgggcaacat cgagagatga gaccctgtct ctacaaaaaa   360

aaatttaaaa attagctggt ggtagtggca tgagcctaga gtcccagccc ttcaggagac   420

tgaagtggga ggatcacttg ggcccaagag ttctagggtt acagtgaggc atgattgcgg   480

ccaccgcact gcagcctggg caacagagtg agacacccat cc                      522


<210> SEQ ID NO 277
<211> LENGTH: 240
<212> TYPE: DNA
<213> ORGANISM: Homo sapiens
<220> FEATURE:
<221> NAME/KEY: misc_feature
<223> OTHER INFORMATION: Incyte ID No: 4220819CT1

<400> SEQUENCE: 277

ttctctgtac tataatagat gatataatcc tttgaaggtg gtataatcct ctgtcacact    60

gctgattgat agagactatt tcaagtcaaa atcctacaaa ttcttggctg ggtgtggtgg   120
```

```
cttacacctg taatcccaac actttgggaa gttgaggcag gaggattgtt tgaggccagg    180

agtttgagac cagcctaggc aacatagcaa gaccccatct ctaccaaaaa aaaaaaaaaa    240


<210> SEQ ID NO 278
<211> LENGTH: 479
<212> TYPE: DNA
<213> ORGANISM: Homo sapiens
<220> FEATURE:
<221> NAME/KEY: misc_feature
<223> OTHER INFORMATION: Incyte ID No: 4220939CT1

<400> SEQUENCE: 278

tgcctcaaaa cattagactt taattccctc acacattcag gtctagaaag gctgaatatg     60

taccaaatgt tatacaactt gctagattta taaaggtaca aattgcaaaa tttaaaacaa    120

tacataatag taacaaaaac aagatataat aatggactct tctttcttgg aacttacaga    180

tagatattaa acatgaatag taatacacac atacattcca ctgtaggtac ttatgaagta    240

aaaccaaaaa gtttcagtgg gagaaaacaa gtcaggttga ctttatgttg tgtggtcaag    300

ccagaataca cggaaatcag aaagtttagc tgagtctgta gacaaggaag ggagagtgga    360

agatgatttc gagggcatgg gaaaaattgg ggaaattcct gaggtgggaa agagttgaca    420

ctcttaaaat aactgaacac cagatgtggg tgggacatga cacggaaagc aggtggtgg     479


<210> SEQ ID NO 279
<211> LENGTH: 500
<212> TYPE: DNA
<213> ORGANISM: Homo sapiens
<220> FEATURE:
<221> NAME/KEY: misc_feature
<223> OTHER INFORMATION: Incyte ID No: 4221286CB1

<400> SEQUENCE: 279

ttgtgcttcc agtcagtaag caagagctac tacaggaatc actttctttt cctttctaag     60

agtatccaac ccacattcat tgtccgttgt ctgaaaaaca gttgtttcat atattctatt    120

cagttttcta atctttcaca gcaggacaat aaattcaggt tatcttaact cctttgtggc    180

cagaaacaag accagttatc agatttttaa ttttgatttt tatcttttac tttaacctct    240

tgaaagtagt agtggtaaaa atcacacatt tttattgggt actttttctg aatacctttg    300

tttatgtagt cttagtgttc tttgttagtc tttgtctttt ttactgaaat ataacaaaaa    360

gtagaggaga ctgattacct agtagagctt tacaggaagt catttggtaa ttgtagaaag    420

atacgagtta ttatagccag cttggcgaga gcattttcct ccaagtatga accttttaat    480

ttccgattag aataccacct                                                500


<210> SEQ ID NO 280
<211> LENGTH: 478
<212> TYPE: DNA
<213> ORGANISM: Homo sapiens
<220> FEATURE:
<221> NAME/KEY: misc_feature
<223> OTHER INFORMATION: Incyte ID No: 4221314CT1

<400> SEQUENCE: 280

tttaaaagct aataaaataa attgaataca acaaacattt attcaataaa ggtcataaat     60

gctttagtcg taatttccca aagcaggaat caacccgata tctatcaata ggaaaatgga    120

taaacaagtt gtaaaggata caatcctaat actactcagc aatacacagc tactgacaca    180

caccacctga gtgaatccta taaatgtatt gagtgagaca gctggaaata aaataaacta    240
```

-continued

```
tttcatatga tttcaggcat agtgaaccaa tggttaaaaa aaaaatggaa tagagatggc    300

ccccgagtga ggaaaaagtt gcctggaaaa taacctgagg aaattttctg gggataatgg    360

gaaacttctg ttcttaaagg atgaagttca tatgaatgta tttatctgtc aaaactgtac    420

agctaagatt tgagctttca tgggatgtac atcagaccac accaaaaaaa aaaaaaaa      478
```

```
<210> SEQ ID NO 281
<211> LENGTH: 322
<212> TYPE: DNA
<213> ORGANISM: Homo sapiens
<220> FEATURE:
<221> NAME/KEY: misc_feature
<223> OTHER INFORMATION: Incyte ID No: 4222520CT1

<400> SEQUENCE: 281

tgaaaacgga ctaatacagt aataaaagaa tatgcacaat attatttaga ttttgctaaa     60

cttttaggta tttgaggacc ttaatattat atatataata ataatatata ttcatttaaa    120

aaatgaccct tggttgcaat taacaaatag tcattgaagt cacttgggca ataaggacaa    180

gcttaatatc atttagactt tgctaaaact ttgagtatct gttgataact ttaagaattc    240

ataaaaagta ttatctcttg gttacaattg agaagtgctt agaattgaag gcagaaaacc    300

attttaaaaa aaaaaaaaaa gg                                              322
```

```
<210> SEQ ID NO 282
<211> LENGTH: 417
<212> TYPE: DNA
<213> ORGANISM: Homo sapiens
<220> FEATURE:
<221> NAME/KEY: misc_feature
<223> OTHER INFORMATION: Incyte ID No: 4223468CT1

<400> SEQUENCE: 282

gcttttaaag atgcctcttt cagtccttgc taggtaaggg aattagaacc attagaattg     60

ctttacaaaa attgaggaaa agattatttg tttagctatt tgtttttagt aaattgcatc    120

ctttgcatta agataaagca gttggccggg cgcggtggct cacgcctgta atcccagcac    180

tttgggaggc cgaggcaggc ggatctcgag gtcaggagat cgagaccatc ctggctaaca    240

cggtgaaacc ccgtctctac tgaaaataca aaaaattagc cgggcgtggt ggcgggcacc    300

tgtaatccca gctacttggg aggctgaggc aggagaatgg cgtgaacccg ggaggcggag    360

cttgcagtga gcagagatcg cgccactgca ctccagactg ggcgaaagag cggccag       417
```

```
<210> SEQ ID NO 283
<211> LENGTH: 615
<212> TYPE: DNA
<213> ORGANISM: Homo sapiens
<220> FEATURE:
<221> NAME/KEY: misc_feature
<223> OTHER INFORMATION: Incyte ID No: 4223734CT1

<400> SEQUENCE: 283

ggctcttatc tgtcttgtgt ctgttctgaa cccactctgg tgtggcagtg tctcagtccc     60

aatctgtgtg atacgtagga cggcacacag cctctcggca agcaggctca ttcctgcacg    120

aagcttgcaa ggcagctctc tctaactggc aaagaccttt cttggtcatg gttttcctcc    180

ttgcaatctg gcctcacttt agggagatat tctcatcagg gaggctgaga ccaactccct    240

ctcctggggg tggcgcctcc ctgacaccag ctgtggtgtg cagatgtgca gtaaatgtcg    300

catcgttatc acttcaaaga taatttcatt cctggaagac tggaaatcct taccctgggt    360
```

```
tttggcaaac acttacatta gagttgctca gtcagttgca gctttaaacc atggcgcccc    420

ctgcccaccc agccagctga taatttatga gaaacaggtg tacaaagaat gagtacattg    480

ggctgcggac ccagatcaaa cttcagaaaa tgcagattac caagggttaa tcatttttga    540

gcaatcttat ttccactgag actgcatctg cacagcaaag caagccactg aggcaaaaag    600

aaaaaaaaaa aaaaa                                                     615


<210> SEQ ID NO 284
<211> LENGTH: 195
<212> TYPE: DNA
<213> ORGANISM: Homo sapiens
<220> FEATURE:
<221> NAME/KEY: misc_feature
<223> OTHER INFORMATION: Incyte ID No: 4224867CT1
<221> NAME/KEY: unsure
<222> LOCATION: 176, 191
<223> OTHER INFORMATION: a, t, c, g, or other

<400> SEQUENCE: 284

gctcgagtag aaaatgaaag ttttctagtc tgagacaaaa tgttagaaat gacagcaaaa     60

tatggcaggg ttttactctt ttgtaggaag ctacataaat tacctcagtc cagacagcac    120

tctaccacat agaagttata gtcgacattt ggggtggtaa gtatttgtca ttgatnaaca    180

cacacacaca nccgg                                                     195


<210> SEQ ID NO 285
<211> LENGTH: 487
<212> TYPE: DNA
<213> ORGANISM: Homo sapiens
<220> FEATURE:
<221> NAME/KEY: misc_feature
<223> OTHER INFORMATION: Incyte ID No: 4256014CB1     Contig3

<400> SEQUENCE: 285

cacaaagaag aactgggtac ccaccagcaa gcatgcagtt actgtgtctt atttctatga     60

cagcacaaga aatgtgtata ggataatcag tttagatggc tcaaaggcaa taataaatag    120

taccatcacc ccaaacatga catttactaa aacatctcag aagtttggcc agtgggctga    180

tagccgggca aacaccgttt atggattggg attctcctct gagcatcatc tttcgaaatt    240

tgcagaaaag tttcaggaat ttaaagaagc tgctcgacta gcaaaggaaa aatcacaaga    300

gaagatggaa cttaccagta caccttcaca ggaatccgca ggcggggatc ttcagtctcc    360

tttaacaccg gaaagtatca acgggacaga tgatgaaaga acacctgatg tgacacagaa    420

ctcagagcca agggctgaac caactcagaa tgcattgcca ttttcacata gggaacaacc    480

tatcttc                                                              487


<210> SEQ ID NO 286
<211> LENGTH: 262
<212> TYPE: DNA
<213> ORGANISM: Homo sapiens
<220> FEATURE:
<221> NAME/KEY: misc_feature
<223> OTHER INFORMATION: Incyte ID No: 4352201CT1

<400> SEQUENCE: 286

cagttttcat tgttttcagt aagctgacct ccaaaggcat agatgtgagc tttcttttga     60

aaggaaatga agtattcacc gttaaggata aggatgtttg taatgtgaca gtgttaatgc    120

tagctaaatg agaaagccat tatgaatact tagactgttg ctacctggga gcattattta    180

ttgacctgtg ccttcgtcag agcttcagat gtgaggggaa tgatgctaat agaatcatgt    240
```

```
acagatgttt gtcattaaaa ag                                              262


<210> SEQ ID NO 287
<211> LENGTH: 535
<212> TYPE: DNA
<213> ORGANISM: Homo sapiens
<220> FEATURE:
<221> NAME/KEY: misc_feature
<223> OTHER INFORMATION: Incyte ID No: 4355247CT1

<400> SEQUENCE: 287

cctttatcca tgaggccttc tcaggctaac atttaaaatg gttaactccc agcccaccat      60

ccctgccagc cccagccccc atgccttgct ttcctttttc cctgtggggc ttctccccat     120

atgacctgtt ataatttact tgtttacagt aagtgaagct cagcaagggc agagagtttc     180

attcgtttgg ctccttgctg gatctgcaat gccagcatac agaaggtgct caaatattgt     240

ataaatcaat aaatgaacaa actagtgaat gatgttgggg agccaccaac agaccagagg     300

ttcctcccct gccctccctt gaagtcatga gcatttcctc tccgttgctc ctttactcac     360

agcctctttc ccacctggta gctaggtaag cagatggaga gtggcatgac tggcaaatcc     420

agcctcgtct gggttgagtt cattcaaatc ccgtttagca gttgggtccc cagctggctg     480

tgacacatcc tggagcagat ttcacaccac tccctgctct tctgcacccc aaatc          535


<210> SEQ ID NO 288
<211> LENGTH: 834
<212> TYPE: DNA
<213> ORGANISM: Homo sapiens
<220> FEATURE:
<221> NAME/KEY: misc_feature
<223> OTHER INFORMATION: Incyte ID No: 4608111CT1

<400> SEQUENCE: 288

gaattcggca cgagcggcac gagtgtagat gtggaagaac aggccacttc aagagaggat      60

gtcctgaact aagaaaggag aaagaagccc ttccacccat aactttcgag gaagaatagg     120

ggggtcaggg gctctgtctc ttgagtccca ccaggagccc ttgataaatt tggaggtggg     180

acctaaacat gagcttatca cctttttagt cgattcagag gctgctcgct cctctgtttg     240

tttccccccg tctaatgttg tctcctcctc agaggaactt ttattctccg gggtaaaagg     300

ggaaggagag gggagaacag cagcataagt ggctggcaga ggcagggaaa gaccagcaga     360

gaggagagag acagaggagg gaaagagaga gagaggaaaa agagagagag agaggaaaaa     420

cagagagagg aagagacaaa gagggagtta cagagagaga gagagagaga gatagaagta     480

gtaaagagca aacaatgtac catattcctt taaagccctc ggtaaattta aaacctttaa     540

tttgaaattg aaggtcttct ctgtgacact ctaacactcc aataccacct tgtctgtagt     600

gtaaccaggg cattgcccga aagctctgag gcccatgaca acccggtgcc ttcctatcaa     660

aaattcttaa cccagttacc catgggtggc ccaagtgaat tcaatctgta gggggcaact     720

ggtttgggta gccgaaagat agtttgaaaa ataacttttt aggagaaacc ttcattggtg     780

agcacacctt cgccagtttc cgaacttagc cctcaggggg aaaaaaaaaa aaaa           834


<210> SEQ ID NO 289
<211> LENGTH: 2100
<212> TYPE: DNA
<213> ORGANISM: Homo sapiens
<220> FEATURE:
<221> NAME/KEY: misc_feature
<223> OTHER INFORMATION: Incyte ID No: 319589CB1
```

<400> SEQUENCE: 289

```
gcgggtttga ctatgcgtcc ttcatcgctc agggcgactc caaacggctc cagctctaac     60
cggtctcctt ctaaacttct tcagcctgga cccatgcacc ggcactgctg gcgttcccag    120
cacacggtat actccattgt ttcctgacaa tccagttgat tcggccaggc tggttgctca    180
gctgtttcac aaacatacag ggctcatgac tcaggactgc tcttcagcct gagacgagct    240
ggtcacctga aggagatggc ggttctctgt caatcattgg cccatagcct caccattctc    300
caagaaccct gatcagagcc tcctcctcca ggaagtcttt cctaactgtg ccagcctcca    360
cctttcctct ggcatttgga tttctgatga ttaggatgcc tctgccacag cagattcatg    420
cttgtgacct ggaatgtcta ctggaaaggt ctgcggctgt ggagaagcag agtcacctct    480
gctttcctgc taccgctgcc tgtgagctga aggggctgaa ccatacactc ctttttctac    540
aaccagcttg catttttttct gcccacaatg agcggggaat caatgaattt cagcgatgtt    600
ttcgactcca gtgaagatta ttttgtgtca gtcaatactt catattactc agttgattct    660
gagatgttac tgtgctcctt gcaggaggtc aggcagttct ccaggctatt tgtaccgatt    720
gcctactcct tgatctgtgt ctttggcctc ctggggaata ttctggtggt gatcaccttt    780
gctttttata agaaggccag gtctatgaca gacgtctatc tcttgaacat ggccattgcg    840
gacatcctct ttgttcttac tctcccattc tgggcagtga gtcatgccac tggtgcgtgg    900
gttttcagca atgccacgtg caagttgcta aaaggcatct atgccatcaa ctttaactgc    960
gggatgctgc tcctgacttg cattagcatg gaccggtaca tcgccattgt acaggcgact   1020
aagtcattcc ggctccgatc cagaacacta ccgcgcagca aaatcatctg ccttgttgtg   1080
tgggggctgt cagtcatcat ctccagctca actttgtct tcaaccaaaa atacaacacc   1140
caaggcagcg atgtctgtga acccaagtac cagactgtct cggagcccat caggtggaag   1200
ctgctgatgt tggggcttga gctactcttt ggtttcttta tccctttgat gttcatgata   1260
ttttgttaca cgttcattgt caaaaccttg gtgcaagctc agaattctaa aaggcacaaa   1320
gccatccgtg taatcatagc tgtggtgctt gtgtttctgg cttgtcagat tcctcataac   1380
atggtcctgc ttgtgacggc tgcaaatttg ggtaaaatga accgatcctg ccagagcgaa   1440
aagctaattg gctatacgaa aactgtcaca gaagtcctgg ctttcctgca ctgctgcctg   1500
aaccctgtgc tctacgcttt tattgggcag aagttcagaa actactttct gaagatcttg   1560
aaggacctgt ggtgtgtgag aaggaagtac aagtcctcag gcttctcctg tgccgggagg   1620
tactcagaaa acatttctcg gcagaccagt gagaccgcag ataacgacaa tgcgtcgtcc   1680
ttcactatgt gatagaaagc tgagtctccc taaggcatgt gtgaaacata ctcatagatg   1740
ttatgcaaaa aaaagtctat ggccaggtat gcatggaaaa tgtgggaatt aagcaaaatc   1800
aagcaagcct ctctcctgcg ggacttaacg tgctcatggg ctgtgtgatc tcttcagggt   1860
ggggtggtct ctgataggta gcattttcca gcactttgca aggaatgttt tgtagctcta   1920
gggtatatat ccgcctggca tttcacaaaa cagcctttgg gaaatgctga attaaagtga   1980
attgttgaca aatgtaaaca ttttcagaaa tattcatgaa gcggtcacag atcacagtgt   2040
cttttggtta cagcacaaaa tgatggcagt ggtttgaaaa actaaaacaa aaaaaaaaaa   2100
```

<210> SEQ ID NO 290
<211> LENGTH: 315
<212> TYPE: DNA
<213> ORGANISM: Homo sapiens
<220> FEATURE:

<221> NAME/KEY: misc_feature
<223> OTHER INFORMATION: Incyte ID No: 884692CB1

<400> SEQUENCE: 290

```
acacatctca ttttcatctt cacaaccagg taggtattat ttagttattg tagaaaggca     60

aagtcattgg ccccaaatta tatagctaaa agaaagtctc tacttgatga gattcaaacc    120

cagatttgtt tggcatgaca gtgataattt tctagattga gataaccaca gcatcggaat    180

tagggccata gcgtgaacca gttctggaca cagttcttgg tccagagctg cccattgtaa    240

gagcagtcta gatgcaatca gggatttaaa tttggatgta gtaagagaca tcatcgatag    300

atcttgctcg gggag                                                     315
```

<210> SEQ ID NO 291
<211> LENGTH: 2799
<212> TYPE: DNA
<213> ORGANISM: Homo sapiens
<220> FEATURE:
<221> NAME/KEY: misc_feature
<223> OTHER INFORMATION: Incyte ID No: 1262948CB1

<400> SEQUENCE: 291

```
tgccgaagag tctggagcgt cggcgctgcg gggccgcggg ggtcgaatgt tcgtggcatc     60

agagagaaag atgagagctc accaggtgct caccttcctc ctgctcttcg tgatcacctc    120

ggtggcctct gaaaacgcca gcacatcccg aggctgtggg ctggacctcc tccctcagta    180

cgtgtccctg tgcgacctgg acgccatctg ggcattgtg gtggaggcgg tggccggggc     240

gggcgccctg atcacactgc tcctgatgct catcctcctg gtgcggctgc ccttcatcaa    300

ggagaaggag aagaagagcc ctgtgggcct ccactttctg ttcctcctgg ggaccctggg    360

cctctttggg ctgacgtttg ccttcatcat ccaggaggac gagaccatct gctctgtccg    420

ccgcttcctc tggggcgtcc tctttgcgct ctgcttctcc tgcctgctga gccaggcatg    480

gcgcgtgcgg aggctggtgc ggcatggcac gggccccgcg ggctggcagc tggtgggcct    540

ggcgctgtgc ctgatgctgg tgcaagtcat catcgctgtg gagtggctgg tgctcaccgt    600

gctgcgtgac acaaggccag cctgcgccta cgagcccatg gactttgtga tggccctcat    660

ctacgacatg gtactgcttg tggtcaccct ggggctggcc ctcttcactc tgtgcggcaa    720

gttcaagagg tggaagctga acggggcctt cctcctcatc acagccttcc tctctgtgct    780

catctgggtg gcctggatga ccatgtacct cttcggcaat gtcaagctgc agcagggggga    840

tgcctggaac gaccccacct tggccatcac gctggcggcc agcggctggg tcttcgtcat    900

cttccacgcc atccctgaga tccactgcac ccttctgcca gccctgcagg agaacacgcc    960

caactacttc gacacgtcgc agcccaggat gcgggagacg gccttcgagg aggacgtgca   1020

gctgccgcgg gcctatatgg agaacaaggc cttctccatg gatgaacaca atgcagctct   1080

ccgaacagca ggatttccca acggcagctt gggaaaaaga cccagtggca gcttggggaa   1140

aagacccagc gctccgttta gaagcaacgt gtatcagcca actgagatgg ccgtcgtgct   1200

caacggtggg accatcccaa ctgctccgcc aagtcacaca ggaagacacc tttggtgaaa   1260

gactttaagt tccagagaat cagaatttct cttaccgatt tgcctccctg gctgtgtctt   1320

tcttgaggga gaaatcggta acagttgccg aaccaggccg cctcacagcc aggaaatttg   1380

gaaatcctag ccaaggggat ttcgtgtaaa tgtgaacact gacgaactga aaagctaaca   1440

ccgactgccc gcccctcccc tgccacacac acagacacgt aataccagac caacctcaat   1500

ccccgcaaac taaagcaaag ctaattgcaa atagtattag gctcactgga aaatgtggct   1560
```

```
gggaagactg tttcatcctc tgggggtaga acagaaccaa attcacagct ggtgggccag   1620

actggtgttg gttggaggtg gggggttccc actcttatca cctctcccca gcaagtgctg   1680

gaccccaggt agcctcttgg agatgaccgt tgcgttgagg acaaatgggg actttgccac   1740

cggcttgcct ggtggtttgc acatttcagg ggggtcagga gagttaagga ggttgtgggt   1800

gggattccaa ggtgaggccc aactgaatcg tggggtgagc tttatagcca gtagaggtgg   1860

agggaccctg gcatgtgcca aagaagaggc cctctgggtg atgaagtgac catcacattt   1920

ggaaagtgat caaccactgt tccttctatg ggctcttgc tctagtgtct atggtgagaa    1980

cacaggcccc gcccccttccc ttgtagagcc atagaaatat tctggcttgg ggcagcagtc  2040

ccttcttccc ttgatcatct cgccctgttc ctacacttac gggtgtatct ccaaatcctc   2100

tcccaatttt attcccttat tcatttcaag agctccaatg gggtctccag ctgaaagccc   2160

ctccgggagg caggttggaa ggcaggcacc acggcaggtt ttccgcgatg atgtcaccta   2220

gcagggcttc aggggttccc actaggatgc agagatgacc tctcgctgcc tcacaagcag   2280

tgacacctcg ggtccttttcc gttgctatgg tgaaaattcc tggatggaat ggatcacatg  2340

agggtttctt gttgcttttg gagggtgtgg gggatatttt gttttggttt ttctgcaggt   2400

tccatgaaaa cagccctttt ccaagcccat tgtttctgtc atggtttcca tctgtcctga   2460

gcaagtcatt cctttgttat ttagcatttc gaacatctcg gccattcaaa gcccccatgt   2520

tctctgcact gtttggccag cataacctct agcatcgatt caaagcagag ttttaacctg   2580

acggcatgga atgtataaat gagggtgggt ccttctgcag atactctaat cactacattg   2640

ctttttctat aaaactaccc ataagccttt aacctttaaa gaaaaatgaa aaaggttagt   2700

gtttgggggc cgggggagga ctgaccgctt cataagccag tacgtctgag ctgagtatgt   2760

ttcaataaac cttttgatat ttaaaaaaaa aaaaaaagg                          2799
```

<210> SEQ ID NO 292
<211> LENGTH: 2385
<212> TYPE: DNA
<213> ORGANISM: Homo sapiens
<220> FEATURE:
<221> NAME/KEY: misc_feature
<223> OTHER INFORMATION: Incyte ID No: 1876370CB1

<400> SEQUENCE: 292

```
caaggctttc tgttgacatt cagtgcagtc tacctgcagc acagcacact ccctttgggc     60

aaggacctga gacccttgtg ctaagtcaag aggctcaatg ggctgcagaa gaactagaga    120

aggaccaagc aaagccatga tatttccatg gaaatgtcag agcacccaga gggacttatg    180

gaacatcttc aagttgtggg ggtggacaat gctctgttgt gatttcctgg cacatcatgg    240

aaccgactgc tggacttacc attattctga aaaacccatg aactggcaaa gggctagaag    300

attctgccga gacaattaca cagatttagt tgccatacaa aacaaggcgg aaattgagta    360

tctggagaag actctgcctt tcagtcgttc ttactactgg ataggaatcc ggaagatagg    420

aggaatatgg acgtgggtgg gaaccaacaa atctcttact gaagaagcag agaactgggg    480

agatggtgag cccaacaaca agaagaacaa ggaggactgc ttggagatct atatcaagag    540

aaacaaagat gcaggcaaat ggaacgatga cggctgccac aaactaaagg cagccctctg    600

ttacacagct tcttgccagc cctggtcatg cagtggccat ggagaatgtg tagaaatcat    660

caataattac acctgcaact gtgatgtggg gtactatggg ccccagtgtc agtttgtgat    720

tcagtgtgag cctttggagg ccccagagct gggtaccatg gactgtactc accctttggg    780
```

-continued

```
aaacttcagc ttcagctcac agtgtgcctt cagctgctct gaaggaacaa acttaactgg    840
gattgaagaa accacctgtg gaccatttgg aaactggtca tctccagaac caacctgtca    900
agtgattcag tgtgagcctc tatcagcacc agatttgggg atcatgaact gtagccatcc    960
cctggccagc ttcagcttta cctctgcatg taccttcatc tgctcagaag gaactgagtt   1020
aattgggaag aagaaaacca tttgtgaatc atctggaatc tggtcaaatc ctagtccaat   1080
atgtcaaaaa ttggacaaaa gtttctcaat gattaaggag ggtgattata accccctctt   1140
cattccagtg gcagtcatgg ttactgcatt ctctgggttg gcatttatca tttggctggc   1200
aaggagatta aaaaaaggca aggaatccaa gagaagtatg aatgacccat attaaatcgc   1260
ccttggtgaa agaaaattct tggaatacta aaaatcatga gatcctttaa atccttccat   1320
gaaacgtttt gtgtggtggc acctcctacg tcaaacatga agtgtgtttc cttcagtgca   1380
tctgggaaga tttctacctg accaacagtt ccttcagctt ccatttcgcc cctcatttat   1440
ccctcaaccc ccagcccaca ggtgtttata cagctcagct tttgtctttt tctgaggaga   1500
aacaaataag accataaagg gaaaggattc atgtggaata taaagatggc tgactttgct   1560
ctttcttgac tcttgttttc agtttcaatt cagtgctgta cttgatgaca gacacttcta   1620
aatgaagtgc aaatttgata catatgtgaa tatggactca gttttcttgc agatcaaatt   1680
tcacgtcgtc ttctgtatac tgtggaggta cactcttata gaaagttcaa aaagtctacg   1740
ctctcctttc tttctaactc cagtgaagta atggggtcct gctcaagttg aaagagtcct   1800
atttgcactg tagcctcgcc gtctgtgaat tggaccatcc tatttaactg gcttcagcct   1860
ccccaccttc ttcagccacc tctctttttc agttggctga cttccacacc tagcatctca   1920
tgagtgccaa gcaaaaggag agaagagaga aatagcctgc gctgtttttt agtttggggg   1980
ttttgctgtt tccttttatg agacccattc ctatttctta tagtcaatgt ttcttttatc   2040
acgatattat tagtaagaaa acatcactga aatgctagct gcaagtgaca tctctttgat   2100
gtcatatgga agagttaaaa caggtggaga aattccttga ttcacaatga aatgctctcc   2160
tttcccctgc ccccagaact tttatccact tacctagatt ctacatattc tttaaatttc   2220
atctcaggcc tccctcaacc ccaccacttc ttttataact agtcctttac taatccaacc   2280
catgatgagc tcctcttcct ggcttcttac tgaaaggtta ccctgtaaca tgcaattttg   2340
catttgaata aagcctgctt tttaagtgtt aaaaaaaaaa aaaaa                  2385
```

<210> SEQ ID NO 293
<211> LENGTH: 1526
<212> TYPE: DNA
<213> ORGANISM: Homo sapiens
<220> FEATURE:
<221> NAME/KEY: misc_feature
<223> OTHER INFORMATION: Incyte ID No: 2088868CB1

<400> SEQUENCE: 293

```
gcaggagcag gagagggaca atggaagctg ccccgtccag gttcatgttc ctcttatttc     60
tcctcacgtg tgagctggct gcagaagttg ctgcagaagt tgagaaatcc tcagatggtc    120
ctggtgctgc ccaggaaccc acgtggctca cagatgtccc agctgccatg gaattcattg    180
ctgccactga ggtggctgtc ataggcttct tccaggattt agaaatacca gcagtgccca    240
tactccatag catggtgcaa aaattcccag gcgtgtcatt tgggatcagc actgattctg    300
aggttctgac acactacaac atcactggga acaccatctg cctctttcgc ctggtagaca    360
atgaacaact gaatttagag gacgaagaca ttgaaagcat tgatgccacc aaattgagcc    420
```

```
gtttcattga gatcaacagc ctccacatgg tgacagagta caaccctgtg actgtgattg    480

ggttattcaa cagcgtaatt cagattcatc tcctcctgat aatgaacaag gcctccccag    540

agtatgaaga gaacatgcac agataccaga aggcagccaa gctcttccag gggaagattc    600

tctttattct ggtggacagt ggtatgaaag aaaatgggaa ggtgatatca tttttcaaac    660

taaaggagtc tcaactgcca gctttggcaa tttaccagac tctagatgac gagtgggata    720

cactgcccac agcagaagtt tccgtagagc atgtgcaaaa cttttgtgat ggattcctaa    780

gtggaaaatt gttgaaagaa aatcgtgaat cagaaggaaa gactccaaag gtggaactct    840

gacttctcct tggaactaca tatggccaag tatctacttt atgcaaagta aaaaggcaca    900

actcaaatct cagagacact aaacaacagg atcactaggc ctgccaacca cacacacacg    960

cacgtgcaca cacgcacgca cgcgtgcaca cacacacgcg cacacacaca cacacacaca   1020

cagagcttca tttcctgtct taaaatctcg ttttctcttc ttccttcttt taaatttcat   1080

atcctcactc cctatccaat ttccttctta tcgtgcattc atactctgta agcccatctg   1140

taacacacct agatcaaggc tttaagagac tcactgtgat gcctctatga aagagaggca   1200

ttcctagaga aagattgttc caatttgtca tttaatatca agtttgtata ctgcacatga   1260

cttacacaca acatagttcc tgctctttta aggttaccta agggttgaaa ctctaccttc   1320

tttcataagc acatgtccgt ctctgactca ggatcaaaaa ccaaaggatg gttttaaaca   1380

cctttgtgaa attgtctttt tgccagaagt taaaggctgt ctccaagtcc ctgaactcag   1440

cagaaataga ccatgtgaaa actccatgct tggttagcat ctccaactcc ctatgtaaat   1500

caacaacctg cataataaat aacaga                                        1526
```

```
<210> SEQ ID NO 294
<211> LENGTH: 2154
<212> TYPE: DNA
<213> ORGANISM: Homo sapiens
<220> FEATURE:
<221> NAME/KEY: misc_feature
<223> OTHER INFORMATION: Incyte ID No: 3550808CB1

<400> SEQUENCE: 294
```

```
gaggacagga tgaggcccgg cctctcattt ctcctagccc ttctgttctt ccttggccaa     60

gctgcagggg atttggggga tgtgggacct ccaattccca gccccggctt cagctctttc    120

ccaggtgttg actccagctc cagcttcagc tccagctcca ggtcgggctc cagctccagc    180

cgcagcttag gcagcggagg ttctgtgtcc cagttgtttt ccaatttcac cggctccgtg    240

gatgaccgtg ggacctgcca gtgctctgtt tccctgccag acaccacctt tcccgtggac    300

agagtggaac gcttggaatt cacagctcat gttctttctc agaagtttga gaaagaactt    360

tctaaagtga gggaatatgt ccaattaatt agtgtgtatg aaaagaaact gttaaaccta    420

actgtccgaa ttgacatcat ggagaaggat accatttctt acactgaact ggacttcgag    480

ctgatcaagg tagaagtgaa ggagatggaa aaactggtca tacagctgaa ggagagtttt    540

ggtggaagct cagaaattgt tgaccagctg gaggtggaga taagaaatat gactctcttg    600

gtagagaagc ttgagacact agacaaaaac aatgtccttg ccattcgccg agaaatcgtg    660

gctctgaaga ccaagctgaa agagtgtgag gcctctaaag atcaaaacac ccctgtcgtc    720

caccctcctc ccactccagg gagctgtggt catggtggtg tggtgaacat cagcaaaccg    780

tctgtggttc agctcaactg gagagggttt tcttatctat atggtgcttg ggtagggat     840

tactctcccc agcatccaaa caaaggactg tattgggtgg cgccattgaa tacagatggg    900
```

-continued

```
agactgttgg agtattatag actgtacaac acactggatg atttgctatt gtatataaat     960

gctcgagagt tgcggatcac ctatggccaa ggtagtggta cagcagttta caacaacaac    1020

atgtacgtca acatgtacaa caccgggaat attgccagag ttaacctgac caccaacacg    1080

attgctgtga ctcaaactct ccctaatgct gcctataata accgcttttc atatgctaat    1140

gttgcttggc aagatattga ctttgctgtg gatgagaatg gattgtgggt tatttattca    1200

actgaagcca gcactggtaa catggtgatt agtaaactca atgacaccac acttcaggtg    1260

ctaaacactt ggtataccaa gcagtataaa ccatctgctt ctaacgcctt catggtatgt    1320

ggggttctgt atgccacccg tactatgaac accagaacag aagagatttt ttactattat    1380

gacacaaaca cagggaaaga gggcaaacta gacattgtaa tgcataagat gcaggaaaaa    1440

gtgcagagca ttaactataa ccccttttgac cagaaacttt atgtctataa cgatggttac    1500

cttctgaatt atgatctttc tgtcttgcag aagccccagt aagctgttta ggagttaggg    1560

tgaaagagaa aatgtttgtt gaaaaaatag tcttctccac ttacttagat atctgcaggg    1620

gtgtctaaaa gtgtgttcat tttgcagcaa tgtttaggtg catagttcta ccacactaga    1680

gatctaggac atttgtcttg atttggtgag ttctcttggg aatcatctgc ctcttcaggc    1740

gcattttgca ataaagtctg tctagggtgg gattgtcaga ggtctagggg cactgtgggc    1800

ctagtgaagc ctactgtgag gaggcttcac tagaagcctt aaattaggaa ttaaggaact    1860

taaaactcag tatggcgtct agggattctt tgtacaggaa atattgccca atgactagtc    1920

cccatccatg tagcaccact aattcttcca tgcctggaag aaacctgggg acttagttag    1980

gtagattaat atctggagct cctcgaggga ccaaatctcc aacttttttt tcccctcact    2040

agcacctgga atgatgcttt gtatgtggca gataagtaaa tttggcatgc ttatatattc    2100

tacatcctga aagtggcctg gttttatgga gaagaggcct ctttatgcag tcaa          2154
```

<210> SEQ ID NO 295
<211> LENGTH: 496
<212> TYPE: DNA
<213> ORGANISM: Homo sapiens
<220> FEATURE:
<221> NAME/KEY: misc_feature
<223> OTHER INFORMATION: Incyte ID No: 1328883CT1

<400> SEQUENCE: 295

```
ggaattgcaa ataacaggaa gaagaaaaat gctgtattgg ctagactcct ttagtgttcc      60

tcattttttt aaaatagtaa tctttgttat aatggagttc catgcacttg aaagtcagat     120

ttgtgatttt cacaattttc acaaacttca ctacaatgtg aagtttggac ttctaaaaca     180

atctctactc cccctcctgg gggttctaca ggaacaagat aatcaaccag tctttgcctc     240

agagtttgtt cttaccagga agtaaaggga gtggggagga ttgtatatgt gagccaccct     300

gcccagcaag accctatttt taaggtgttt agattagcag atattcttta agtaagcatc     360

tttaatcctt catgggcact tgaaaaaaga ataaccatca ttttggatga agtgagtatt     420

acagcctggg caacagagtg agactcagaa aaaaaaattg gaagaggtaa tttgtaggag     480

taaaaaaaaa aatagg                                                     496
```

<210> SEQ ID NO 296
<211> LENGTH: 251
<212> TYPE: DNA
<213> ORGANISM: Homo sapiens
<220> FEATURE:
<221> NAME/KEY: misc_feature -continued
<223> OTHER INFORMATION: Incyte ID No: 3458089H1

<400> SEQUENCE: 296
cgccgcgggc ggcacctgga agctgctggg ctcagtggtc tacgcgcata gcaaggagct 60
gatcaccgcc tggtacatcg ggttcctggt gctcatcttc gcctccttcc tggtctacct 120
ggctgagaag gacgccaact ccgacttctc ctcctacgcc gactcgctct ggtgggggac 180
gattacattg acaaccatcg gctatggtga caagacaccg cacacatggg ctgggcaggt 240
cctggctgct g 251

<210> SEQ ID NO 297
<211> LENGTH: 250
<212> TYPE: DNA
<213> ORGANISM: Homo sapiens
<220> FEATURE:
<221> NAME/KEY: misc_feature
<223> OTHER INFORMATION: Incyte ID No: 1329138CT1

<400> SEQUENCE: 297
gttgtgtgtt tggtcacagt gccaatttaa actgggttga tctgtcttac atggctgtta 60
tggcactgaa ggatatgaag catttgaaat gctgacattt tggaatattc atttaaaaat 120
aggctggggc cggacatggc tcacacttgt aatcccagcg cgttgggagg ctgaggcggg 180
tggatcacct gaggtcagga gtttgagacc aacctggcca acatgacgag accccgtctc 240
tatgaaaata 250

<210> SEQ ID NO 298
<211> LENGTH: 557
<212> TYPE: DNA
<213> ORGANISM: Homo sapiens
<220> FEATURE:
<221> NAME/KEY: misc_feature
<223> OTHER INFORMATION: Incyte ID No: 1514470CT1

<400> SEQUENCE: 298
gcaggggcca gtccctccac cctcaactca gcctccatct ggcagggcaa tggccccttc 60
cctcagattg cctgtcccct cgtggtgcct tctccttcat caggcaacct ataattcttg 120
tggaagggag ggacggcgtg tccccgggcc ctctgatggt tcccttaccc ttagggtgga 180
ccaaattgtg ggtcgggggc ccggggacag gaaggcccgg gagaagggcg acaaggggcc 240
ctccgacgcg gaggtggtgg atgaaatcag catgatggga cgcgtggtca aggtggagaa 300
gcaggtgcag tccatcgagc acaagctgga cctgctgttg ggcttctatt cgcgctgcct 360
gcgctctggc acctcggcca gcctgggcgc cgtgcaagtg ccgctgttcg accccgacat 420
cacctccgac taccacagct ctgtggacca cgaggacatc tccgtctctg cacagacgct 480
cagcatctcc cgctcggtca gcacaacatg gactgagggc ttctcagagg caggcagcaa 540
cggcagctcg cggctgg 557

<210> SEQ ID NO 299
<211> LENGTH: 197
<212> TYPE: DNA
<213> ORGANISM: Homo sapiens
<220> FEATURE:
<221> NAME/KEY: misc_feature
<223> OTHER INFORMATION: Incyte ID No: 1513293H1
<221> NAME/KEY: unsure
<222> LOCATION: 122, 126
<223> OTHER INFORMATION: a, t, c, g, or other

<400> SEQUENCE: 299

```
gcaggggcca gtccctccac cctcaactca gcctccatct ggcagggcaa tggccccttc     60

cctcagattg cctgtcccct cgtggtgcct tctccttcat caggcaacct ataattcttg    120

tngaanggag ggacggcgtg tccccgggcc ctctgatggt tcccttaccc ttagggtgga    180

ccaaattgtg ggtcggg                                                   197


<210> SEQ ID NO 300
<211> LENGTH: 441
<212> TYPE: DNA
<213> ORGANISM: Homo sapiens
<220> FEATURE:
<221> NAME/KEY: misc_feature
<223> OTHER INFORMATION: Incyte ID No: 1514470F6
<221> NAME/KEY: unsure
<222> LOCATION: 4, 23, 31, 33, 122, 411, 429, 438
<223> OTHER INFORMATION: a, t, c, g, or other

<400> SEQUENCE: 300

gcangggcca gtccctccac ccncaactca ncntccatct ggcagggcaa tggccccttc     60

cctcagattg cctgtcccct cgtggtgcct tctccttcat caggcaacct ataattcttg    120

tngaagggag ggacggcgtg tccccgggcc ctctgatggt tcccttaccc ttagggtgga    180

ccaaattgtg ggtcgggggc ccggggacag gaaggcccgg gagaagggcg acaaggggcc    240

ctccgacgcg gaggtggtgg atgaaatcag catgatggga cgcgtggtca aggtggagaa    300

gcaggtgcag tccatcgagc acaagctgga cctgctgttg ggcttctatt cgcgcttcct    360

gcgctctggc acctcggcca gcctgggcgc cgtgcaagtg ccgtgttcga ncccgacatc    420

accttcgant aaccacantc c                                              441


<210> SEQ ID NO 301
<211> LENGTH: 203
<212> TYPE: DNA
<213> ORGANISM: Homo sapiens
<220> FEATURE:
<221> NAME/KEY: misc_feature
<223> OTHER INFORMATION: Incyte ID No: 1514470H1
<221> NAME/KEY: unsure
<222> LOCATION: 122
<223> OTHER INFORMATION: a, t, c, g, or other

<400> SEQUENCE: 301

gcaggggcca gtccctccac cctcaactca gcctccatct ggcagggcaa tggccccttc     60

cctcagattg cctgtcccct cgtggtgcct tctccttcat caggcaacct ataattcttg    120

tngaagggag ggacggcgtg tccccgggcc ctctgatggt tcccttaccc ttagggtgga    180

ccaaattgtg ggtcgggggc ccg                                            203


<210> SEQ ID NO 302
<211> LENGTH: 281
<212> TYPE: DNA
<213> ORGANISM: Homo sapiens
<220> FEATURE:
<221> NAME/KEY: misc_feature
<223> OTHER INFORMATION: Incyte ID No: 3372628H1

<400> SEQUENCE: 302

gccccgtccc caggtgcagt ccatcgagca caagctggac ctgctgttgg gcttctattc     60

gcgctgcctg cgctctggca cctcggccag cctgggcgcc gtgcaagtgc cgctgttcga    120

ccccgacatc acctccgact accacagccc tgtggaccac gaggacatct ccgtctccgc    180

acagacgctc agcatctccc gctcggtcag caccaacatg gactgaggga cttctcagag    240
```

```
gcagggcagc acacggccag ccccgcggcc tggcgctccg a                     281


<210> SEQ ID NO 303
<211> LENGTH: 582
<212> TYPE: DNA
<213> ORGANISM: Homo sapiens
<220> FEATURE:
<221> NAME/KEY: misc_feature
<223> OTHER INFORMATION: Incyte ID No: 4970006CT1

<400> SEQUENCE: 303

ggaaaagggc aaatcacatc agataagaag agccgagaga aaataacagc agaacatgag      60

accacagacg atctcagtat gctcggtcgg gtggtcaagg ttgaaaaaca ggtacagtcc     120

atagaatcca agctggactg cctactagac atctatcaac aggtccttcg gaaaggctct     180

gcctcagccc tcgctttggc ttcattccag atcccacctt ttgaatgtga acagacatct     240

gactatcaaa gccctgtgga tagcaaagat ctttcgggtt ccgcacaaaa cagtggctgc     300

ttatccagat caactagtgc caacatctcg agaggcctgc agttcattct gacgccaaat     360

gagttcagtg cccagacttt ctacgcgctt agccctacta tgcacagtca agcaacacag     420

gtgccaatta gtcaaagcga tggctcagca gtggcagcca ccaacaccat tgcaaaccaa     480

ataaatacgg caccaaagcc agcagcccaa caactttaca gatcttcctc ctccagctct     540

tgaggagcta gaatacaggg agatgccaca tgccagttaa tt                        582


<210> SEQ ID NO 304
<211> LENGTH: 284
<212> TYPE: DNA
<213> ORGANISM: Homo sapiens
<220> FEATURE:
<221> NAME/KEY: misc_feature
<223> OTHER INFORMATION: Incyte ID No: 4970006H1
<221> NAME/KEY: unsure
<222> LOCATION: 3-5, 96-97, 229
<223> OTHER INFORMATION: a, t, c, g, or other

<400> SEQUENCE: 304

ggnnnagggc aaatcacatc agataagaag agccgagaga aaataacagc agaacatgag      60

accacagacg atctcagtat gctcggtcgg gtggtnnagg ttgaaaaaca ggtacagtcc     120

atagaatcca agctggactg cctactagac atctatcaac aggtccttcg gaaaggctct     180

gcctcagccc tcgctttggc ttcattccag atcccacctt ttgaatgtna acagacatct     240

gactatcaaa gccctgtgga tagcaaagat ctttcgggtt ccgc                      284


<210> SEQ ID NO 305
<211> LENGTH: 575
<212> TYPE: DNA
<213> ORGANISM: Homo sapiens
<220> FEATURE:
<221> NAME/KEY: misc_feature
<223> OTHER INFORMATION: Incyte ID No: 4970006F6
<221> NAME/KEY: unsure
<222> LOCATION: 486, 510, 552, 573
<223> OTHER INFORMATION: a, t, c, g, or other

<400> SEQUENCE: 305

ggaaaagggc aaatcacatc agataagaag agccgagaga aaataacagc agaacatgag      60

accacagacg atctcagtat gctcggtcgg gtggtcaagg ttgaaaaaca ggtacagtcc     120

atagaatcca agctggactg cctactagac atctatcaac aggtccttcg gaaaggctct     180

gcctcagccc tcgctttggc ttcattccag atcccacctt ttgaatgtga acagacatct     240
```

-continued

```
gactatcaaa gccctgtgga tagcaaagat ctttcgggtt ccgcacaaaa cagtggctgc    300

ttatccagat caactagtgc caacatctcg agaggcctgc agttcatctg acgccaaatg    360

agttcagtgc ccagactttc tacggcttag cctactatgc acagtcaagc aacacaggtg    420

ccaatagtca aagcgatggc tcagcagtgg cagccaccaa caccattgca accaaattaa    480

tacggnaccc aagccagcag gccccacaan ttacagtctc ctctcagctc ttgaggggta    540

ggaattacag gnagatgccc catggcccgt tantt                               575
```

COMPOSITION FOR DETECTION OF GENES ENCODING MEMBRANE-ASSOCIATED PROTEINS

This application claims the benefit of U.S. Provisional Application No. 60/118,318, filed on Feb. 1, 1999.

FIELD OF THE INVENTION

The present invention relates to a composition comprising a plurality of polynucleotide sequences for use in research and diagnostic applications.

BACKGROUND OF THE INVENTION

DNA-based arrays can provide a simple way to explore the expression of a single polymorphic gene or a large number of genes. When the expression of a single gene is explored, DNA-based arrays are employed to detect the expression of specific gene variants. For example, a p53 tumor suppressor gene array may be used to determine whether individuals are carrying mutations that predispose them to cancer. The array has over 50,000 DNA targets to analyze more than 400 distinct mutations of p53. A cytochrome p450 gene array is useful to determine whether individuals have one of a number of specific mutations that could result in increased drug metabolism, drug resistance, or drug toxicity.

DNA-based array technology is especially relevant to screen expression of a large number of genes rapidly. There is a growing awareness that gene expression is affected in a global fashion and that genetic predisposition, disease, or therapeutic treatment may affect, directly or indirectly, the expression of a large number of genes. In some cases the interactions may be expected, such as where the genes are part of the same signaling pathway. In other cases, such as when some of the genes participate in separate signaling pathways, the interactions may be totally unexpected. Therefore, DNA-based arrays can be used to investigate how genetic predisposition, disease, or therapeutic treatment affect the coregulation and expression of a large number of genes.

It would be advantageous to prepare DNA-based arrays that can be used for monitoring the expression of a large number of membrane-associated proteins. Proteins which span or are associated with cell membranes include receptors, ion channels and symporters, cytokines and their suppressors, monomeric or heterotrimeric G- and ras-related proteins, lectins such as selectin, oncogenes and their suppressors, and the like. Receptors include G protein coupled, four transmembrane, and tyrosine kinase receptors. Some of these proteins may span a cellular membrane and some may be secreted. The secreted proteins typically include signal sequences that direct them to their final cellular or extracellular destination.

The present invention provides for a composition comprising a plurality of polynucleotide sequences for use in detecting changes in expression of a large number of genes encoding proteins which are membrane-associated proteins, receptors and ion channels. Such a composition can be employed for the diagnosis or treatment of any disease—a pancreatic disease, a cancer, an immunopathology, a neuropathology and the like—where a defect in the expression of a gene encoding membrane-associated proteins is involved.

SUMMARY OF THE INVENTION

In one aspect, the present invention provides a composition comprising a plurality of polynucleotide sequences, wherein each of said polynucleotide sequences comprises at least a fragment of a gene encoding membrane-associated proteins, receptors and ion channels.

In one preferred embodiment, the plurality of polynucleotide sequences comprises at least a fragment of one or more of the sequences, SEQ ID NOs:1–305, presented in the Sequence Listing. In a second preferred embodiment, the composition comprises a plurality of polynucleotide sequences comprising at least a fragment of a gene encoding a membrane-associated protein. In a third preferred embodiment, the composition comprises a plurality of polynucleotide sequences comprising at least a fragment of a gene encoding a receptor. In a fourth preferred embodiment, the composition comprises a plurality of polynucleotide sequences comprising at least a fragment of a gene encoding ion channels. In a fifth preferred embodiment, the composition comprises a plurality of polynucleotide sequences comprising at least a fragment of at least one or more of the sequences of SEQ ID NOs:1–288. In a sixth preferred embodiment, the composition comprises a plurality of polynucleotide sequences comprising at least a fragment of at least one or more of the sequences of SEQ ID NOs:289–294. In a seventh preferred embodiment, the composition comprises a plurality of polynucleotide sequences comprising at least a fragment of at least one or more of the sequences of SEQ ID NOs:295–305. In one aspect, the fragment is selected from the group consisting of SEQ ID NOs:295–297, or SEQ ID NOs:298–305. In an eighth preferred embodiment, the composition is a polynucleotide probe. In one aspect, the composition is immobilized on a substrate. In a ninth preferred embodiment, the composition is an hybridizable array element.

The composition, a hybridizable array element, is useful to monitor the expression of a plurality of expressed polynucleotides. The microarray is used in the diagnosis and treatment of a pancreatic disease, a cancer, an immunopathology, a neuropathology, and the like.

In another aspect, the present invention provides an expression profile that can reflect the expression levels of a plurality of polynucleotide sequences in a sample. The expression profile comprises a microarray and a plurality of detectable complexes. Each detectable complex is formed by hybridization of at least one probe polynucleotide sequence to at least one target polynucleotide sequence and further comprises a labeling moiety for detection.

DESCRIPTION OF THE SEQUENCE LISTING, FIGURES, AND TABLES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of nucleotide sequences obtained by sequencing and assembling clone inserts (isolates) from various cDNA libraries. Each sequence is identified by a sequence identification number (SEQ ID NO:) and by clone number.

FIGS 1A and 1B are an alignment of SEQ ID NOs:298–302 produced using GELVIEW Fragment Assembly System software (Genetics Computer Group (GCG), Madison Wis.).

FIGS. 2A and 2B are an alignment of SEQ ID NOs:303–305 produced using GELVIEW Fragment Assembly System software (GCG).

Table 1 is a list of the sequences disclosed herein. By column, the table contains: 1) SEQ ID NO: as shown in the Sequence Listing; 2) Incyte Clone NO; 3) PRINT ID, designation of the relevant PROSITE group; 4) PRINT DESCRIPTION; 5) PRINT STRENGTH, the degree of correlation to the PROSITE group, >1300 is strong and 1000 to 1300 is weak; 6) PRINT SCORE, where >1300 is strong and 1000 to 1300 is suggestive; 7) TM, the presence of at least one transmembrane domain; and 8) SIGNAL PEPTIDE, the presence of a signal peptide. The table is arranged so that SEQ ID NOs:1–305 contain at least a fragment of a gene encoding a membrane-associated protein, some of which are receptors, and some, ion channels.

DESCRIPTION OF THE INVENTION

Definitions

The term "microarray" refers to an ordered arrangement of hybridizable array elements. The elements are arranged so that there are preferably at least one or more different elements, more preferably at least 100 elements, even more preferably at least 1,000 elements, and most preferably at least 10,000 elements on a one $cm^2$ substrate surface. The maximum number of array elements is unlimited, but is at least 100,000. Furthermore, the hybridization signal from each array element is individually distinguishable. In a preferred embodiment, the array elements comprise polynucleotide sequences.

A "polynucleotide" refers to a chain of nucleotides. Preferably, the chain has from about five to 10,000 nucleotides, more preferably from about 50 to 3,500 nucleotides. The term "probe" refers to a polynucleotide sequence capable of hybridizing with a target sequence to form a polynucleotide probe/target complex under hybridization conditions. A "target polynucleotide" refers to a chain of nucleotides to which a polynucleotide probe can hybridize by base pairing. In some instances, the sequences will be completely complementary (no mismatches) when aligned; in others, there may be up to a 10% mismatch.

A "plurality" refers preferably to a group of at least one or more members, more preferably to a group of at least about 100, even more preferably to a group of at least about 1,000 members, and most preferably to a group of at least about 10,000 members. The maximum number of members is unlimited, but is at least about 100,000 members.

A "fragment" means a stretch of at least about 100 consecutive nucleotides. A "fragment" can also mean a stretch of at least about 100 consecutive nucleotides that contains one or more deletions, insertions or substitutions. A "fragment" can also include the entire open reading frame of a gene. Preferred fragments are those that lack secondary structure as identified by using computer software programs such as OLIGO 4.06 Primer Analysis software (National Biosciences, Plymouth Minn.), LASERGENE software (DNASTAR, Madison Wis.), MACDNASIS (Hitachi Software Engineering Co., Ltd., San Bruno Calif.) and the like.

The term "gene" or "genes" refers to polynucleotide sequence which may be the partial or complete and may comprise regulatory, untranslated, or coding regions. The phrase "genes encoding membrane-associated proteins, receptors, or ion channels" refers to genes comprising sequences that contain conserved protein motifs or domains that were identified by BLAST (Basic Local Alignment Search Tool; Altschul (1993) J Mol Evol 36:290–300; and Altschul et al. (1990) J Mol Biol 215:403–410), PRINTS, or other analytical tools. Additionally, "genes encoding membrane-associated proteins, receptors, or ion channels" refers to genes which may produce proteins which span the cell membrane or have signal sequences which direct them to their final cellular or extracellular destination.

The Invention

The present invention provides a composition comprising a plurality of polynucleotide sequences comprising at least a fragment of a gene encoding a protein which is a receptor, ion channel, or associated with cell membrane. Preferably, the plurality of polynucleotide sequences comprise at least a fragment of one or more of the sequences (SEQ ID NOs:1–305) presented in the Sequence Listing. In one preferred embodiment, the composition comprises a plurality of polynucleotide sequences, wherein each sequence comprises at least a fragment of a sequence selected from the group consisting of SEQ ID NOs:1–294. In a second preferred embodiment, the composition comprises a plurality of polynucleotide sequences, wherein each sequence comprises at least a fragment of a sequence selected from the group consisting of SEQ ID NOs:295–305.

A microarray can be used for large scale genetic or gene expression analysis of a large number of polynucleotide sequences. Such an analysis can be used in the diagnosis of diseases and in the monitoring of treatments where altered expression of genes encoding receptors, ion channels, or membrane-associated proteins cause disease, such as pancreatic disease, cancer, an immunopathology, neuropathology, and the like. Further, the microarray can be employed to investigate an individual's predisposition to a disease, such as pancreatic disease, cancer, an immunopathology, or a neuropathology. Furthermore, the microarray can be employed to investigate cellular responses to infection, drug treatment, and the like.

When the composition of the invention is employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment.

The composition comprising a plurality of polynucleotide sequences can also be used to purify a subpopulation of mRNAs, cDNAs, genomic fragments, and the like, in a sample. Typically, samples will include polynucleotides of interest and additional nucleic acids which may contribute to background signal in a hybridization. Therefore, it may be advantageous to remove these additional nucleic acids before hybridization. One method for removing the additional nucleic acids is to hybridize the sample containing probe polynucleotides with immobilized polynucleotide targets. Those nucleic acids which do not hybridize to the polynucleotide targets are washed away. At a later point, the immobilized target polynucleotides can be released in the form of purified target polynucleotides.

Method for Selecting Polynucleotide Sequences

This section describes the selection of the plurality of polynucleotide sequences. In one embodiment, the sequences are selected based on the presence of shared signal sequence motifs. For example, signal sequences generally contain 15 to 60 amino acids and are located at the N-terminal end of the protein. The signal sequence consists of three regions: 1) an n-region located adjacent to the N-terminus which is composed of one to five amino acids and usually carries a positive charge, 2) the h-region which is composed of 7 to 15 hydrophobic amino acids and creates a hydrophobic core; and 3) the c region which is located between the h-region and the cleavage site and is composed of three to seven polar, but mostly uncharged, amino acids. The signal sequence is removed from the protein during posttranslational processing by cleavage at the cleavage site.

A transmembrane protein is characterized by a polypeptide chain which is exposed on both sides of a membrane. The cytoplasmic and extracellular domains are separated by at least one membrane-spanning segment which traverses the hydrophobic environment of the lipid bilayer. The membrane-spanning segment is composed of amino acid residues with nonpolar side chains, usually in the form of an $\alpha$ helix. Segments which contain about 20–30 hydrophobic residues are long enough to span a membrane as an $\alpha$ helix, and they can often be identified by means of a hydropathy plot.

Receptor sequences are recognized by one or more hydrophobic transmembrane regions, cysteine disulfide bridges between extracellular loops, an extracellular N-terminus, and a cytoplasmic C-terminus. For example, in G protein-coupled receptors (GPCRs), the N-terminus interacts with ligands, the disulfide bridge interacts with agonists and antagonists, the second cytoplasmic loop has a conserved, acidic-Arg-aromatic triplet which may interact with the G proteins, and the large third intracellular loop interacts with G proteins to activate second messengers such as cyclic AMP, phospholipase C, inositol triphosphate, or ion channel proteins (Watson and Arkinstall (1994) *The G-protein Linked Receptor Facts Book*, Academic Press, San Diego Calif.). Other exemplary classes of receptors such as the tetraspanins (Maecker et al. (1997) FASEB J 11:428–442), calcium dependent receptors (Speiss (1990) Biochem 29:10009–18) and the single transmembrane receptors may be similarly characterized relative to their intracellular and extracellular domains, known motifs, and interactions with other molecules.

An ion channel is a transmembrane protein that forms a hydrophilic pore through which ions can cross the lipid bilayer of the membrane. An ion channel usually shows some degree of ion specificity, and up to a million ions per second may flow down their electrochemical gradients through the open pore. Ion channels are gated and allow ions to pass only under defined circumstances. Gated channels may be either voltage-gated, such as the sodium channel of neurons, or ligand-gated, such as the acetylcholine receptor of cholinergic synapses.

Membrane-associated proteins, receptors or ion channels may act directly as inhibitors or as stimulators of cell proliferation, growth, attachment, angiogenesis, and apoptosis, or indirectly by modulating the effects of transcription factors, matrix and adhesion molecules, cell cycle regulators, and other molecules in cell signaling pathways. In addition, cell signaling molecules may act as ligands or ligand cofactors for receptors which modulate cell growth, proliferation, and differentiation. These molecules may be identified by sequence homology to molecules whose function has been characterized, and by the identification of their conserved domains. Membrane-associated proteins, receptors or ion channels may be characterized using programs such as BLAST, PRINTS, or Hidden Markov Models (HMM). Fragments which include characterized, conserved regions of membrane-associated proteins, receptors, or ion channels may be used in hybridization technologies to identify similar proteins.

A large number of clones from a variety of cDNA libraries can be screened using software well known in the art to discover sequences with conserved protein domains or motifs. Such sequences may be screened using the BLOCK 2 Bioanalysis program (Incyte Pharmaceuticals, Palo Alto Calif.), a motif analysis program based on sequence information contained in the SWISSPROT and PROSITE databases, which is useful for determining the function of uncharacterized proteins translated from genomic or cDNA sequences (Bairoch et al. (1997) Nucleic Acids Res 25:217–221; Attwood et al. (1997) J Chem Inf Comput Sci 37:417–424). PROSITE is particularly useful to identify functional or structural domains that cannot be detected using common motifs because of extreme sequence divergence. The method, which is based on weight matrices, calibrates the motifs against the SWISS-PROT database to obtain a measure of the chance distribution of the matches. Similarly, databases such as PRINTS store conserved motifs useful in the characterization of proteins (Attwood et al. (1998) Nucl Acids Res 26:304–308). These conserved motifs are used in the selection and design of probes. The PRINTS database can be searched using the BLIMPS search program. The PRINTS database of protein family "fingerprints" complements the PROSITE database and utilizes groups of conserved motifs within sequence alignments to build characteristic signatures of different polypeptide families. Alternatively, HMMs can be used to find shared motifs, specifically consensus sequences (Pearson and Lipman (1988) Proc Natl Acad Sci 85:2444–2448; Smith and Waterman (1981) J Mol Biol 147:195–197). Although HMMs were initially developed to examine speech recognition patterns, they have been used in biology to analyze protein and DNA sequences and to model protein structure. HMMs have a formal probabilistic basis and use position-specific scores for amino acids or nucleotides. The algorithms are flexible in that they incorporate information from newly identified sequences to build even more successful patterns. HMMs are useful to identify the transmembrane regions and signal peptides.

In another embodiment, the sequences disclosed in the Sequence Listing can be searched against GenBank and SWISSPROT databases using BLAST. Then, the descriptions of those sequences with homology to the disclosed sequences may be scanned using keywords such as receptor, transmembrane, receptor, channel, oncogene, inhibitor, and the like.

Sequences identified by the methods described above are provided in SEQ ID NOs:1–305 in the Sequence Listing. Table 1 provides the annotation to the referenced PRINTS sequences and specifies whether they possess transmembrane and signal peptide motifs. The resulting composition can comprise polynucleotide sequences that are not redundant, i.e., there is no more than one polynucleotide sequence to represent a particular gene. Alternatively, the composition can contain polynucleotide probes or microarray elements that are redundant, i.e., a gene is represented by more than one polynucleotide sequence.

The selected polynucleotide sequences may be manipulated further to optimize their performance as hybridization probes. To optimize probe selection, the sequences are examined using a computer algorithms, which are well known in the art, to identify fragments of genes without potential secondary structure. Such computer algorithms are found in OLIGO 4.06 Primer Analysis software (National Biosciences) or LASERGENE software (DNASTAR). These programs can search nucleotide sequences to identify stem loop structures and tandem repeats and to analyze G+C content of the sequence (those sequences with a G+C content greater than 60% are excluded). Alternatively, the probes can be optimized by trial and error. Experiments can be performed to determine whether the probes hybridize optimally to target sequences under experimental conditions.

Where the greatest numbers of different polynucleotide sequences are desired, the sequences are extended to assure that different polynucleotide sequences are not derived from the same gene, i.e., the polynucleotide sequences are not redundant. The probe sequences may be extended utilizing the partial nucleotide sequences derived from clone isolates by employing methods well known in the art. For example, one method which may be employed, "restriction-site" PCR, uses universal primers to retrieve unknown sequence adjacent to a known locus (Sarkar (1993) PCR Methods Applic 2: 318–322).

Polynucleotide Sequences

This section describes the polynucleotide sequences. The polynucleotide sequences can be genomic DNA, cDNA, mRNA, or any RNA-like or DNA-like material, such as peptide nucleic acids, branched DNAs, and the like. The polynucleotide sequences can be sense or antisense, complementary sequences. Where target polynucleotides are double stranded, the probes may be either sense or antisense strands. Where the target polynucleotides are single stranded, the probes are complementary single strands. In one embodiment, the polynucleotide sequences are cDNAs, the size of which may vary, and are preferably from 1000 to 10,000 nucleotides, more preferably from 150 to 5000 nucleotides. In a second embodiment, the polynucleotide sequences are contained within plasmids. In this case, the size of the inserted cDNA sequence, excluding the vector DNA and its regulatory sequences, may vary from about 50 to 12,000 nucleotides, more preferably from about 150 to 5000 nucleotides.

The polynucleotide can be prepared by a variety of synthetic or enzymatic schemes which are well known in the art. Sequences can be synthesized, in whole or in part, using chemical or enzymatic methods well known in the art (Caruthers et al. (1980) Nucl Acids Symp Ser (7)215–233; Ausubel et al. (1997) *Short Protocols in Molecular Biology*, John Wiley & Sons, New York N.Y.).

Nucleotide analogues, which can base pair with the target nucleotide sequences, can be incorporated into the probe sequences by methods well known in the art. For example, certain guanine nucleotides can be substituted with hypoxanthine which hydrogen bonds with cytosine, but these bonds are less stable than those formed between guanine and cytosine. Alternatively, adenine nucleotides can be substituted with 2,6-diaminopurine which forms stronger bonds with thymidine than those between adenine and thymidine. Additionally, the polynucleotide sequences can include nucleotides that have been derivatized chemically or enzymatically. Typical chemical modifications include derivatization with acyl, alkyl, aryl or amino groups.

The polynucleotide sequences can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide sequences are bound. Preferably, the substrates are optically transparent.

Sequences can be synthesized, in whole or in part, on the surface of a substrate using a chemical coupling procedure and a piezoelectric printing apparatus, such as that described in PCT publication WO95/251116 (Baldeschweiler et al.). Alternatively, the target can be synthesized on a substrate surface using a self-addressable electronic device that controls when reagents are added (Heller et al. U.S. Pat. No. 5,605,662).

Complementary DNA (cDNA) can be arranged and immobilized on a substrate. The sequences can be immobilized by covalent means such as by chemical bonding procedures or UV. In one such method, a cDNA is bound to a glass surface which has been modified to contain epoxide or aldehyde groups. In another case, a cDNA target is placed on a polylysine coated surface and UV cross-linked (Shalon et al. WO95/35505). In yet another method, a DNA is actively transported from a solution to a given position on a substrate by electrical means (U.S. Pat. No. 5,605,662). Alternatively, individual DNA clones can be gridded on a filter. Cells are lysed, proteins and cellular components degraded, and the DNA coupled to the filter by UV cross-linking.

Furthermore, the sequences do not have to be directly bound to the substrate, but rather can be bound to the substrate through a linker group. The linker groups are typically about 6 to 50 atoms long, and they provide exposure to the attached polynucleotide sequence. Preferred linker groups include ethylene glycol oligomers, diamines, diacids and the like. Reactive groups on the substrate surface react with one of the terminal portions of the linker to bind the linker to the substrate. The other terminal portion of the linker is adapted to bind the polynucleotide sequence.

The polynucleotide sequences can be attached to a substrate by dispensing reagents for target synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

Sample Preparation

In order to conduct sample analysis, a sample containing nucleic acids is provided. The samples can be obtained from any bodily fluid (blood, urine, saliva, phlegm, gastric juices, etc.), cultured cells, biopsies, or other tissue preparations. DNA or RNA can be isolated from the sample according to any of a number of methods well known to those of skill in the art. For example, methods of purification of nucleic acids are described in Tijssen (1993; *Laboratory Techniques in Biochemistry and Molecular Biology: Hybridization With Nucleic Acid Probes, Part I. Theory and Nucleic Acid Preparation*, Elsevier Science, New York N.Y.). In one case, total RNA is isolated using the TRIZOL reagent (Life Technologies, Gaithersburg Md.), and mRNA is isolated using oligo d(T) column chromatography or glass beads. Alternatively, when probe polynucleotides are derived from an mRNA, the probe polynucleotides can be DNA reverse transcribed from the mRNA, an RNA transcribed from that cDNA, a DNA amplified from that DNA, an RNA transcribed from the amplified DNA, and the like. When the target polynucleotide is derived from cDNA, the target polynucleotide can be DNA amplified from DNA or DNA reverse transcribed from RNA. In yet another alternative, the polynucleotide sequences are prepared by more than one method.

When polynucleotide sequences are amplified, it is desirable to amplify the nucleic acid sample and maintain the relative abundances represented in the original sample including low abundance transcripts. Total mRNA can be amplified by reverse transcription using a reverse transcriptase and a primer consisting of oligo d(T) and a sequence encoding the phage T7 promoter to provide a single stranded DNA template. The second DNA strand is polymerized using a DNA polymerase and a RNAse which assists in breaking up the DNA/RNA hybrid. After synthesis of the double stranded DNA, T7 RNA polymerase can be added, and RNA transcribed from the second DNA strand template (Van Gelder et al. U.S. Pat. No. 5,545,522). RNA can be amplified in vitro, in situ or in vivo (Eberwine U.S. Pat. No. 5,514,545).

It is also advantageous to include quantitation controls within the sample to assure that amplification and labeling procedures do not change the true distribution of probe polynucleotides in a sample. For this purpose, a sample is spiked with a known amount of a control probe polynucleotide and the composition of target polynucleotide sequences includes reference target sequences which specifically hybridize with the control probe polynucleotides. After hybridization and processing, the hybridization signals obtained should reflect accurately the amount of control probe polynucleotides added to the sample.

Prior to hybridization, it may be desirable to fragment the probe polynucleotides. Fragmentation improves hybridization by minimizing secondary structure and cross-hybridization to polynucleotides in the sample with low or no complementarity. Fragmentation can be performed by mechanical or chemical means.

The probe polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Exemplary dyes include quinoline dyes, triarylmethane dyes, phthaleins, azo dyes, cyanine dyes and the like. Preferably, fluorescent markers absorb light above about 300 nm, preferably above 400 nm, and usually emit light at wavelengths at least greater than 10 nm above the wavelength of the light absorbed. Preferred fluorescent markers include fluorescein, phycoerythrin, rhodamine, lissamine, and Cy3 and Cy5 (Amersham Pharmacia Biotech, Piscataway N.J.).

Labeling can be carried out during an amplification reaction, such as polymerase chain and in vitro transcription reactions, or by nick translation or 5' or 3'-end-labeling reactions. In one case, labeled nucleotides are used in an in vitro transcription reaction. When the label is incorporated after or without an amplification step, the label is incorporated by using terminal transferase or by kinasing the 5' end of the polynucleotide sequence and then incubating overnight with a labeled oligonucleotide in the presence of T4 RNA ligase.

Alternatively, the labeling moiety can be incorporated after hybridization once a probe/target complex has formed. In one case, biotin is first incorporated during an amplification step as described above. After the hybridization reaction, unbound nucleic acids are rinsed away so that the only biotin present is attached to probe polynucleotides complexed with the target polynucleotides. An avidin-conjugated fluorophore, such as avidin-phycoerythrin, that binds with high affinity to biotin is added. In another case, the labeling moiety is incorporated by intercalation into bound probe/target complexes. In this case, an intercalating dye such as a psoralen-linked dye can be employed.

Under some circumstances it may be advantageous to immobilize the probe polynucleotides on a substrate and have the polynucleotide targets bind to the immobilized probe polynucleotides. In such cases the probe polynucleotides can be attached to a substrate as described above.

Hybridization and Detection

Hybridization causes a denatured polynucleotide probe and a denatured complementary target to form a stable duplex through base pairing. Hybridization methods are well known to those skilled in the art. (See, e.g., Ausubel, supra, units 2.8–2.11, 3.18–3.19 and 4–6–4.9.) Conditions can be selected for hybridization where completely complementary probe and target can hybridize, i.e., each base pair must interact with its complementary base pair. Alternatively, conditions can be selected where probe and target have mismatches but are still able to hybridize. Suitable conditions can be selected, for example, by varying the concentrations of salt in the prehybridization, hybridization, and wash solutions or by varying the hybridization and wash temperatures. With some membranes, the temperature can be decreased by adding formamide to the prehybridization and hybridization solutions.

Hybridization can be performed at low stringency with buffers, such as 5×SSC with 1% sodium dodecyl sulfate (SDS) at 60° C., which permits hybridization between probe and target sequences that contain some mismatches to form probe/target complexes. Subsequent washes are performed at higher stringency with buffers such as 0.2×SSC with 0.1% SDS at either 45° C. (medium stringency) or 68° C. (high stringency), to maintain hybridization of only those probe/target complexes that contain completely complementary sequences. Background signals can be reduced by the use of detergents such as SDS, Sarcosyl, or Triton X-100, or a blocking agent, such as salmon sperm DNA.

Hybridization specificity can be evaluated by comparing the hybridization of control probe sequences to control target sequences that are added to a sample in a known amount. The control probe may have one or more sequence mismatches compared with the corresponding control target. In this manner, it is possible to evaluate whether only complementary probes are hybridizing to the targets or whether mismatched hybrid duplexes are forming.

Hybridization reactions can be performed in absolute or differential hybridization formats. In the absolute hybridization format, probe polynucleotides from one sample are hybridized to microarray elements, and signals detected after hybridization complexes form. Signal strength correlates with probe polynucleotide levels in a sample. In the differential hybridization format, differential expression of a set of genes in two biological samples is analyzed. Probe polynucleotides from the two samples are prepared and labeled with different labeling moieties. A mixture of the two labeled probe polynucleotides is hybridized to the microarray elements, and signals are examined under conditions in which the emissions from the two different labels are individually detectable. Targets in the microarray that are hybridized to substantially equal numbers of probes derived from both biological samples give a distinct combined fluorescence (Shalon WO95/35505). In a preferred embodiment, the labels are fluorescent labels with distinguishable emission spectra, such as a lissamine conjugated nucleotide analog and a fluorescein conjugated nucleotide analog. In another embodiment Cy3/Cy5 fluorophores (Amersham Pharmacia Biotech) are employed.

After hybridization, the microarray is washed to remove nonhybridized nucleic acids, and complex formation between the hybridizable array elements and the probe polynucleotides is examined. Methods for detecting complex formation are well known to those skilled in the art. In a preferred embodiment, the probe polynucleotides are labeled with a fluorescent label, and measurement of levels and patterns of fluorescence indicative of complex formation is accomplished by fluorescence microscopy, preferably confocal fluorescence microscopy. An argon ion laser excites the fluorescent label, emissions are directed to a photomultiplier, and the amount of emitted light is detected and quantitated. The detected signal should be proportional to the amount of probe/target polynucleotide complexes at each position of the microarray. The fluorescence microscope can be associated with a computer-driven scanner device to generate a quantitative two-dimensional image of hybridization intensity. The scanned image is examined to determine the abundance/expression level of each hybridized probe polynucleotide.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray.

Expression Profiles

Expression profiles using the composition of this invention may be used to detect changes in the expression of genes implicated in disease. These genes include genes whose altered expression is correlated with pancreatic disease, cancer, immunopathology, neuropathology, and the like.

The expression profile comprises the polynucleotide sequences of the Sequence Listing. The expression profile also includes a plurality of detectable complexes. Each complex is formed by hybridization of one or more polynucleotide sequences or array elements to one or more complementary probe polynucleotides. At least one of the polynucleotide sequences, preferably a plurality of polynucleotide sequences, is hybridized to a complementary target polynucleotide forming at least one, and preferably a plurality, of complexes. A complex is detected by the incorporation of at least one labeling moiety, described above, in the complex. Expression profiles provide "snapshots" that reflect unique expression patterns that are characteristic of a disease or condition.

After performing hybridization experiments and interpreting the signals produced by complexes on a microarray, particular polynucleotide sequences can be identified based on their expression patterns. Such polynucleotide sequences can be used to clone a full length sequence for the gene, to produce a polypeptide, to develop a diagnostic panel for a particular disease, to choose a gene for potential therapeutic use, and the like.

Additional Utility of the Invention

Microarrays containing the sequences of the Sequence Listing can be employed in several applications including diagnostics, prognostics and treatment regimens, drug discovery and development, toxicological and carcinogenicity studies, forensics, pharmacogenomics and the like. In one situation, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic. The invention can also be used to monitor the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach may be more sensitive and rapid than waiting for the patient to show inadequate improvement, or to manifest side effects, before altering the course of treatment.

Alternatively, animal models which mimic a disease can be used, rather than patients, to characterize expression profiles associated with a particular disease or condition. This gene expression data may be useful in diagnosing and monitoring the course of disease in the model, in determining gene that are candidates for intervention, and in testing novel treatment regimens. Subsequently, the expression profile following protocols and treatments successful in the model system may be used on and monitored in human patients.

The expression of genes encoding membrane-associated proteins, receptors, and ion channels was highly associated with pancreatic tissue; ~45% of the sequences of the Sequence Listing were expressed in pancreatic tissues. In particular, the microarray and expression profile is useful to diagnose a conditions of the pancreas such as diabetes, pancreatitus, pancreatic cholera, hyperlipidemia, fibrocystic disease, and cancers and tumors of the pancreas.

The expression of genes encoding membrane-associated proteins, receptors, and ion channels is closely associated with immune conditions, disorders and diseases; ~20% of the sequences of the Sequence Listing were expressed in tissues from patients with immunological conditions such as AIDS, Addison's disease, ARDS, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

The expression of genes encoding membrane-associated proteins, receptors, and ion channels is closely associated with cancers; ~10% of the sequences of the Sequence Listing were expressed in cancerous tissues. In particular, the microarray and expression profile is useful to diagnose a cancer such as adenocarcinoma, leukemia, lymphoma, melanoma, myeloma, sarcoma and teratocarcinoma. Such cancers include, but are not limited to, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid and uterus.

The expression of genes encoding membrane-associated proteins, receptors, and ion channels is also closely associated with the immune response. Therefore, the microarray can be used to diagnose immunopathologies including, but not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, and protozoal infections; and trauma.

Neuropathologies are also effected by the expression of genes encoding membrane-associated proteins, receptors, and ion channels; in fact, ~1% of the sequences of the Sequence Listing were expressed in neuronal tissues. Thus, the microarray can be used to diagnose neuropathologies including, but not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

Also, researchers can use the microarray to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to determine the molecular mode of action of a drug. It is understood that this invention is not limited to the particular devices, machines, materials and methods described. Although preferred embodiments are described; devices, machines, materials and methods similar or equivalent to these embodiments may be used to practice the invention. The preferred embodiments are not intended to limit the scope of the invention which is limited only by the appended claims.

The singular forms "a", "an", and "the" include plural reference unless the context clearly dictates otherwise. All technical and scientific terms have the meanings commonly understood by one of ordinary skill in the art. All patents mentioned herein are incorporated by reference for the purpose of describing and disclosing the devices, machines, materials and methods which are presented and which might be used in connection with the invention. Nothing in the specification is to be construed as an admission that the invention is not entitled to antedate such disclosure by virtue of prior invention.

EXAMPLES

For purposes of example, the preparation and sequencing of the PANCNOT07 cDNA library is described. Preparation and sequencing of cDNAs in libraries in the LIFESEQ database (Incyte Pharmaceuticals) have varied over time, and the gradual changes involved use of kits, plasmids, and machinery available at the particular time the library was made and analyzed.

I cDNA Library Construction

The PANCNOT07 cDNA library was constructed from pancreas tissue obtained from a 25-week-old Caucasian male fetus. The frozen tissue was homogenized and lysed using a POLYTRON homogenizer (PT-3000; Brinkmann Instruments, Westbury N.J.) in guanidinium isothiocyanate solution. The lysate was centrifuged over a 5.7 M CsCl cushion using an SW28 rotor in a L8-70M ultracentrifuge (Beckman Coulter, Fullerton Calif.) for 18 hours at 25,000 rpm at ambient temperature. The RNA was extracted with acid phenol (pH 4.7), precipitated using 0.3 M sodium acetate and 2.5 volumes of ethanol, resuspended in RNAse-free water, and treated with DNase at 37° C. Extraction and precipitation were repeated as before. The mRNA was isolated with the OLIGOTEX kit (Qiagen, Chatsworth Calif.) and used to construct the cDNA library.

The mRNA was handled according to the recommended protocols in the SUPERSCRIPT Plasmid system (Life Technologies). The cDNAs were fractionated on a SEPHAROSE CL4B column (Amersham Pharmacia Biotech), and those cDNAs exceeding 400 bp were ligated into pINCY1 plasmid (Incyte Pharmaceuticals). The plasmid was then transformed into DH5$\alpha$ competent cells (Life Technologies).

II Isolation and Sequencing of cDNA Clones

Plasmid DNA was released from the cells and purified using the REAL Prep 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours; and at the end of incubation, the cells were lysed with 0.3 ml of lysis buffer; and 3) following isopropanol precipitation, the DNA pellet was resuspended in 0.1 ml of distilled water. After the last step in the protocol, samples were transferred to a 96-well block for storage at 4° C.

The cDNAs were sequenced by the method of Sanger and Coulson (1975, J Mol Biol 94:441–448). A MICROLAB 2200 (Hamilton, Reno Nev.) in combination with DNA Engine thermal cyclers (PTC200; MJ Research, Watertown Mass.) were used to prepare the DNA. After thermal cycling, the A, C, G, and T reactions with each DNA template were combined. Then, 50 $\mu$l 100% ethanol was added, and the solution was spun at 4° C. for 30 min. The supernatant was decanted, and the pellet was rinsed with 100 $\mu$l 70% ethanol. After being spun for 15 min, the supernatant was discarded and the pellet was dried for 15 min under vacuum. The DNA sample was dissolved in 3 $\mu$l of formaldehyde/50 mM EDTA and loaded into wells in volumes of 2 $\mu$l per well for sequencing on ABI 377 DNA Sequencing systems (PE Biosystems, Foster City Calif.).

Most of the sequences were sequenced using standard ABI protocols and kits (Cat. Nos. 79345, 79339, 79340, 79357, 79355; PE Biosystems) at solution volumes of 0.25x–1.0x concentrations. Some of the sequences were sequenced using solutions and dyes from Amersham Pharmacia Biotech).

III Characterization of cDNA Clones

The nucleotide sequences of the Sequence Listing, as well as the amino acid sequences deduced from them, were used as query sequences against GenBank, SwissProt, BLOCKS, and PRINTS databases. The sequences in these databases, which contain previously identified and annotated sequences, were searched for regions of similarity using BLAST or FASTA (Pearson, W. R. (1990) Methods Enzymol 183:63–98; and Smith and Waterman (1981) Adv Appl Math 2:482–489).

VII. Extension of cDNA Sequences

The original nucleic acid sequence was extended using the Incyte cDNA clone and oligonucleotide primers. One primer was synthesized to initiate 5' extension of the known fragment, and the other, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected cDNA libraries, such as a pancreas library, were used to extend the sequence. If more than one extension was necessary, additional or nested sets of primers were designed. Preferred libraries are ones that have been size-selected to include larger cDNAs. Also, random primed libraries are preferred because they will contain more sequences with the 5' and upstream regions of genes. A randomly primed library is particularly useful if an oligo d(T) library does not yield a full-length cDNA. Genomic libraries are useful for extension 5' of the promoter binding region to obtain regulatory elements.

High fidelity amplification was obtained by PCR using methods well known in the art. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, TAQ DNA polymerase (Amersham Pharmacia Biotech), ELONGASE enzyme (Life Technologies), and Pfu DNA polymerase (Stratagene, San Diego Calif.), with the following parameters for primer pair PCI A and PCI B: Step 1: 94° C., 3 min; Step 2: 94° C., 15 sec; Step 3: 60° C., 1 min; Step 4: 68° C. 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% v/v; Molecular Probes, Eugene Oreg.) dissolved in 1×TE and 0.5 μl of undiluted PCR product into each well of an opaque fluorimeter plate (Corning Costar, Acton Mass.) and allowing the DNA to bind to the reagent. The plate was scanned in a Fluroskan II (Labsystems Oy, Helsinki, FI) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with AGARACE enzyme (Promega, Madison Wis.). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, and individual colonies were picked and cultured overnight at 37° C. in 384-well plates in LB/2x carbenicillin liquid media.

The cells were lysed, and DNA was amplified by PCR using TAQ DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified using PICOGREEN reagent (Molecular Probes) as described above. Samples with low DNA recoveries were reamplified using the same conditions described above. Samples were diluted with 20% dimethysulphoxide (1:2, v/v), and sequenced using DYENAMIC energy transfer sequencing primers and the DYENAMIC DIRECT cycle sequencing kit (Amersham Pharmacia Biotech) or the ABI PRISM BIG-DYE Terminator cycle sequencing kit (PE Biosystems). The extended sequences were assembled with the original clone using CONSED, PHRAP or GELVIEW software (GCG) and reanalyzed using BLAST, FASTA, or similar sequence analysis programs well known in the art. (See, e.g., Ausubel, supra, unit 7.7, pp. 7.65–69.)

IV Selection of Sequences

The sequences found in the Sequence Listing were selected because they possessed annotation, motifs, domains, regions or other patterns consistent with genes encoding proteins associated with membranes, receptors, or ion channels. The PRINTS database was searched using the BLIMPS search program to obtain protein family "finger-prints". The PRINTS database complements the PROSITE database and contains groups of conserved motifs within sequence alignments which are used to build characteristic signatures of different polypeptide families. For PRINTS analyses, the cutoff scores for local similarity were >1300=strong, 1000–1300=suggestive; for global similarity, p<exp-3; and for strength (degree of correlation >1300=strong, 1000–1300=weak.

PRINTS screening was carried out electronically to identify those sequences shown in the Sequence Listing with similarity to membrane-associated proteins, receptors, and ion channels. The protein groupings screened included extracellular messengers (including cytokines, growth factors, hormones, neuropeptides, oncogenes, and vasomediators), receptors (including GPCRs, tetraspannins, receptor kinases and nuclear receptors), ion channels, and proteins associated with signaling cascades (including kinases, phosphatases, G proteins, and second messengers such as cyclic AMP, phospholipase C, inositol triphosphate, and the like).

VIII Labeling of Probes and Hybridization Analyses

Blotting

Polynucleotide sequences are isolated from a biological source and applied to a solid matrix (a blot) suitable for standard nucleic acid hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20×saline sodium citrate (SSC). Alternatively, the target nucleic acids are individually ligated to a vector and inserted into bacterial host cells to form a library. Target nucleic acids are arranged on a blot by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 (Amersham Pharmacia Biotech). Purified target nucleic acids are robotically arrayed onto a glass microscope slide (Corning Science Products, Acton Mass.). The slide was previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

Probe Preparation cDNA probe sequences are made from mRNA templates. Five micrograms of mRNA is mixed with 1 μg random primer (Life Technologies), incubated at 70° C. for 10 minutes, and lyophilized. The lyophilized sample is resuspended in 50 μl of 1×first strand buffer (cDNA synthesis system; Life Technologies) containing a dNTP mix, [α-$^{32}$P] dCTP, dithiothreitol, and MMLV reverse transcriptase (Stratagene), and incubated at 42° C. for 1–2 hours. After incubation, the probe is diluted with 42 μl $dH_2O$, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 microcolumn (Amersham Pharmacia Biotech). Probes can be labeled with fluorescent markers, Cy3-dCTP or Cy5-dCTP (Amersham Pharmacia Biotech), in place of the radionuclide, [$^{32}$P]dCTP.

Hybridization

Hybridization is carried out at 65° C. in a hybridization buffer containing 0.5 M sodium phosphate (pH 7.2), 7% SDS, and 1 mM EDTA. After the blot is incubated in hybridization buffer at 65° C. for at least 2 hours, the buffer is replaced with 10 ml of fresh buffer containing the probe sequences. After incubation at 65° C. for 18 hours, the hybridization buffer is removed, and the blot is washed sequentially under increasingly stringent conditions, up to 40 mM sodium phosphate, 1% SDS, 1 mM EDTA at 65° C. To detect signal produced by a radiolabeled probe hybridized on a membrane, the blot is exposed to a PHOSPHORIMAGER cassette (Amersham Pharmacia Biotech), and the image is analyzed using IMAGEQUANT data analysis software (Molecular Dynamics). To detect signals produced by a fluorescent probe hybridized on a microarray, the blot is examined by confocal laser microscopy, and images are collected and analyzed using GEMTOOLS gene expression analysis software (Incyte Pharmaceuticals).

TABLE I

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| SEQ ID NO:1 | 8915 | PR00554C | ADENOSINE A2B RECEPTOR SIGNATURE | 1189 | 1319 | yes | yes |
| SEQ ID NO:2 | 68454 | PR00572B | INTERLEUKIN 8A RECEPTOR SIGNATURE | 1120 | 1184 | | |
| SEQ ID NO:3 | 98991 | PR00897E | VASOPRESSIN VIB RECEPTOR SIGNATURE | 1159 | 1135 | | |
| SEQ ID NO:4 | 121140 | PR00247B | CAMP-TYPE GPCR SIGNATURE | 1230 | 1244 | yes | |
| SEQ ID NO:5 | 129059 | PR00535A | MELANOCORTIN RECEPTOR SIGNATURE | 1169 | 1120 | | |
| SEQ ID NO:6 | 222732 | PR00580 | PROSTANOID EPI RECEPTOR SIGNATURE | 1278 | 1114 | | |
| SEQ ID NO:7 | 222748 | PR00635A | AT1 ANGIOTENSIN II RECEPTOR SIGNATURE | 1280 | 1356 | yes | yes |
| SEQ ID NO:8 | 224587 | PR00555C | ADENOSINE A3 RECEPTOR SIGNATURE | 1332 | 1341 | yes | |
| SEQ ID NO:9 | 225146 | PR00522G | CANNABINOID RECEPTOR TYPE 1 SIGNATURE | 1341 | 1282 | | |
| SEQ ID NO:10 | 225640 | PR00592B | EXTRACELLULAR CALCIUM-SENSING RECEPTOR SIGNAT | 1421 | 1279 | | |
| SEQ ID NO:11 | 225650 | PR00648D | GPR3 ORPHAN RECEPTOR SIGNATURE | 1146 | 1302 | yes | |
| SEQ ID NO:12 | 226179 | PR00641H | EBI1 ORPHAN RECEPTOR SIGNATURE | 1259 | 1215 | | |
| SEQ ID NO:13 | 226815 | PR00644E | GPR ORPHAN RECEPTOR SIGNATURE | 1453 | 1250 | | yes |
| SEQ ID NO:14 | 227559 | PR00554G | ADENOSINE A2B RECEPTOR SIGNATURE | 1259 | 1234 | | |
| SEQ ID NO:15 | 227799 | PR00366A | ENDOTHELIN RECEPTOR SIGNATURE | 1337 | 1279 | yes | |
| SEQ ID NO:16 | 227892 | PR00531A | HISTAMINE H2 RECEPTOR SIGNATURE | 1183 | 1197 | yes | |
| SEQ ID NO:17 | 228282 | PR00565C | DOPAMINE 1A RECEPTOR SIGNATURE | 1221 | 1213 | | |
| SEQ ID NO:18 | 229665 | PR00648D | GPR3 ORPHAN RECEPTOR SIGNATURE | 1146 | 1233 | yes | |
| SEQ ID NO:19 | 229779 | PR00537C | MU OPIOID RECEPTOR SIGNATURE | 1348 | 1216 | yes | |
| SEQ ID NO:20 | 240829 | PR00856I | PROSTACYCLIN (PROSTANOID IP) RECEPTOR SIGNATURE | 1131 | 1273 | | yes |
| SEQ ID NO:21 | 341490 | PR00531A | HISTAMINE H2 RECEPTOR SIGNATURE | 1183 | 1256 | yes | yes |
| SEQ ID NO:22 | 402456 | PR00555F | ADENOSINE A3 RECEPTOR SIGNATURE | 1259 | 1121 | | |
| SEQ ID NO:23 | 420765 | PR00536E | MELANOCYTE STIMULATING HORMONE RECEPTOR SIGNA | 1313 | 1170 | | |
| SEQ ID NO:24 | 481770 | PR00558B | ALPHA-2A ADRENERGIC RECEPTOR SIGNATURE | 1519 | 1108 | | |
| SEQ ID NO:25 | 548654 | PR00531A | HISTAMINE H2 RECEPTOR SIGNATURE | 1183 | 1240 | | yes |
| SEQ ID NO:26 | 632097 | PR00715E | CATION-DEPENDENT MANNOSE-6-PHOSPHATE RECEPTOR | 1440 | 1300 | yes | yes |
| SEQ ID NO:27 | 647580 | PR00586B | PROSTANOID EP4 RECEPTOR SIGNATURE | 1452 | 1317 | | yes |
| SEQ ID NO:28 | 647628 | PR00514D | 5-HYDROXYTRYPTAMINE 1D RECEPTOR SIGNATURE | 1252 | 1263 | yes | yes |
| SEQ ID NO:29 | 647931 | PR00596D | URIDINE NUCLEOTIDE RECEPTOR SIGNATURE | 1255 | 1221 | | |
| SEQ ID NO:30 | 648153 | PR00647I | SENR ORPHAN RECEPTOR SIGNATURE | 1291 | 1213 | | |
| SEQ ID NO:31 | 648838 | PR00751E | THYROTROPHIN-RELEASING HORMONE | 1433 | 1221 | | |

TABLE I-continued

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| | | | RECEPTOR SIGNATURE | | | | |
| SEQ ID NO:32 | 649152 | PR00554G | ADENOSINE A2B RECEPTOR SIGNATURE | 1259 | 1078 | | |
| SEQ ID NO:33 | 649682 | PR00255B | NATRIURETIC PEPTIDE RECEPTOR SIGNATURE | 1264 | 1213 | | |
| SEQ ID NO:34 | 649917 | PR00596D | URIDINE NUCLEOTIDE RECEPTOR SIGNATURE | 1255 | 1154 | | |
| SEQ ID NO:35 | 650726 | PR00490C | SECRETIN RECEPTOR SIGNATURE | 1238 | 1195 | | |
| SEQ ID NO:36 | 652013 | PR00491C | VASOCATIVE INTESTINAL PEPTIDE RECEPTOR SIGNAT | 1121 | 1155 | | yes |
| SEQ ID NO:37 | 738964 | PR00542F | MUSCARINIC M5 RECEPTOR SIGNATURE | 1218 | 1185 | | |
| SEQ ID NO:38 | 743323 | PR00899G | FUNGAL PHEROMONE STE3 GPCR SIGNATURE | 1132 | 1218 | | |
| SEQ ID NO:39 | 753592 | PR00587A | SOMATOSTATIN RECEPTOR TYPE I SIGNATURE | 1312 | 1121 | | |
| SEQ ID NO:40 | 797777 | PR00512F | 5-HYDROXYTRYPTAMINE 1A RECEPTOR SIGNATURE | 1388 | 1257 | | yes |
| SEQ ID NO:41 | 885098 | PR00642C | EDG1 ORPHAN RECEPTOR SIGNATURE | 1193 | 1213 | | |
| SEQ ID NO:42 | 947812 | PR00636C | AT2 ANGIOTENSIN II RECEPTOR SIGNATURE | 1317 | 1277 | | |
| SEQ ID NO:43 | 948051 | PR00554A | ADENOSINE A2B RECEPTOR SIGNATURE | 1109 | 1255 | | |
| SEQ ID NO:44 | 948581 | PR00539E | MUSCARINIC M2 RECEPTOR SIGNATURE | 1322 | 1244 | yes | |
| SEQ ID NO:45 | 948700 | PR00554C | ADENOSINE A2B RECEPTOR SIGNATURE | 1189 | 1316 | | |
| SEQ ID NO:46 | 948883 | PR00531E | HISTAMINE H2 RECEPTOR SIGNATURE | 1324 | 1241 | yes | |
| SEQ ID NO:47 | 948935 | PR00663D | GALANIN RECEPTOR SIGNATURE | 1168 | 1282 | | |
| SEQ ID NO:48 | 949387 | PR00639D | NEUROMEDIN B RECEPTOR SIGNATURE | 1198 | 1216 | yes | |
| SEQ ID NO:49 | 951797 | PR00900G | PHEROONE A RECEPTOR SIGNATURE | 996 | 1211 | yes | |
| SEQ ID NO:50 | 997947 | PR00928E | GRAVES DISEASE CARRIER PROTEIN SIGNATURE | 1410 | 1283 | yes | |
| SEQ ID NO:51 | 1212964 | PR00564D | BURKITT'S LYMPHOMA RECEPTOR SIGNATURE | 1295 | 1291 | yes | |
| SEQ ID NO:52 | 1214535 | PR00527A | GASTRIN RECEPTOR SIGNATURE | 1327 | 1185 | | |
| SEQ ID NO:53 | 1219856 | PR00587A | SOMATOSTATIN RECEPTOR TYPE I SIGNATURE | 1312 | 1181 | | |
| SEQ ID NO:54 | 1288503 | PR00663G | GALANIN RECEPTOR SIGNATURE | 1160 | 1452 | yes | yes |
| SEQ ID NO:55 | 1298179 | PR00666C | PINEAL OPSIN SIGNATURE | 1257 | 1296 | yes | |
| SEQ ID NO:56 | 1305513 | PR00639D | NEUROMEDIN B RECEPTOR SIGNATURE | 1198 | 1238 | | yes |
| SEQ ID NO:57 | 1318926 | PR00639D | NEUROMEDIN B RECEPTOR SIGNATURE | 1198 | 1299 | yes | |
| SEQ ID NO:58 | 1328744 | PR00641A | EBI1 ORPHAN RECEPTOR SIGNATURE | 1325 | 1267 | yes | yes |
| SEQ ID NO:59 | 1328845 | PR00554D | ADENOSINE A2B RECEPTOR SIGNATURE | 1208 | 1221 | yes | yes |
| SEQ ID NO:60 | 1329044 | PR00900G | PHEROMONE A RECEPTOR SIGNATURE | 996 | 1235 | yes | yes |
| SEQ ID NO:61 | 1329081 | PR00522G | CANNABINOID RECEPTOR TYPE I SIGNATURE | 1341 | 1249 | yes | |
| SEQ ID NO:62 | 1329095 | PR00639D | NEUROMEDIN B RECEPTOR SIGNATURE | 1198 | 1137 | | |
| SEQ ID NO:63 | 1329404 | PR00637D | TYPE 3 BOMBESIN RECEPTOR SIGNATURE | 1131 | 1246 | | |
| SEQ ID NO:64 | 1329477 | PR00517F | 5-HYDROXYTRYPTAMINE 2C RECEPTOR SIGNATURE | 1259 | 1310 | yes | |
| SEQ ID NO:65 | 1329584 | PR00856I | PROSTACYCLIN PROSTANOID IP) RECEPTOR SIGNATU | 1131 | 1176 | | |
| SEQ ID NO:66 | 1329652 | PR00646B | RDC1 ORPHAN RECEPTOR SIGNATURE | 1307 | 1226 | yes | yes |
| SEQ ID NO:67 | 1329778 | PR00562F | BETA-2 ADRENERGIC RECEPTOR SIGNATURE | 1360 | 1292 | yes | |
| SEQ ID NO:68 | 1329830 | PR00642B | EDG1 ORPHAN RECEPTOR SIGNATURE | 1218 | 1325 | yes | |
| SEQ ID NO:69 | 1329851 | PR00582B | PROSTANOID EP3 RECEPTOR SIGNATURE | 1750 | 1276 | yes | yes |
| SEQ ID NO:70 | 1329862 | PR00580C | PROSTANOID EP1 RECEPTOR SIGNATURE | 1278 | 1253 | | yes |
| SEQ ID NO:71 | 1329971 | PR00547A | X OPIOID RECEPTOR SIGNATURE | 1342 | 1233 | | |
| SEQ ID NO:72 | 1329994 | PR00564D | BURKITT'S LYMPHOMA RECEPTOR SIGNATURE | 1295 | 1315 | yes | yes |
| SEQ ID NO:73 | 1329995 | PR00490F | SECRETIN RECEPTOR SIGNATURE | 1239 | 1275 | | yes |
| SEQ ID NO:74 | 1330007 | PR00899K | FUNGAL PHEROMONE STE3 GPCR SIGNATURE | 1057 | 1244 | yes | |
| SEQ ID NO:75 | 1330016 | PR00514D | 5-HYDROXYTRYPTAMINE 1D RECEPTOR SIGNATURE | 1252 | 1255 | yes | |
| SEQ ID NO:76 | 1330023 | PR00647I | SENR ORPHAN RECEPTOR SIGNATURE | 1291 | 1258 | yes | |
| SEQ ID NO:77 | 1330061 | PR00586H | PROSTANOID EP4 RECEPTOR SIGNATURE | 1526 | 1219 | | |
| SEQ ID NO:78 | 1330108 | PR00424B | ADENOSINE RECEPTOR SIGNATURE | 1339 | 1240 | yes | yes |
| SEQ ID NO:79 | 1330215 | PR00642B | EDG1 ORPHAN RECEPTOR SIGNATURE | 1218 | 1237 | yes | |
| SEQ ID NO:80 | 1330424 | PR00248F | METABOTROPIC GLUTAMATE GPCR SIGNATURE | 1498 | 1262 | yes | |
| SEQ ID NO:81 | 1330429 | PR00568D | DOPAMINE D3 RECEPTOR SIGNATURE | 1445 | 1226 | yes | yes |
| SEQ ID NO:82 | 1330478 | PR00571G | ENDOTHELIN-B RECEPTOR SIGNATURE | 1420 | 1253 | yes | |
| SEQ ID NO:83 | 1330641 | PR00424F | ADENOSINE RECEPTOR SIGNATURE | 1205 | 1241 | | |
| SEQ ID NO:84 | 1330656 | PR00554B | ADENOSINE A2B RECEPTOR SIGNATURE | 1090 | 1227 | yes | |
| SEQ ID NO:85 | 1330683 | PR00699F | *C. ELEGANS* INTEGRAL MEMBRAND PROTEIN SRG SIGNA | 1214 | 1220 | yes | |
| SEQ ID NO:86 | 1330740 | PR00639D | NEUROMEDIN B RECEPTOR SIGNATURE | 1198 | 1209 | | yes |
| SEQ ID NO:87 | 1330847 | PR00641F | EBI1 ORPHAN RECEPTOR SIGNATURE | 1290 | 1260 | yes | yes |
| SEQ ID NO:88 | 1330861 | PR00424B | ADENOSINE RECEPTOR SIGNATURE | 1339 | 1310 | | yes |
| SEQ ID NO:89 | 1330882 | PR00559C | ALPHA-2B ADRENERGIC RECEPTOR SIGNATURE | 1284 | 1208 | | |
| SEQ ID NO:90 | 1330907 | PR00568A | DOAPMINE D3 RECEPTOR SIGNATURE | 1427 | 1248 | | yes |
| SEQ ID NO:91 | 1330918 | PR00908H | THROMBIN RECEPTOR SIGNATURE | 1409 | 1300 | yes | yes |
| SEQ ID NO:92 | 1330930 | PR00645I | LCR1 ORPHAN RECEPTOR SIGNATURE | 1511 | 1272 | yes | yes |
| SEQ ID NO:93 | 1330957 | PR00261E | LOW DENSITY LIPOPROTEIN (LDL) RECEPTOR SIGNAT | 1459 | 1236 | yes | |
| SEQ ID NO:94 | 1330969 | PR00515C | 5-HYDROXYTRYPTAMINE 1F RECEPTOR SIGNATURE | 1351 | 1264 | | |
| SEQ ID NO:95 | 1331030 | PR00715E | CATION-DEPENDENT MANNOSE-6-PHOSPHATE RECEPTOR | 1440 | 1300 | yes | |
| SEQ ID NO:96 | 1331172 | PR00667B | RETINAL PIGMENT EPITHELIUM-RETINAL GPCR SIGNA | 1190 | 1237 | yes | |

TABLE I-continued

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| SEQ ID NO:97 | 1331278 | PR00854B | PROSTAGLANDIN D RECEPTOR SIGNATURE | 1257 | 1288 | | yes |
| SEQ ID NO:98 | 1331316 | PR00596D | URIDINE NUCLEOTIDE RECEPTOR SIGNATURE | 1255 | 1294 | | |
| SEQ ID NO:99 | 1331330 | PR00699E | *C. ELEGANS* INTEGRAL MEMBRANE PROTEIN SRG SIGNA | 1137 | 1196 | yes | |
| SEQ ID NO:100 | 1331371 | PR00240D | ALPHA-1A ADRENERGIC RECEPTOR SIGNATURE | 1470 | 1238 | yes | |
| SEQ ID NO:101 | 1331411 | PR00542F | MUSCARINIC M5 RECEPTOR SIGNATURE | 1218 | 1284 | yes | |
| SEQ ID NO:102 | 1331481 | PR00641B | EBI1 ORPHAN RECEPTOR SIGNATURE | 1354 | 1244 | | |
| SEQ ID NO:103 | 1331917 | PR00572B | INTERLEUKIN 8A RECEPTOR SIGNATURE | 1120 | 1229 | yes | yes |
| SEQ ID NO:104 | 1332023 | PR00240D | ALPHA-1A ADRENERGIC RECEPTOR SIGNATURE | 1470 | 1307 | yes | yes |
| SEQ ID NO:105 | 1332138 | PR00752F | VASOPRESSIN V1A RECEPTOR SIGNATURE | 1304 | 1226 | yes | |
| SEQ ID NO:106 | 1332171 | PR00715I | CATION-DEPENDENT MANNOSE-6-PHOSPHATE RECEPTOR | 1392 | 1205 | | |
| SEQ ID NO:107 | 1332391 | PR00522G | CANNABINOID RECEPTOR TYPE 1 SIGNATURE | 1341 | 1285 | | yes |
| SEQ ID NO:108 | 1332480 | PR00643D | G1D ORPHAN RECEPTOR SIGNATURE | 1317 | 1210 | | |
| SEQ ID NO:109 | 1332803 | PR00258D | SPERACT RECEPTOR SIGNATURE | 1254 | 1230 | | yes |
| SEQ ID NO:110 | 1332830 | PR00652F | 5-HYDROXYTRYPTAMINE 7 RECEPTOR SIGNATURE | 1488 | 1194 | | |
| SEQ ID NO:111 | 1332955 | PR00639D | NEUROMEDIN B RECEPTOR SIGNATURE | 1198 | 1295 | yes | yes |
| SEQ ID NO:112 | 1332966 | PR00574D | BLUE-SENSITIVE OPSIN SIGNATURE | 1263 | 1300 | yes | |
| SEQ ID NO:113 | 1332981 | PR00589E | SOMATOSTATIN RECEPTOR TYPE 3 SIGNATURE | 1340 | 1253 | | yes |
| SEQ ID NO:114 | 1333006 | PR00643H | G10D ORPHAN RECEPTOR SIGNATURE | 1453 | 1285 | | yes |
| SEQ ID NO:115 | 1333107 | PR00539E | MUSCARINIC M2 RECEPTOR SIGNATURE | 1322 | 1371 | | |
| SEQ ID NO:116 | 1333116 | PR00568D | DOPAMINE D3 RECEPTOR SIGNATURE | 1445 | 1206 | | |
| SEQ ID NO:117 | 1333133 | PR00643H | G10D ORPHAN RECEPTOR SIGNATURE | 1453 | 1246 | | |
| SEQ ID NO:118 | 1352448 | PR00527I | GASTRIN RECEPTOR SIGNATURE | 1633 | 1234 | yes | yes |
| SEQ ID NO:119 | 1385827 | PR00539E | MUSCARINIC M2 RECEPTOR SIGNATURE | 1322 | 1368 | yes | yes |
| SEQ ID NO:120 | 1385922 | PR00571G | ENDOTHELIN-B RECEPTOR SIGNATURE | 1420 | 1193 | | |
| SEQ ID NO:121 | 1386485 | PR00574D | BLUE-SENSITIVE OPSIN SIGNATURE | 1263 | 1317 | | |
| SEQ ID NO:122 | 1386553 | PR00857C | MELATONIN RECEPTOR SIGNATURE | 1472 | 1238 | | yes |
| SEQ ID NO:123 | 1386660 | PR00647I | SENR ORPHAN RECEPTOR SIGNATURE | 1291 | 1251 | | |
| SEQ ID NO:124 | 1386859 | PR00645G | LCR1 ORPHAN RECEPTOR SIGNATURE | 1454 | 1230 | | |
| SEQ ID NO:125 | 1387302 | PR00592B | EXTRACELLULAR CALCIUM-SENSING RECEPTOR SIGNAT | 1421 | 1203 | | yes |
| SEQ ID NO:126 | 1388063 | PR00665G | OXYTOCIN RECEPTOR SIGNATURE | 1246 | 1335 | yes | |
| SEQ ID NO:127 | 1422814 | PR00647I | SENR ORPHAN RECEPTOR SIGNATURE | 1291 | 1292 | | |
| SEQ ID NO:128 | 1423820 | PR00574D | BLUE-SENSITIVE OPSIN SIGNATURE | 1263 | 1177 | yes | |
| SEQ ID NO:129 | 1429651 | PR00554G | ADENOSINE A2B RECEPTOR SIGNATURE | 1259 | 1275 | yes | yes |
| SEQ ID NO:130 | 1436525 | PR00568D | DOPAMINE D3 RECEPTOR SIGNATURE | 1445 | 1216 | | yes |
| SEQ ID NO:131 | 1453124 | PR00649G | GPR6 ORPHAN RECEPTOR SIGNATURE | 1103 | 1292 | yes | |
| SEQ ID NO:132 | 1460891 | PR00854B | PROSTAGLANDIN D RECEPTOR SIGNATURE | 1257 | 1245 | | |
| SEQ ID NO:133 | 1465590 | PR00539E | MUSCARINIC M2 RECEPTOR SIGNATURE | 1322 | 1229 | yes | yes |
| SEQ ID NO:134 | 1466523 | PR00560D | ALPHA-2C ADRENERGIC RECEPTOR SIGNATURE | 1642 | 1319 | | |
| SEQ ID NO:135 | 1466902 | PR00240D | ALPHA-1A ADRENERGIC RECEPTOR SIGNATURE | 1470 | 1271 | | |
| SEQ ID NO:136 | 1468040 | PR00537C | MU OPIOID RECEPTOR SIGNATURE | 1348 | 1316 | yes | |
| SEQ ID NO:137 | 1480833 | PR00571G | ENDOTHELIN-B RECEPTOR SIGNATURE | 1420 | 1325 | | |
| SEQ ID NO:138 | 1516908 | PR00530I | HISTAMINE H1 RECEPTOR SIGNATURE | 1295 | 1276 | | yes |
| SEQ ID NO:139 | 1518320 | PR00343A | SELECTIN SUPERFAMILY COMPLEMENT-BINDING REPEA | 1245 | 1412 | | yes |
| SEQ ID NO:140 | 1529624 | PR00522G | CANNABINOID RECEPTOR TYPE 1 SIGNATURE | 1341 | 1350 | | |
| SEQ ID NO:141 | 1590311 | PR00639D | NEUROMEDIN B RECEPTOR SIGNATURE | 1198 | 1168 | | |
| SEQ ID NO:142 | 1590335 | PR00666B | PINEAL OPSIN SIGNATURE | 1253 | 1224 | | |
| SEQ ID NO:143 | 1590422 | PR00240F | ALPHA-1A ADRENERGIC RECEPTOR SIGNATURE | 1323 | 1226 | | |
| SEQ ID NO:144 | 1590455 | PR00637D | TYPE 3 BOMBESIN RECEPTOR SIGNATURE | 1131 | 1182 | | |
| SEQ ID NO:145 | 1590464 | PR00637D | TYPE 3 BOMBESIN RECEPTOR SIGNATURE | 1131 | 1268 | | yes |
| SEQ ID NO:146 | 1590496 | PR00908H | THROMBIN RECEPTOR SIGNATURE | 1409 | 1226 | yes | |
| SEQ ID NO:147 | 1590713 | PR00641F | EBI1 ORPHAN RECEPTOR SIGNATURE | 1290 | 1211 | | |
| SEQ ID NO:148 | 1590769 | PR00572B | INTERLEUKIN 8A RECEPTOR SIGNATURE | 1120 | 1122 | | |
| SEQ ID NO:149 | 1590779 | PR00642C | EDG1 ORPHAN RECEPTOR SIGNATURE | 1193 | 1246 | | |
| SEQ ID NO:150 | 1590931 | PR00646F | RDC1 ORPHAN RECEPTOR SIGNATURE | 1188 | 1165 | | |
| SEQ ID NO:151 | 1590958 | PR00261C | LOW DENSITY LIPOPROTEIN (LDL) RECEPTOR SIGNAT | 1576 | 1234 | | |
| SEQ ID NO:152 | 1590973 | PR00350C | VITAMIN D RECEPTOR SIGNATURE | 1416 | 1283 | yes | yes |
| SEQ ID NO:153 | 1591090 | PR00643G | G10D ORPHAN RECEPTOR SIGNATURE | 1383 | 1292 | | |
| SEQ ID NO:154 | 1591713 | PR00553B | ADENOSINE A2A RECEPTOR SIGNATURE | 1258 | 1292 | yes | yes |
| SEQ ID NO:155 | 1642794 | PR00527B | GASTRIN RECEPTOR SIGNATURE | 1431 | 1353 | | |
| SEQ ID NO:156 | 1687080 | PR00855A | PROSTAGLANDIN F RECEPTOR SIGNATURE | 1361 | 1248 | yes | yes |
| SEQ ID NO:157 | 1722845 | PR00248C | METABOTROPIC GLUTAMATE GPCR SIGNATURE | 1402 | 1328 | yes | yes |
| SEQ ID NO:158 | 1732911 | PR00587A | SOMATOSTATIN RECEPTOR TYPE 1 SIGNATURE | 1312 | 1221 | | |
| SEQ ID NO:159 | 1785913 | PR00554C | ADENOSINE A2B RECEPTOR SIGNATURE | 1189 | 1201 | | |
| SEQ ID NO:160 | 1809069 | PR00643G | G10D ORPHAN RECEPTOR SIGNATURE | 1383 | 1367 | yes | yes |
| SEQ ID NO:161 | 1867626 | PR00665F | OXYTOCIN RECEPTOR SIGNATURE | 1290 | 1353 | yes | |
| SEQ ID NO:162 | 1880501 | PR00715I | CATION-DEPENDENT MANNOSE-6-PHOSPHATE RECEPTOR | 1392 | 1257 | yes | yes |
| SEQ ID NO:163 | 1881009 | PR00531A | HISTAMINE H2 RECEPTOR SIGNATURE | 1183 | 1269 | | yes |
| SEQ ID NO:164 | 1909132 | PR00637D | TYPE 3 BOMBESIN RECEPTOR SIGNATURE | 1131 | 1221 | | yes |
| SEQ ID NO:165 | 1955094 | PR00580 | PROSTANOID EP1 RECEPTOR SIGNATURE | 1160 | 1197 | | yes |
| SEQ ID NO:166 | 1955688 | PR00647I | SENR ORPHAN RECEPTOR SIGNATURE | 1291 | 1193 | yes | |

TABLE I-continued

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| SEQ ID NO:167 | 1956694 | PR00517F | 5-HYDROXYTRYPTAMINE 2C RECEPTOR SIGNATURE | 1259 | 1255 | | |
| SEQ ID NO:168 | 1957189 | PR00366A | ENDOTHELIN RECEPTOR SIGNATURE | 1337 | 1232 | | |
| SEQ ID NO:169 | 1957920 | PR00350B | VITAMIN D RECEPTOR SIGNATURE | 1494 | 1267 | | |
| SEQ ID NO:170 | 1957977 | PR00559C | ALPHA-2B ADRENERGIC RECEPTOR SIGNATURE | 1284 | 1157 | | yes |
| SEQ ID NO:171 | 1958505 | PR00571G | ENDOTHELIN-B RECEPTOR SIGNATURE | 1420 | 1188 | | |
| SEQ ID NO:172 | 1972687 | PR00553B | ADENOSINE A2A RECEPTOR SIGNATURE | 1258 | 1275 | yes | yes |
| SEQ ID NO:173 | 1975013 | PR00554D | ADENOSINE A2B RECEPTOR SIGNATURE | 1208 | 1312 | yes | |
| SEQ ID NO:174 | 2010369 | PR00645I | LCR1 ORPHAN RECEPTOR SIGNATURE | 1511 | 1277 | yes | yes |
| SEQ ID NO:175 | 2019481 | PR00641A | EBI1 ORPHAN RECEPTOR SIGNATURE | 1325 | 1178 | | |
| SEQ ID NO:176 | 2022460 | PR00574D | BLUE-SENSITIVE OPSIN SIGNATURE | 1263 | 1279 | yes | |
| SEQ ID NO:177 | 2022624 | PR00857C | MELATONIN RECEPTOR SIGNATURE | 1472 | 1232 | yes | yes |
| SEQ ID NO:178 | 2022628 | PR00244A | NEUROKININ RECEPTOR SIGNATURE | 1316 | 1174 | | |
| SEQ ID NO:179 | 2022630 | PR00525E | DELTA OPIOID RECEPTOR SIGNATURE | 1139 | 1261 | | yes |
| SEQ ID NO:180 | 2022631 | PR00645I | LCR1 ORPHAN RECEPTOR SIGNATURE | 1511 | 1299 | yes | yes |
| SEQ ID NO:181 | 2023275 | PR00667B | RETINAL PIGMENT EPITHELIUM-RETINAL GPCR SIGNA | 1190 | 1217 | | |
| SEQ ID NO:182 | 2023747 | PR00568D | DOPAMINE D3 RECEPTOR SIGNATURE | 1445 | 1244 | | |
| SEQ ID NO:183 | 2044305 | PR00751B | THYROTROPHIN-RELEASING HORMONE RECEPTOR SIGNA | 1443 | 1209 | yes | yes |
| SEQ ID NO:184 | 2069971 | PR00644E | GPR ORPHAN RECEPTOR SIGNATURE | 1453 | 1307 | yes | |
| SEQ ID NO:185 | 2070872 | PR00245C | OLFACTORY RECEPTOR SIGNATURE | 1364 | 1286 | yes | yes |
| SEQ ID NO:186 | 2072228 | PR00553A | ADENOSINE A2A RECEPTOR SIGNATURE | 1377 | 1218 | yes | |
| SEQ ID NO:187 | 2085633 | PR00752E | VASOPRESSIN V1A RECEPTOR SIGNATURE | 1193 | 1250 | | yes |
| SEQ ID NO:188 | 2088104 | PR00641A | EBI1 ORPHAN RECEPTOR SIGNATURE | 1325 | 1305 | yes | yes |
| SEQ ID NO:189 | 2091133 | PR00562C | BETA-2 ADRENERGIC RECEPTOR SIGNATURE | 1457 | 1302 | | |
| SEQ ID NO:190 | 2123514 | PR00587A | SOMATOSTATIN RECEPTOR TYPE 1 SIGNATURE | 1312 | 1252 | yes | |
| SEQ ID NO:191 | 2150261 | PR00176C | SODIUM/NEUROTRANSMITTER SYMPORTER SIGNATURE | 1414 | 1576 | yes | yes |
| SEQ ID NO:192 | 2170670 | PR00896H | VASOPRESSIN RECEPTOR SIGNATURE | 1331 | 1271 | yes | yes |
| SEQ ID NO:193 | 2199484 | PR00559B | ALPHA-2B ADRENERGIC RECEPTOR SIGNATURE | 1285 | 1195 | | yes |
| SEQ ID NO:194 | 2204242 | PR00896H | VASOPRESSIN RECEPTOR SIGNATURE | 1331 | 1305 | | |
| SEQ ID NO:195 | 2236316 | PR00554B | ADENOSINE A2B RECEPTOR SIGNATURE | 1090 | 1192 | yes | |
| SEQ ID NO:196 | 2237722 | PR00855H | PROSTAGLANDIN F RECEPTOR SIGNATURE | 1467 | 1218 | | |
| SEQ ID NO:197 | 2238625 | PR00585A | PROSTANOID EP3 RECEPTOR TYPE 3 SIGNATURE | 1230 | 1237 | | yes |
| SEQ ID NO:198 | 2242277 | PR00255B | NATRIURETIC PEPTIDE RECEPTOR SIGNATURE | 1264 | 1180 | yes | |
| SEQ ID NO:199 | 2244782 | PR00590A | SOMATOSTATIN RECEPTOR TYPE 4 SIGNATURE | 1253 | 1260 | | |
| SEQ ID NO:200 | 2272244 | PR00568D | DOPAMINE D3 RECEPTOR SIGNATURE | 1445 | 1365 | yes | yes |
| SEQ ID NO:201 | 2284108 | PR00652F | 5-HYDROXYTRYPTAMINE 7 RECEPTOR SIGNATURE | 1488 | 1317 | yes | yes |
| SEQ ID NO:202 | 2287109 | PR00641H | EBI1 ORPHAN RECEPTOR SIGNATURE | 1259 | 1305 | | |
| SEQ ID NO:203 | 2289873 | PR00596D | URIDINE NUCLEOTIDE RECEPTOR SIGNATURE | 1255 | 1254 | yes | yes |
| SEQ ID NO:204 | 2375491 | PR00592B | EXTRACELLULAR CALCIUM-SENSING RECEPTOR SIGNAT | 1421 | 1286 | | |
| SEQ ID NO:205 | 2376547 | PR00539E | MUSCARINIC M2 RECEPTOR SIGNATURE | 1322 | 1222 | | |
| SEQ ID NO:206 | 2377774 | PR00240F | ALPHA-1A ADRENERGIC RECEPTOR SIGNATURE | 1323 | 1215 | yes | yes |
| SEQ ID NO:207 | 2378093 | PR00854A | PROSTAGLANDIN D RECEPTOR SIGNATURE | 1169 | 1350 | yes | yes |
| SEQ ID NO:208 | 2378367 | PR00571A | ENDOTHELIN-B RECEPTOR SIGNATURE | 1357 | 1278 | | yes |
| SEQ ID NO:209 | 2378405 | PR00647I | SENR ORPHAN RECEPTOR SIGNATURE | 1291 | 1195 | | |
| SEQ ID NO:210 | 2378406 | PR00555C | ADENOSINE A3 RECEPTOR SIGNATURE | 1332 | 1369 | | |
| SEQ ID NO:211 | 2381364 | PR00666B | PINEAL OPSIN SIGNATURE | 1253 | 1249 | | yes |
| SEQ ID NO:212 | 2381732 | PR00663D | GALANIN RECEPTOR SIGNATURE | 1168 | 1242 | | |
| SEQ ID NO:213 | 2383045 | PR00522C | CANNABINOID RECEPTOR TYPE 1 SIGNATURE | 1317 | 1223 | | |
| SEQ ID NO:214 | 2470285 | PR00373D | GLYCOPROTEIN HORMONE RECEPTOR SIGNATURE | 1458 | 1537 | yes | yes |
| SEQ ID NO:215 | 2488060 | PR00558G | ALPHA-2A ADRENERGIC RECEPTOR SIGNATURE | 1396 | 1282 | yes | yes |
| SEQ ID NO:216 | 2503084 | PR00752E | VASOPRESSIN V1A RECEPTOR SIGNATURE | 1193 | 1235 | yes | |
| SEQ ID NO:217 | 2511221 | PR00565B | DOPAMINE 1A RECEPTOR SIGNATURE | 1289 | 1266 | yes | yes |
| SEQ ID NO:218 | 2512109 | PR00636B | AT2 ANGIOTENSIN II RECEPTOR SIGNATURE | 1305 | 1267 | | |
| SEQ ID NO:219 | 2553280 | PR00530I | HISTAMINE H1 RECEPTOR SIGNATURE | 1295 | 1275 | yes | |
| SEQ ID NO:220 | 2603450 | PR00373D | GLYCOPROTEIN HORMONE RECEPTOR SIGNATURE | 1458 | 1419 | yes | yes |
| SEQ ID NO:221 | 2605934 | PR00539C | MUSCARINIC M2 RECEPTOR SIGNATURE | 1365 | 1286 | yes | |
| SEQ ID NO:222 | 2674641 | PR00752E | VASOPRESSIN V1A RECEPTOR SIGNATURE | 1193 | 1228 | yes | yes |
| SEQ ID NO:223 | 2681738 | PR00258C | SPERACT RECEPTOR SIGNATURE | 1210 | 1307 | yes | yes |
| SEQ ID NO:224 | 2723293 | PR00554B | ADENOSINE A2B RECEPTOR SIGNATURE | 1090 | 1240 | yes | |
| SEQ ID NO:225 | 2762348 | PR00560D | ALPHA-2C ADRENERGIC RECEPTOR SIGNATURE | 1642 | 1284 | yes | yes |
| SEQ ID NO:226 | 2773609 | PR00854B | PROSTAGLANDIN D RECEPTOR SIGNATURE | 1257 | 1269 | | |
| SEQ ID NO:227 | 2776266 | PR00854B | PROSTAGLANDIN D RECEPTOR SIGNATURE | 1257 | 1269 | | |
| SEQ ID NO:228 | 2777115 | PR00527A | GASTRIN RECEPTOR SIGNATURE | 1327 | 1286 | | |
| SEQ ID NO:229 | 2812882 | PR00566B | DOPAMINE 1B RECEPTOR SIGNATURE | 1121 | 1215 | | yes |
| SEQ ID NO:230 | 2821121 | PR00560D | ALPHA-2C ADRENERGIC RECEPTOR SIGNATURE | 1642 | 1251 | yes | yes |
| SEQ ID NO:231 | 2848989 | PR00561F | BETA-1 ADRENERGIC RECEPTOR SIGNATURE | 1445 | 1293 | | |
| SEQ ID NO:232 | 2854471 | PR00643C | G1D ORPHAN RECEPTOR SIGNATURE | 1286 | 1051 | | |
| SEQ ID NO:233 | 2854670 | PR00571A | ENDOTHELIN-B RECEPTOR SIGNATURE | 1357 | 1222 | yes | |
| SEQ ID NO:234 | 2855520 | PR00590C | SOMATOSTATIN RECEPTOR TYPE 4 SIGNATURE | 1325 | 1255 | | |
| SEQ ID NO:235 | 2855815 | PR00558G | ALPHA-2A ADRENERGIC RECEPTOR SIGNATURE | 1396 | 1184 | | yes |
| SEQ ID NO:236 | 2857653 | PR00854B | PROSTAGLANDIN D RECEPTOR SIGNATURE | 1257 | 1302 | yes | yes |
| SEQ ID NO:237 | 2866122 | PR00350C | VITAMIN D RECEPTOR SIGNATURE | 1416 | 1264 | | |

TABLE I-continued

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| SEQ ID NO:238 | 2925464 | PR00585A | PROSTANOID EP3 RECEPTOR TYPE 3 SIGNATURE | 1230 | 1214 | yes | yes |
| SEQ ID NO:239 | 2954714 | PR00241C | ANGIOTENSIN II RECEPTOR SIGNATURE | 1246 | 1213 | | |
| SEQ ID NO:240 | 2986560 | PR00855A | PROSTAGLANDIN F RECEPTOR SIGNATURE | 1361 | 1330 | | |
| SEQ ID NO:241 | 3068234 | PR00642D | EDG1 ORPHAN RECEPTOR SIGNATURE | 1208 | 1319 | yes | yes |
| SEQ ID NO:242 | 3077943 | PR00647I | SENR ORPHAN RECEPTOR SIGNATURE | 1291 | 1268 | | |
| SEQ ID NO:243 | 3144006 | PR00715G | CATION-DEPENDENT MANNOSE-6-PHOSPHATE RECEPTOR | 1366 | 1247 | | |
| SEQ ID NO:244 | 3226980 | PR00527A | GASTRIN RECEPTOR SIGNATURE | 1327 | 1222 | yes | |
| SEQ ID NO:245 | 3290614 | PR00522G | CANNABINOID RECEPTOR TYPE 1 SIGNATURE | 1341 | 1263 | | |
| SEQ ID NO:246 | 3291235 | PR00240D | ALPHA-1A ADRENERGIC RECEPTOR SIGNATURE | 1470 | 1269 | | yes |
| SEQ ID NO:247 | 3324775 | PR00490F | SECRETIN RECEPTOR SIGNATURE | 1239 | 1217 | | yes |
| SEQ ID NO:248 | 3333159 | PR00581A | PROSTANOID EP2 RECEPTOR SIGNATURE | 1113 | 1243 | yes | |
| SEQ ID NO:249 | 3393404 | PR00343A | SELECTIN SUPERFAMILY COMPLEMENT-BINDING REPEA | 1245 | 1606 | yes | yes |
| SEQ ID NO:250 | 3429408 | PR00643G | G10D ORPHAN RECEPTOR SIGNATURE | 1383 | 1204 | | |
| SEQ ID NO:251 | 3447545 | PR00642E | EDG1 ORPHAN RECEPTOR SIGNATURE | 1216 | 1341 | | |
| SEQ ID NO:252 | 3486012 | PR00343C | SELECTIN SUPERFAMILY COMPLEMENT-BINDING REPEA | 1254 | 1343 | | |
| SEQ ID NO:253 | 3513925 | PR00261C | LOW DENSITY LIPOPROTEIN (LDL) RECEPTOR SIGNATURE | 1576 | 1256 | | |
| SEQ ID NO:254 | 3542591 | PR00573C | INTERLEUKIN 8B RECEPTOR SIGNATURE | 1042 | 1231 | | yes |
| SEQ ID NO:255 | 3556218 | PR00373F | GLYCOPROTEIN HORMONE RECEPTOR SIGNATURE | 1570 | 1293 | yes | |
| SEQ ID NO:256 | 3665056 | PR00366A | ENDOTHELIN RECEPTOR SIGNATURE | 1337 | 1251 | yes | |
| SEQ ID NO:257 | 4043152 | PR00514D | 5-HYDROXYTRYPTAMINE 1D RECEPTOR SIGNATURE | 1252 | 1304 | | yes |
| SEQ ID NO:258 | 4080842 | PR00424B | ADENOSINE RECEPTOR SIGNATURE | 1339 | 1117 | | |
| SEQ ID NO:259 | 4081268 | PR00564G | BURKITT'S LUMPHOMA RECEPTOR SIGNATURE | 1305 | 1216 | | yes |
| SEQ ID NO:260 | 4082591 | PR00640F | GASTRIN-RELEASING PEPTIDE RECEPTOR SIGNATURE | 1243 | 1311 | | |
| SEQ ID NO:261 | 4084463 | PR00539C | MUSCARINIC M2 RECEPTOR SIGNATURE | 1365 | 1258 | yes | |
| SEQ ID NO:262 | 4085069 | PR00663E | GALANIN RECEPTOR SIGNATURE | 1216 | 1210 | | |
| SEQ ID NO:263 | 4129226 | PR00250F | FUNGAL PHEROMONE MATING FACTOR STE2 GPCR SIGN | 1166 | 1178 | | |
| SEQ ID NO:264 | 4129407 | PR00564D | BURKITT'S LYMPHOMA RECEPTOR SIGNATURE | 1295 | 1222 | | |
| SEQ ID NO:265 | 4130289 | PR00539E | MUSCARINIC M2 RECEPTOR SIGNATURE | 1322 | 1236 | yes | yes |
| SEQ ID NO:266 | 4130748 | PR00751E | THYROTROPHIN-RELEASING HORMONE RECEPTOR SIGNA | 1433 | 1245 | | |
| SEQ ID NO:267 | 4131249 | PR00240F | ALPHA-1A ADRENERGIC RECEPTOR SIGNATURE | 1323 | 1305 | yes | |
| SEQ ID NO:268 | 4132125 | PR00581E | PROSTANOID EP2 RECEPTOR SIGNATURE | 1195 | 1157 | | |
| SEQ ID NO:269 | 4132371 | PR00350C | VITAMIN D RECEPTOR SIGNATURE | 1416 | 1321 | | yes |
| SEQ ID NO:270 | 4132403 | PR00248E | METABOTROPIC GLUTAMATE GPCR SIGNATURE | 1306 | 1167 | | |
| SEQ ID NO:271 | 4132547 | PR00559E | ALPHA-2B ADRENERGIC RECEPTOR SIGNATURE | 1546 | 1214 | | |
| SEQ ID NO:272 | 4133631 | PR00928F | GRAVES DISEASE CARRIER PROTEIN SIGNATURE | 1555 | 1238 | | |
| SEQ ID NO:273 | 4166159 | PR00855H | PROSTAGLANDIN F RECEPTOR SIGNATURE | 1467 | 1236 | | |
| SEQ ID NO:274 | 4167883 | PR00537C | MU OPIOID RECEPTOR SIGNATURE | 1348 | 1185 | | |
| SEQ ID NO:275 | 4220523 | PR00537C | MU OPIOID RECEPTOR SIGNATURE | 1348 | 1227 | yes | |
| SEQ ID NO:276 | 4220713 | PR00366G | ENDOTHELIN RECEPTOR SIGNATURE | 1420 | 1276 | | |
| SEQ ID NO:277 | 4220819 | PR00855H | PROSTAGLANDIN F RECEPTOR SIGNATURE | 1467 | 1263 | | |
| SEQ ID NO:278 | 4220939 | PR00571A | ENDOTHELIN-B RECEPTOR SIGNATURE | 1357 | 1235 | yes | |
| SEQ ID NO:279 | 4221286 | PR00574D | BLUE-SENSITIVE OPSIN SIGNATURE | 1263 | 1254 | yes | |
| SEQ ID NO:280 | 4221314 | PR00530I | HISTAMINE H1 RECEPTOR SIGNATURE | 1295 | 1263 | yes | yes |
| SEQ ID NO:281 | 4222520 | PR00350C | VITAMIN D RECEPTOR SIGNATURE | 1416 | 1202 | | |
| SEQ ID NO:282 | 4223468 | PR00592A | EXTRACELLULAR CALCIUM-SENSING RECEPTOR SIGNAT | 1379 | 1206 | | |
| SEQ ID NO:283 | 4223734 | PR00652F | 5-HYDROXYTRYPTAMINE 7 RECEPTOR SIGNATURE | 1488 | 1213 | | |
| SEQ ID NO:284 | 4224867 | PR00244E | NEUROKININ RECEPTOR SIGNATURE | 1282 | 1266 | | |
| SEQ ID NO:285 | 4256014 | PR00665F | OXYTOCIN RECEPTOR SIGNATURE | 1290 | 1353 | yes | |
| SEQ ID NO:286 | 4352201 | PR00643H | G10D ORPHAN RECEPTOR SIGNATURE | 1453 | 1297 | | |
| SEQ ID NO:287 | 4355247 | PR00536E | MELANOCYTE STIMULATING HORMONE RECEPTOR SIGNA | 1313 | 1353 | yes | |
| SEQ ID NO:288 | 4608111 | PR00596A | URIDINE NUCLEOTIDE RECEPTOR SIGNATURE | 1217 | 1273 | yes | yes |
| SEQ ID NO:289 | 319589 | PR00635F | AT1 ANGIOTENSIN II RECEPTOR SIGNATURE | 1424 | 1398 | yes | yes |
| SEQ ID NO:290 | 884692 | PR00255B | NATRIURETIC PEPTIDERECEPTOR SIGNATURE | 1264 | 1239 | | yes |
| SEQ ID NO:291 | 1262948 | PR00248C | METABOTROPIC GLUTAMATE GPCR SIGNATURE | 1402 | 1369 | yes | yes |
| SEQ ID NO:292 | 1876370 | PR00343A | SELECTIN SUPERFAMILY COMPLEMENT-BINDING | 1245 | 1616 | yes | yes |
| SEQ ID NO:293 | 2088868 | PR00522G | CANNABINOID RECEPTOR TYPE 1 SIGNATURE | 1341 | 1329 | yes | yes |
| SEQ ID NO:294 | 3550808 | PR00594B | P2U PURINOCEPTOR SIGNATURE | 1452 | 1255 | yes | yes |
| SEQ ID NO:295 | 1328883 | PR00169H | POTASSIUM CHANNEL SIGNATURE | 1749 | 1204 | | |
| SEQ ID NO:296 | 3458089 | PR00169G | POTASSIUM CHANNEL SIGNATURE | 1540 | 1390 | yes | no |
| SEQ ID NO:297 | 1329138 | PR00168F | SLOW VOLTAGE-GATED POTASSIUM CHANNEL SIGNATUR | 1307 | 1176 | | |
| SEQ ID NO:298 | 1514470 | PR00944B | COPPER ION BINDING PROTEIN SIGNATURE | 1319 | 1255 | no | yes |
| SEQ ID NO:299 | 1513293 | PR00944B | COPPER ION BINDING PROTEIN SIGNATURE | | | | |
| SEQ ID NO:300 | 1514470F6 | PR00944B | COPPER ION BINDING PROTEIN SIGNATURE | | | | |
| SEQ ID NO:301 | 1514470H1 | PR00944B | COPPER ION BINDING PROTEIN SIGNATURE | | | | |

TABLE I-continued

| SEQ ID NO | INCYTE CLONE NO | PRINT ID | PRINT DESCRIPTION | PRINT STRENGTH | PRINT SCORE | TM | SIGNAL PEPTIDE |
|---|---|---|---|---|---|---|---|
| SEQ ID NO:302 | 3372628 | PR00944B | COPPER ION BINDING PROTEIN SIGNATURE | | | | |
| SEQ ID NO:303 | 4970006 | PR00944B | COPPER ION BINDING PROTEIN SIGNATURE | 1319 | 1255 | no | no |
| SEQ ID NO:304 | 4970006H1 | PR00944B | COPPER ION BINDING PROTEIN SIGNATURE | | | | |
| SEQ ID NO:305 | 4970006F6 | PR00944B | COPPER ION BINDING PROTEIN SIGNATURE | | | | |

What is claimed is:

1. A combination comprising a plurality of polynucleotide sequences, wherein the polynucleotide sequences consist of SEQ ID NOs:1–305.

2. The combination of claim 1, wherein each polynucleotide sequence is a probe.

3. The combination of claim 2, wherein each polynucleotide sequence is immobilized on a substrate.

4. The combination of claim 1, wherein each polynucleotide sequence is an array element.

5. A composition consisting of the polynucleotide sequence of SEQ ID NO:184.

* * * * *